US 11,684,614 B2

(12) United States Patent
Abergel et al.

(10) Patent No.: US 11,684,614 B2
(45) Date of Patent: Jun. 27, 2023

(54) FORMULATIONS OF HYDROXYPYRIDONATE ACTINIDE/LANTHANIDE DECORPORATION AGENTS

(71) Applicant: THE REGENTS OF THE UNIVERSITY OF CALIFORNIA, Oakland, CA (US)

(72) Inventors: Rebecca J. Abergel, Kensington, CA (US); Taylor A. Choi, South San Francisco, CA (US); Kenneth N. Raymond, Berkeley, CA (US); David K. Shuh, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 113 days.

(21) Appl. No.: 16/330,601

(22) PCT Filed: Sep. 5, 2017

(86) PCT No.: PCT/US2017/050121
§ 371 (c)(1),
(2) Date: Mar. 5, 2019

(87) PCT Pub. No.: WO2018/048812
PCT Pub. Date: Mar. 15, 2018

(65) Prior Publication Data
US 2021/0283115 A1     Sep. 16, 2021

(51) Int. Cl.
*A61K 31/444* (2006.01)
*A61P 39/04* (2006.01)
(Continued)

(52) U.S. Cl.
CPC .......... *A61K 31/444* (2013.01); *A61K 9/0019* (2013.01); *A61K 9/0056* (2013.01);
(Continued)

(58) Field of Classification Search
CPC .. A61K 31/444; A61K 9/2018; A61K 9/1652; A61K 9/0019; A61K 9/2054;
(Continued)

(56) References Cited

U.S. PATENT DOCUMENTS 3,323,857 A     6/1967  Bauer
3,634,113 A     1/1972  Fhrenbacher
(Continued)

FOREIGN PATENT DOCUMENTS

CN     104825389         8/2015
CN     104825389  A      8/2015
(Continued)

OTHER PUBLICATIONS

Sam II, AD et al. Safety of gadolinium contrast angiography in patients with chronic renal Insufficiency Journal of Vascular Surgery, vol. 38, pp. 313-318, (2003).
(Continued)

*Primary Examiner* — Carlos A Azpuru
(74) *Attorney, Agent, or Firm* — Knobbe, Martens, Olson & Bear LLP

(57) ABSTRACT

Provided herein are pharmaceutical formularions comprising a 1,2-HOPO chelating agent and/or 3,2-HOPO chelating agent.

18 Claims, 47 Drawing Sheets

(51) Int. Cl.
*A61K 9/00* (2006.01)
*A61K 9/16* (2006.01)
*A61K 9/20* (2006.01)

(52) U.S. Cl.
CPC .......... *A61K 9/0095* (2013.01); *A61K 9/1611* (2013.01); *A61K 9/1623* (2013.01); *A61K 9/1652* (2013.01); *A61K 9/2009* (2013.01); *A61K 9/2018* (2013.01); *A61K 9/2054* (2013.01); *A61P 39/04* (2018.01)

(58) Field of Classification Search
CPC .. A61K 9/1623; A61K 9/2009; A61K 9/0056; A61K 9/0095; A61K 9/1611; A61P 39/04; A61P 39/08
See application file for complete search history.

(56) References Cited

U.S. PATENT DOCUMENTS

| | | | |
|---|---|---|---|
| 4,025,602 | A | 5/1977 | Campbell |
| 4,278,559 | A | 7/1981 | Levenson et al. |
| 4,698,431 | A | 10/1987 | Raymond et al. |
| 4,891,075 | A | 1/1990 | Dakubu |
| 5,442,116 | A | 8/1995 | Welch et al. |
| 5,482,570 | A | 1/1996 | Saurer et al. |
| 5,510,091 | A | 4/1996 | Rais |
| 5,571,894 | A | 11/1996 | Wels et al. |
| 5,587,458 | A | 12/1996 | King et al. |
| 5,591,828 | A | 1/1997 | Bosslet et al. |
| 5,624,901 | A | 4/1997 | Raymond et al. |
| 5,634,901 | A | 6/1997 | Alba et al. |
| 5,753,204 | A | 5/1998 | Huston et al. |
| 5,826,161 | A | 10/1998 | Madic et al. |
| 5,869,046 | A | 2/1999 | Presta et al. |
| 5,892,029 | A | 4/1999 | Raymond et al. |
| 6,221,476 | B1 | 4/2001 | Bruening et al. |
| 6,843,917 | B1 | 1/2005 | Guy et al. |
| 6,846,915 | B2 | 1/2005 | Raymond et al. |
| 8,361,794 | B2 | 1/2013 | Jakobsen et al. |
| 8,475,747 | B1 | 7/2013 | Johnson et al. |
| 8,557,601 | B2 | 10/2013 | Raymond et al. |
| 8,933,526 | B2 | 1/2015 | Tsakalakos et al. |
| 9,123,846 | B2 | 9/2015 | Le Perchec et al. |
| 9,472,694 | B2 | 10/2016 | Dionne et al. |
| 9,556,122 | B2 | 1/2017 | Raymond et al. |
| 10,982,136 | B2 | 4/2021 | Agbo et al. |
| 2002/0122752 | A1 | 9/2002 | Fukasawa et al. |
| 2005/0008570 | A1 | 1/2005 | Raymond et al. |
| 2009/0184051 | A1 | 7/2009 | Heres et al. |
| 2009/0320646 | A1 | 12/2009 | Yaita et al. |
| 2010/0015725 | A1 | 1/2010 | Raymond et al. |
| 2010/0261902 | A1 | 10/2010 | Xu |
| 2010/0317117 | A1 | 12/2010 | Peterson |
| 2011/0250138 | A1 | 10/2011 | Fan et al. |
| 2012/0132277 | A1 | 5/2012 | Sulima et al. |
| 2012/0214843 | A1* | 8/2012 | Durbin-Heavey ...... A61P 39/04 514/335 |
| 2014/0039169 | A1 | 2/2014 | Raymond et al. |
| 2014/0235680 | A1 | 8/2014 | Bergeron et al. |
| 2016/0289223 | A1 | 10/2016 | Bergeron |
| 2016/0362491 | A1 | 12/2016 | Mudde et al. |
| 2017/0298272 | A1 | 10/2017 | Agbo et al. |
| 2017/0360956 | A1 | 12/2017 | Butlin et al. |
| 2019/0183868 | A1 | 6/2019 | Abergel et al. |
| 2019/0287691 | A1 | 9/2019 | Abergel et al. |
| 2019/0382470 | A1 | 12/2019 | Himmler et al. |
| 2021/0009510 | A1 | 1/2021 | Abergel et al. |
| 2022/0152003 | A1 | 5/2022 | Abergel et al. |

FOREIGN PATENT DOCUMENTS

| | | |
|---|---|---|
| CN | 104998251 | 10/2015 |
| CN | 104998251 A | 10/2015 |
| EP | 0404097 B1 | 6/1990 |
| EP | 1755586 A2 | 2/2007 |
| EP | 3452040 A1 | 3/2019 |
| EP | 3509595 A1 | 7/2019 |
| EP | 3519034 A1 | 8/2019 |
| EP | 3520117 A2 | 8/2019 |
| JP | 2008-525812 | 7/2008 |
| JP | 2019-514944 A | 6/2019 |
| JP | 2019-532040 A | 11/2019 |
| JP | 2019-532182 A | 11/2019 |
| WO | WO 1993/01161 A1 | 1/1993 |
| WO | WO 1993/16185 A2 | 8/1993 |
| WO | 2006/028523 A2 * | 3/2006 |
| WO | WO 2006/028523 | 3/2006 |
| WO | WO 2006/072620 A1 | 7/2006 |
| WO | WO 2007/098934 A1 | 9/2007 |
| WO | WO 2010/129962 | 11/2010 |
| WO | 2010/129962 A2 * | 11/2011 |
| WO | WO 2015/077655 A1 | 5/2015 |
| WO | WO 2017/105565 | 6/2017 |
| WO | WO 2017/192581 A1 | 11/2017 |
| WO | WO 2018/048812 A1 | 3/2018 |
| WO | WO 2018/063638 A1 | 4/2018 |
| WO | WO 2018/097871 A2 | 5/2018 |

OTHER PUBLICATIONS

Office Action dated Jan. 2, 2020 in U.S. Appl. No. 15/442,441.
Office Action dated Apr. 9, 2020 in U.S. Appl. No. 15/442,441.
Office Action dated Mar. 10, 2020 in U.S. Appl. No. 16/097,782.
Office Action dated Oct. 15, 2019 in U.S. Appl. No. 16/097,782.
Office Action dated Jun. 25, 2019 in U.S. Appl. No. 16/097,782.
Supplementary Partial European Search Report, re Application No. 17873523.9, dated May 27, 2020.
Office Action dated May 14, 2021 in European Patent Application No. 17793154.0.
Durbin, P. et al., "Octadentate catecholamide ligands for Pu (IV) based on linear or preorganized molecular backbones", Human Toxicology, Macmillan Publishers, Basingstoke GB, vol. 15, No. 4, pp. 352-360, 1996.
Gans, et al., GLEE, a new computer program for glass electrode calibration, Talanta, vol. 51, No. 1, pp. 33-37, 2000.
Uhlir, Linda et al., "Specific sequestering agents for the actinides. 21. Synthesis and initial biological testing of octadentate mixed catecholate-hydroxypyridinonate ligands", Journal of Medicinal Chemistry, vol. 36, No. 4, pp. 504-509, 1993.
Office Action dated Jul. 22, 2020 in U.S. Appl. No. 16/097,782.
European Search Report, re Application No. 17873523.9, dated Aug. 27, 2020.
Supplementary Partial European Search Report, re Application No. 17857076.8, dated Oct. 7, 2020.
Extended European Search Report dated Jan. 19, 2021 in Application No. 17857076.8.
Abergel, et al. Biomimetic Actinide Chelators: An Update on the Preclinical Development of the Orally Active Hydroxypyridonate Decorporation Agents 3,4,3-L/(1,2-HOPO) and 5-LIO(Me-3,2-HOPO). Health Physics, vol. 99, No. 3, pp. 401-417, 2010.
Abergel, et al. Using the Antenna Effect as a Spectroscopic Tool; Photophysics and Solution Thermodynamics of the Model Luminescent Hydroxypyridonate Complex [EuIII(3,4,3-LI(1,2-HOPO))], Inorganic Chemistry, vol. 48, No. 23, pp. 10868-10870, 2009.
Abergei, et al., Multidentate Terephthalamidate and Hydroxypyridonate Ligands: Towards New Orally Active Chelators, Hemoglobin, vol. 35, No. 3, pp. 276-290, 2011.
Agbo et al., Enhanced ultraviolet photon capture in ligand-sensitized nanocrystals, ACS Photonics, vol. 3, pp. 547-552, 2016.
Agbo et al., Ligand-Sensitized Lanthanide Nanocrystals: Merging Solid-State Photophysics and Molecular Solution Chemistry, Inorganic Chemistry, vol. 55, No. 20, pp. 9973-9980, 2016.
Agency for Toxic Substances and Disease Registry (ATSDR), Toxicological profile for Plutonium. 2010, U.S. Department of Health and Human Services, Public Health Service: Atlanta, GA.

(56) References Cited

OTHER PUBLICATIONS

Alderighi, et al., Hyperquad Simulation and Speciation (HySS): A Utility Program for the Investigation of Equilibria Involving Soluble and Partially Soluble Species, Coordination Chemistry Reviews, vol. 184, pp. 311-318, 1999.

Allred, B. et al. Siderocalin-mediated recognition, sensitization, and cellular uptake of actinides. Proceedings of the National Academy of Sciences of the United States of America, vol. 112, pp. 10342, 2015.

An, et al., Elimination Profiles After Delayed Treatment With 3,4,3L/(1,2HOPO) in Female and Male Swiss-Webster Mice. International Journal of Radiation Biology, vol. 90, No. 11, pp. 1055-1061, 2014.

An, et al., From Early Prophylaxis to Delayed Treatment: Establishing The Plutonium Decorporation Activity Window of Hydroxypyridinonate Chelating Agents, Chemico-Biological Interactions, Elsevier Science Ireland, IR, vol. 267, pp. 80-88, 2016.

Ansari, et al., Extraction of actinides using N, N,N , N-Tetraoctyl Diglycolamide (TODGA): A Thermodynamic Study Radiochimica. Acta Journal, vol. 94, pp. 307-312, 2006.

Ansari, et al., N,N,N',N'-Tetraoctyl Diglycolamide (TODGA): A Promising Extractant for Actinide-Partitioning from High-Level Waste (HLW), Solvent Extraction and Ion Exchange, pp. 463-479, 2006.

Antonio, M. et al., Berkelium redox speciation, Radiochim. Acta, vol. 90, pp. 851-856, (2006).

Argonne National Laboratory Division of Biological and Medical Research, Annual Report, Argonne National Laboratory. Division of Biological and Medical Research: Argonne, Illinois. 1979.

Baco, et al., Diphenyl-Benzo[1,3]dioxole-4-Carboxylic Acid Pentafluorophenyl Ester: A Convenient Catechol Precursor in the Synthesis of Siderophore Vectors Suitable for Antibiotic Trojan Horse Strategies, Organic and Biomolecular Chemistry, vol. 12, pp. 749, 2014.

Banker, et al., Pharmaceutics and Pharmacy Practice, pp. 238-250, 1982.

Banski, M. et al., NaYF4 nanocrystals with TOPO ligands: synthesis-dependent structural and luminescent properties, Physical Chemistry Chemical Physics, vol. 15, No. 47, pp. 19232-19241, 2013.

Baral, T. et al., Experimental Therapy of African Trypanosomiasis With a Nanobody-Conjugated Human Trypanolytic Factor, Nature Medicine, vol. 12, pp. 580-584, 2006.

Barthelemy, et al., Journal of Biological Chemistry, pp. 3283-3639, 2008.

Baybarz, et al. Absorption Spectra of Bk(III) and Bk(IV) in Several Media, Journal of Inorganic and Nuclear Chemistry, vol. 34, pp. 739-746, 1972.

Bhattacharyya, M. et al., Action of DTPA on Hepatic Plutonium: III. Evidence for a Direct Chelation Mechanism for DTPA-Induced Excretion of Monomeric Plutonium into Rat Bile, Radiation Research, vol. 80, pp. 108-115, 1979.

Binz, et al., Engineering Novel Binding Proteins From Nonimmunoglobulin Domains, Nature Biotechnology, vol. 23, pp. 1257-1268, 2005.

Bird, et al., Single-chain antigen-binding proteins, Science, vol. 242, No. 4877, pp. 423-426, 1988.

Boersma, et al., DARPins and Other Repeat Protein Scaffolds: Advances in Engineering and Applications, Current Opinion in Biotechnology, vol. 22, No. 4, pp. 849-857, 2011.

Bunin, et al., Dose-Dependent Efficacy and Safety Toxicology of Hydroxypyridinonate Actinide Decorporation Agents in Rodents: Towards a Safe and Effective Human Dosing Regimenm Radiation Research, vol. 179, No. 2, pp. 171-182, 2013.

Bünzlil, et al., Lanthanide Luminescence for Biomedical Analyses and Imaging, Chemical Reviews, vol. 110, No. 5, pp. 2729-2755, 2010.

Bünzlil, et al. Taking Advantage of Luminescent Lanthanide Ions, Chemical Society Reviews, vol. 34, No. 12, pp. 1048-1077, 2005.

Carnall, et al., A Systematic Analysis of the Spectra the Trivalent Actinide Chlorides in D3h Site Symetry, Argonne National Laboratory, Argonne , Illinois, USA, 1989.

Carott, et al., Distribution of plutonium, americium and interfering fission products between nitric acid and a mixed organic phase of TODGA and DMDOHEMA in kerosene, and implications for the design of the "EURO-GANEX" process, Hydrometallurgy, vol. 152, pp. 139-148, 2015.

Carrot, et al. Neptunium Extraction and Stability in the GANEX Solvent: 0.2 M TODGA/0.5 M DMDOHEMA/ Kerosene, Solvent Extraction and Ion Exchange, 2012.

Captain, et al., Engineered Recognition of Tetravalent Zirconium and Thorium by Chelator-Protein Systems: Toward Flexible Radiotherapy and Imaging Platforms, Inorganic Chemistry, vol. 55, pp. 11930-11936, 2016.

Cassatt, et al., Medical Countermeasures Against Nuclear Threats: Radionuclide Decorporation Agents., Radiation Research, vol. 170, No. 4, pp. 540-548, 2008.

Chang, et al., Analytical Methods for the Bioavailability Evaluation of Hydroxypyridinonate Actinide Decorporation Agents in Pre-Clinical Pharmacokinetic Studies, Journal Chromatography Separation Technique Journal, 2012.

Chen, et al. Core/Shell NaGdF4:Nd3+/NaGdF4 Nanocrystals with Efficient Near-Infrared to Near-Infrared Downconversion Photoluminescence for Bioimaging Applications, ACS Nano, vol. 6, No. 4, pp. 2969-2977, 2012.

Choi, et al., Biodistribution of the Multidentate Hydroxypyridinonate Ligand [(14) CJ-3,4,3-L/(1,2-HOPO), A Potent Actinide Decorporation Agent, Drug Development Research, vol. 76, No. 3, pp. 107-122, 2015.

Choi, et al., In vitro metabolism and stability of the actinide chelating agent 3,4,3-Lf {1,2-l-/OPO). Journal of pharmaceutical sciences, vol. 104, No. 5, pp. 1832-1838, 2015.

Choi, et al., Understanding the Health Impacts and Risks of Exposure to Radiation, in Reflections on the Fukushima Daiichi Nuclear Accident, Chemical Sciences Division, Lawrence Berkeley National Laboratory, pp. 259-281, 2015.

Chudinov, et al., The separation of berkelium (III) from cerium (III), Journal of Radioanalytical and Nuclear Chemistry, vol. 10, pp. 41-46, 1972.

Cortez-Retamozo, V. et al., Efficient Cancer Therapy with a Nanobody-Based Conjugate, Cancer Research, vol. 64, pp. 2853-2857, 2004.

Cotton, et al., Wiley, 2006. http://www.wiley.com/WileyCDA/WileyTitle/productCd-0470010053.html.

Daumann, et al. New Insights into Structure and Luminescence of Eu(III) and Sm(III) Complexes of the 3,4,3-Li(1,2-HOPO) Ligand, Journal of the American Chemical Society, vol. 137, pp. 2816-2819, 2015.

Deblonde, et al., A New Strategy for the Purification of Heavy Actinides and Medical Radioisotopes, Advanced Techniques in Actinide Spectroscopy, 2018.

Deblonde, et al., Chelation and stabilization of berkelium in oxidation state +IV, Nature Chemistry, vol. 9, pp. 843-849, 2017.

Deblonde, et al., Complexation, Characterization and Separation of the Lanthanides and Actinides: Shedding Light to Subtle Differences within the f-element Series, Actinides and Rare Earths Focus Topic, 2018.

Deblonde, et al., Solution Thermodynamic Stability of Complexes Formed with the Octadentate Hydroxypyridinonate Ligand 3,4,3-LI(1,2-HOPO): A Critical Feature for Efficient Chelation of Lanthanide(IV) and Actinide(IV) Ions, Inorganic Chemistry, vol. 52, pp. 8805-8811, 2013.

Deblonde, et al., 1387—Hydropyridinonate ligands: From iron(III) to berkelium(IV) chemistry, Abstract.

Deblonde, et al., Inducing Selectivity and Chirality in Group IV Metal Coordination With High-Denticity Hydroxypyridinones†, Dalton Transactions, No. 23, 2019.

Deblonde, et al., Solution Thermodynamics and Kinetics of Metal Complexation with a Hydroxypyridinone Chelator Designed for Thorium-227 Targeted Alpha Therapy, Inorganic Chemistry, vol. 57, pp. 14337-14346, 2018.

Deblonde, et al., Solution thermodynamics of hydropyridinonate 4f and 5f complexes, 28th Rare Earth Research Conference, 2017.

(56) References Cited

OTHER PUBLICATIONS

Deblonde, et al., Toxic heavy metal—Pb, Cd, Sn—complexation by the octadentate hydroxypyridinonate ligand archetype 3,4,3-LI(1,2-HOPO)†, New Journal of Chemistry, vol. 42, pp. 7649-7658, 2018.
Deblonde, et al., Ultra-selective Ligand-driven Separation of Strategic Actinides, Nature Communications, 2019.
Deblonde, et al., Inorganic chemistry, vol. 52, No. 15, pp. 8805-8811, 2013.
Delmau, et al., Extraction of Trivalent Actinides and Lanthanides from Californium Campaign Rework Solution Using TODGA-based Solvent Extraction System, Oak Ridge National Laboratory, 2017.
Deri, et al., Alternative Chelator for 89Zr Radiopharmaceuticals: Radiolabeling and Evaluation of 3,4,3-(LI-1,2-HOPO), Journal of Medicinal Chemistry, vol. 57, No. 11, pp. 4849-4860, 2014.
Deri, et al., Bioconjugate Chemistry, vol. 26, No. 12, pp. 2579-2591, 2015.
Deri, et al., A Superior Bifunctional Chelator for 89Zr ImmunoPET, Bioconjugate Chemistry, vol. 26, No. 12, pp. 2579-2591, 2015.
Designing a Process for Selecting a Site for a Deep-Mined, Geologic Repository for High Level Radioactive Waste and Spent Nuclear Fuel, United States Nuclear Waste Technical Review Board, pp. 1-228, 2015.
Durbin, et al. Actinides in Animals and Man, in The Chemistry of the Actinide and Transactinide Elements, L.R. Morss, N.M. Edelstein, and J. Fuger, Editors, pp. 3339-3340, 2006.
Durbin, et al., Gross Composition and Plasma and Extracellular Water Volumes of Tissues of a Reference Mouse, Health Physics, vol. 63, No. 4, pp. 427-442, 1992.
Durbin, et al., Lecture: The Quest For Therapeutic Actinide Chelators, Health Physics, vol. 95, No. 5, pp. 465-492, 2008.
Dutta, et al., Studies on separation of 90Y and 90Sr separation from hydrochloric acid solutions using TODGA as the extractant by SLM method, Procedia Chemistry, vol. 7, pp. 191-194, 2012.
Fritsch, et al., Simplified Structure of a New Model to Describe Urinary Excretion of Plutonium After Systemic, Liver or Pulmonary Contamination of Rats Associated With Ca-DTPA Treatments, Radiation Research, vol. 171, No. 6, pp. 674-686, 2009.
Fritsch, et al., Structure of a Single Model to Describe Plutonium and Americium Decorporation by DTPA treatments, Health Physics, vol. 99, No. 4, pp. 553-559, 2010.
Gans, et al., Investigation of Equilibria in Solution. Determination of Equilibrium Constants with the Hyperquad Suite of Programs, Talanta, vol. 43, pp. 1739-1753, 1996.
Gennaro, et al., Remington: The Science and Practice of Pharmacy, 20th ed, 2003.
Goetz, et al., The Neutrophil Lipocalin NGAL is a Bacteriostatic Agent That Interferes With Siderophore-Mediated Iron Acquisition, Molecular Cell, vol. 10, pp. 1033-1043, 2002.
Gorden, et al., Rational Design of Sequestering Agents for Plutonium and Other Actinides, Chemical Reviews, vol. 103, pp. 4207-4282, 2003.
Grappin, et al., Treatment of actinide exposures: A review oJCa-DTPA injections inside CEA-COGEMA plants, Radiation Protection Dosimetry, vol. 127, pp. 435-439, 2007.
Gregoric, et al., Characterization and Leaching of Neodymium Magnet Waste and Solvent Extraction of the Rare-Earth Elements Using TODGA, Journal of Sustain. Metall, vol. 3, pp. 638-645, 2017.
Grimes, et al., Trivalent Lanthanide/Actinide Separation Using Aqueous-Modified TALSPEAK Chemistry, Solvent Extraction and Ion Exchange, vol. 32, No. 4, pp. 378-390, 2014.
Gutmacher, et al., The absorption spectra of Bk3+ and Bk4+ in solution, Journal of Inorganic and Nuclear Chemistry, vol. 29, pp. 2341-2345, 1967.
Gutmacher, et al., Stability of Tetravalent Berkelium in Acid Solution and the Absorption Spectra of Bk(IV) and Bk(III), Journal of Inorganic and Nuclear Chemistry, pp. 979-994, 1973.
Harvey, Production of Actinium-225 via High Energy Proton Induced Spallation of Thorium-232. Final Technical Report DE-SC0003602, NorthStar Medical Radioisotopes, LLC, https ://world wide web .osti.gov/scitech/servlets/purl/1032445/).
Hobart, et al., The Chemistry of the Actinide and Transactinide Elements—Chapter X—Berkelium, Springer, 2006.
Hoet, et al., Generation of High-Affinity Human Antibodies by Combining Donor-Derived and Synthetic Complementarity-Determining-Region Diversity, Nature Biotechnology, vol. 23, pp. 344-348, 2005.
Holliger, et al., Diabodies: small bivalent and bispecific antibody fragments, Proceedings of the National Academy of Sciences of the USA, vol. 90, pp. 6444-6448, 1993.
Hudson, et al., Engineered antibodies, Nature Medicine, vol. 9, pp. 129-134, 2003.
Husain, et al., Extraction chromatography of lanthanides using N,N,N',N'-tetraoctyl diglycolamide (TODGA) as the stationary phase, Desalination, vol. 229, pp. 294-301, 2008.
Huston, et al., Protein Engineering of Antibody Binding Sites: Recovery of Specific Activity in an Anti-Digoxin Single-Chain Fv Analogue Produced in *Escherichia coli*, Proceedings of the National Academy of Sciences of the USA, vol. 85, pp. 5879-5883, 1988.
Iqbal, et al., Synthesis and Am/Eu extraction of novel TODGA derivatives, Supramolecualr Chemistry, vol. 22, pp. 827-837, 2010.
Jang, et al. Bright dual-mode green emission from selective set of dopant ions in β-Na(Y,Gd)F4:Yb,Er/β-NaGdF4:Ce,Tb core/shell nanocrystals, Optics Express, vol. 20, No. 15, pp. 17107-17118, (2012).
Jarvis, et al., Significance of Single Variables in Defining Adequate Animal Models to Assess the Efficacy of New Radionuclide Decorporation Agents: Using the Contamination Dose as an Example. Drug Development Research, vol. 73, No. 5, pp. 281-299, 2012.
Burgaada, et al., Journal of Labelled Compounds and Radiopharmaceuticals, vol. 44, pp. 13-19, 2001.
Jursich, et al., Laser induced fluorescence of 249 Bk 4+ in CeF 4, Inorganica Chim. Acta. vol. 139, pp. 273-274. 1987.
Konzen, et al, Development of the Plutonium-DTPA Biokinetic Model. Health Physics, vol. 108, No. 6, pp. 565-573, 2015.
Kurkoti, et al., Gadolinium and nephrogenic systemic fibrosis: Association or causation. 1-10 Nephrology, vol. 13, pp. 235-241, 2008.
Kullgren, et al., Actinide Chelation: Biodistribution and In Vivo Complex Stability of the Targeted Metal Ions, Toxicology Mechanisms and Methods, vol. 23, No. 1, pp. 18-26, 2013.
Lakowicz, et al., Energy Transfer, Principles of Fluorescence Spectroscopy, pp. 367-394, 2006.
Lake, et al., Construction and Binding Analysis of Recombinant Single-Chain TCR Derived From Tumor-Infiltrating Lymphocytes and a Cytotoxic T Lymphocyte Clone Directed Against MAGE-1, International Immunology, vol. 11, pp. 745-751, 1999.
Lakshminarayana, et al., Cooperative downconversion luminescence in Pr3+/Yb3+:SiO2—Al2O3—BaF2—GdF3 glasses, Journal of Materials Research, vol. 23, Issue 11, pp. 3090-3095, 2008.
Li, et al., Engineering Homogeneous Doping in Single Nanoparticle to Enhance Upconversion Efficiency, Nano Lett., vol. 14, No. 6, pp. 3634-3639, 2014.
Li, et al., Enhanced NIR downconversion luminescence by precipitating nano Ca5(P04)3F crystals in Eu2+-Yb3+ co-doped glass, Spectrochimica Acta Part A: Molecular and Biomolecular Spectroscopy, vol. 114, pp. 575-578, 2013.
Li, et al. Nd3+ Sensitized Up/Down Converting Dual-Mode Nanomaterials for Efficient In-vitro and In-vivo Bioimaging Excited at 800 nm, Scientific Reports, vol. 3, pp. 3536, 2013.
Liu, et al. A Stratgey to Achieve Efficent Dual-Mode Luminscence of EU3+ in Lanthanides Doped Multifunctional NAGdF4 Nanocrystals, Adv Matter, vol. 22, pp. 3266-3271, 2010.
Liu, et al. Morphology and Phase-Controlled Synthesis of Monodisperse Lanthanide-Doped NaGdF4 Nanocrystals with Multicolor Photo Luminsence, Journal of Materials Chemistry, vol. 19, pp. 489-496, 2009.
Liu et al., Procedures for a fast separation of berkelium from complex mixtures of reaction products, J. Radioanal. Nucl. Chem. 76, pp. 119-124, 1983.
Lohithakshan, et al., Solvent extraction studies of plutonium(IV) and americium(III) in room temperature ionic liquid (RTIL) by

(56) References Cited

OTHER PUBLICATIONS di-2-ethyl hexyl phosphoric acid (HDEHP) as Extractant, Journal of Radioanalytical and Nuclear Chemistry, vol. 301, pp. 153-157, 2014.

Loomis, et al., Inorganic Chemistry, vol. 30, No. 5, pp. 906-911, 1991.

Lumetta, et al., An Advanced TALSPEAK Concept Using 2-Ethylhexylphosphonic Acid Mono-2-Ethylhexyl Ester as the Extractant, Solvent Extraction and Ion Exchange, vol. 33, No. 3, pp. 211-223, 2015.

Lundberg, et al., Structural Study of the N,N'-Dimethylpropyleneurea Solvated Lanthanoid(III) Ions in Solution and Solid State with an Analysis of the Ionic Radii of Lanthanoid(III) Ions, Inorganic Chemistry, vol. 49, pp. 4420-4432, 2010.

Lundberg, et al., The size of actinoid(III) ions—structural analysis vs. common misinterpretations, Coordination Chemistry Reviews, vol. 318, pp. 131-134, 2016.

Martell, et al., NIST Standard Reference Database; National Institute of Standards and Technology: Gaithersburg, MD.

Maynard, et al., High-Level Bacterial Secretion of Single-Chain Aβ T-Cell Receptors, Journal of Immunological Methods, vol. 306, pp. 51-67, 2005.

Mimum, et al., Bimodal imaging using neodymium doped gadolinium fluoride nanocrystals with near-infrared to near-infrared downconversion luminescence and magnetic resonance properties, Journals of Materials Chemistry B, vol. 1, pp. 5702-5710, 2013.

Milyukova, et al. Extraction of Bk(IV) with POM—Milyukova, 1986.pdf, J. Radioanal. Nucl. Chern. 104 pp. 81-90, (1986).

Modolo, et al., Recovery of Actinides and Lanthanides From High-Level Liquid Waste by Extraction Chromatography Using TODGA+TBP Impregnated Resins, Radiochimica Acta, vol. 95, pp. 391-397, 2007.

Modolo, et al., Development of a TODGA based Process for Partitioning of Actinides from a PUREX Raffinate Part I: Batch Extraction Optimization Studies and Stability Tests, Solvent Extraction and Ion Exchange, 2007.

Moore, et al. An octadentate luminescent Eu(III) 1,2-HOPO chelate with potent aqueous stability, Inorganic Chemistry, vol. 46, No. 14, pp. 5468-5470, 2007.

Moore, et al., Application of dual affinity retargeting molecules to achieve optimal redirected T-cell killing of B-cell lymphoma, Blood, vol. 117, pp. 4542-4551, 2011.

Moore, et al. Liquid-liquid Extraction Method for the Separation of Cerium (IV) From Berkelium (IV) and Other Elements, Analytical Chemistry, vol. 41, pp. 1658-1661, 1969.

Moore, et al., New Method for Rapid Separation of Berkelium (IV) From Cerium (IV) By Anion Exchange, Analytical Chemistry, vol. 39, pp. 1874-1876, 1967.

Moos, et al., Radiation Drugs—A Hot Topic. Drug Development Research, vol. 73, No. 5, pp. 229-231, 2012.

Morita, et al. Development of Todga Extraction Process for High-Level Liquid Waste—Preliminary Evaluation of Actinide Separation by Calculation, 2000.

Morris, et al., Voltammetric Investigation of the Berkelium(IV/III) Couple in Concentrated Aqueous Carbonate Solutions, Radiochimica Acta, pp. 125-134, 1990.

Morss et al., The Chemistry of the Actinide and Transactinide Elements, 4th ed, Springer,(2010).

Nash, et al., The Chemistry of Talspeak: A Review of the Science, Solvent Extraction. Ion Exchange Journal, vol. 33, No. 1, pp. 1-55, 2015.

NCRP, Management of Persons Contaminated with Radionuclides: Handbook, in NCRP Publication. 2008: Bethesda.

Nord, et al., A combinatorial library of an α-helical bacterial receptor domain, Protein Engineering, Design and Selection, vol. 8, No. 6, pp. 601, 1995.

Nord, et al., Binding proteins selected from combinatorial libraries of an α-helical bacterial receptor domain, Nature Biotechnology, vol. 15, pp. 772-777, 1997.

Nord, et al., Recombinant human factor VIII-specific affinity ligands selected from phage-displayed combinatorial libraries of protein A, European Journal of Biochemistry, vol. 268, pp. 4269-4277, 2001.

Nugent, et al., Electron-transfer and fd Absorption Bands of Some Lanthanide and Actinide Complexes and the Standard (II-III) Oxidation Potential for Each Member of the Lanthanide and Actinide Series, The Journal of Physical Chemistry A, vol. 77, pp. 1528-1539, 1973.

Nugent, et al., Intramolecular Energy Transfer and Sensitized Luminescence in Actinide (III). Beta.-Diketone Chelates, The Journal of Physical Chemistry A, vol. 73, pp. 1540-1549, 1969.

Ostapenko, et al., Extraction Chromatographic Behavior of Actinium and REE on DGA, Ln and TRU Resins in Nitric Acid Solutions, Journal of Radioanalytical and Nuclear Chemistry, vol. 306, pp. 707-711, 2015.

Oxford Dictionary of Biochemistry and Molecular Biology Ed. Anthony Smith, Oxford University Press, Oxford, 2004.

Parker, S et al., The McGraw-Hill Dictionary of chemical Terms, 1985.

Payne, et al. Possible Stabilization of the Tetravalent Oxidation State of Berkelium and Californium in Acetonitrile With Triphenylarsine Oxide, Inorganica Chimica Acta, vol. 139 , pp. 111-112, 1987.

Peppard, et al. Isolation of Berkelium by Solvent Extraction of the Tetravalent Species, Journal of Inorganic and Nuclear Chemistry, vol. 4, pp. 344-348, 1957.

Pham, et al., A Macrocyclic Chelator with Unprecedented Th4+ Affinity, Journal of the American Chemical Society, vol. 136, No. 25, pp. 9106-9115, 2014.

PLUECKTHON The Pharmacology of Monoclonal Antibodies, vol. 113, Rosenburg and Moore, 269-315, 1994.

Pokhrel, et al. Stokes emission inGdF3:Nd3+ nanoparticles for bioimaging probe, Nanoscale, vol. 6, No. 3, pp. 1667-1674, 2014.

Pourmand, et al., Distribution coefficients of 60 elements on TODGA resin: Application to Ca, Lu, Hf, U and Th isotope geochemistry, Taianta, vol. 81, pp. 741-753, 2010.

Radchenko et al., Application of Ion Exchange and Extraction Chromatography to the Separation of Actinium From Proton-Irradiated Thorium Metal for Analytical Purposes, Journal of Chromatography, pp. 55-63, 2015.

Remington's Pharmaceutical Sciences, 18th Ed. Mack Printing Company, 1990.

Ricano, et al. Combinatorial Design of Multimeric Chelating Peptoids for Selective Metal Coordination, Chemical Science, 2019.

Shannon, et al., Revised Effective Ionic Radii and Systematic Studies of Interatomic Distances in Halides and Chalcogenides, Acta Crystallographica A32, pp. 751-757, 1976.

Shockley, et al. Detailed Balance Limit of Efficiency of p-n Junction Solar Cells, Journal of Applied Physics, vol. 32, No. 3, pp. 510-519, 1961.

Smith, et al., NIST Critically selected stability constants of metal complexes database, NIST standard reference database, 2004.

Stather, et al., Use of DTPAfor increasing the rate of elimination ofplutonium-238 and americium-241from rodents after their inhalation as the nitrates, Human & Experimental Toxicology, vol. 4, No. 6, pp. 573-582, 1985.

Stockley, et al., Absorption Spectra of the Bk(IV)-Bk(III) in several media, Journal of Inorganic and Nuclear Chemistry, vol. 34, pp. 739-746, 1972.

Sturzbecher-Hoehne, et al., Highly Luminescent and Stable Hydroxypyridinonate Complexes: A Step Towards New Curium Decontamination Strategies, Chemistry—A European Journal, vol. 20, No. 32, pp. 9962-9968, 2014.

Sturzbecher-Hoehne, et al., Hydroxypyridinonate Complex Stability of Group (IV) Metals and Tetravalent f-Block Elements: The Key to the Next Generation of Chelating Agents for Radiopharmaceuticals, Inorganic chemistry, vol. 54, No. 7, pp. 3462-3468, 2015.

Sturzbecher-Hoehne, et al. 3,4,3-LI(1,2-HOPO): In vitroformation of highly stable lanthanide complexes translates into efficacious in vivo europium decorporation, Dalton Trans., vol. 40, No. 33, pp. 8340-8346, 2011.

(56) References Cited

OTHER PUBLICATIONS

Sturzbecher-Hoehne, et al Intramolecular Sensitization of Americium Luminescence in Solution: Shining Light on Short-Lived Forbidden 5f Transitions, Dalton Transactions, vol. 45, pp. 9912-9919, 2016.
Sturzbecher-Hoehne, et al., Solution Thermodynamic Evaluation of Hydroxypyridinonate Chelators 3,4,3-LI(1,2-HOPO) and 5-LIO(Me-3,2-HOPO) for UO2(VI) and Th(IV) Decorporation, Radiochimica Acta, vol. 101,No. 6, pp. 359-366, 2013.
Suzuki, et al., Extraction and separation of Am(III) and Sr(II) by N,N,N ,N -tetraoctyl-3-oxapentanediamide (TODGA), Radiochimica Acta vol. 92, pp. 463-466, 2004.
Tachimori, et al. Modification of Todga-N-Dodecane Solvent With a Monoamide for High Loading of Lanthanides(III) and Actinides(III), Solvent Extraction and Ion Exchange, 2007.
Taylor, et al., Treatment of Human Contamination With Plutonium and Americium: Would Orally Administered Ca- or Zn-DTPA be effective? Radiation Protection Dosimetry, vol. 127, pp. 469-471, 2007.
Thompson, et al, Element 97, Physics Review, vol. 77, pp. 838, 1950.
Thompson, et al, Chemical properties of Berkelium, Journal of the American Chemical Society, vol. 72, pp. 2798-2801, 1950.
Trissel, L. et al., ASHP Handbook on Injectable Drugs 4th ed, pp. 622-630, 1986.
Turanov, et al., Synergistic Extraction of U(VI), Th(IV), and Lanthanides(III) from Nitric Acid Solutions Using Mixtures of TODGA and Dinonylnaphthalene Sulfonic Acid, Solvent Extraction and Ion Exchange, 2018.
Umeda, et al., Separation of Americium from Plutonium-Solvent Extraction Raffinate by Extraction Chromatography using TODGA Absorbent, Atlantate, 2004.
U.S. Food and Drug Administration, Guidance for Industry Calcium DTPA and Zinc DTPA Drug Products—Submitting a New Drug Application. 2004.
US. Food and Drug Administration, Guidance for Industry Internal Radioactive Contamination—Development of Decorporation Agents. 2006.
U.S. Food and Drug Administration, Guidance for Industry Product Development Under the Animal Rule 2015.
U.S. Food and Drug Administration, Approval of New Drugs When Human Efficacy Studies Are Not Ethical or Feasible. 2015, U.S. FDA: Washington, DC.
Van Der Ende, et al., Lanthanide ions as spectral converters for solar cells, Physical Chemistry Chemical Physics, vol. 11, pp. 11081-11095, 2009.
Van Wijngaarden, et al. Energy Transfer Mechanism for Downconversion in the (Pr3+, Yb3+) couple, Physics Review, vol. 81, Issue 15, pp. 155112, 2010.
Wadsworth, et al., Present Status of Cerium (IV)-Cerium (III) Potentials, Analytical Chemistry, vol. 29, pp. 1824-1825, 1957.
Wai, et al., Carboxylate-Derived Calixarenes With High Selectivity For Actinium-225, Chemical Communications pp. 377-378, 1998.
Wang, et al. Down- and Up-Conversion Photoluminescence, Cathodoluminescence and Paramagnetic Properties of NaGdF4 : Yb3+,Er3+ Submicron Disks Assembled From Primary nanocrystals, Journal of Materials Chemistry, Issue 16, pp. 3178-3185, 2010.
Wang, et al. Extraction of Trivalent Americium and Europium With TODGA Homologs From HNO3 Solution, Journal of Radioanalytical and Nuclear Chemistry, vol. 313, pp. 309-318, 2017.
Wang, et al. Preparation of Core-Shell NaGdF4 Nanoparticles Doped with Luminescent Lanthanide Ions to be Used as Upconversion-Based Probes, Nature Protocols, vol. 9, No. 7, pp. 1634-1644, 2014.
Wawrzynczyk, et al. Ligand-dependent luminescence of ultra-small Eu3+-doped NaYF4 nanoparticles, Journal of Nanoparticle Research, vol. 15, pp. 1707, 2013.
Weidle et al., The Emerging Role of New Protein Scaffold-based Agents for Treatment of Cancer, Cancer Genomics and Proteomics. vol. 10, pp. 155, 2013.
Weitl, et al., Specific sequestering agents for the actinides. 3. Polycatecholate ligands derived from 2,3-dihydroxy-5-sulfobenzoyl conjugates of diaza- and tetraazaalkanes, Journal of the American Chemical Society, vol. 102. No. 7, pp. 2289-2293, 1980.
Welcher, F. J. The analytical uses of ethylenediamine tetraacetic acid; 1958.
Wermuth, C. et al., Designing Prodrugs and Bioprecursors, pp. 561-586, 2003.
Whitaker, et al., Applications of Diglycolamide Based Solvent Extraction Processes in Spent Nuclear Fuel Reprocessing, Part 1: Todga, Solvent Extraction and Ion Exchange, 2018.
Whitcomb, et al., A Public Health Perspective on the U.S. Response to the Fukushima radiological emergency. Health Phys, vol. 108, No. 3, pp. 357-363, 2015.
White, et al., Specific Sequestering Agents for the Actinides. 16. Synthesis and Initial Biological Testing of Polydentate Oxohydroxypyridinecarboxylate Ligands, Journal of Medicinal Chemistry, vol. 31, No. 1, pp. 11-18, 1988.
Wilden, A. et al. Unprecedented Inversion of Selectivity and Extraordinary Difference in the Complexation of Trivalent f-Elements by Diastereomers of a Methylated Diglycolamide, Chemistry a European Journal, 2019.
Xu, et al., Specific Sequestering Agents for the Actinides. 28. Synthesis and Initial Evaluation of Multidentate 4-Carbamoyl-3-hydroxy-1-methyl-2(1H)-pyridinone Ligands for in Vivo Plutonium (IV) Chelation, Journal of Medicinal Chemistry, vol. 38, No. 14, pp. 2606-2614, 1988.
Yantasee, et al., Novel Sorbents for Removal of Gadolinium-Based Contrast Agents in Sorbent Dialysis and Hemoperfusion: Preventive Approaches to Nephrogenic Systemic Fibrosis (NSF), Nanomedicine, vol. 6, No. 1, pp. 1-8, 2010.
Ye, et al. Down conversion luminescence of Tb3+—Yb3+ codoped SrF2 precipitated glass ceramics, Journal of Non-Crystalline Solids, vol. 357, Issues 11-13, pp. 2268-2271, 2011.
Ye, et al. Enhanced cooperative quantum cutting in Tm3+—Yb3+ codoped glass ceramics containing LaF3nanocrystals, Optics Express, vol. 16, No. 12, pp. 8989-8994, 2008.
Zou, et al. Broadband Dye-Sensitized Upconversion of Near-Infrared Light, Nature Photonics, vol. 6, pp. 560-564, 2012.
Zhang et al, Novel enterobactin analogues as potential therapeutic chelating agents: Synthesis, thermodynamic and antioxidant studies Scientific Reports, vol. 6, pp. 1-12, 2016.
Zhu, et al. An active-core/active-shell structure with enhanced quantum-cutting luminescence in Pr—Yb co-doped monodisperse nanoparticles, Nanoscale, vol. 6, pp. 10500-10504, 2014.
Zhu, X et al. Cumulative study on solvent extraction of elements by N,N,N ,N-tetraoctyl-3-oxapentanediamide (TODGA) from nitric acid into n-dodecane, Analytica Chimica Acta 527, pp. 163-168, 2004.
International Preliminary Report on Patentability dated Nov. 6, 2018 in International Patent Application No. PCT/US2017/030628.
International Preliminary Report on Patentability dated Mar. 12, 2019 in International Patent Application No. PCT/US2017/050121.
International Preliminary Report on Patentability dated Apr. 11, 2019 in International Patent Application No. PCT/US2017/048910.
International Preliminary Report on Patentability dated Apr. 11, 2019 in International Patent Application No. PCT/US2017/048934.
International Search Report and Written Opinion dated Jul. 27, 2017 in International Patent Application No. PCT/US2017/030628.
International Search Report and Written Opinion dated Nov. 13, 2017 in International patent application PCT/US2017/050121.
International Search Report dated Dec. 21, 2017 in International Patent Application No. PCT/US2017/048910.
International Search Report dated May 11, 2018 in International Patent Application No. PCT/US2017/048934.
Office Action dated Nov. 21, 2018 in U.S. Appl. No. 15/442,441.
Office Action dated May 6, 2019 in U.S. Appl. No. 15/442,441.
Office Action dated Aug. 23, 2019 in U.S. Appl. No. 15/442,441.
Supplementary European Search Report, dated Nov. 15, 2019, in European Application No. EP 17793154.
Extended European Search Report dated Mar. 24, 2020 in European App. No. 17849400.1.
Office Action dated Aug. 16, 2021 in U.S. Appl. No. 16/097,782.

(56) References Cited

OTHER PUBLICATIONS

Office Action dated Jun. 10, 2021 in U.S. Appl. No. 16/365,132.
Naasani, Imad et al., Improving the Oral Bioavailability of Sulpiride by Sodium Oleate in Rabbits, J. Pharm., vol. 47, pp. 469-473, 1995.
Office Action dated Jul. 28, 2021 in JP 2019-512761.
Japanese Office Action dated Oct. 26, 2021 in JP 2019-516989.
Office Action dated Oct. 26, 2021 in Japanese Application No. 2019-516989.
Office Action dated Dec. 14, 2021 in U.S. Appl. No. 16/336,665.
Final Office Action dated Jan. 19, 2022 in U.S. Appl. No. 16/097,782.
Pharmaceutics, 1997, vol. 57 No. Suppl, pp. 62-63.
Notice of Reasons for Rejection dated Apr. 26, 2021 in Japanese Patent Application No. JP 2018-557384.
Notice of Reasons for Rejection dated Mar. 10, 2022 in Japanese Patent Application No. 2018-557384.
Intention to Grant dated May 18, 2022, in European Application No. 17849400.1.
Moore et al., "Eu(III) complexes of functionalized octadentate 1-Hydroxypyridin-2-ones: Stability, bioconjugation, and luminescence resonance energy transfer studies", Iorg. Chem. Vol. 49(21):9928-9939 (2010).
Rees et al., "Evaluating the potential of chelation therapy to prevent and treat gadolinium deposition from MRI contrast agents", Scientific Reports, published online Mar. 13, 2018, www.nature.com/scientificreports, in 9 pages.
Final Office Action dated Jul. 15, 2022 in U.S. Appl. No. 16/336,665.
Non-Final Office Action dated Feb. 25, 2022, in U.S. Appl. No. 16/365,132.
Office Action with English translation in Japanese Application No. 2019-516989, dated Aug. 5, 2022.
Decision to Grant in European Application No. 17849400.1, dated Oct. 7, 2022, in 2 pages.
Office Action issued in European Application No. 17793154.0, dated Sep. 20, 2022, in 4 pages.
Decision of Refusal in Japanese Application No. 2018-557384, dated Sep. 29, 2022, with English translation, in 5 pages.
Office Action dated Jan. 31, 2023, in Japanese Application No. 2022-008581.
Notice of Allowance dated Jan. 30, 2023, in U.S. Appl. No. 16/365,132.
Chatterjee et al., "Excipients and Active Pharmaceutical Ingredients", American Association of Pharmauceticals Scientists, Chapter 24, pp. 347-361 (2014).
Corrected Notice of Allowability in U.S. Appl. No. 16/365,132, dated Mar. 21, 2023.
Non-Final Office Action dated Mar. 30, 2023, in U.S. Appl. No. 16/097,782.
Non-Final Office Action dated Mar. 28, 2023, in U.S. Appl. No. 16/336,665.
Notice of Allowance in Japanese Application No. 2019-516989, dated Mar. 29, 2023.

* cited by examiner

FORMULATIONS OF HYDROXYPYRIDONATE ACTINIDE/LANTHANIDE DECORPORATION AGENTS

STATEMENT OF GOVERNMENTAL SUPPORT

The invention was made with government support under National Institute of Allergy and Infectious Diseases Contract #HHSN272201000046C and Biomedical Advanced Research and Development Authority Contract #IPIAA12OS99609, through the U.S. Department of Energy under Contract #DE-AC02-05CH11231. The government has certain rights in the invention.

CROSS REFERENCE TO RELATED APPLICATIONS

This application is the U.S. National Stage Application under 35 U.S.C. § 371 of International Application No. PCT/US2017/050121, filed on Sep. 5, 2017, designating the U.S. and published in English as WO 2018/048812 A1 on Mar. 15, 2018, which claims the benefit of U.S. Provisional Application No. 62/384,087, filed on Sep. 6, 2016, which is hereby incorporated by reference in its entirety.

BACKGROUND

Field of the Invention

This invention relates generally to formulations for the treatment of metal poisoning.

Description of the Related Art

Exposure to radionuclides accidentally or deliberately scattered by a radiological dispersion device or deposited from a nuclear power plant accident or nuclear device detonation could result in the contamination of a large population. As internalized radionuclides are highly toxic and may cause both acute and chronic radiation injury, such contamination event would have dramatic public health consequences. Decorporation by chelating agents is the only way to reduce exposure of certain incorporated isotope, and diethylenetriaminepentaacetic acid (DTPA) has been the standard therapy for actinide/lanthanide decorporation since its development and use by the U.S. Atomic Energy Commission in the 1950's.

SUMMARY OF THE PREFERRED EMBODIMENTS

Embodiments herein provide for a pharmaceutical composition that comprises a 1,2-HOPO chelating agent in an amount from about 300 to about 1500 mg; and sodium oleate. In some embodiments, the 1,2-HOPO chelating agent is 3,4,3-L1-1,2-HOPO. In some embodiments, sodium oleate is present at about 70 to about 130 mg. In some embodiments, sodium oleate is present at 8 to 12% of a total weight of the composition. In some embodiments, sodium oleate is about 11% of a total weight of the composition. In some embodiments, the 3,4,3-L1-1,2-HOPO chelating agent is present in an amount from 100 to 1500 mg. In some embodiments, the 3,4,3-L1-1,2-HOPO chelating agent is present in an amount from 400 to 1200 mg. In some embodiments, the 3,4,3-L1-1,2-HOPO chelating agent is present in an amount from 100 to 300 mg. In some embodiments, the 3,4,3-L1-1,2-HOPO chelating agent is present in an amount of 600 mg. In some embodiments, the 3,4,3-L1-1,2-HOPO chelating agent is present in an amount from 100 to 1500 mg. In some embodiments, the 3,4,3-L1-1,2-HOPO chelating agent is present in an amount from 400 to 1200 mg. In some embodiments, the 3,4,3-L1-1,2-HOPO chelating agent is present in an amount from 100 to 300 mg. In some embodiments, the 3,4,3-L1-1,2-HOPO chelating agent is present in an amount of 600 mg. In some embodiments, the pharmaceutical composition is packaged as a tablet. In some embodiments, the pharmaceutical composition is within a capsule. In some embodiments, the pharmaceutical composition is within one or more granules. In some embodiments, the pharmaceutical composition is packaged as a tablet. In some embodiments, the pharmaceutical composition is within a capsule. In some embodiments, the pharmaceutical composition is within one or more granules.

This is especially useful when administered to a subject that has been exposed to, has been in contact with, or contaminated by one or more known or unknown actinides and/or lanthanides, or a mixture thereof.

BRIEF DESCRIPTION OF THE DRAWINGS

The foregoing aspects and others will be readily appreciated by the skilled artisan from the following description of illustrative embodiments when read in conjunction with the accompanying drawings.

treatment was administered i.p. or p.o. once-daily for 6 days, starting at 24 hours post-exposure and mice were euthanized at 11 days.

Figure 12A:
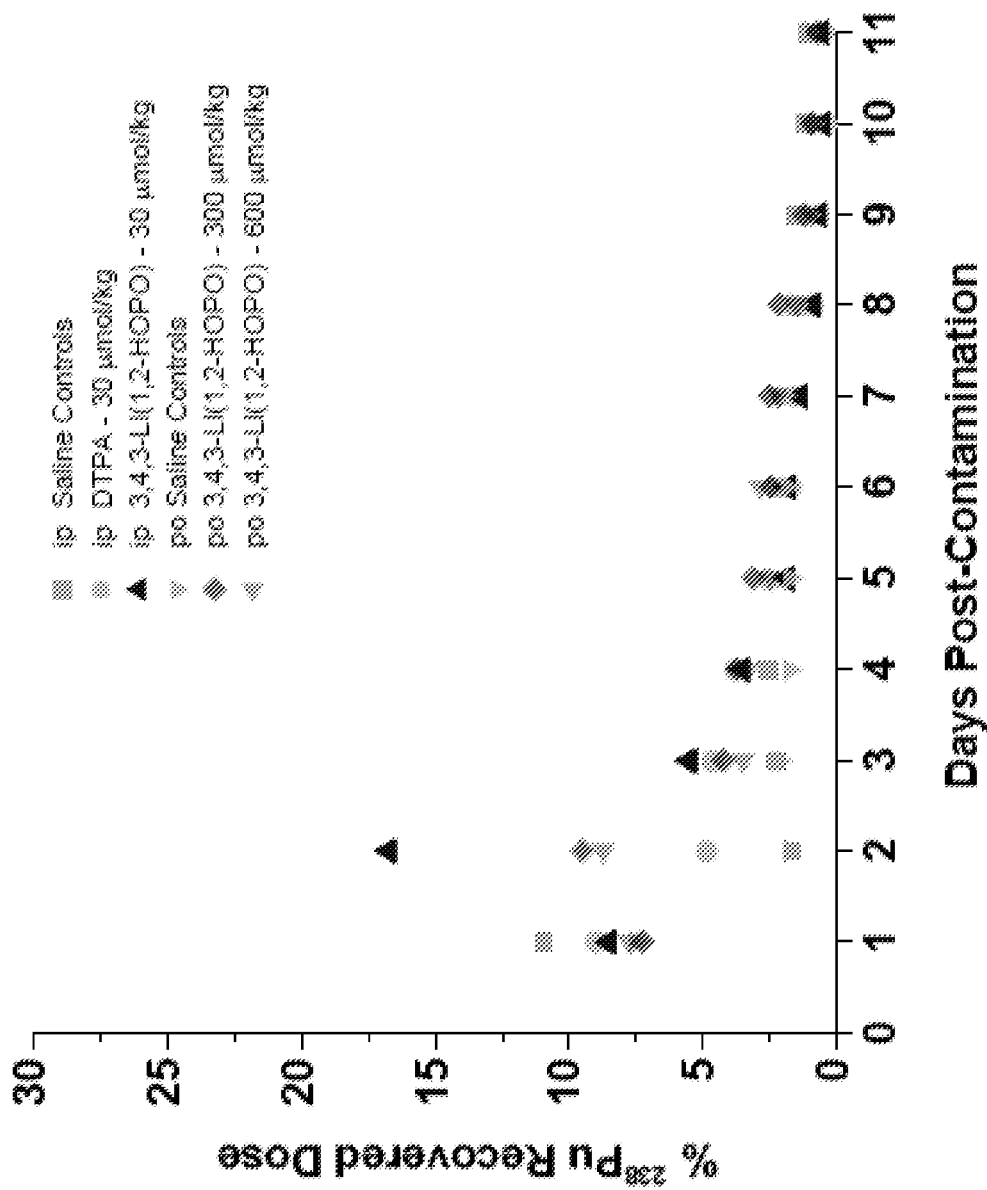
FIG. 12A shows the daily fecal excretion rate at necropsy of young adult female Swiss-Webster mice injected i.v. with $^{238}$Pu-citrate. Saline, DTPA or 3,4,3-L1(1,2-HOPO)
Figure 12B:
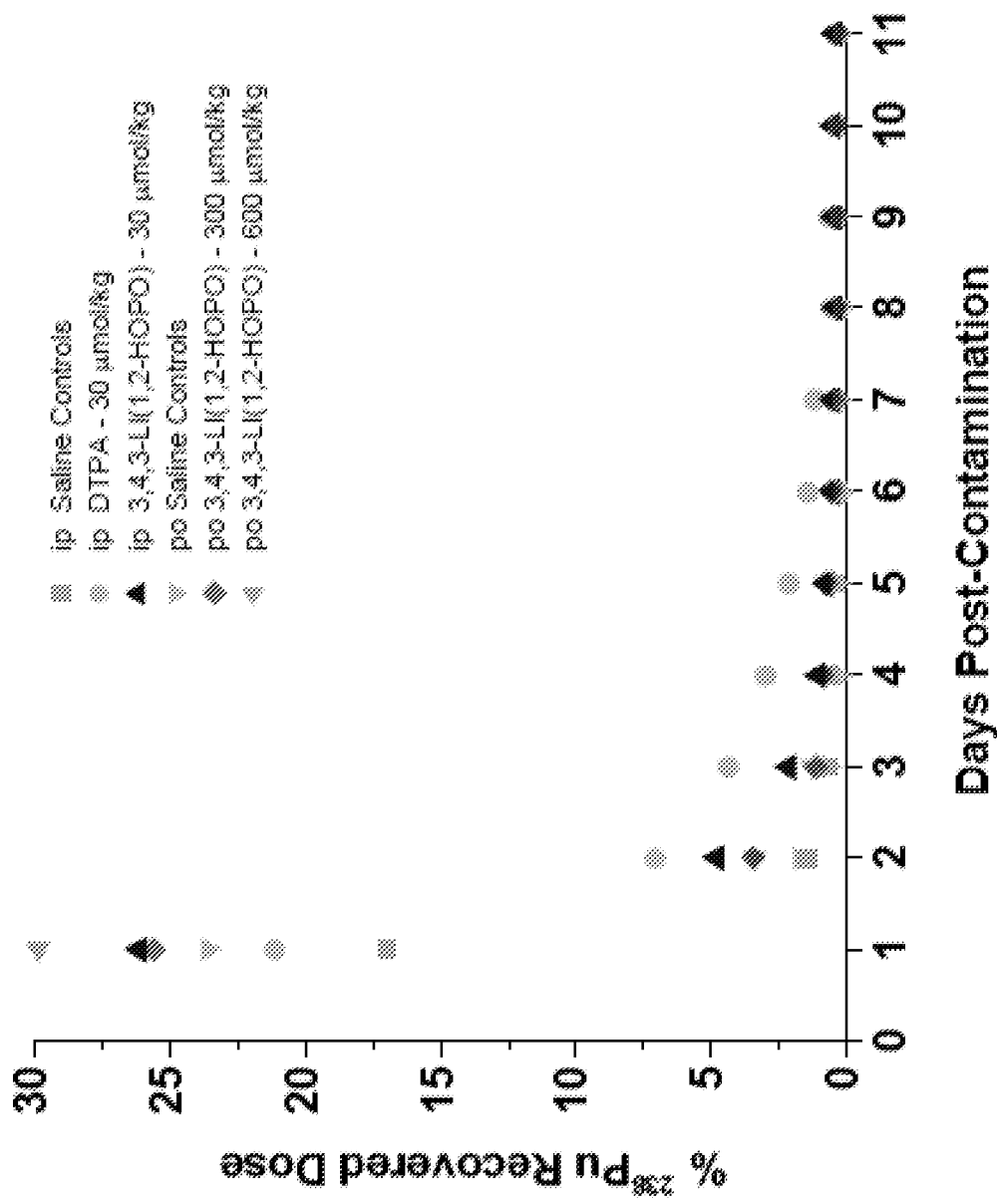

FIG. 12B shows the daily urinary excretion rate at necropsy of young adult female Swiss-Webster mice injected i.v. with $^{238}$Pu-citrate. Saline, DTPA or 3,4,3-L1(1,2-HOPO) treatment was administered i.p. or p.o. once-daily for 6 days, starting at 24 hours post-exposure and mice were euthanized at 11 days.

Figure 12C:
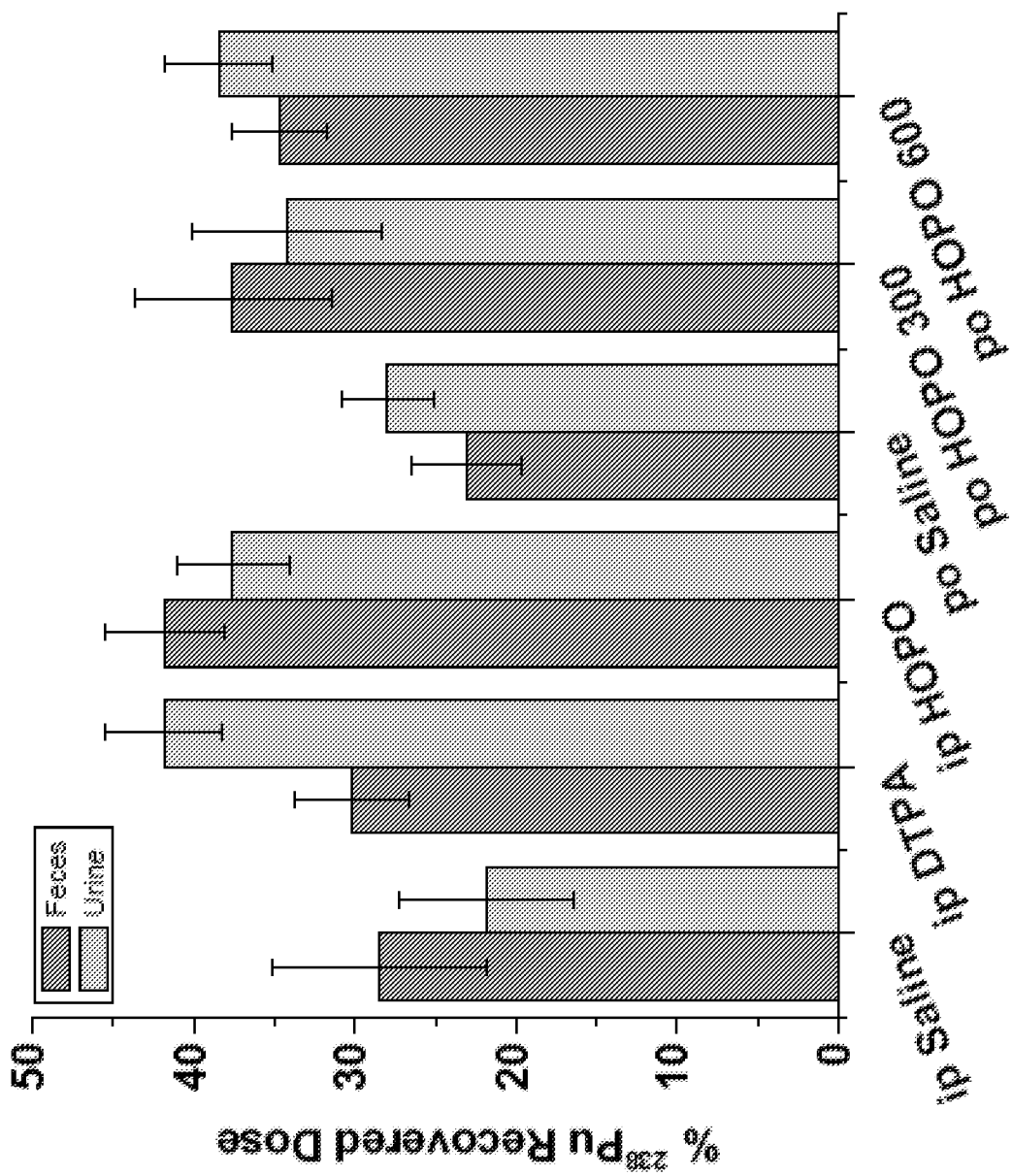

FIG. 12C shows the cumulative excretion at necropsy on day 11 for FIG. 12A and FIG. 12B.

Figure 13A:
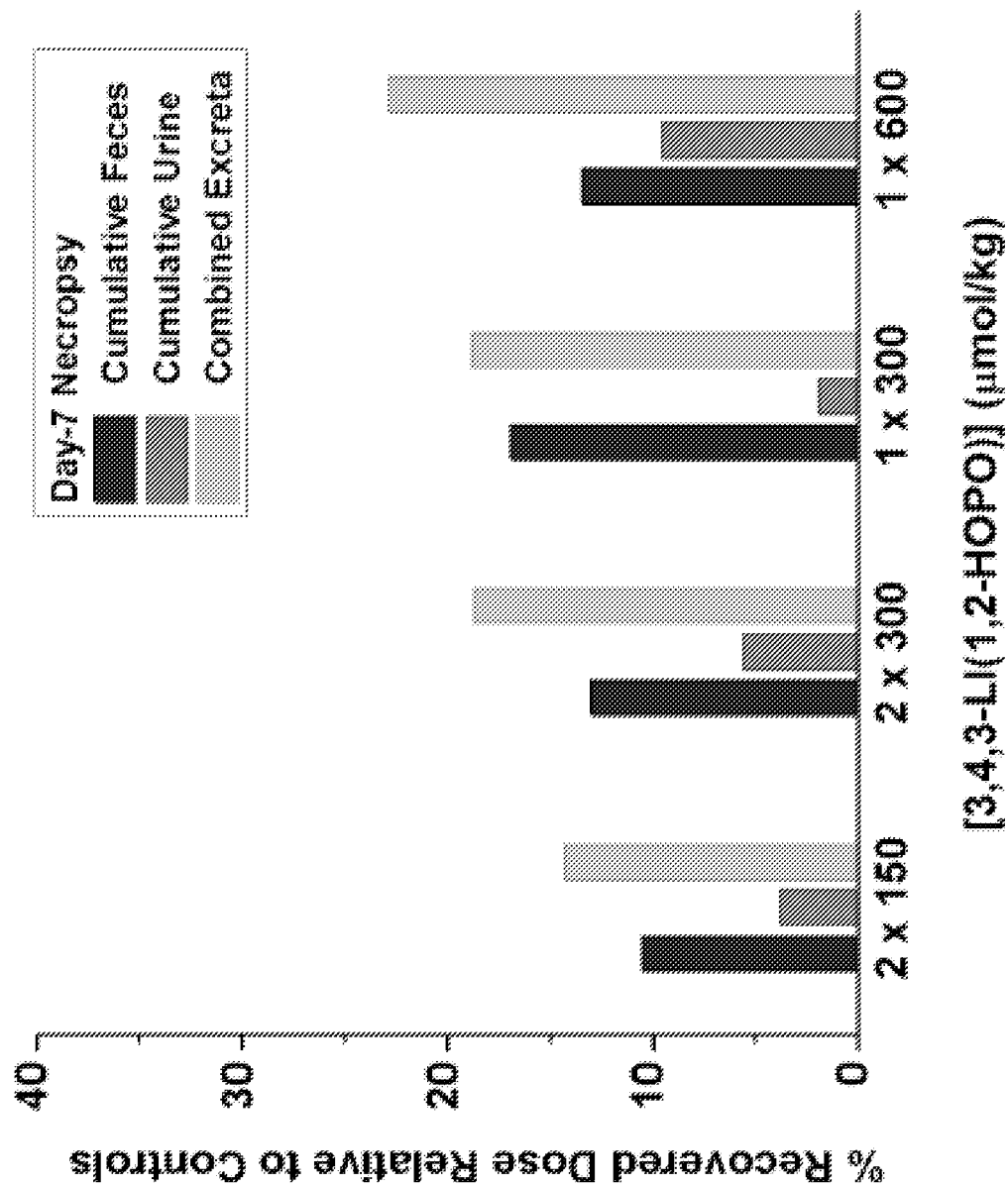

FIG. 13A shows cumulative excretion in treated groups relative to control at day 7 post-contamination for young adult female Swiss-Webster injected i.v. with $^{238}$Pu-citrate. DTPA or 3,4,3-L1(1,2-HOPO) treatment was administered p.o. for six days, once-daily or twice-daily, starting at 24 hours post-exposure and mice were euthanized at 7 days.

Figure 13B:
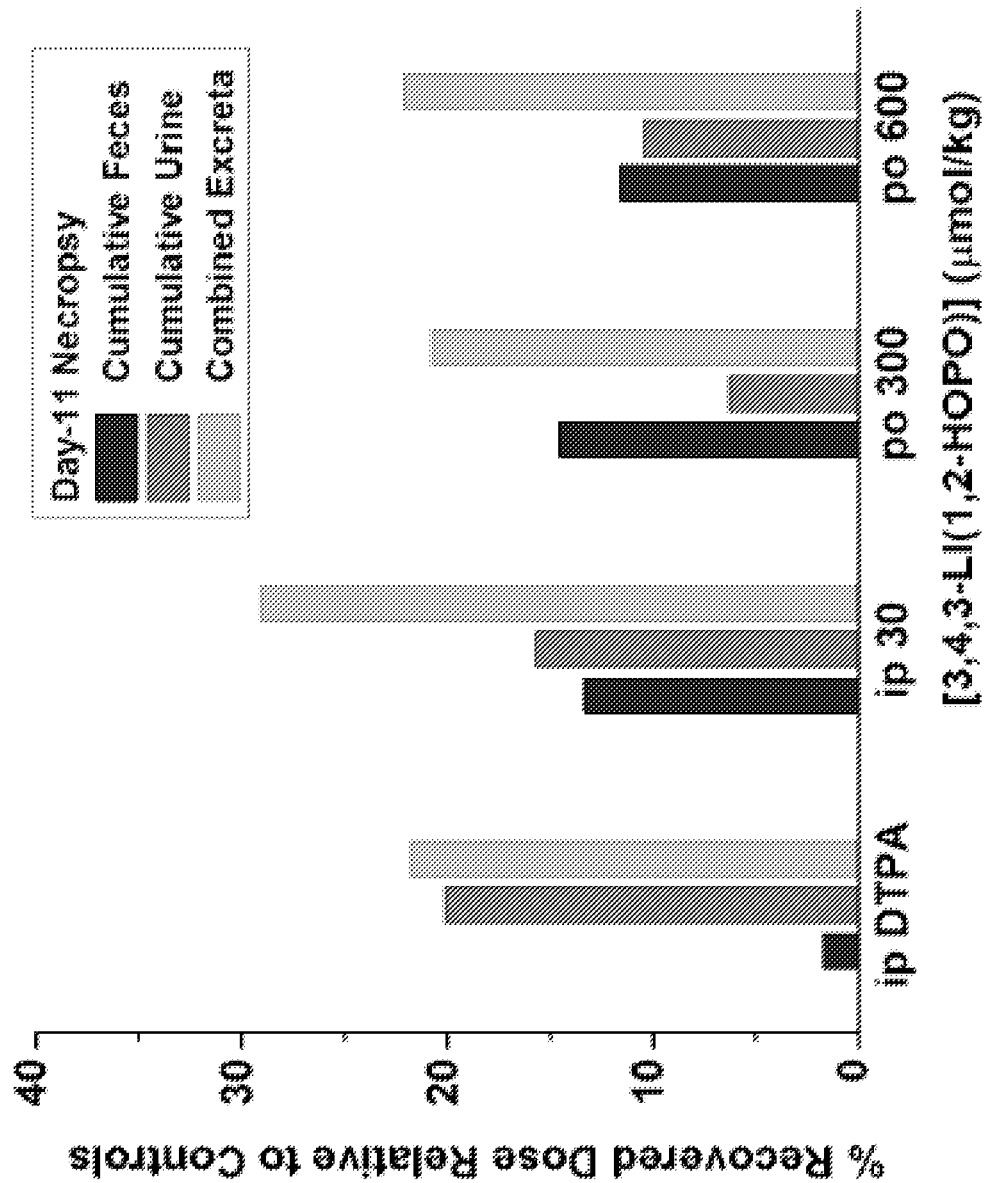

FIG. 13B shows cumulative excretion in treated groups relative to control at day 11 post-contamination for young adult female Swiss-Webster injected i.v. with $^{238}$Pu-citrate. DTPA or 3,4,3-L1(1,2-HOPO) treatment was administered i.p. or p.o. for six days, once-daily, starting at 24 hours post-exposure and mice were euthanized at 11 days.

Figure 14A:
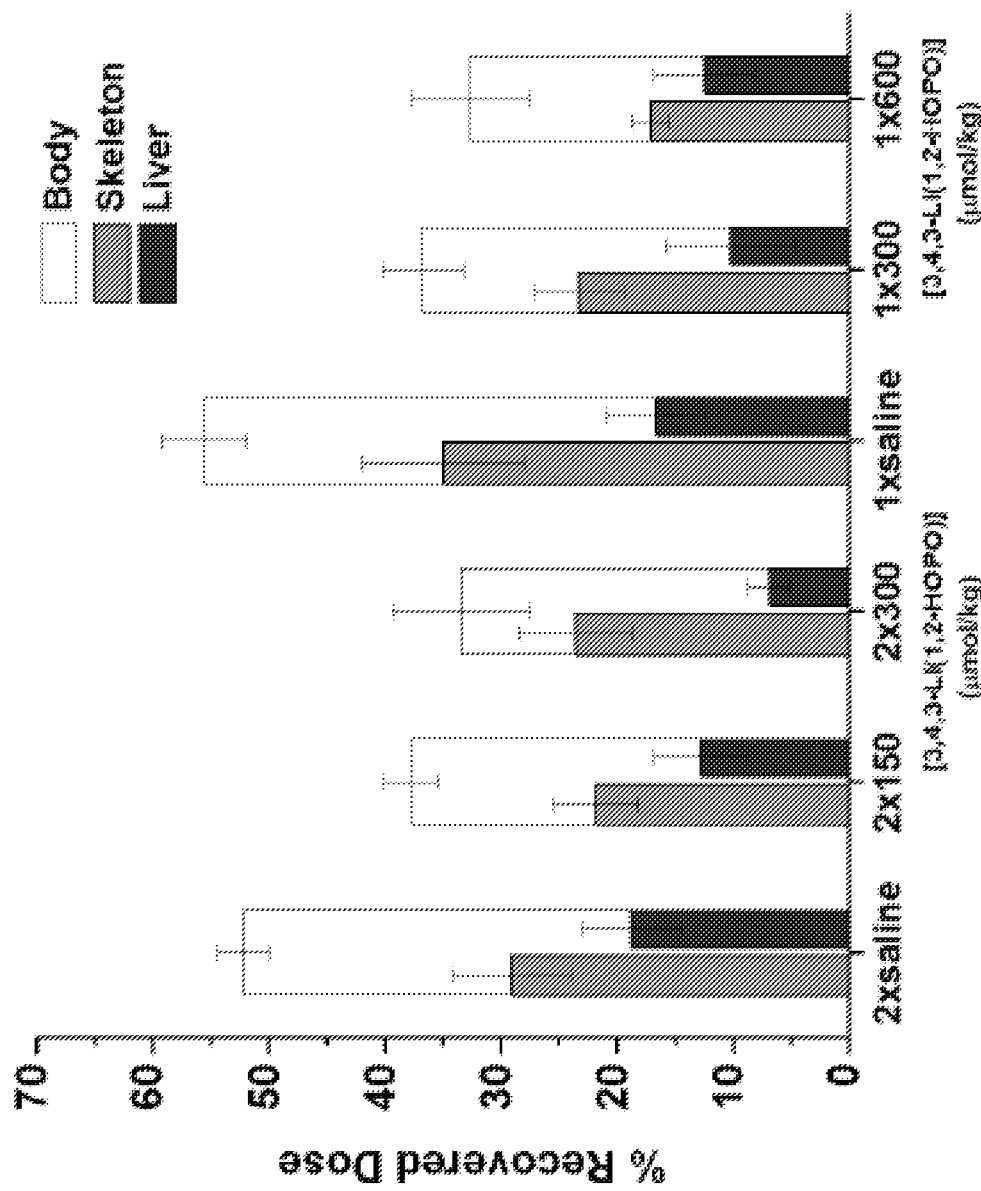

FIG. 14A shows body, skeleton and liver retention in treated groups at 7 days post-contamination for young adult female Swiss-Webster injected i.v. with $^{238}$Pu-citrate. Saline, DTPA or 3,4,3-L1(1,2-HOPO) treatment was administered p.o. for six days, once-daily or twice-daily, starting at 24 hours post-exposure and mice were euthanized at 7 days.

Figure 14B:
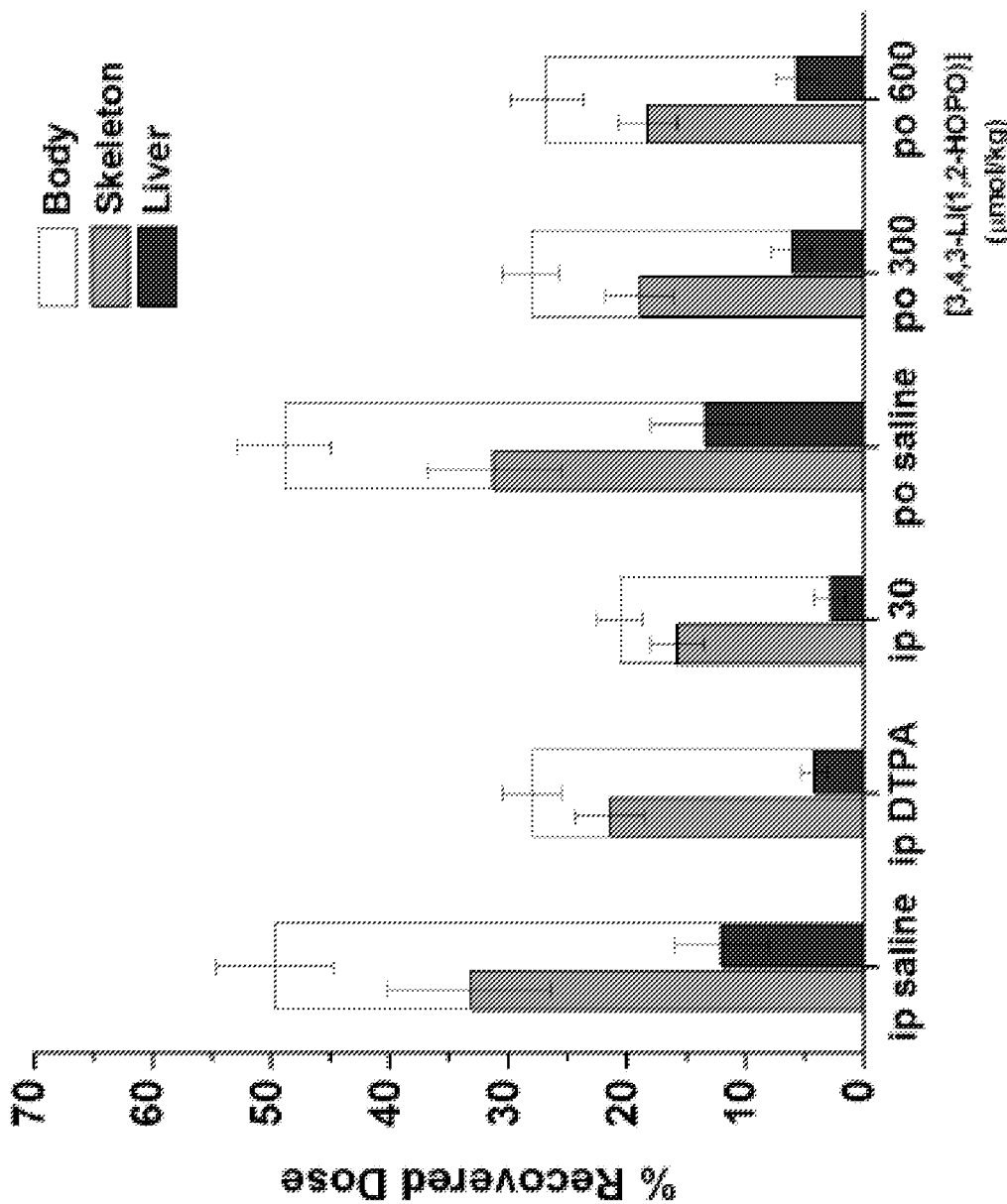

FIG. 14B shows body, skeleton and liver retention in treated groups at day 11 post-contamination for young adult female Swiss-Webster injected i.v. with $^{238}$Pu-citrate. Saline, DTPA or 3,4,3-L1(1,2-HOPO) treatment was administered i.p. or p.o. for six days, once-daily, starting at 24 hours post-exposure and mice were euthanized at 11 days.

Figure 15A:
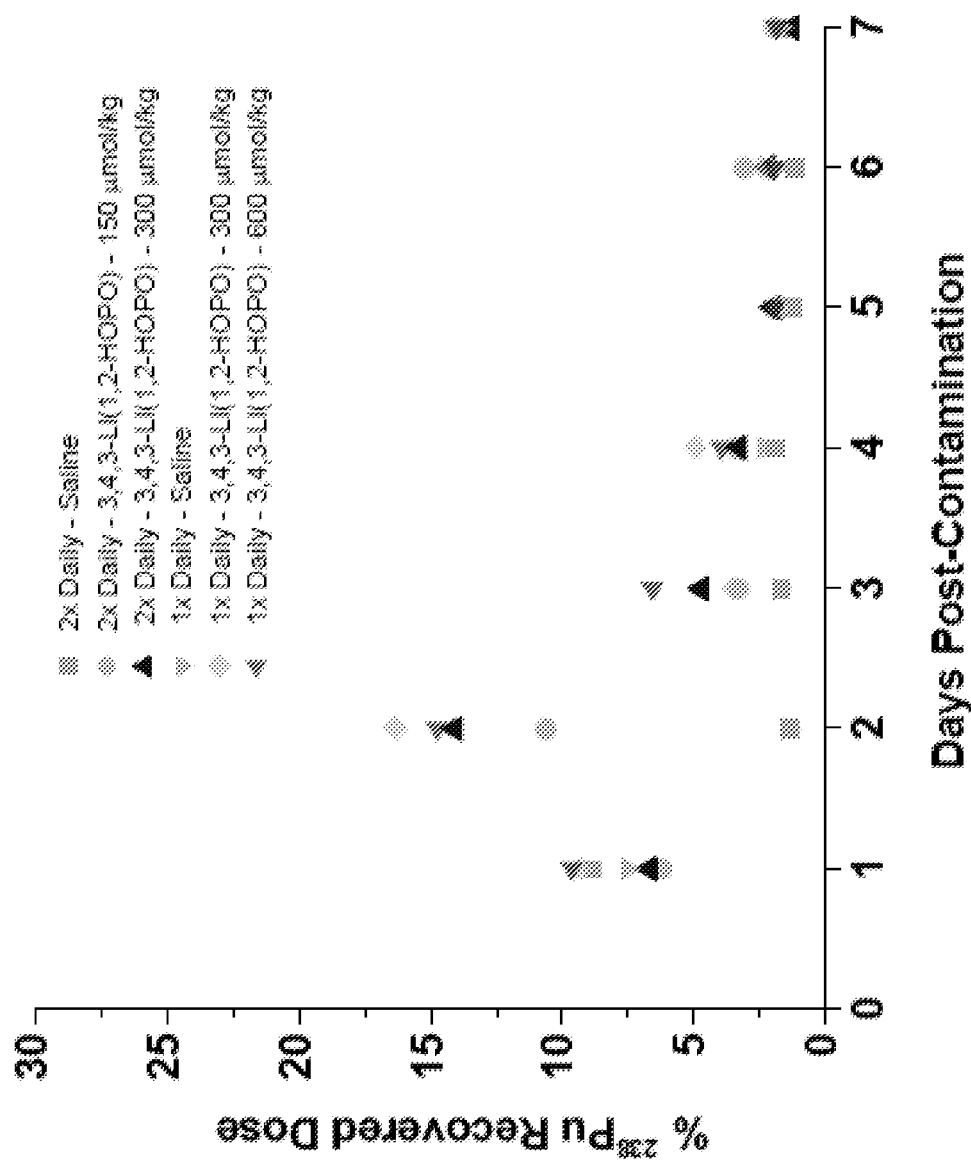

FIG. 15A shows the daily fecal excretion rate at necropsy of young adult male Swiss-Webster mice injected i.v. with $^{238}$Pu-citrate. 3,4,3-L1(1,2-HOPO) treatment was administered p.o. twice-daily or once-daily for 6 days, starting at 24 hours post-exposure and mice were euthanized at 7 days.

Figure 15B:
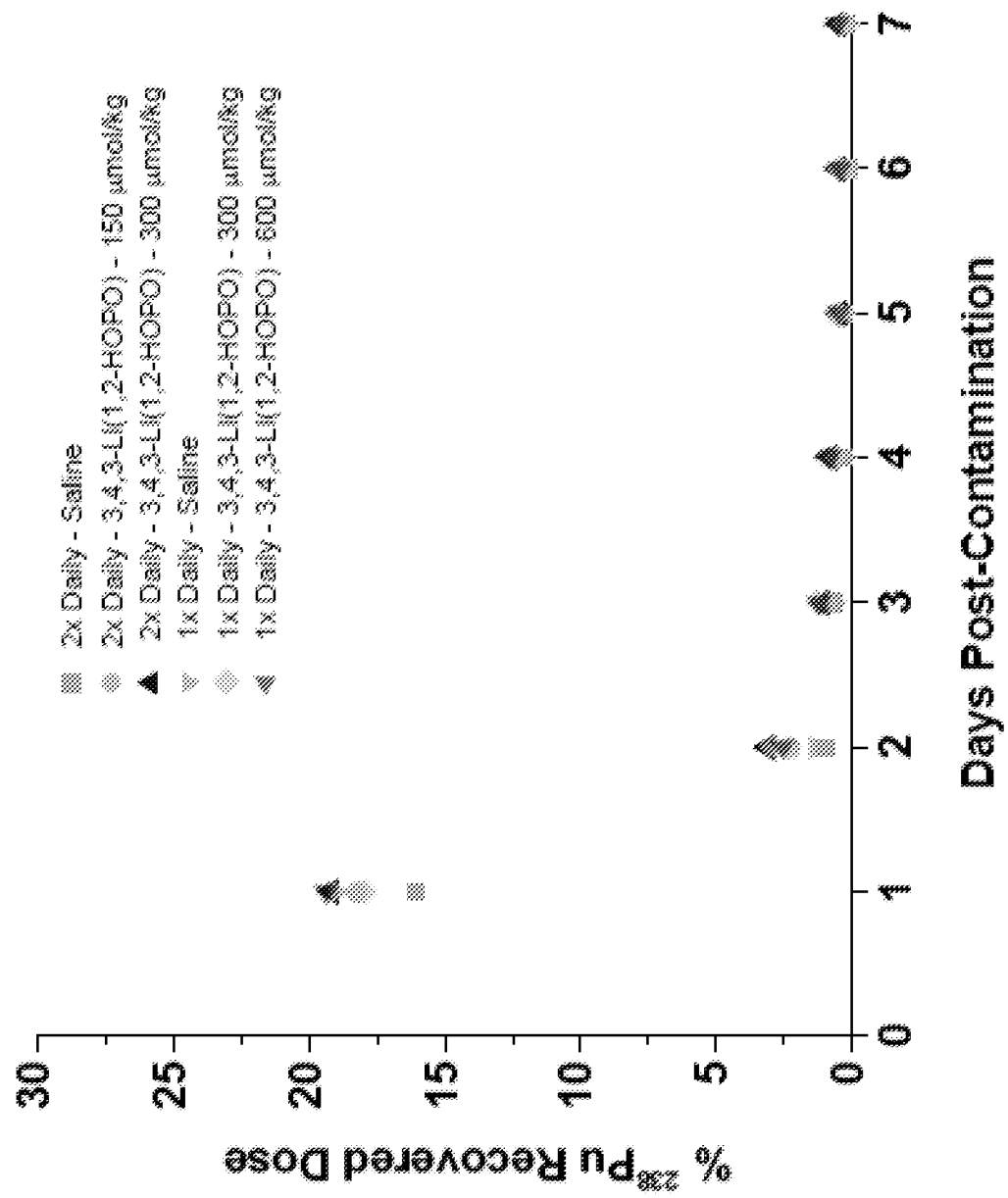

FIG. 15B shows the daily urinary excretion rate at necropsy of young adult male Swiss-Webster mice injected i.v. with $^{238}$Pu-citrate. 3,4,3-L1(1,2-HOPO) treatment was administered p.o. twice-daily or once-daily for 6 days, starting at 24 hours post-exposure and mice were euthanized at 7 days.

Figure 15C:
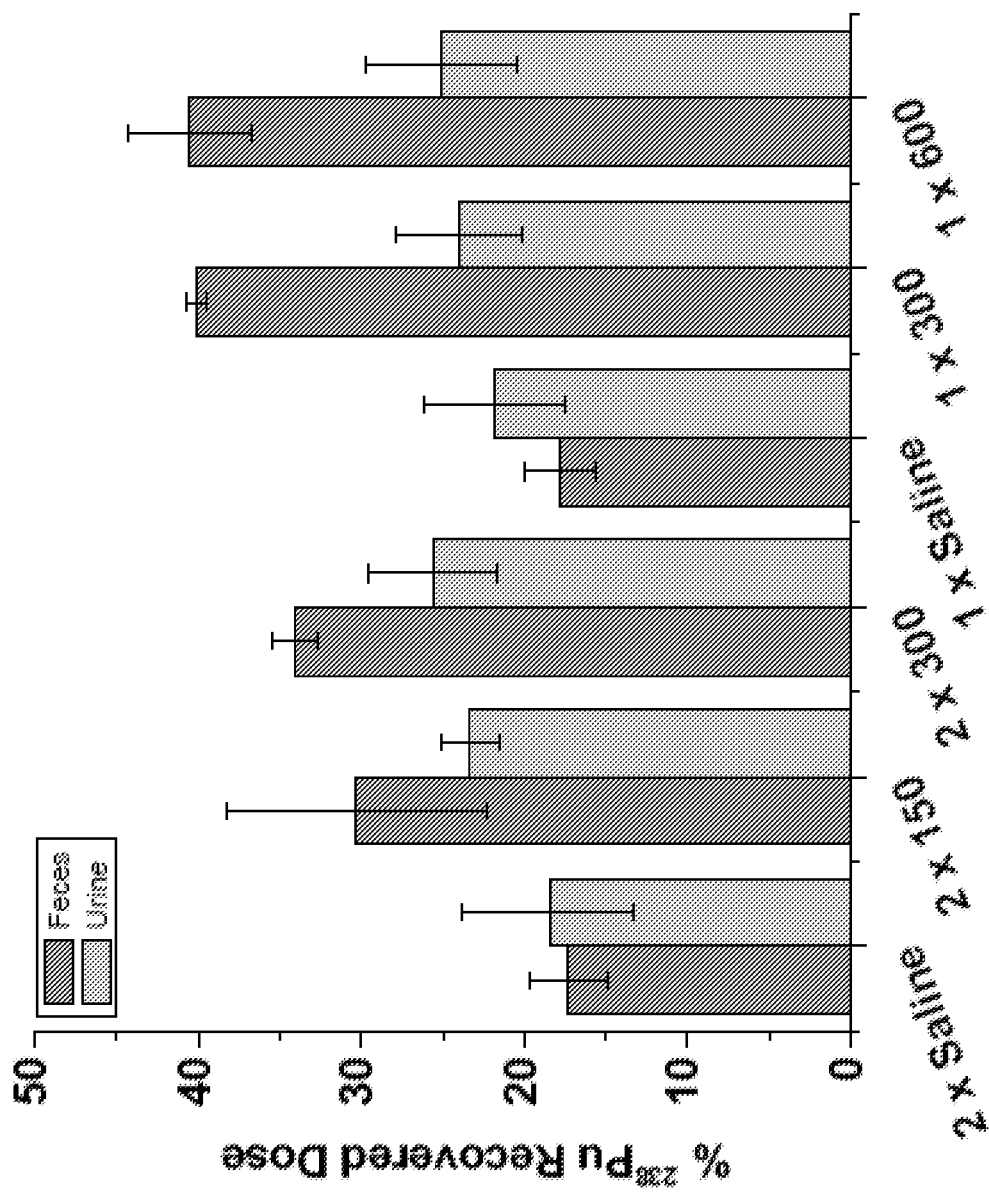

FIG. 15C shows the cumulative excretion at necropsy on day 7 for FIG. 15A and FIG. 15B.

Figure 16A:
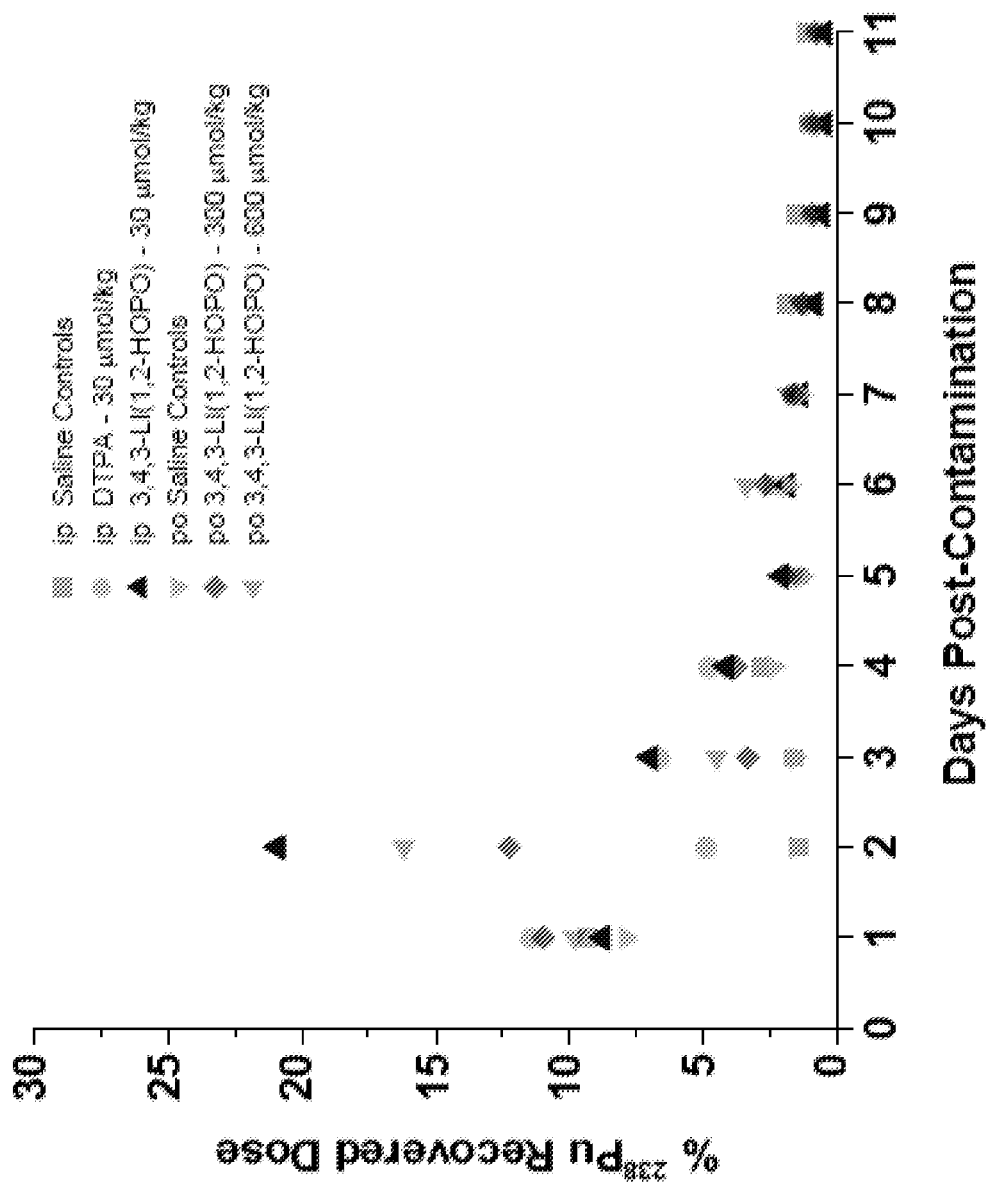

FIG. 16A shows the daily fecal excretion rate at necropsy of young adult male Swiss-Webster mice injected i.v. with $^{238}$Pu-citrate. Saline, DTPA or 3,4,3-L1(1,2-HOPO) treatment was administered i.p. or p.o. once-daily for 6 days, starting at 24 hours post-exposure and mice were euthanized at 11 days.

Figure 16B:
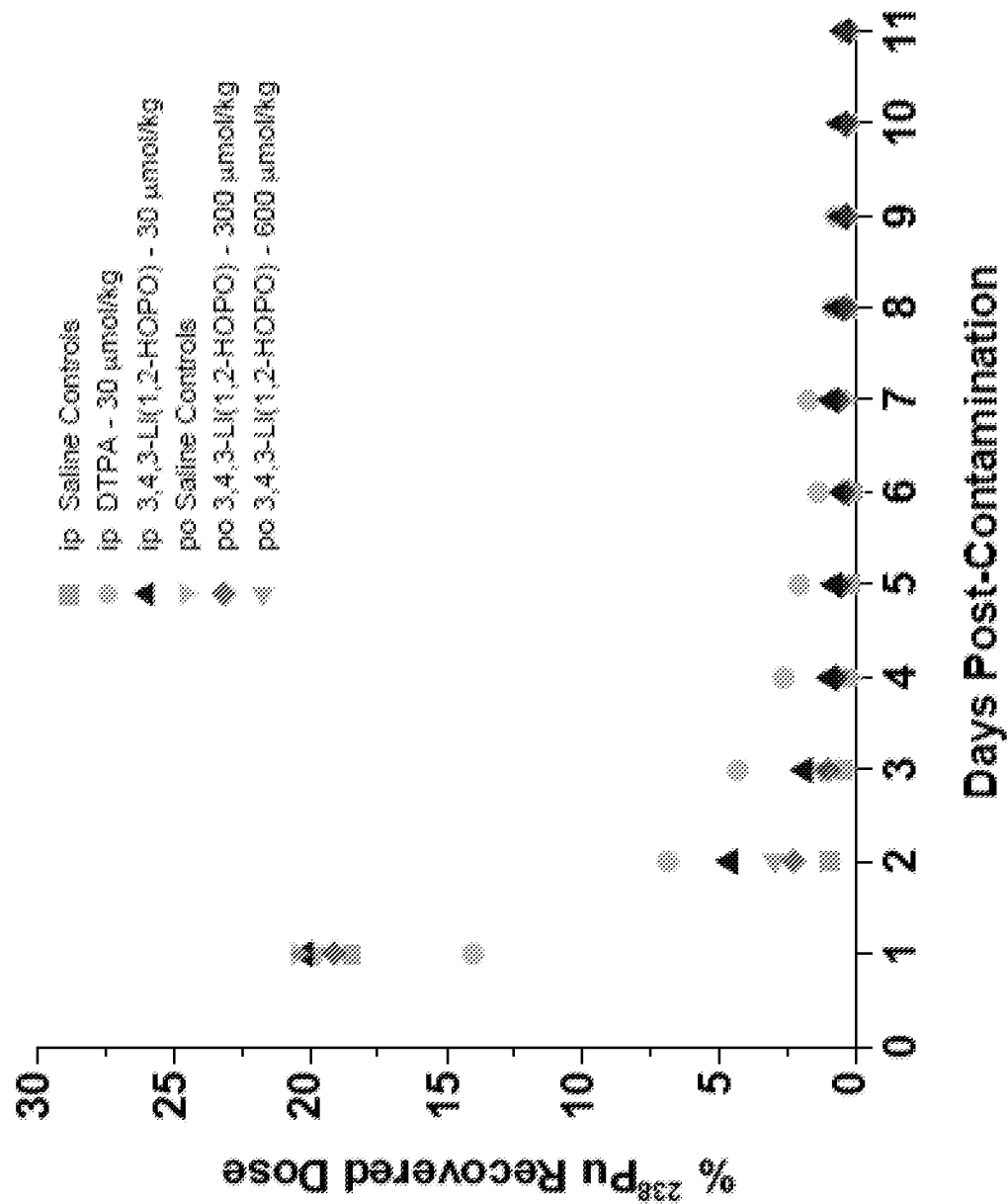

FIG. 16B shows the daily urinary excretion rate at necropsy of young adult male Swiss-Webster mice injected i.v. with $^{238}$Pu-citrate. Saline, DTPA or 3,4,3-L1(1,2-HOPO) treatment was administered i.p. or p.o. once-daily for 6 days, starting at 24 hours post-exposure and mice were euthanized at 11 days.

Figure 16C:
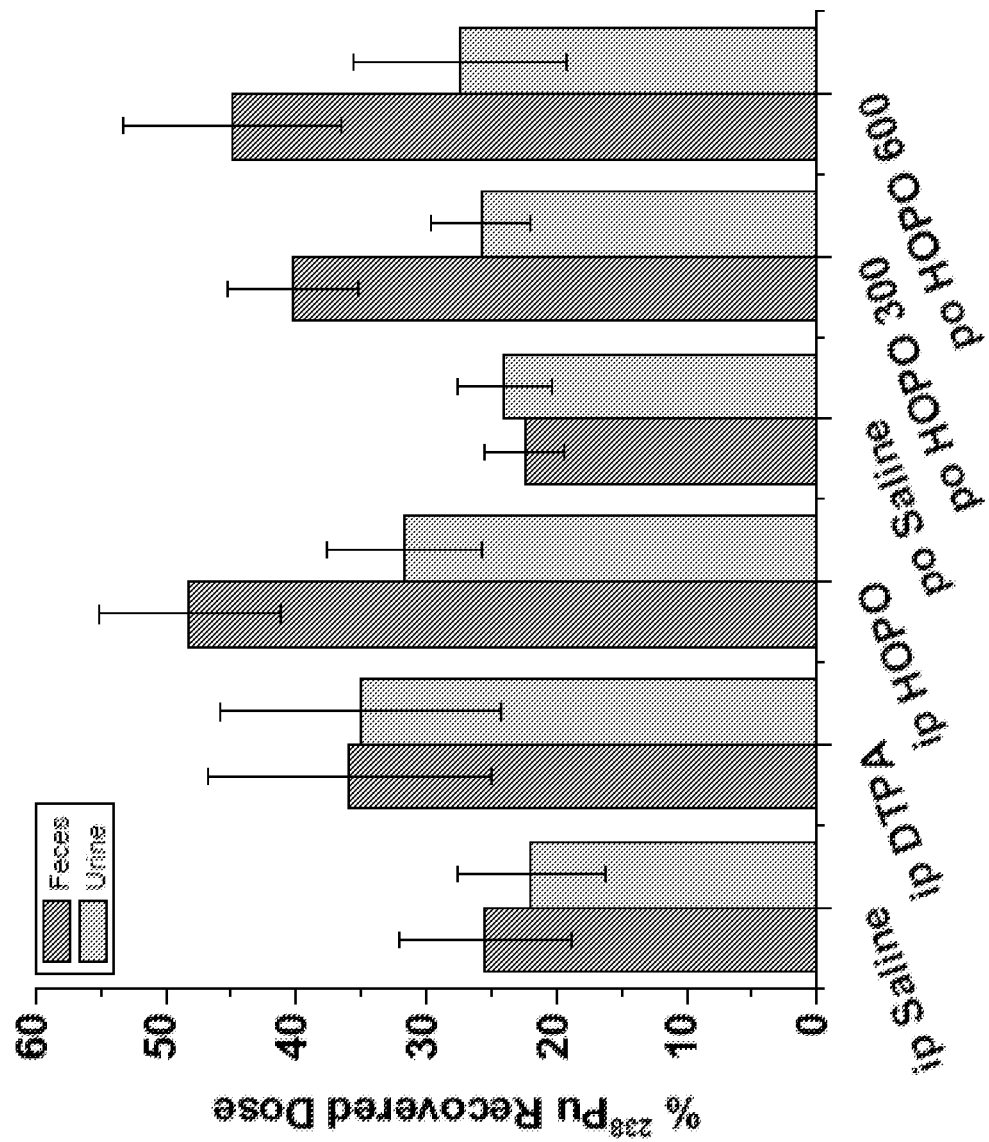

FIG. 16C shows the cumulative excretion at necropsy on day 11 for FIG. 16A and FIG. 16B.

Figure 17A:
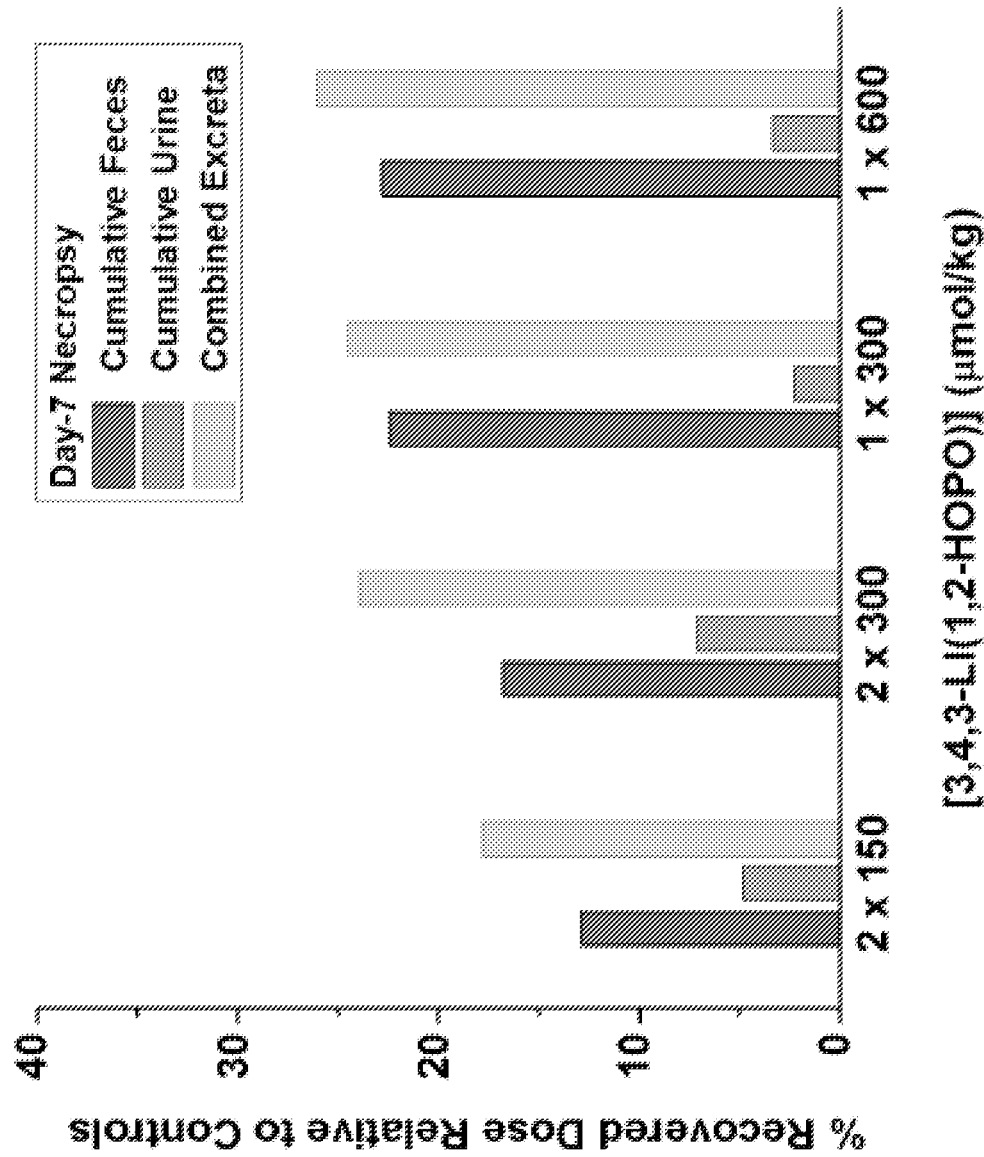

FIG. 17A shows cumulative excretion in treated groups relative to control at day 7 post-contamination for young adult male Swiss-Webster injected i.v. with $^{238}$Pu-citrate. DTPA or 3,4,3-L1(1,2-HOPO) treatment was administered p.o. for six days, once-daily or twice-daily, starting at 24 hours post-exposure and mice were euthanized at 7 days.

Figure 17B:
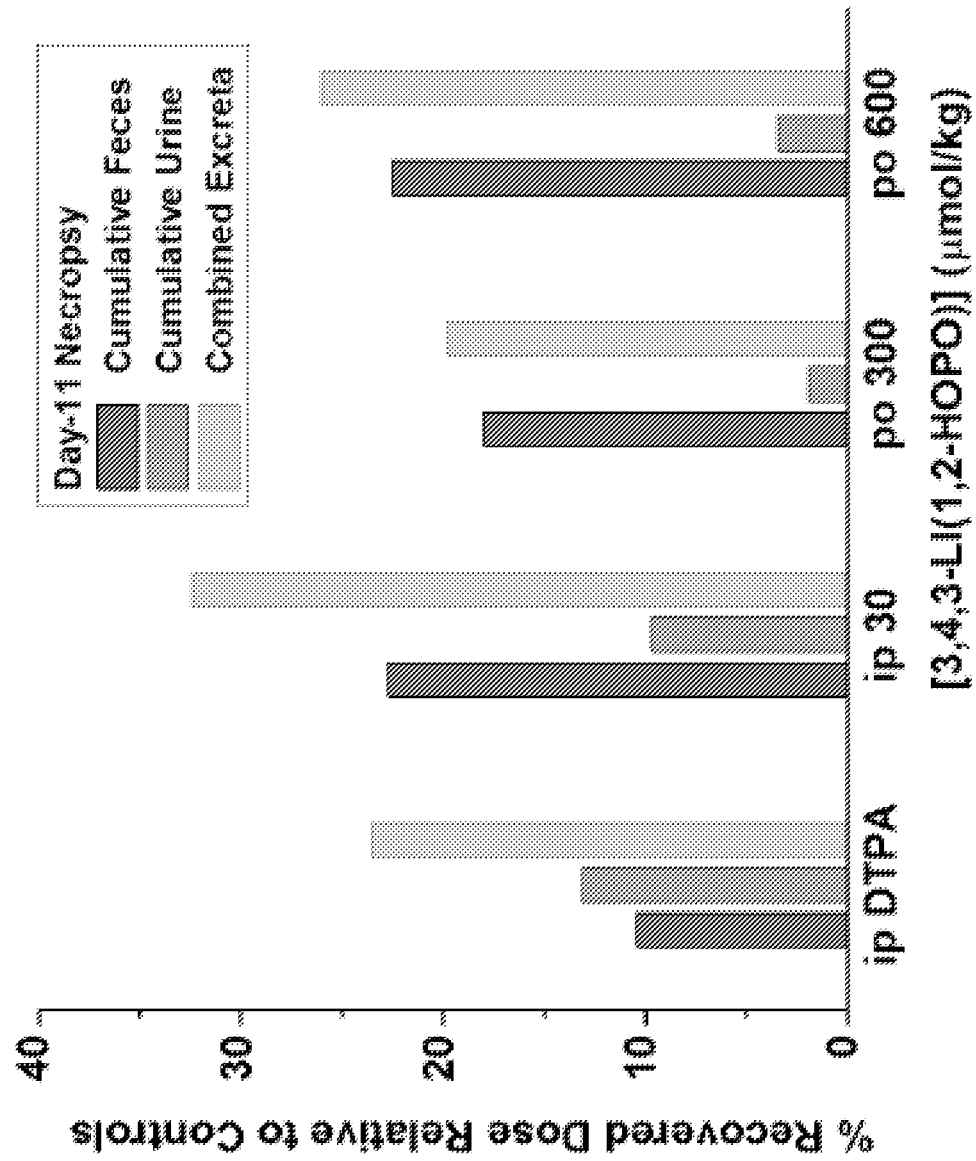

FIG. 17B shows cumulative excretion in treated groups relative to control at day 11 post-contamination for young adult male Swiss-Webster injected i.v. with $^{238}$Pu-citrate. DTPA or 3,4,3-L1(1,2-HOPO) treatment was administered i.p. or p.o. for six days, once-daily, starting at 24 hours post-exposure and mice were euthanized at 11 days.

Figure 18A:
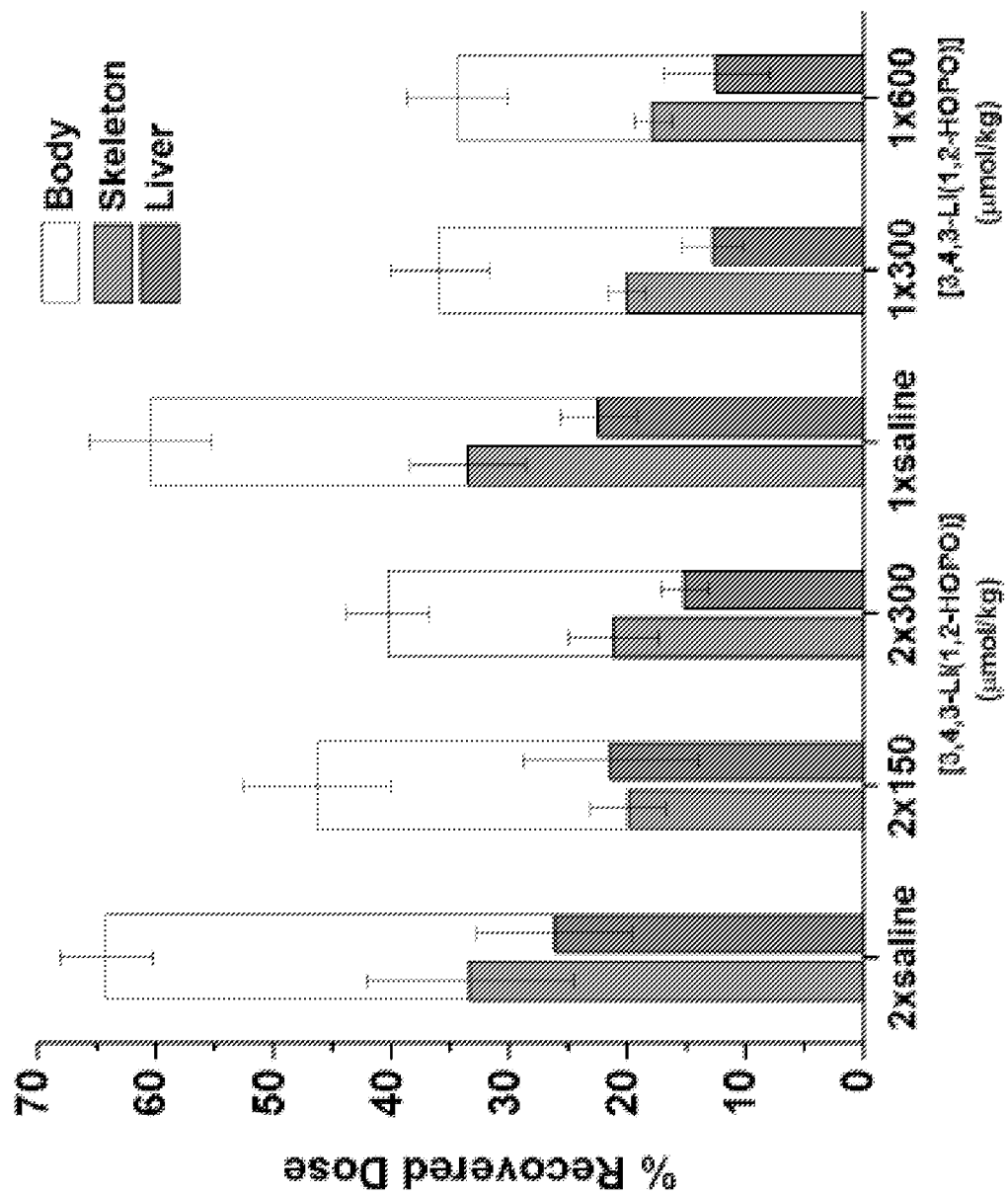

FIG. 18A shows body, skeleton and liver retention in treated groups at 7 days post-contamination for young adult male Swiss-Webster injected i.v. with $^{238}$Pu-citrate. Saline, DTPA or 3,4,3-L1(1,2-HOPO) treatment was administered p.o. for six days, once-daily or twice-daily, starting at 24 hours post-exposure and mice were euthanized at 7 days.

Figure 18B:
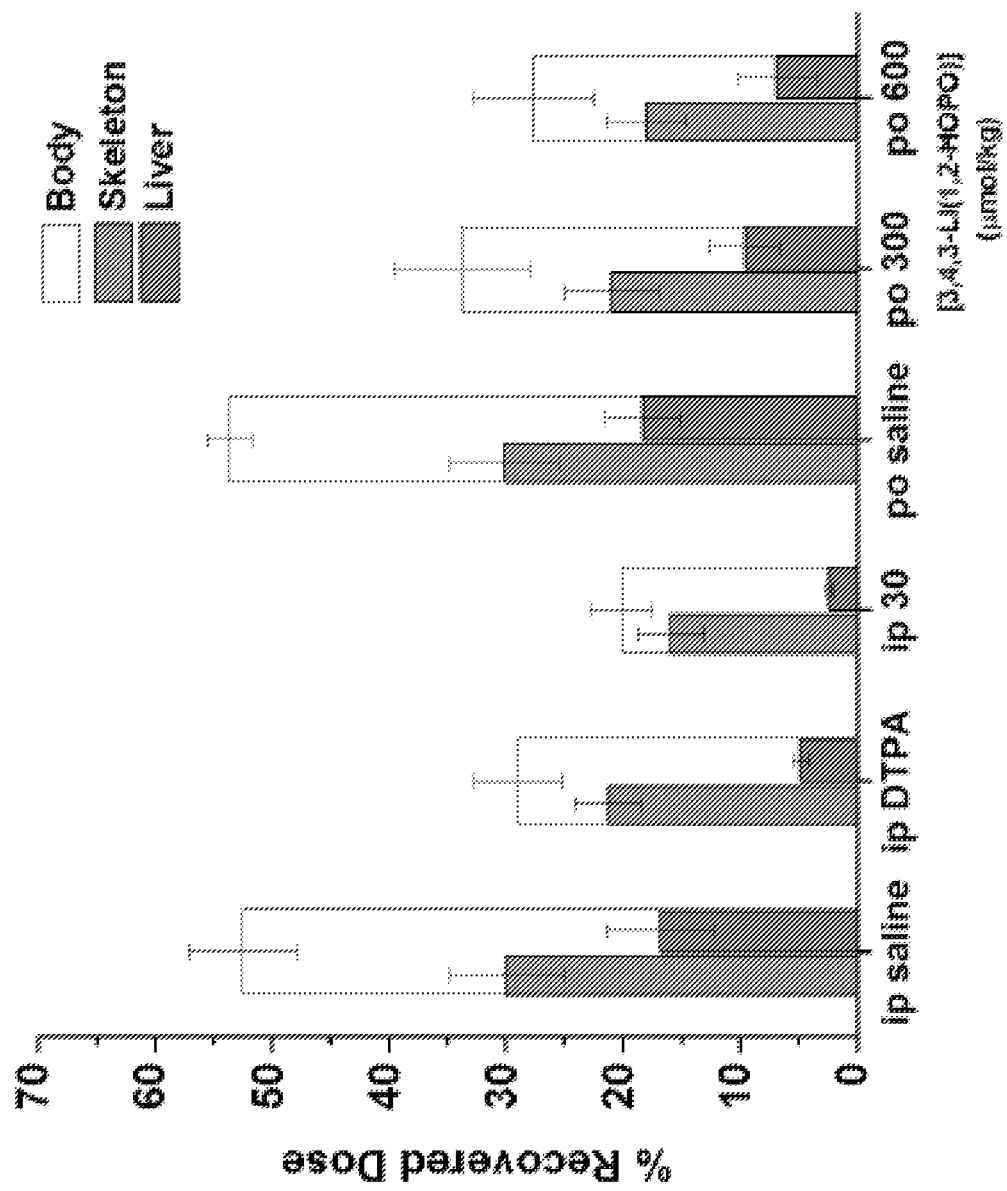

FIG. 18B shows body, skeleton and liver retention in treated groups at day 11 post-contamination for young adult male Swiss-Webster injected i.v. with $^{238}$Pu-citrate. Saline, DTPA or 3,4,3-L1(1,2-HOPO) treatment was administered i.p. or p.o. for six days, once-daily, starting at 24 hours post-exposure and mice were euthanized at 11 days.

FIG. 19A-FIG. 19F show data related to retention in liver and kidneys and excretion of radioactivity from $[_{14}C]$-3,4,3-L1(1,2-HOPO) in male and female mice after i.v., i.p., or p.o. administration. Data expressed as µg-eq (mean±SD, n=3) for tissue content and as percentage of administered dose (% AD) for excreta; excreta of each three-mouse group were pooled and standard deviations are not available.

Figure 19A:
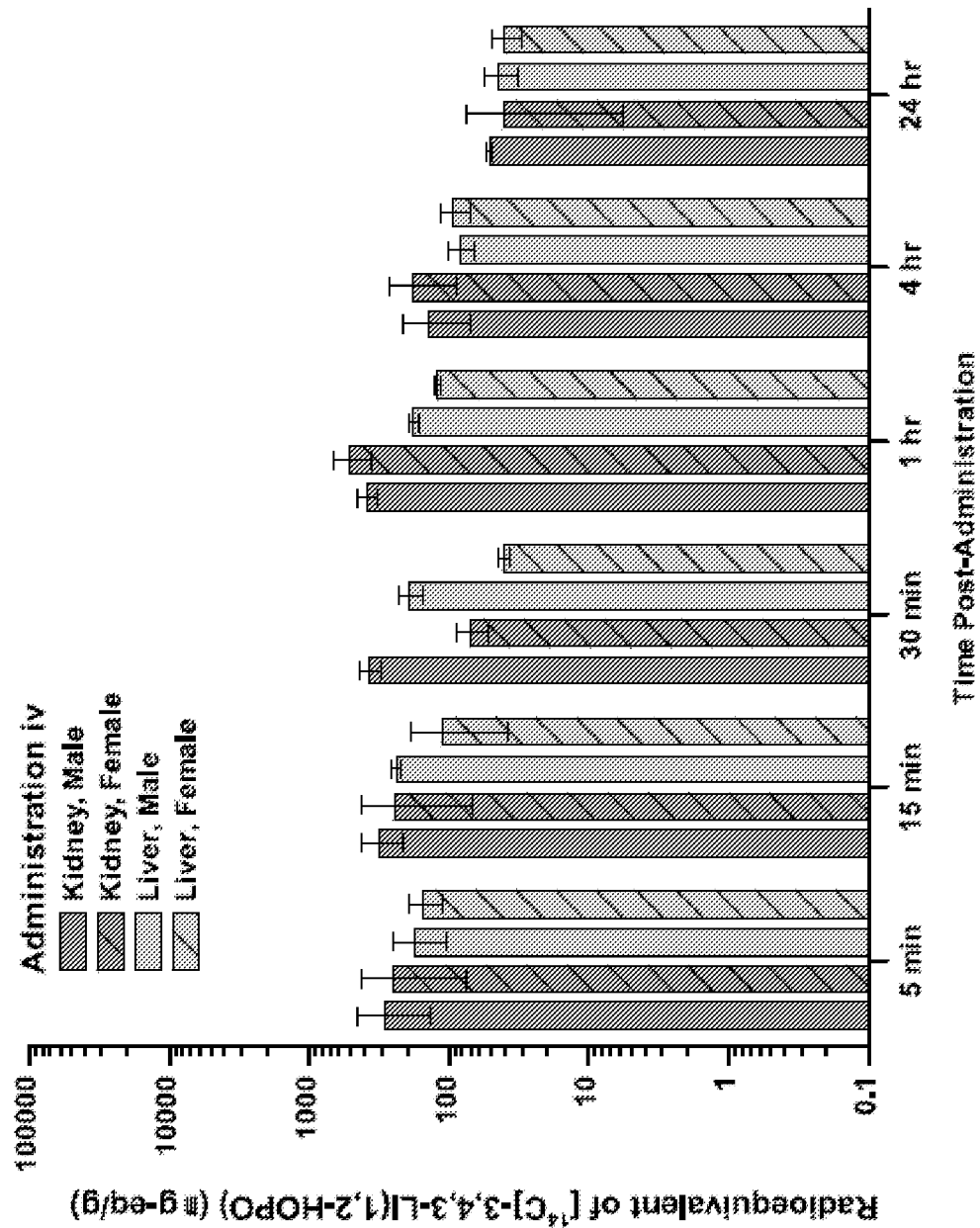

FIG. 19A show data related to retention in liver and kidneys of radioactivity from $[_{14}C]$-3,4,3-L1(1,2-HOPO) in male and female mice after i.v. administration.

Figure 19B:
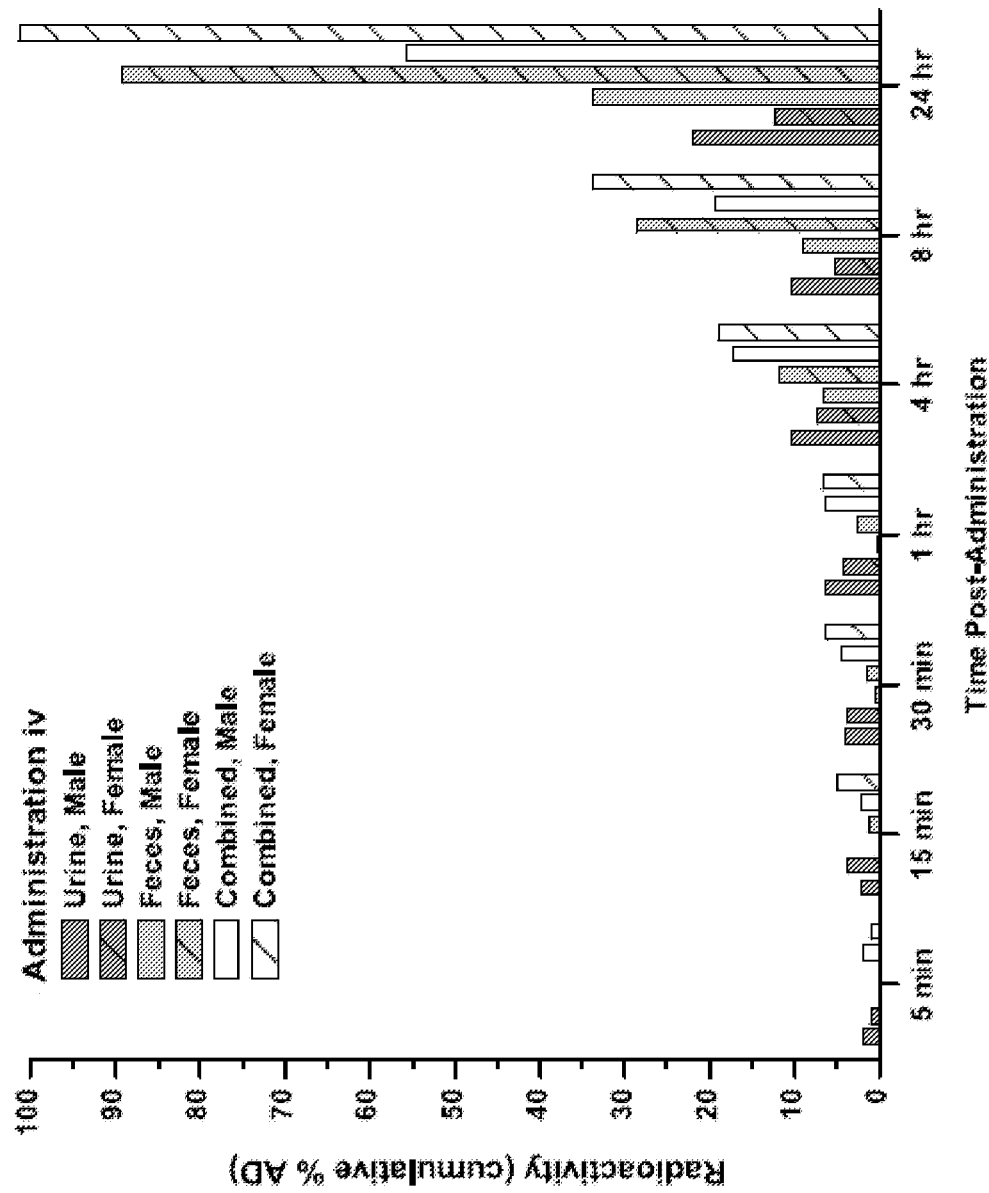

FIG. 19B show data related to excretion of radioactivity from $[_{14}C]$-3,4,3-L1(1,2-HOPO) in male and female mice after i.v. administration.

Figure 19C:
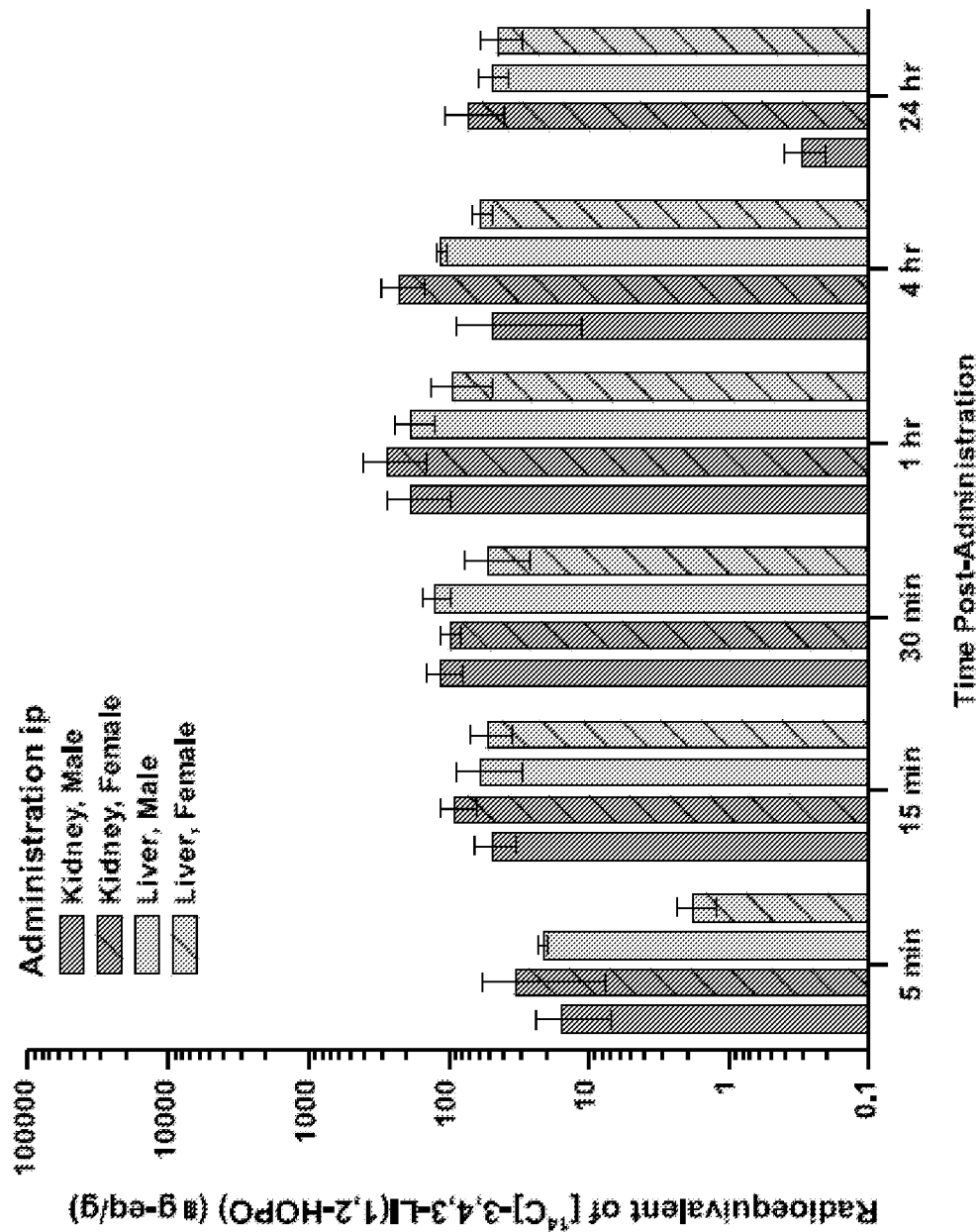

FIG. 19C show data related to retention in liver and kidneys of radioactivity from $[_{14}C]$-3,4,3-L1(1,2-HOPO) in male and female mice after i.p. administration.

Figure 19D:
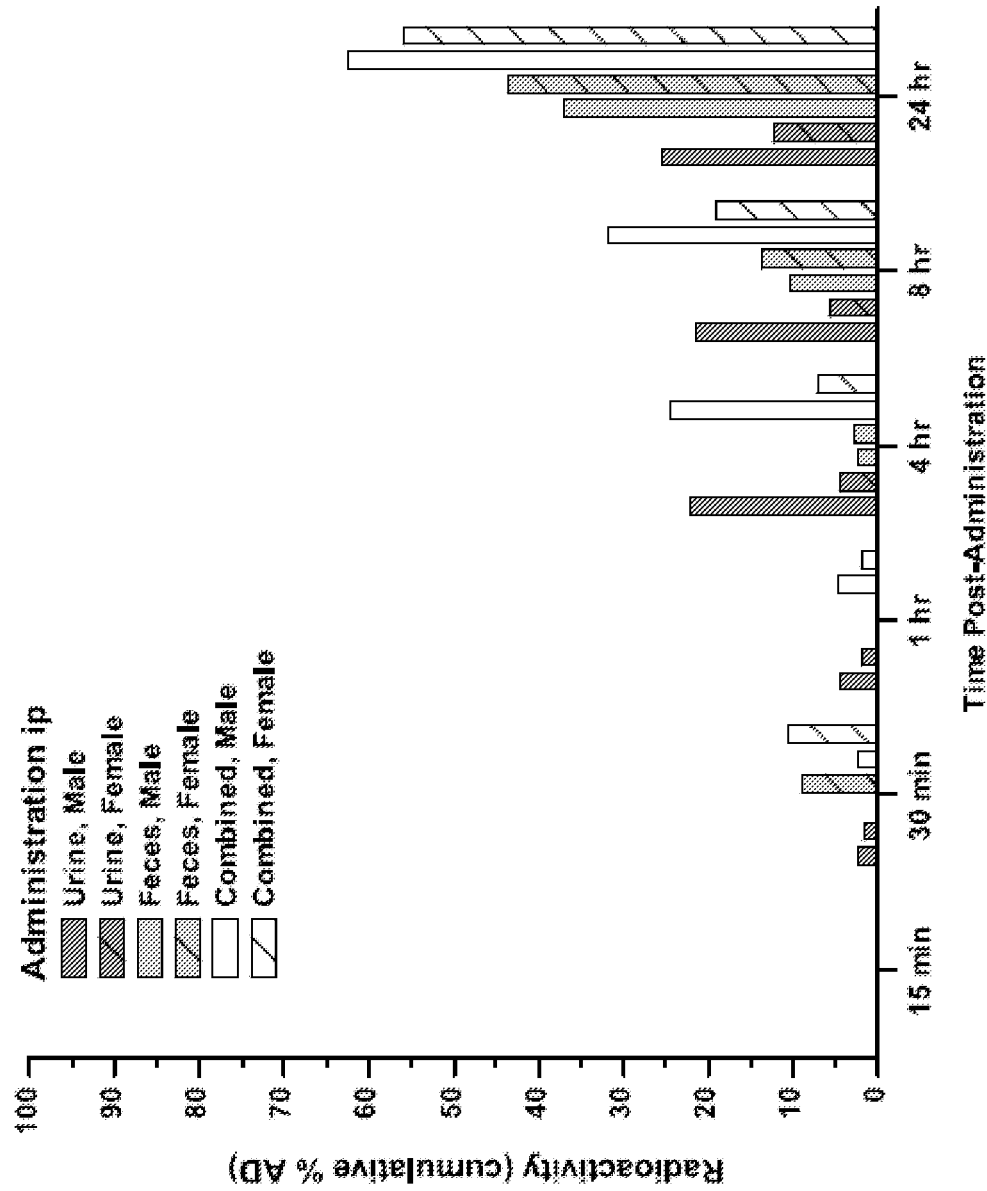

FIG. 19D show data related to excretion of radioactivity from $[_{14}C]$-3,4,3-L1(1,2-HOPO) in male and female mice after i.p. administration.

Figure 19E:
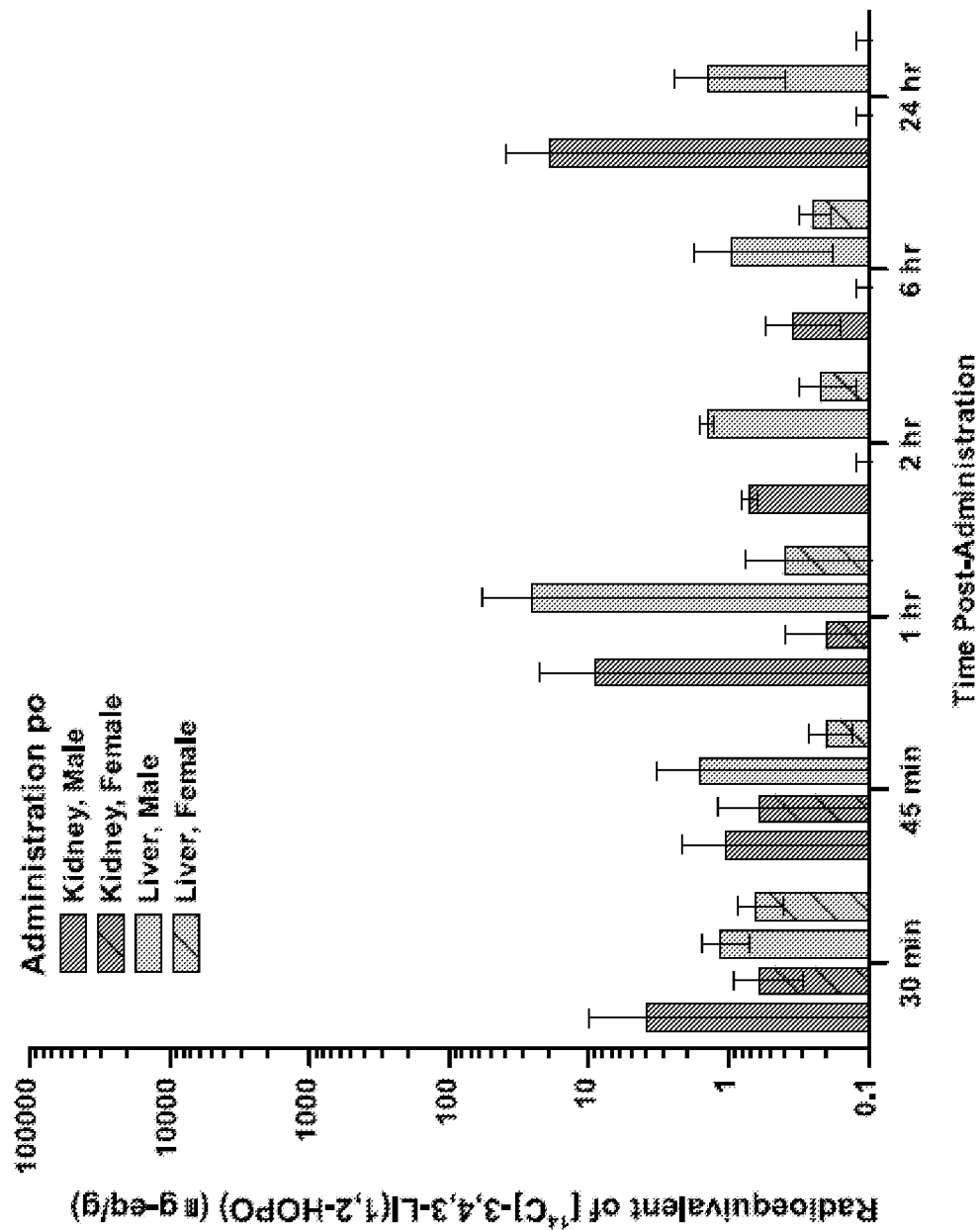

FIG. 19E show data related to retention in liver and kidneys of radioactivity from $[_{14}C]$-3,4,3-L1(1,2-HOPO) in male and female mice after p.o. administration.

Figure 19F:
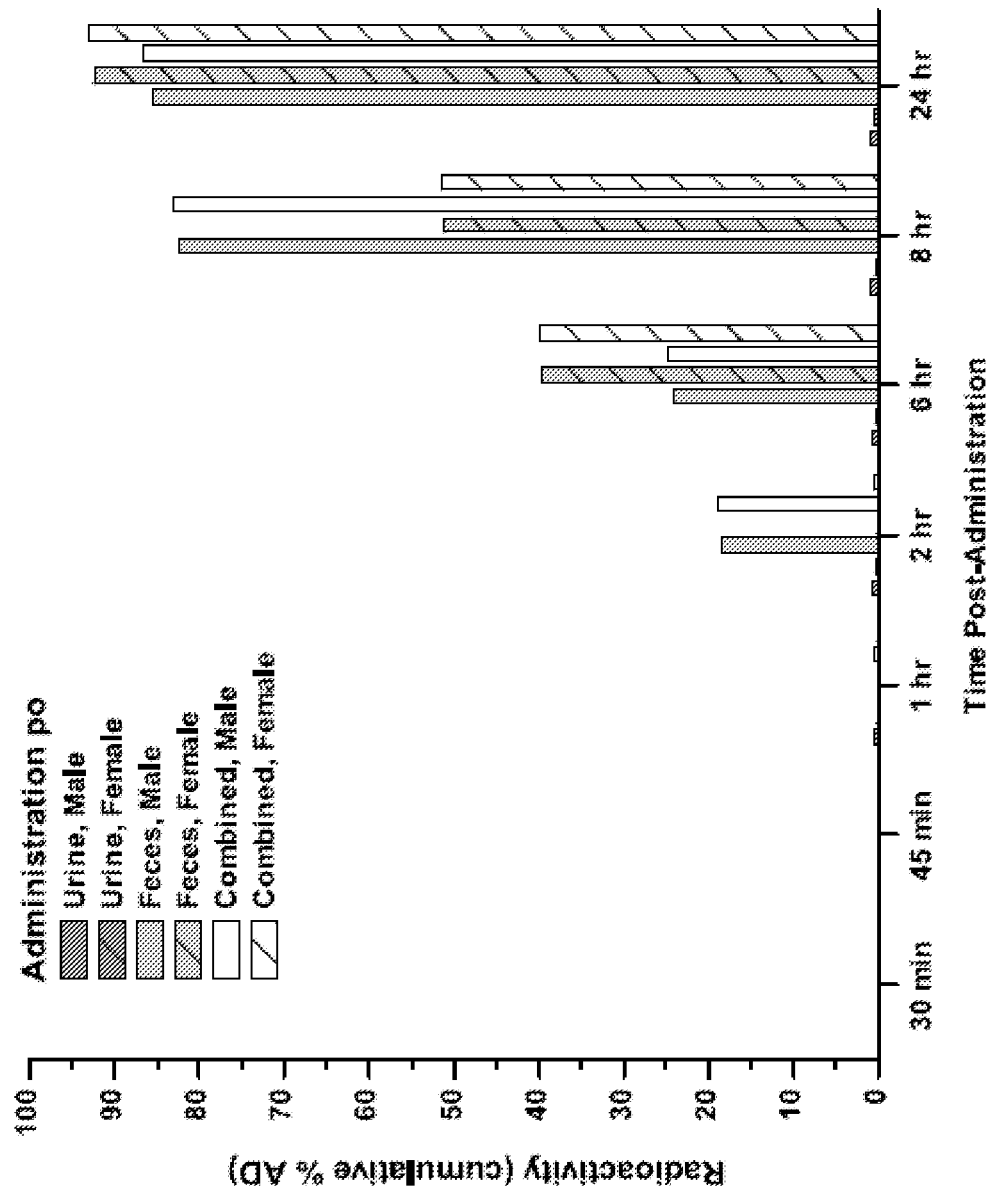

FIG. 19F show data related to excretion of radioactivity from $[_{14}C]$-3,4,3-L1(1,2-HOPO) in male and female mice after p.o. administration.

FIG. 20A-FIG. 20D show data related to retention and excretion of radioactivity from $[_{14}C]$-3,4,3-L1(1,2-HOPO) in male and female rats after i.v. or p.o. administration. Groups of two or three rats were administered a single dose of $[_{14}C]$-3,4,3-L1(1,2-HOPO) and were euthanized at three time points between 2 hr and 24 hr postdose. Data expressed as µg-eq (mean±SD) for tissue content and as percentage of administered dose (% AD; mean±SD) for excreta.

Figure 20A:
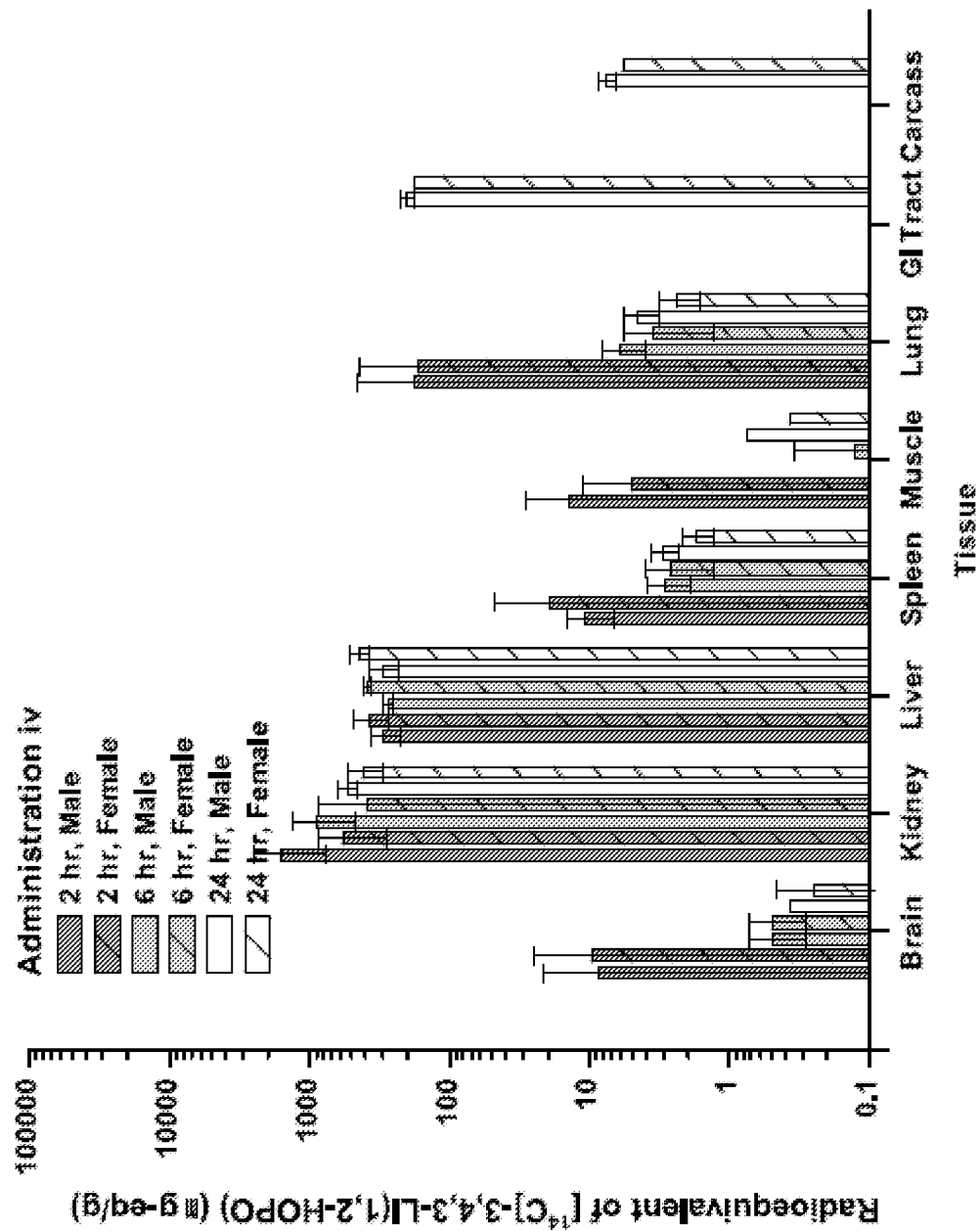

FIG. 20A show data related to retention of radioactivity from $[_{14}C]$-3,4,3-L1(1,2-HOPO) in male and female rats after i.v. administration.

Figure 20B:
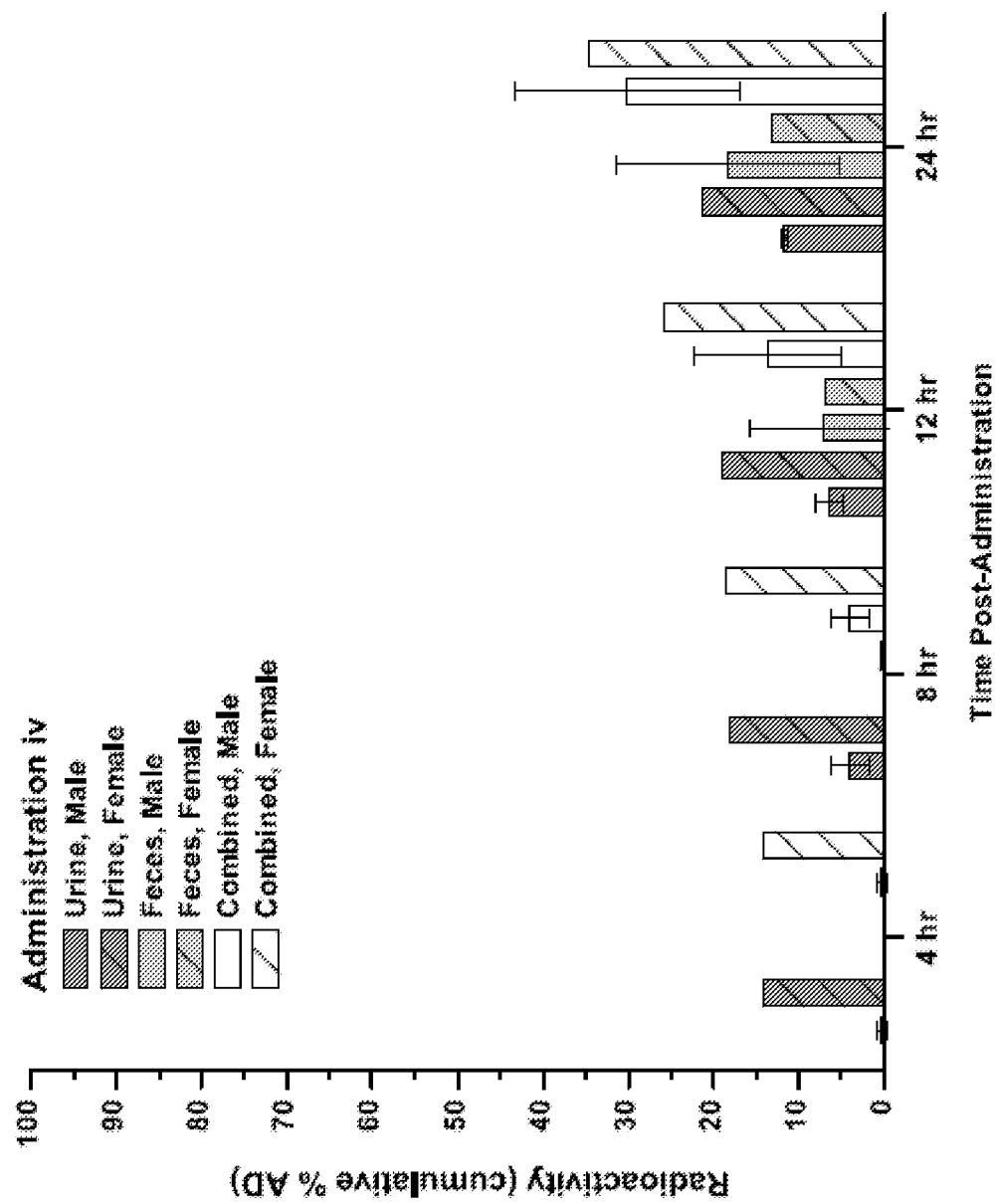

FIG. 20B show data related to excretion of radioactivity from $[_{14}C]$-3,4,3-L1(1,2-HOPO) in male and female rats after i.v. administration.

Figure 20C:
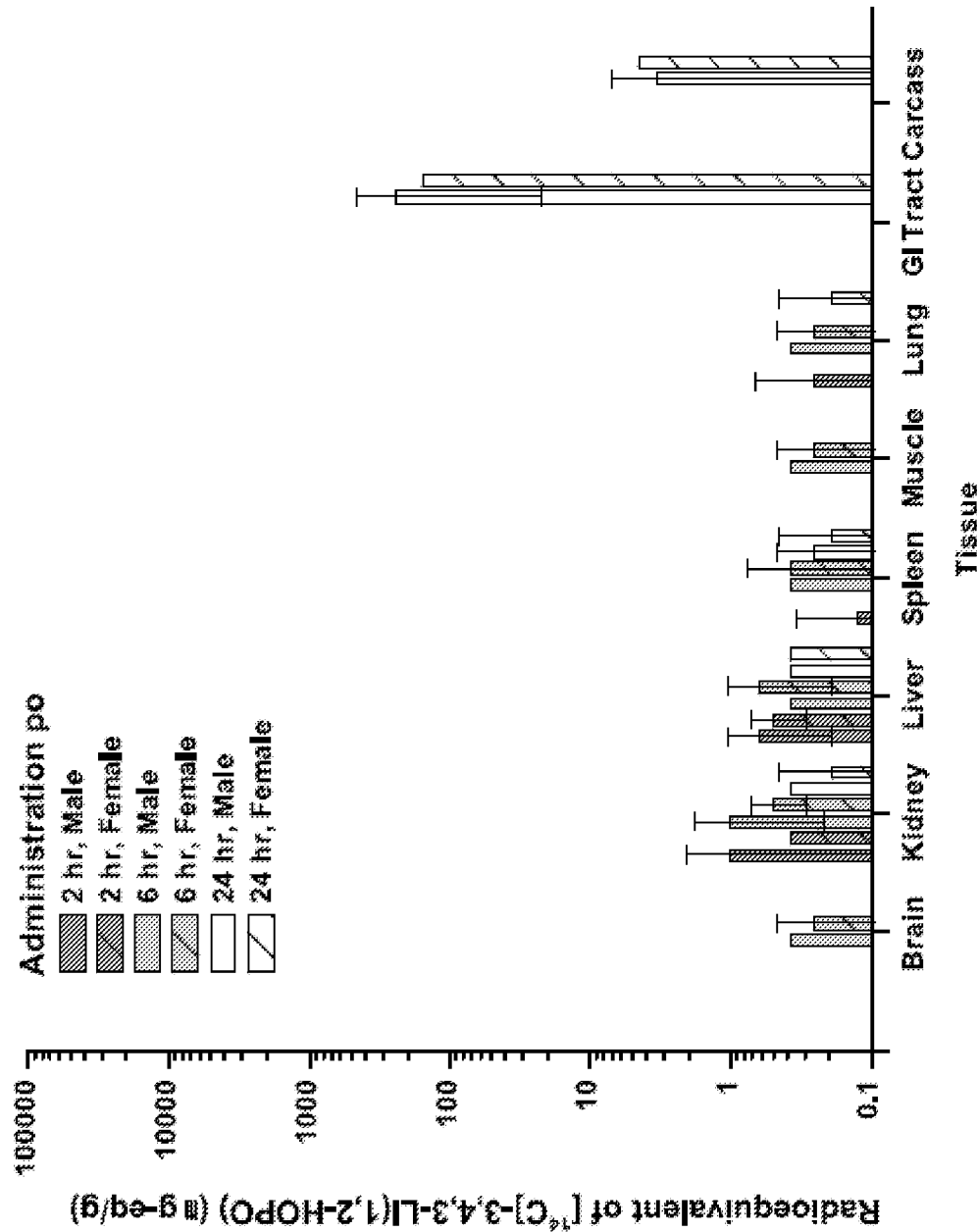

FIG. 20C show data related to retention of radioactivity from $[_{14}C]$-3,4,3-L1(1,2-HOPO) in male and female rats after p.o. administration.

Figure 20D:
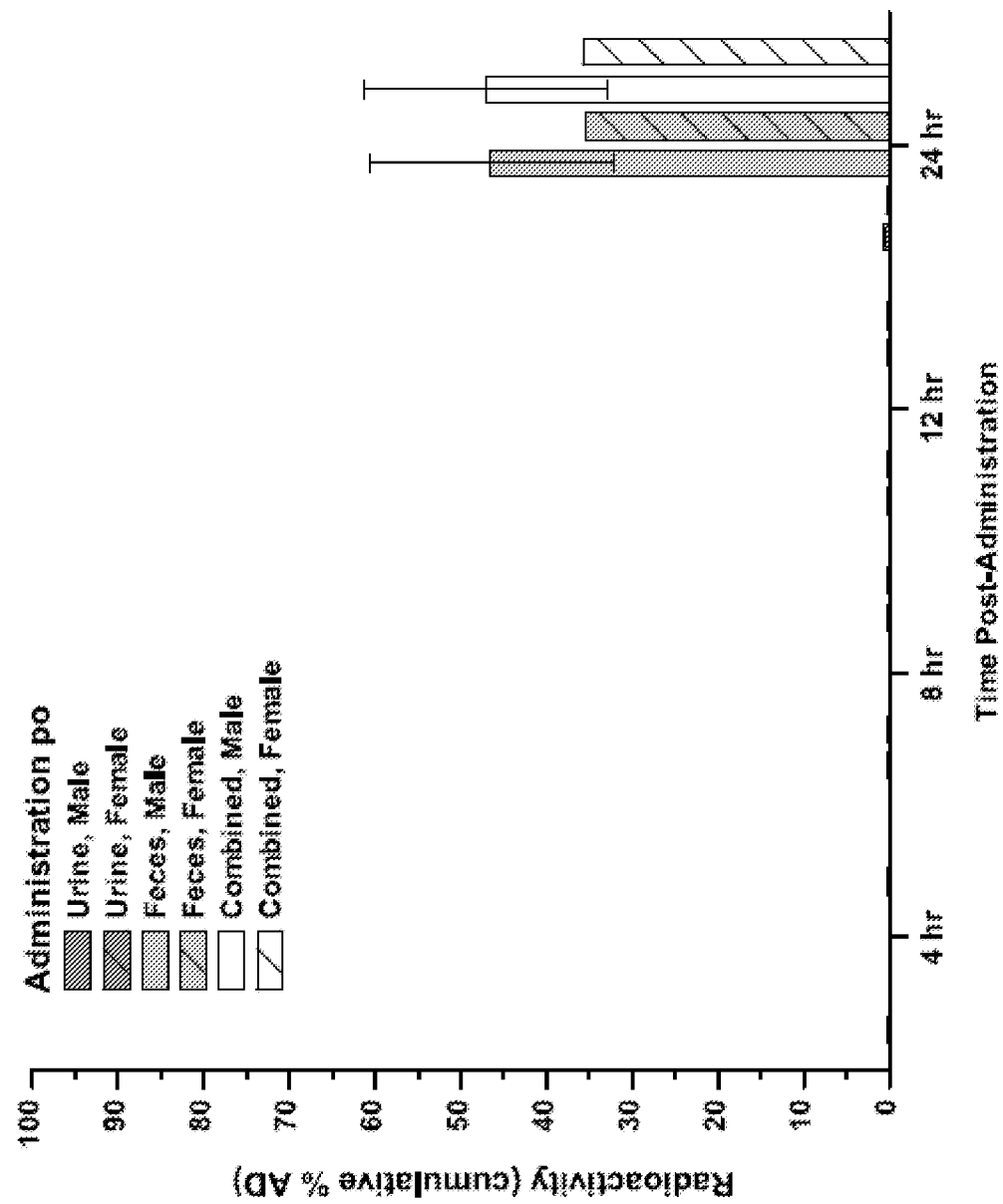

FIG. 20D show data related to excretion of radioactivity from $[_{14}C]$-3,4,3-L1(1,2-HOPO) in male and female rats after p.o. administration.

Figure 21A:
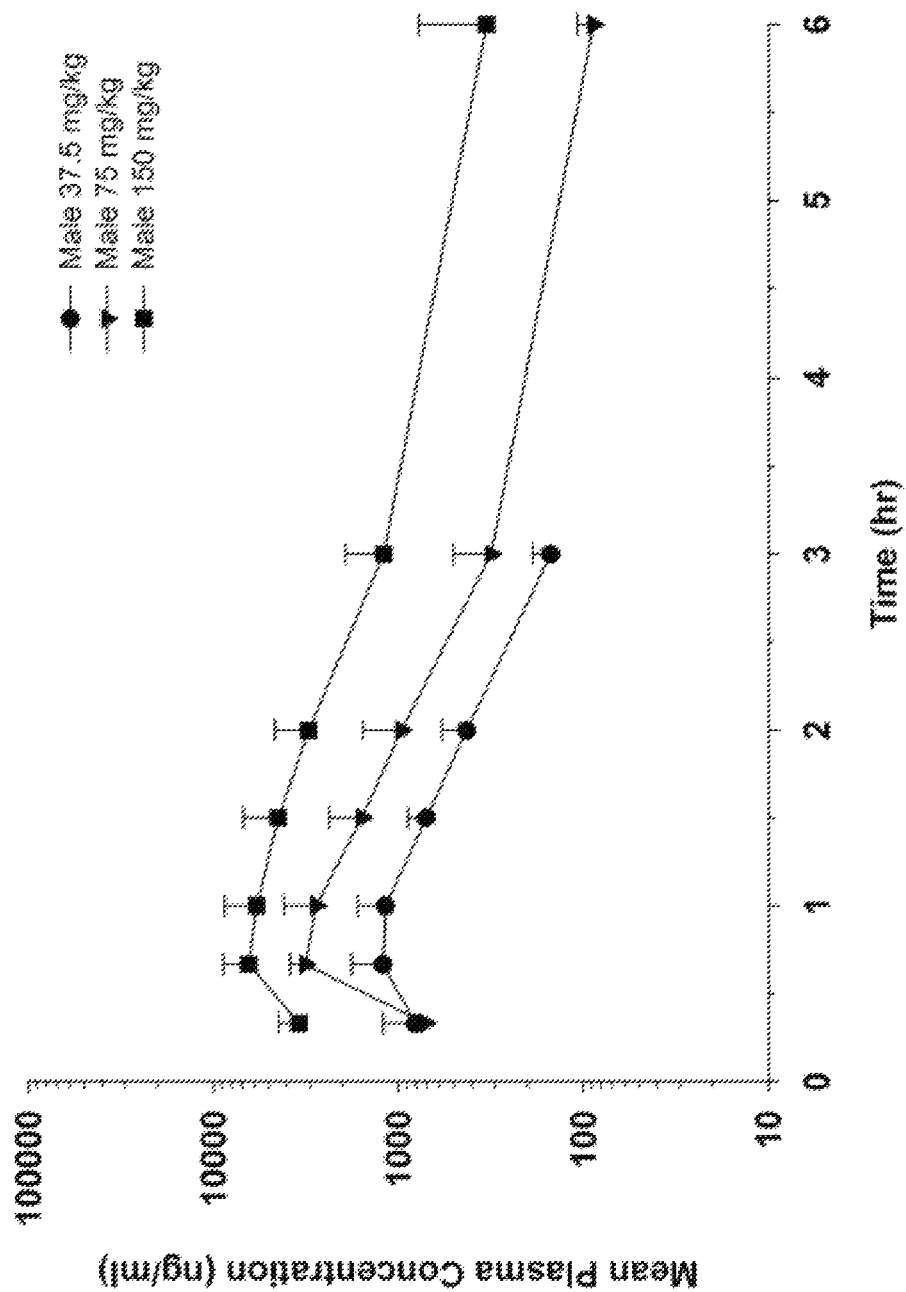
Figure 21B:
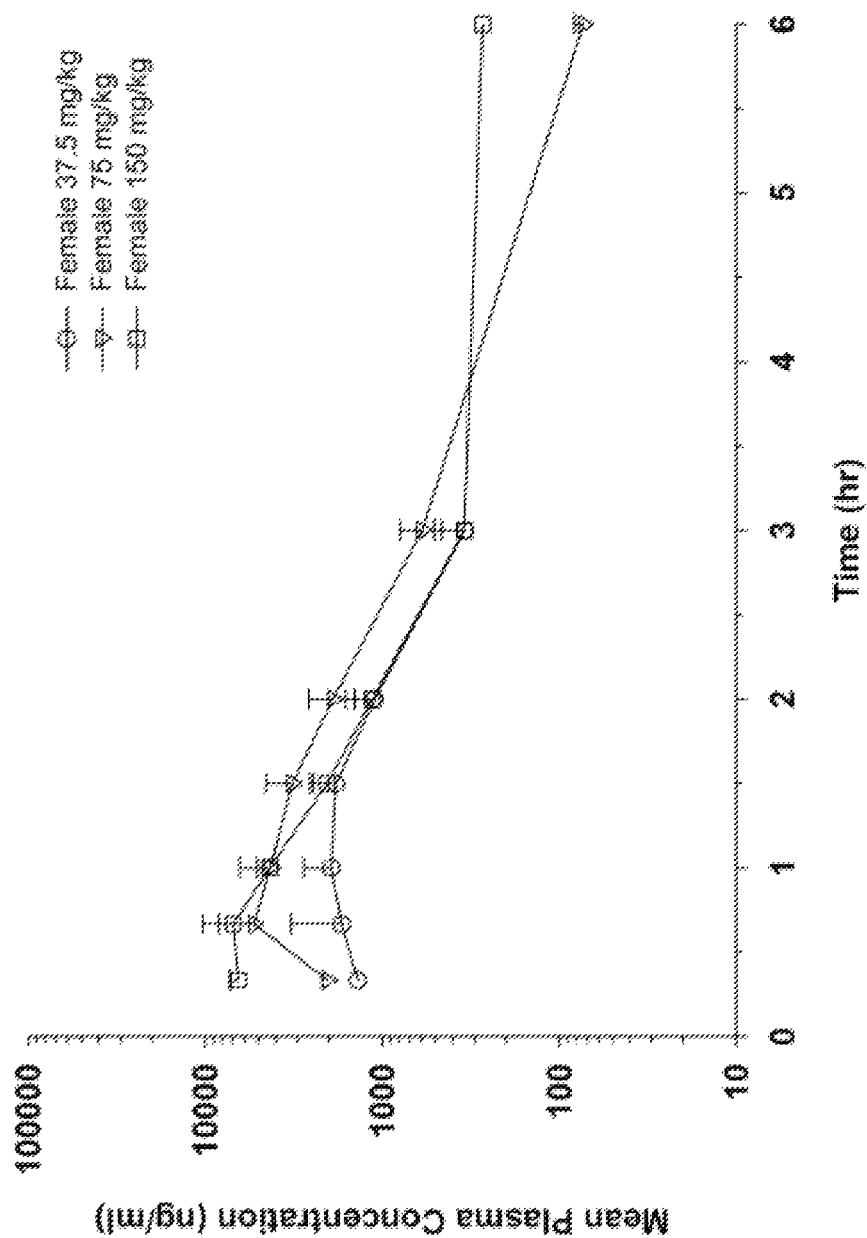

FIG. 21A and FIG. 21B show time-course of mean plasma concentrations of 3,4,3-L1(1,2-HOPO) in male (FIG. 21A)

and female (FIG. 21B) beagle dogs after a single oral dose of 37.5, 75, or 150 mg/kg 3,4,3-L1(1,2-HOPO). Mean (±SD) data (n≤3) are plotted against the nominal blood collection times. Plasma concentrations from the 37.5 mg/kg group were not plotted at 6 hr because they were below the lower limit of quantification.

FIG. 21A shows clearance of 3,4,3-L1(1,2-HOPO) in plasma of male dogs.

FIG. 21B shows clearance of 3,4,3-L1(1,2-HOPO) in plasma of female dogs

Figure 22:
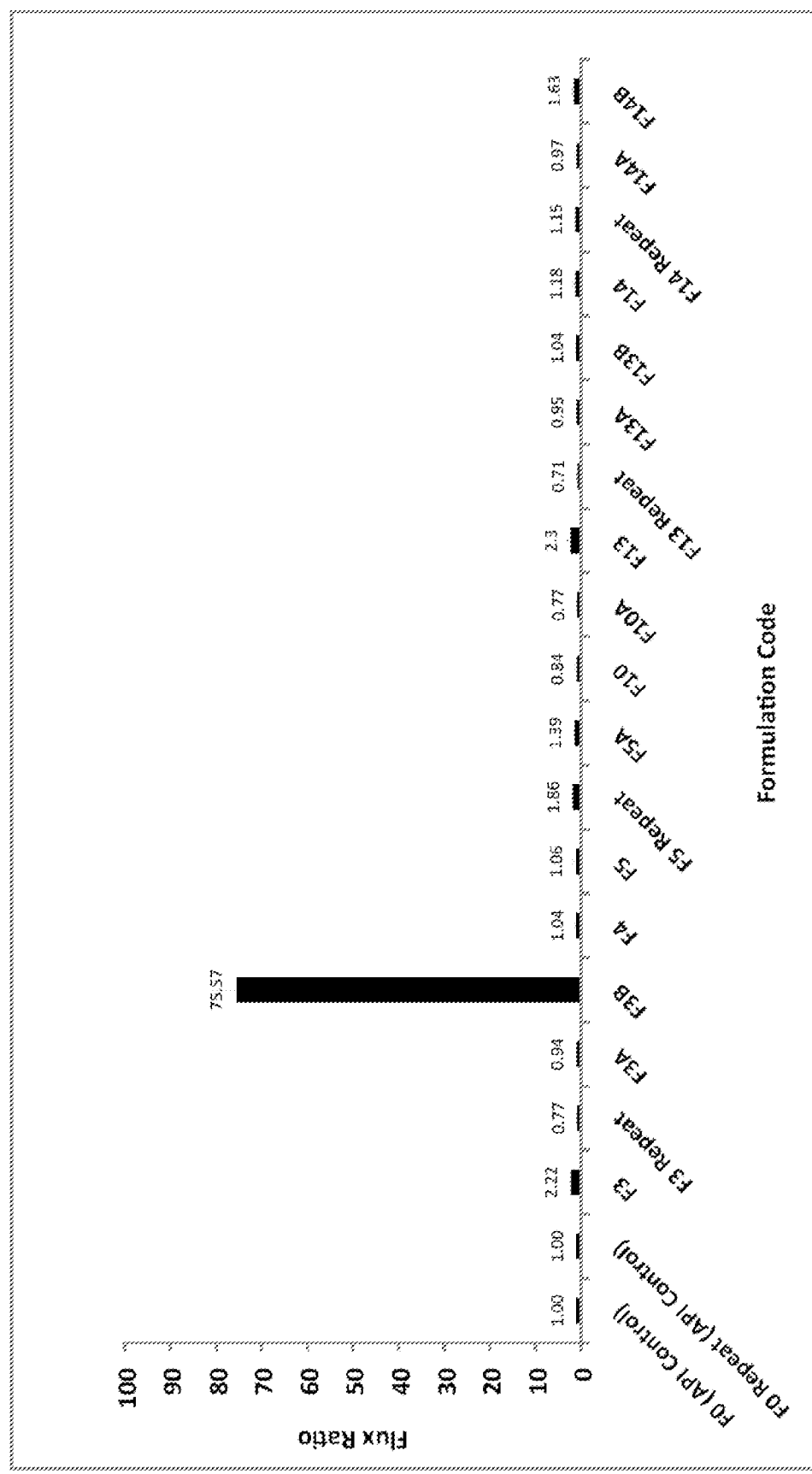

FIG. 22 shows flux ratio comparison of 3,4,3-L1(1,2-HOPO) formulations.

Figure 23:
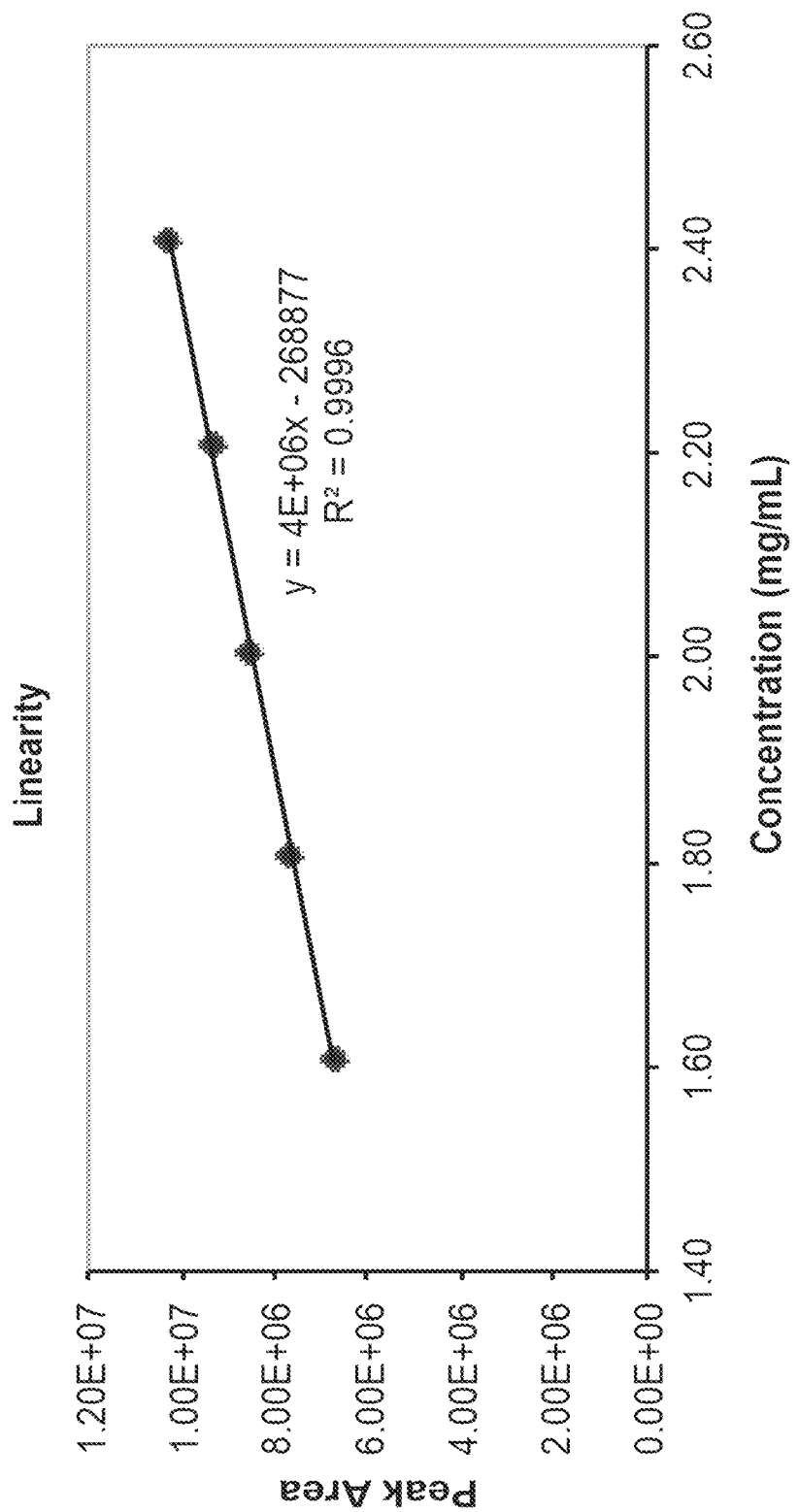

FIG. 23 shows linearity results for 3,4,3-L1(1,2-HOPO) at T=0.

Figure 24:
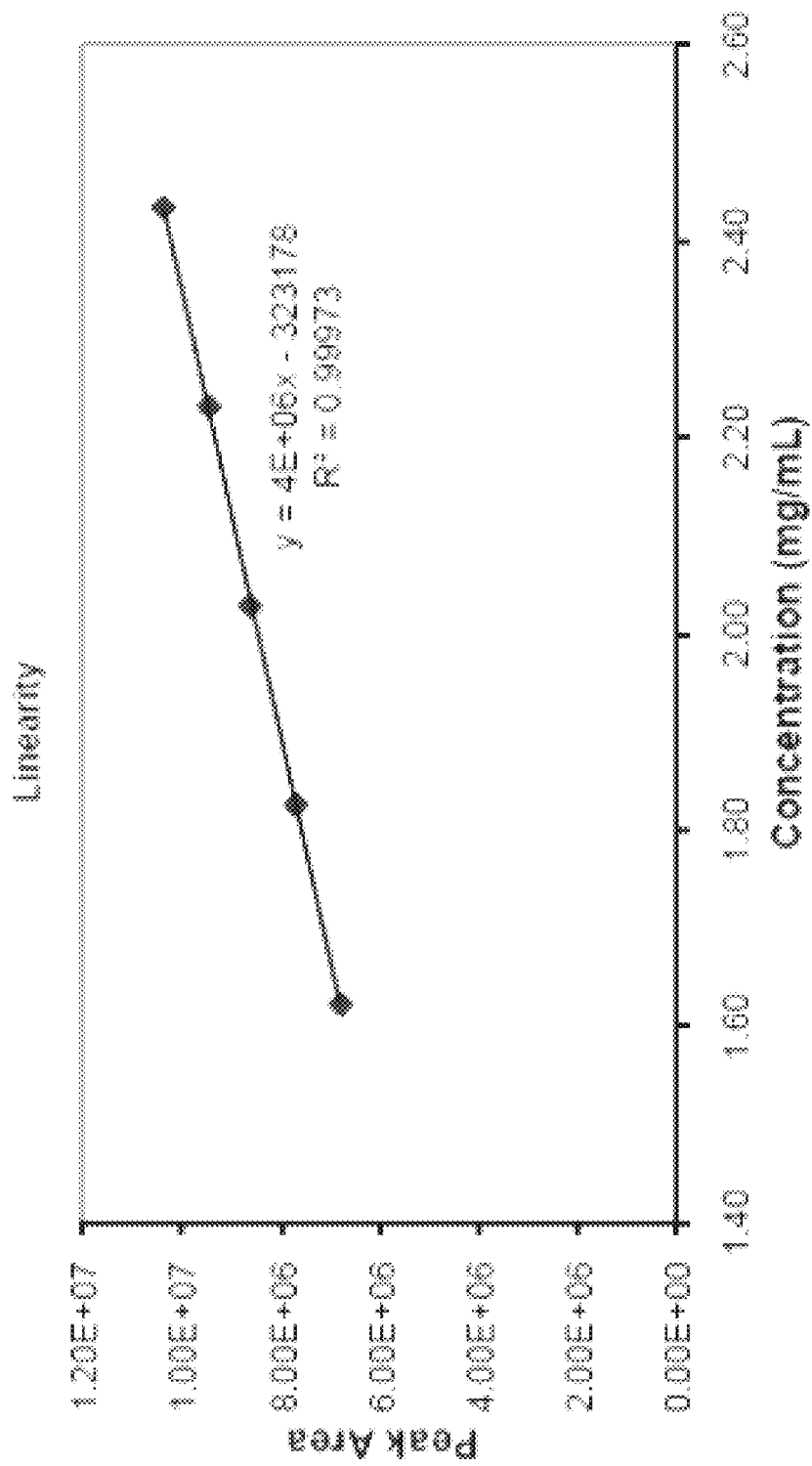

FIG. 24 shows linearity results for 3,4,3-L1(1,2-HOPO) at T=2 weeks.

Figure 25:
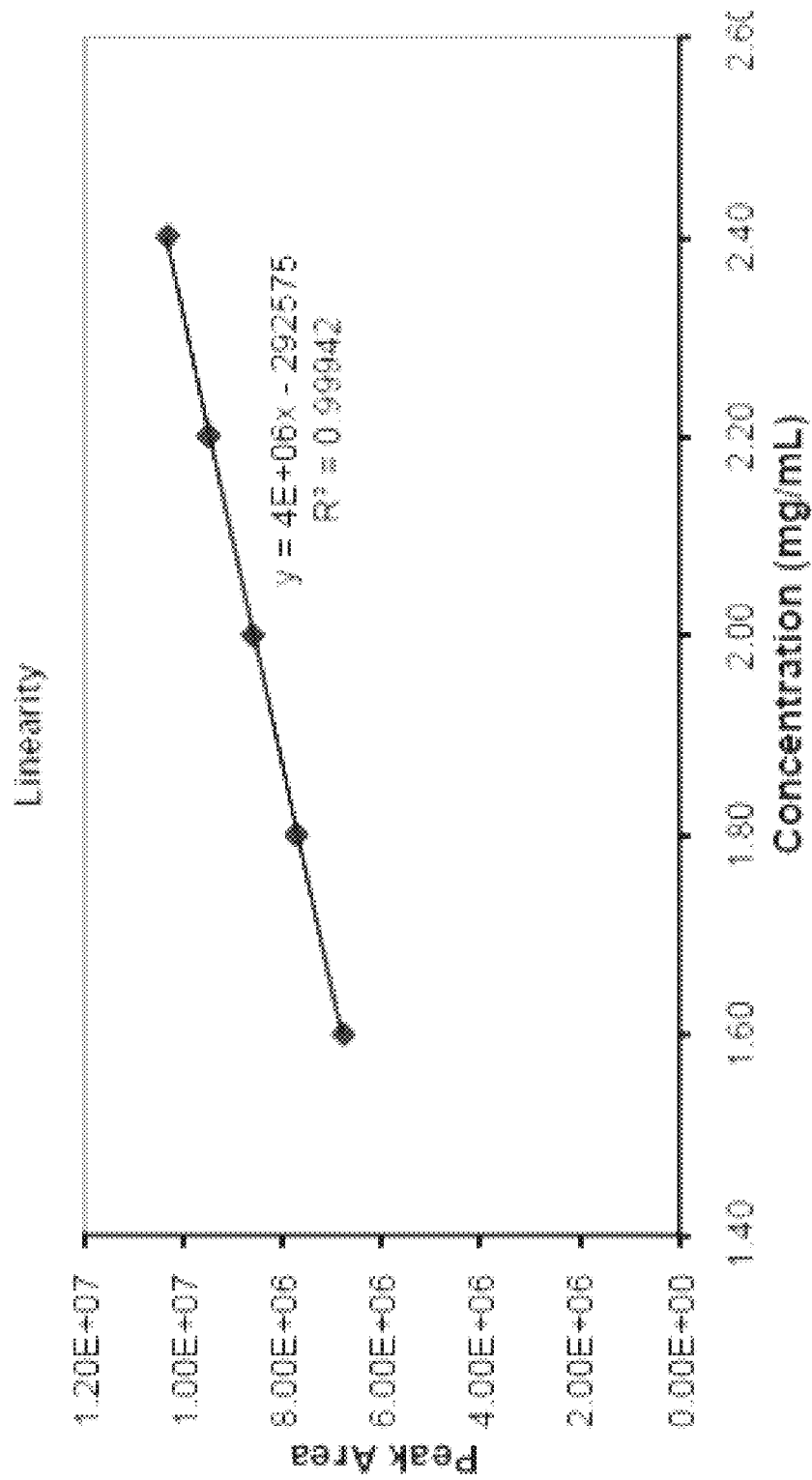

FIG. 25 shows linearity results for 3,4,3-L1(1,2-HOPO) at T=4 weeks.

Figure 26:
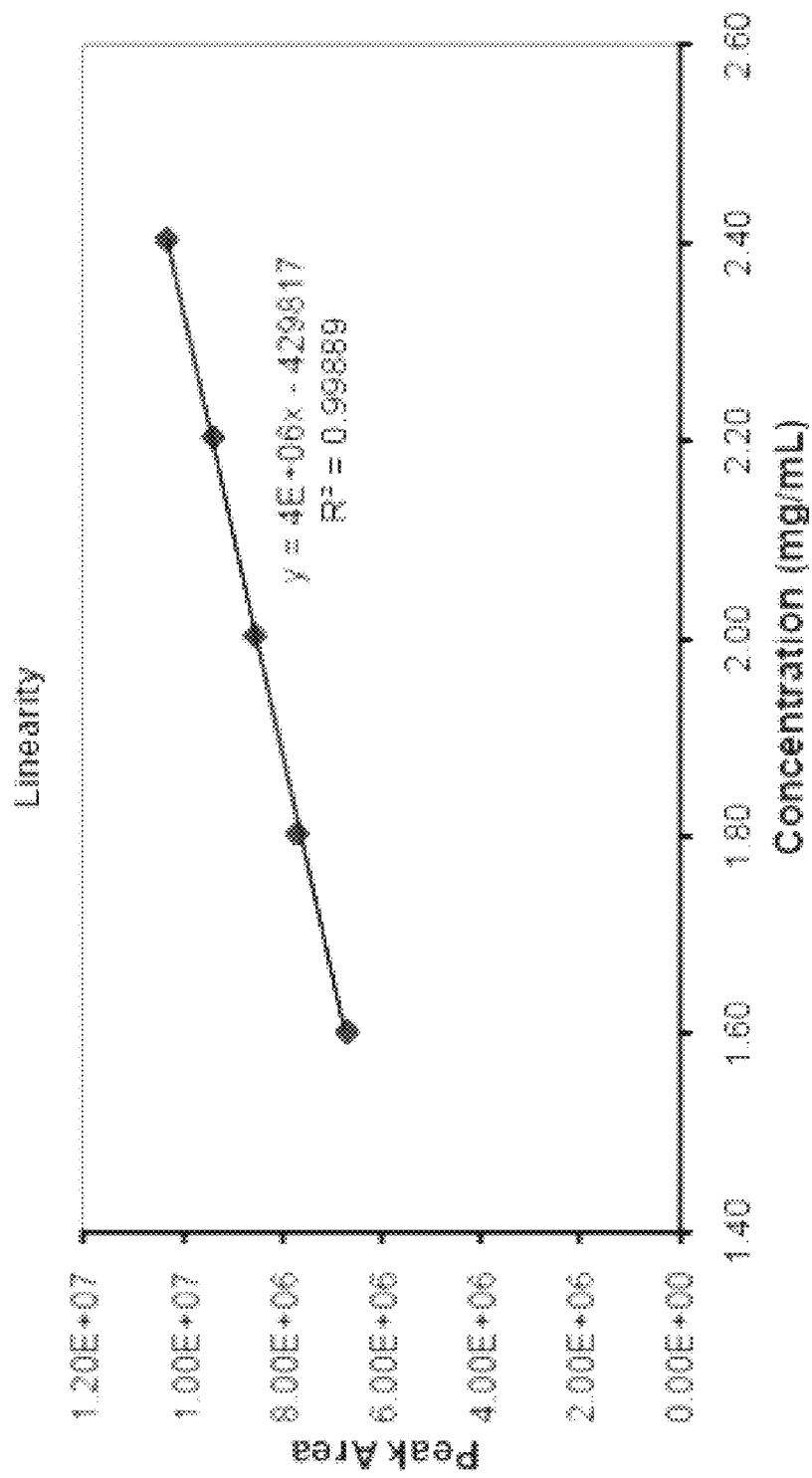

FIG. 26 shows linearity results for 3,4,3-L1(1,2-HOPO) at T=8 weeks.

DETAILED DESCRIPTION OF VARIOUS EMBODIMENTS

The potential consequences of a major radiological event are not only large-scale external radiation exposure of the population, but also uncontrolled dissemination of, and internal contamination with, radionuclides. When planning an emergency response to radiological and nuclear incidents, one must consider the need for treatment for contaminated individuals. In addition to meeting the desired criteria for post-exposure treatments such as safety, ease of administration, and broad-spectrum efficacy against multiple radionuclides and levels of challenge, ideal countermeasures can include rapid onset; induce minimal to no performance-decrementing side effects; be compatible with current military Chemical, Biological, Radiological, Nuclear, and Explosive countermeasures; and require minimal logistical burdens. Hydroxypyridinone-based actinide decorporation agents have shown the most promise as decorporation strategies for various radionuclides of concern, including the actinides plutonium and americium.

Provided herein are various formulations for decorporation agents.

The following disclosure provides a brief set of definitions, then provides further detail regarding the various formulations of the chelators provided herein, and then provides a set of Examples regarding various embodiments.

Definitions

The term "emergency" encompasses: (a) The event of an accidental release of the radioisotopes in the environment due to any nuclear accident. (b) Any accidental release of the hazardous nuclides in the environment. (c) A nuclear fallout including that occurring in the normal course of an experimental, diagnostic or therapeutic purpose. (d) Any kind of accidental uptake and retention of the radionuclides by the human or animal subjects. (e) Any other kind of exposure to the volatile radionuclides. (f) Any kind of a radiological accident.

The term "pharmaceutically acceptable salt," as used herein, and particularly when referring to a pharmaceutically acceptable salt of a compound, including 3,4,3-L1(1,2-HOPO), and refers to any pharmaceutically acceptable salts of a compound, and preferably refers to an acid addition salt of a compound.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound can comprise at least 0.5% to 1%, 1% to 5%, 5% to 10%, 10% to 20%, 20% to 50%, 50% to 70%, 70% to 90%, 90% to 95%, 95% to 99%, and 99% to 100%. In some embodiments, the amount of the compound will be at least 50% or 75% of the mass, by weight, of a given sample. A "functional purity" is a measurement of the amount of a particular compound in a sample or product in relation to other compounds in a sample that can adversely impact the function of the compound. Thus, other components in a sample that do not interfere with the compound's activity (e.g., water), will not be used in determining the purity of a sample or product.

The terms "derivative," "variant," or other similar term refers to a compound that is an analog of the other compound.

The term "and/or" designates both the option of "and" as well as the option of "or" in that particular circumstance. However, unless otherwise specified in the specification, the use of the term "or" or "and" encompasses a description of both option as well. Thus, the use of the term "or" should not be taken as excluding the option of "and", unless additional context indicates that it should (this definition does not apply to the language in the claims). The use of the singular or plural forms of a term encompasses both options (singlular or plural) as well as both options combined (singular and plural), unless indicated otherwise.

The term "inhibition" as used herein, refers to any statistically significant decrease in the detrimental impact of the metal, including full blocking of the activity. For example, "inhibition" can refer to a decrease of about 10%, 20%, 30%, 40%, 50%, 60%, 70%, 80%, 90%, or 100% in the detrimental impact of the metal.

The term "patient" includes human and other mammalian subjects that receive either prophylactic or therapeutic treatment.

The terms "treat" or "prevent" do not require complete treatment or complete prevention under all conditions. A slowing of the onset of a disorder or its symptoms or a decrease in the number of the symptoms can be adequate "prevention" in some embodiments. Similarly, a decrease in the severity of the symptoms of the disorder can also be an effective treatment for a disorder. "Prophylactic treatment" denotes that the compound is administered prior to exposure to the detrimental compound (e.g., metal such as plutonium or a MRI imaging agent). Treatment may also be in response to exposure, e.g., responsive therapy. Treat also encompasses remediation, decorporation, and/or decontamination.

"Therapeutically effective amount" means that amount of the chelating agents, such as 3,4,3-L1(1,2-HOPO), 5-LIO (Me-3,2-HOPO) and/or DTPA, that elicit the biological or medicinal response in a tissue system, animal or human sought by a researcher, veterinarian, medical doctor or other clinician, which response includes alleviation of the symptoms of the disease or disorder being treated. The specific amount of chelating agents needed to elicit the biological or medicinal response will depend on a number of factors, including but not limited to the disease or disorder being treated, the chelating agents being administered, the method of administration, and the condition of the patient.

"Mammal" when used herein refers to any animal that is considered a mammal. Preferably, the mammal is human.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), (incorporated herein by reference).

The term "heavy metal" denotes one or more of a transition metal, a metalloid, a metallic element within groups 13, 14, and 15 of the Periodic Table, an actinide or a lanthanide. Heavy metals include, for example, gadolinium, lead, tin, cadmium, yttrium, scandium, and plutonium.

Pharmaceutical Formulations

In some embodiments, the pharmaceutical composition of formulation comprises a chelating agent and one or more additional ingredient. In some embodiments, the chelating agent is a 1,2-HOPO chelating agent. In some embodiments, the chelating agent is 3,4,3-L1-1,2-HOPO.

In some embodiments, the pharmaceutical composition comprises a 1,2-HOPO chelating agent in an amount from about 300 to about 1500 mg and sodium oleate. In some embodiments, the pharmaceutical composition the 1,2-HOPO chelating agent is 3,4,3-L1-1,2-HOPO.

In some embodiments, any amount of sodium oleate can be used, as appropriate for the intended use. In some embodiments, the amount of sodium oleate present is between about 50 to about 150, for example about 70 to about 130 mg. In some embodiments, sodium oleate is present at about 5 to about 20% of a total weight of the composition, for example, about 8 to 12% of a total weight of the composition or about 11% of a total weight of the composition. Other amounts described herein are also applicable for various applications.

In some embodiments, the 3,4,3-L1-1,2-HOPO chelating agent is present in an amount from about 50 to about 2000 mg, for example, about 100 to 1500 mg, about 400 to 1200 mg, about 100 to 300 mg, or at about an amount of 600 mg. Other amounts described herein are also applicable for various applications.

The amount of the chelating agents that may be combined with the pharmaceutically acceptable carrier to produce a single dosage form will vary depending upon the subject treated and the particular mode of administration. Suitable dosage levels of the chelating agents include from about 1 mg to about 500 mg per kg body weight per day. In some embodiments, the suitable dosage level is from about 20 mg to about 100 mg per kg body weight per day. In some embodiments, the suitable dosage level is from about 10 mol to about 100 µmol per kg body weight for 3,4,3-L1-1,2-HOPO. In some embodiments, the suitable dosage level is from about 30 µmol to about 200 µmol per kg body weight for 5-LIO-Me-3,2-HOPO. Dosage unit forms will generally contain from about 20 mg to about 100 mg of the chelating agents. In addition, the pharmaceutical composition can be administered on an intermittent basis, i.e., at daily, semi-weekly, or weekly intervals. It will be understood, however, that the specific dose level for a particular subject will depend on a variety of factors. These factors include the activity of the specific compound employed; the age, body weight, general health, sex, and diet of the subject; the time and route of administration and the rate of excretion of the chelating agents; the combination of chelating agents employed in the treatment; and, the severity of the particular disease or condition for which therapy is sought.

In some embodiments, the pharmaceutical composition is packaged as a tablet, within a capsule, and/or within one or more granules.

Suitable modes of administration of the pharmaceutical composition include, but are not limited to, oral, topical, aerosol, inhalation by spray, parenteral, subcutaneous, intravenous, intramuscular, interperitoneal, rectal, and vaginal administration. The term parenteral, as used herein, includes subcutaneous injections, and intravenous, intrathecal, intramuscular, and intrasternal injection or infusion techniques. A particular mode of administration is one that brings a compound of this invention to the actual or potential site(s) of radionuclide contamination in the subject. The pharmaceutical composition can be in a solid, semi-solid, and/or liquid form. In some embodiments, any of the above formulations can be used for any of the metals provided herein.

In some embodiments, the formulation can include a pharmaceutically acceptable carrier. The pharmaceutically acceptable carriers described herein, for example, vehicles, adjuvants, excipients, and diluents, are well known to those who are skilled in the art and are readily available. In some embodiments, the carrier is chemically inert to a compound of this invention and has no detrimental side effects or toxicity under the conditions of use. In some embodiments, the pharmaceutically acceptable carrier is free of pyrogen. The pharmaceutically acceptable carriers which can be used include, but are not limited to, water, glucose, lactose, gum acacia, gelatin, mannitol, starch paste, magnesium trisilicate, talc, corn starch, keratin, colloidal silica, potato starch, and urea.

The pharmaceutical compositions suitable for oral administration include, but are not limited to, (a) liquid formulations; (b) capsules, sachets, tablets, lozenges, and troches, each containing a predetermined amount of the active ingredient, as solids or granules; (c) powders; (d) suspensions; and (e) suitable emulsions. Liquid formulations may include diluents, such as water and alcohols, and optionally a pharmaceutically acceptable surfactant. Capsule forms can be of the ordinary hard- or soft-shelled gelatin type containing, for example, surfactants, lubricants, and inert fillers. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and the like. The tablet can further comprise one or more colorants, diluents, buffering agents, disintegrating agents, moistening agents, preservatives, or flavoring agents.

The pharmaceutical composition, alone or in combination with other suitable components, can be made into aerosol formulations to be administered via inhalation. These aerosol formulations can be placed into pressurized acceptable propellants (such as dichlorodifluoromethane, propane, nitrogen, and the like) or non-pressured preparations (such as in a nebulizer or an atomizer). When the site(s) of infection of a subject is the lungs, a preferred mode of administration is inhalation of an aerosol formulation either orally or nasally. in particular, the aerosol formulation may comprises particles of a respirable size, including, but not limited to, mean particle sizes of 5 µm to 500 µm.

The pharmaceutical composition can be an injectable formulation. The requirements for effective carriers for injectable compositions are well known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)). In particular embodiments, injectable compositions are administered intravenously. Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The pharmaceutical composition can further comprise an excipient. Excipients that may be used include one or more carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

In some embodiments, the pharmaceutical composition can comprise one or more of the following formulations in table 1 and/or table 2:

TABLE 1

COMPOSITION OF EMBODIMENTS OF FORMULATIONS OF 3,4,3-LI(1,2-HOPO)

| | Quantity in unit dosage form (mg) | | | | |
|---|---|---|---|---|---|
| Ingredients | Prototype Powder for Reconstitution Formulation ID# A11 (mg) | Immediate Release Tablets Formulation ID# T51 (mg) | Chewable Tablets Formulation ID# C21 (mg) | Capsules (500 mg) 3,4,3-LI(1,2-HOPO) Blend Lot#FLBN-20131029-1 - 00 gelatin capsule (mg) | Capsules (100 mg) 3,4,3-LI(1,2-HOPO) Blend Lot#FLBN-20131029-1 - 4 gelatin capsule (mg) |
| 3,4,3-LI-(1,2-HOPO) | 500.0 | 500.0 | 500.0 | 500.0 | 100.0 |
| Sodium Oleate | 46.0 | 46.0 | 46.0 | 55.6 | 11.1 |
| Microcrystalline Cellulose and Carboxymethyl Cellulose, NF (Avicel RC-591) | 500.0 | — | — | — | — |
| Croscarmellose Sodium, NF (Ac-Di-Sol) | — | 92.0 | 75.0 | — | — |
| Microcrystalline Cellulose, NF (Avicel PH 102) | — | 501.0 | — | — | — |
| Colloidal silicone dioxide, (Cab-O-Sil M5 P) | — | 6.0 | — | — | — |
| Coprocessed Microcrystalline Cellulose and Guar gum, (Avicel CE-15) | — | — | 927.0 | — | — |
| Mannitol, (Mannogem Granular 2080) | — | — | 927.0 | — | — |
| Magnesium stearate, NF (HyQual) | — | 6.0 | 25.0 | — | — |
| Unit Weight (mg) | 1046.0 | 1151.0 | 2500.0 | 555.6 | 111.1 |

TABLE 2

| Ingredients | Dosage Form→ Formulation ↓ ID→ | Powder in Bottle | | Granules | | Chewable Tablets | | | Conventional Tablets | |
|---|---|---|---|---|---|---|---|---|---|---|
| | | A2 | A11 | G11 | G12 | C11 | C13 | C21 | T50 | T51 |
| Intra-Granular Materials (for granules and conventional tablets) | | 1.000 | 1.000 | 1.000 | 1.000 | 0.500 | 0.500 | 0.500 | 0.500 | 0.500 |
| 3,4,3-LI(1,2-HOPO) | | 0.092 | 0.092 | 0.092 | 0.092 | 0.046 | 0.046 | 0.046 | 0.046 | 0.046 |
| Sodium Oleate | | — | 1.000 | — | — | — | — | — | — | — |
| Microcrystalline Cellulose and Carboxymethyl Cellulose, NF (Avivel RC-591) | | — | — | 0.075 | 0.075 | 0.075 | — | 0.075 | 0.084 | 0.092 |

TABLE 2-continued

| Ingredients | Dosage Form→ Formulation ID→ | Powder in Bottle | | Granules | | Chewable Tablets | | | Conventional Tablets | |
|---|---|---|---|---|---|---|---|---|---|---|
| | | A2 | A11 | G11 | G12 | C11 | C13 | C21 | T50 | T51 |
| Croscarmellose Sodium, NF (Ac-Di-Sol) | | — | — | 1.833 | — | 1.854 | — | 0.927 | — | — |
| Microcrystalline Cellulose and guar gum, NF (Avicel CE-15) | | — | — | — | 1.533 | — | — | — | — | — |
| Lactose Monohydrate, NF (Pharmatose 300M) | | — | — | — | — | — | 1.929 | — | — | — |
| Lactose Monohydrate, Povidone and Crospovidone, NF (Ludipress) | | — | — | — | — | — | — | 0.9227 | — | — |
| Mannitol, USP (mannogem) | | — | — | — | — | 0.025 | 0.025 | 0.025 | — | — |
| Magnesium sterate, NF (HyQual) | | — | — | — | — | — | — | — | 0.410 | 0.501 |
| Microcrystalline Cellulose, NF (Avicel PH 102) | | — | — | — | — | — | — | — | 0.005 | 0.006 |
| Colloidal silicone dioxide, NF (Cab-O-Sil M5P) | | — | — | — | — | — | — | — | — | — |
| Purified water, USP | | — | — | Q.S. | Q.S. | — | — | — | — | — |
| Magensium sterate, NF (HyQual) | | — | — | — | — | — | — | — | — | — |
| Extra-Granular Materials (for granules and conventional tablets) | | | | | | | | | | |
| Hypromellose, 50 cps | | — | — | — | 0.300 | — | — | — | — | — |
| Magensium sterate, NF (HyQual) | | — | — | — | — | — | — | — | 0.005 | 0.006 |
| Unit weight (g) | | 1.092 | 2.0962 | 3.000 | 3.000 | 2.500 | 2.500 | 2.500 | 1.050 | 1.15 |

All of these oral dosage forms were found suitable for further development. Following extensive evaluation of dosage configuration, capsules containing 3,4,3-L1(1,2-HOPO) blended with excipient sodium oleate were deemed to be the optimal dosage form for both the clinic and a potential mass casualty situation for the following reasons: 1) This capsule dosage form allows more flexibility with regards to dose level adjustments than tablet dosage forms. 2) Taste issues resulting in unwanted reactions are minimized in comparison to chewable tablets, powder in bottle dissolved in water, or dispersible granules dissolved in water. 3) Capsules require less clean potable water and a greater accuracy in dose administration than the other dosage forms. 4) Capsules may be adapted to pediatric formulations, with regards to dose level adjustments and administration (by opening the capsules, and blending the powder with yoghurt or apple sauce-type mixtures.

In some embodiments, any of the ratios provided in any of the formulations can be maintained, while the amount of the active ingredient is increased or decreased.

In some embodiments, a formulation can comprise a pharmaceutically suitable composition of 3,4,3-L1(1,2-HOPO) and one or more excipients. In some embodiments, the pharmaceutically suitable excipients include, but are not limited to, mannitol, lactose monohydrate, compressible sugar, microcrystalline cellulose, hypromellose, povidone, pregelatinized starch, croscarmellose sodium, sodium starch glycolate, crospovidone, colloidal silicon dioxide, magnesium stearate, hydrogenated vegetable oil (type 1), and polysorbate 80.

In some embodiments, different forms of the formulation can be used, including i) powder, (ii) orally dispersible/dissolvable granules, (iii) chewable tablets, and/or (iv) conventional immediate release tablets. Based on the studies performed in the examples, nine formulation prototypes showed immediate drug release behavior and desired physical properties and were selected for API verification, gastric fluid dissolution, and related substance testing following defined liquid chromatography methods. Among these selected compositions, two are powder in bottle formulations, two are granule formulations, three are chewable tablet formulations, and two are conventional tablet formulations. The respective compositions of these formulations are summarized in the examples and in tables 1 and 2 above. All assays confirmed that these prototypes are suitable for further development.

In some embodiments, a powder formulation can comprise a pharmaceutically suitable composition of 3,4,3-L1 (1,2-HOPO), sodium oleate, and optionally, a mixture of microcrystalline cellulose and carboxymethyl cellulose. In some embodiments, the composition can include 1 g of 3,4,3-L1(1,2-HOPO) and 0.092 g of sodium oleate. In some embodiments, the composition can include 1 g of 3,4,3-L1 (1,2-HOPO), 0.092 g of sodium oleate, and 1 g of microcrystalline cellulose and carboxymethyl cellulose. In some embodiments, the composition can include 1 g of 3,4,3-L1 (1,2-HOPO), 0.092 g of sodium oleate, and between 0 g and 1 g of microcrystalline cellulose and carboxymethyl cellulose. Weights are listed in grams per unit of formulation.

In some embodiments, the formulation can be an orally dispersible/dissolvable granule formulation. It can include (by weight of ingredients per unit of formulation) 3,4,3-L1 (1,2-HOPO)—1 g, Sodium oleate—0.092 g, Croscarmellose Sodium—0.075 g, and microcrystalline cellulose & guar gum—1.833 g. In some embodiments, the formulation can include 3,4,3-L1(1,2-HOPO)—1 g, Sodium oleate—0.092 g, croscarmellose Sodium—0.075 g, lactose monohydrate—1.533 mg/ml, and hypromellose—0.3 g.

In some embodiments, an orally dispersible/dissolvable granule formulation can comprise a pharmaceutically suitable composition of 3,4,3-L1(1,2-HOPO), sodium oleate, croscarmellose sodium, a mixture of microcrystalline cellulose and guar gum, lactose monohydrate, and hypromellose. In some embodiments, the composition can include 1 g of 3,4,3-L1(1,2-HOPO), 0.092 g of sodium oleate, 0.075 g of croscarmellose sodium, between 0 and 1.833 g of microcrystalline cellulose and guar gum, between 0 and 1.533 mg/ml of lactose monohydrate, and between 0 and 0.3 g of hypromellose. All weights are listed in grams per unit of formulation, unless otherwise noted.

In some embodiments, the formulation can be a chewable tablet formulation. In some embodiments, a chewable tablet formulation can comprise a pharmaceutically suitable composition of 3,4,3-L1(1,2-HOPO), sodium oleate, croscarmellose sodium, a mixture of microcrystalline cellulose and guar gum, magnesium stearate, a mixture of lactose monohydrate, povidone, and crospovidone, and mannitol. In some embodiments, the composition can include 0.5 g of 3,4,3-L1(1,2-HOPO), 0.046 g of sodium oleate, 0.075 g of croscarmellose sodium, 1.854 g of microcrystalline cellulose and guar gum, and 0.025 g of magnesium stearate. In some embodiments, the composition can include 0.5 g of 3,4,3-L1(1,2-HOPO), 0.046 g of sodium oleate, 1.929 g of lactose monohydrate, povidone, and crospovidone, and 0.025 g of magnesium stearate. In some embodiments, the composition can include 0.5 g of 3,4,3-L1(1,2-HOPO), 0.046 g of sodium oleate, 0.075 g of croscarmellose sodium, 0.927 g of microcrystalline cellulose and guar gum, 0.9227 g mannitol, and 0.025 g of magnesium stearate. In some embodiments, the composition can include 0.5 g of 3,4,3-L1(1,2-HOPO), 0.046 g of sodium oleate, between 0 and 0.075 g of croscarmellose sodium, between 0 and 1.854 g of microcrystalline cellulose and guar gum, 0.025 g of magnesium stearate, between 0 and 1.929 g of lactose monohydrate, povidone, and crospovidone, and between 0 and 0.9227 g of mannitol. All weights are listed in grams per unit of formulation.

In some embodiments, an immediate release tablet formulation can comprise a pharmaceutically suitable composition of 3,4,3-L1(1,2-HOPO), sodium oleate, croscarmellose sodium, microcrystalline cellulose, colloidal silicon dioxide, and magnesium stearate. In some embodiments, the composition can include 0.5 g of 3,4,3-L1(1,2-HOPO), 0.046 g of sodium oleate, 0.084 g of croscarmellose sodium, 0.41 g of microcrystalline cellulose, 0.005 g of colloidal silicon dioxide, and 0.005 g of magnesium stearate. In some embodiments, the composition can include 0.5 g of 3,4,3-L1(1,2-HOPO), 0.046 g of sodium oleate, 0.092 g of croscarmellose sodium, 0.501 g of microcrystalline cellulose, 0.006 g of colloidal silicon dioxide, and 0.006 g of magnesium stearate. In some embodiments, the composition can include 0.5 g of 3,4,3-L1(1,2-HOPO), 0.046 g of sodium oleate, between 0.084 and 0.092 g of croscarmellose sodium, between 0.41 g and 0.501 g of microcrystalline cellulose, between 0.005 g and 0.006 g of colloidal silicon dioxide, and between 0.005 g and 0.006 g of magnesium stearate. All weights are listed in grams per unit of formulation.

In some embodiments, the formulations can be stable under 25° C./60% RH and 40° C./75% RH storage conditions over six months or longer. Such stable formulations can be a powder formulation, a chewable tablet formulation, an immediate release tablet formulation, a 500 mg capsule formulation, and a 100 mg capsule formulation. The respective compositions of these prototype formulations are summarized below.

In some embodiments, a powder formulation can comprise a pharmaceutically suitable composition of 3,4,3-L1 (1,2-HOPO), sodium oleate, and a mixture of microcrystalline cellulose and carboxymethyl cellulose. In some embodiments, the composition can include 500 mg of 3,4, 3-L1(1,2-HOPO), 46 mg of sodium oleate, and 500 mg of microcrystalline cellulose and carboxymethyl cellulose. All weights are listed in milligrams per unit of formulation.

In some embodiments, a chewable tablet formulation can comprise a pharmaceutically suitable composition of 3,4,3-L1(1,2-HOPO), sodium oleate, croscarmellose sodium, a mixture of microcrystalline cellulose and guar gum, mannitol, and magnesium stearate. In some embodiments, the composition can include 500 mg of 3,4,3-L1(1,2-HOPO), 46 mg of sodium oleate, 75 mg of croscarmellose sodium, 927 mg of microcrystalline cellulose and guar gum, 927 mg of mannitol, and 25 mg of magnesium stearate. All weights are listed in milligrams per unit of formulation.

In some embodiments, an immediate release tablet formulation can comprise a pharmaceutically suitable composition of 3,4,3-L1(1,2-HOPO), sodium oleate, croscarmellose sodium, microcrystalline cellulose, colloidal silicon dioxide, and magnesium stearate. In some embodiments, the composition can include 500 mg of 3,4,3-L1(1,2-HOPO), 46 mg of sodium oleate, 92 mg of croscarmellose sodium, 501 mg of microcrystalline cellulose, 6 mg of colloidal silicon dioxide, and 6 mg of magnesium stearate. Weights are listed in milligrams per unit of formulation.

In some embodiments, a 500 mg capsule formulation can be provided that includes a pharmaceutically suitable composition of 3,4,3-L1(1,2-HOPO) and sodium oleate. In some embodiments, the composition can include 500 mg of 3,4, 3-L1(1,2-HOPO) and 55.6 mg of sodium oleate.

In some embodiments, a 100 mg capsule formulation can be provided that comprises a pharmaceutically suitable composition of 3,4,3-L1(1,2-HOPO) and sodium oleate. In some embodiments, the composition can include 100 mg of 3,4,3-L1(1,2-HOPO) and 11.1 mg of sodium oleate.

The formulations can be configured for administration parenterally (ip) or orally (po) via consecutive injections or gavages at various doses, including, but not limited to: human doses of 2.5, 12.5, 25, and 50 µmol/kg, using the accepted conversion system of mouse doses into human equivalent doses—HED—based on body surface area). The parenteral formulation can be pure 3,4,3-L1(1,2-HOPO), while the oral formulation can include a 90:10 weight ratio of 3,4,3-L1(1,2-HOPO) and sodium oleate.

In some embodiments, an intraperitoneal injection formulation can comprise a pharmaceutically suitable composition of 3,4,3-L1(1,2-HOPO). In some embodiments, the composition can include 3,4,3-L1(1,2-HOPO) at a concentration of 30 µmol/kg ip (equivalent approximate human dose: 2.5 µmol/kg).

In some embodiments, an oral formulation can comprise a pharmaceutically suitable composition of 3,4,3-L1(1,2-HOPO) and sodium oleate. In some embodiments, the composition can include a 90:10 weight ratio of 3,4,3-L1 (1,2-HOPO) and sodium oleate. In some embodiments, the composition can include 3,4,3-L1(1,2-HOPO) at a concentration of 150 µmol/kg po. In some embodiments, the composition can include 3,4,3-L1(1,2-HOPO) at a concentration of 300 µmol/kg po. In some embodiments, the composition can include 3,4,3-L1(1,2-HOPO) at a concentration of 300 µmol/kg po. In some embodiments, the composition can include 3,4,3-L1(1,2-HOPO) at a concentration between 150 µmol/kg po and 600 µmol/kg po.

In some embodiments, an intraperitoneal injection, oral, or intravenous injection formulation can comprise a pharmaceutically suitable composition of $[_{14}C]$-3,4,3-L1(1,2-HOPO) and sodium oleate. In some embodiments, the composition can include $[_{14}C]$-3,4,3-L1(1,2-HOPO) at a dosage of 1 µmol/kg and 0% sodium oleate. In some embodiments, the composition can include [$_{14}$C]-3,4,3-L1 (1,2-HOPO) at a dosage of 1 µmol/kg and 10% sodium oleate. In some embodiments, the composition can include [$_{14}$C]-3,4,3-L1(1,2-HOPO) at a dosage of 1800 µmol/kg and 0% sodium oleate. In some embodiments, the composition can include [$_{14}$C]-3,4,3-L1(1,2-HOPO) at a dosage of 1800 µmol/kg and 10% sodium oleate. In some embodiments, the composition can include [$_{14}$C]-3,4,3-L1(1,2-HOPO) at a dosage between 1 µmol/kg and 1800 µmol/kg and between 0 and 10% sodium oleate.

In some embodiments, an orally administered capsule formulation can comprise a pharmaceutically suitable composition of 3,4,3-L1(1,2-HOPO). In some embodiments, the composition can include 50 µmol/kg of 3,4,3-L1(1,2-HOPO). In some embodiments, the composition can include 100 µmol/kg of 3,4,3-L1(1,2-HOPO). In some embodiments, the composition can include 200 µmol/kg of 3,4,3-L1(1,2-HOPO). In some embodiments, the composition can include between 50 µmol/kg and 200 µmol/kg of 3,4,3-L1 (1,2-HOPO).

As outlined in the examples (Examples 10-11), the enhancement of the permeability of the active pharmaceutical ingredient 3,4,3-L1(1,2-HOPO) using oral permeation enhancers was evaluated. Fifteen different permeation enhancers were evaluated for their ability at increasing the permeability of 3,4,3-L1(1,2-HOPO), using an in vitro PAMPA assay with artificial GIT lipid membranes. A significant increase was observed in permeability for one formulation containing 10 mg/mL of Polysorbate 80 and 1 mg/mL of API. All other tested formulations showed no or minor improvement in permeability.

In some embodiments, a formulation can comprise a pharmaceutically suitable composition of 3,4,3-L1(1,2-HOPO) and one or more excipient. In some embodiments, the excipients may include, but are not limited to, sodium lauryl sulfate, caprolactam, polysorbate 80, sodium deoxycholate, isopropyl myristate, 1-phenylpiperazine, piperine, menthone, labrafac lipophile WL 1349, gelucire 44/14, labrafil M2130 CS, labrafil M2125 CS, maisine 35-1, peceol, labrasol, sodium decyl sulfate, sodium octyl sulfate, decyltrimethylammonium bromide, span-80 (Sorbitan monooleate), Triton X-100, sodium glycocholate hydrate, cholic acid, heptanoic acid, isopropyl palmitate, methyl laurate, sodium oleate, urea, 1-octyl-2-pyrrolidone, 1-methylpiperazine, 1-methyl-2-pyrrolidinone, n-caproic acid, sodium salicylate, (±)-limonene, L-fenchone, cineole, pinene oxide, 2-octyl-1-dodecanol, cumin seed oil, caproyl PGMC, caproyl 90 (propylene glycol dicaprylate), lauroglycol FCC, lauroglycol 90, labrafac PG, transcutol, gelucire 50/13, and labrafil M1944 CS.

In some embodiments, the composition can include 3,4, 3-L1(1,2-HOPO) at a concentration of 1 mg/ml and polysorbate 80 at a concentration of 10 mg/ml. In some embodiments, the composition can include 3,4,3-L1(1,2-HOPO) at a concentration of 1 mg/ml and 2-octyl-1-dodecanol at a concentration of 2.5 mg/ml. In some embodiments, the composition can include 3,4,3-L1(1,2-HOPO) at a concentration of 1 mg/ml and sodium oleate at a concentration of 2.5 mg/ml.

In some embodiments, a formulation can comprise a pharmaceutically suitable composition of 3,4,3-L1(1,2-HOPO) and one or more excipients. In some embodiments, pharmaceutically suitable excipients include, but are not limited to, sodium oleate, sodium lauryl sulfate, caprolactam, polysorbate 80, sodium deoxycholate, isopropyl myristate, 1-phenylpiperazine, piperine, menthone, labrafac lipophile, gelucire 44/14, labrafil M2130 CS, labrafil M2125 CS, maisine 35-1, peceol, labrasol, sodium decyl sulfate, sodium octyl sulfate, decyltrimethylammonium bromide, span-80 (sorbitan monooleate), triton X-100, sodium glycocholate hydrate, cholic acid, heptanoic acid, isopropyl palmitate, methyl laurate, sodium oleate, urea, 1-octyl-2-pyrrolidone, 1-methylpiperazine, 1-methyl-2-pyrrolidinone, n-caproic acid, sodium salicylate, (±)-limonene, L-fenchone, cineole, pinene oxide, 2-octyl-1-dodecanol, cumin seed oil, caproyl PGMC, caproyl 90 (Propylene glycol dicaprylate), lauroglycol FCC, lauroglycol 90, labrafac PG, transcutol, gelucire 50/13, labrafil M1944 CS, mannitol, compressible sugar, coprocessed microcrystalline cellulose and guar gum, coprocessed lactose monohydrate and povidone, microcrystalline cellulose, lactose monohydrate, povidone, HPMC, hypromellose, pregelatinized starch, croscarmellose sodium, sodium starch glycolate, crospovidone, colloidal silicon dioxide, magnesium stearate, microcrystalline cellulose and carboxymethyl cellulose, hydrogenated vegetable oil, type 1, co-processed lactose monohydrate, povidone and crospovidone, co-processed microcrystalline cellulose and carboxymethyl cellulose, maltodextrin, sodium citrate, and/or sodium chloride.

In some embodiments, a formulation can comprise a pharmaceutically suitable composition of 3,4,3-L1(1,2-HOPO) and one or more permeation enhancers. In some embodiments, the permeation enhancers include, but are not limited to, sodium oleate, sodium lauryl sulfate, caprolactam, polysorbate 80, sodium deoxycholate, isopropyl myristate, 1-phenylpiperazine, piperine, menthone, labrafac lipophile, gelucire 44/14, labrafil M2130 CS, labrafil M2125 CS, maisine 35-1, peceol, labrasol, sodium decyl sulfate, sodium octyl sulfate, decyltrimethylammonium bromide, span-80 (sorbitan monooleate), triton X-100, sodium glycocholate hydrate, cholic acid, heptanoic acid, isopropyl palmitate, methyl laurate, sodium oleate, urea, 1-octyl-2-pyrrolidone, 1-methylpiperazine, 1-methyl-2-pyrrolidinone, n-caproic acid, sodium salicylate, (±)-limonene, L-fenchone, cineole, pinene oxide, 2-octyl-1-dodecanol, cumin seed oil, caproyl PGMC, caproyl 90 (Propylene glycol dicaprylate), lauroglycol FCC, lauroglycol 90, labrafac PG, transcutol, gelucire 50/13, and/or labrafil M1944 CS.

In some embodiments, the composition can include between 1% and 10% sodium oleate by weight. In some embodiments, the composition can include between 5 mg and 100 mg of sodium oleate.

In some embodiments, the composition can include sodium lauryl sulfate at a concentration of 0.1 mg/ml. In some embodiments, the composition can include caprolactam at a concentration of 2.5 mg/ml.

In some embodiments, the composition can include polysorbate 80 at a concentration of 2.5 mg/ml. In some embodiments, the composition can include polysorbate 80 at a concentration of 2 mg/ml. In some embodiments, the composition can include polysorbate 80 at a concentration of 10 mg/ml. In some embodiments, the composition can include polysorbate 80 at a concentration between 2 mg/ml and 10 mg/ml.

In some embodiments, the composition can include sodium deoxycholate at a concentration of 2.5 mg/ml. In some embodiments, the composition can include sodium deoxycholate at a concentration of 10 mg/ml. In some embodiments, the composition can include sodium deoxycholate at a concentration between 2.5 mg/ml and 10 mg/ml.

In some embodiments, the composition can include isopropyl myristate at a concentration of 2.5 mg/ml. In some embodiments, the composition can include isopropyl myristate at a concentration of 10 mg/ml. In some embodiments, the composition can include isopropyl myristate at a concentration between 2.5 mg/ml and 10 mg/ml.

In some embodiments, the composition can include 1-phenylpiperazine at a concentration of 2.5 mg/ml.

In some embodiments, the composition can include piperine at a concentration of 2.5 mg/ml.

In some embodiments, the composition can include menthone at a concentration of 2.5 mg/ml.

In some embodiments, the composition can include labrafac lipophile WL 1349 at a concentration of 5 mg/ml.

In some embodiments, the composition can include gelucire 44/14 at a concentration of 5 mg/ml. In some embodiments, the composition can include gelucire 44/14 at a concentration of 20 mg/ml. In some embodiments, the composition can include gelucire 44/14 at a concentration between 1 mg/ml and 40 mg/ml.

In some embodiments, the composition can include labrafil M2130 CS at a concentration of 5 mg/ml. In some embodiments, the composition can include labrafil M2125 CS at a concentration of 5 mg/ml.

In some embodiments, the composition can include maisine 35-1 at a concentration of 5 mg/ml. In some embodiments, the composition can include maisine 35-1 at a concentration of 20 mg/ml. In some embodiments, the composition can include maisine 35-1 at a concentration between 1 mg/m and 40 mg/ml.

In some embodiments, the composition can include peceol 35-1 at a concentration of 5 mg/ml. In some embodiments, the composition can include peceol 35-1 at a concentration of 20 mg/ml. In some embodiments, the composition can include peceol 35-1 at a concentration between 1 mg/m and 40 mg/ml.

In some embodiments, the composition can include labrasol at a concentration of 5 mg/ml. In some embodiments, the composition can include sodium decyl sulfate at a concentration of 0.2 mg/ml. In some embodiments, the composition can include sodium octyl sulfate at a concentration of 0.2 mg/ml. In some embodiments, the composition can include decyltrimethylammonium bromide at a concentration of 1 mg/ml. In some embodiments, the composition can include span-80 (sorbitan monooleate) at a concentration of 2.5 mg/ml. In some embodiments, the composition can include triton X-100 at a concentration of 2.5 mg/ml. In some embodiments, the composition can include sodium glycocholate hydrate at a concentration of 1.0 mg/ml. In some embodiments, the composition can include cholic acid at a concentration of 2.5 mg/ml. In some embodiments, the composition can include heptanoic acid at a concentration of 2.5 mg/ml.

In some embodiments, the composition can include isopropyl palmitate at a concentration of 2.5 mg/ml. In some embodiments, the composition can include methyl laurate at a concentration of 2.5 mg/ml. In some embodiments, the composition can include sodium oleate at a concentration of 2.5 mg/ml. In some embodiments, the composition can include urea at a concentration of 2.5 mg/ml. In some embodiments, the composition can include 1-octyl-2-pyrrolidone at a concentration of 2.5 mg/ml. In some embodiments, the composition can include 1-methylpiperazine at a concentration of 2.5 mg/ml. In some embodiments, the composition can include 1-methyl-2-pyrrolidinone at a concentration of 2.5 mg/ml. In some embodiments, the composition can include n-caproic acid at a concentration of 2.5 mg/ml. In some embodiments, the composition can include sodium salicylate at a concentration of 2.5 mg/ml. In some embodiments, the composition can include (±)-limonene at a concentration of 2.5 mg/ml. In some embodiments, the composition can include L-fenchone at a concentration of 2.5 mg/ml. In some embodiments, the composition can include cineole at a concentration of 2.5 mg/ml. In some embodiments, the composition can include pinene oxide at a concentration of 2.5 mg/ml. In some embodiments, the composition can include 2-octyl-1-dodecanol at a concentration of 2.5 mg/ml. In some embodiments, the composition can include cumin seed oil at a concentration of 2.5 mg/ml. In some embodiments, the composition can include caproyl PGMC at a concentration of 5 mg/ml. In some embodiments, the composition can include caproyl 90 (propylene glycol dicaprylate) at a concentration of 5 mg/ml.

In some embodiments, the composition can include lauroglycol FCC at a concentration of 5 mg/ml. In some embodiments, the composition can include lauroglycol 90 at a concentration of 5 mg/ml. In some embodiments, the composition can include labrafac PG at a concentration of 5 mg/ml. In some embodiments, the composition can include transcutol at a concentration of 5 mg/ml. In some embodiments, the composition can include gelucire 50/13 at a concentration of 5 mg/ml. In some embodiments, the composition can include labrafil M1944 CS at a concentration of 5 mg/ml.

In some embodiments, a formulation can comprise a pharmaceutically suitable composition of 3,4,3-L1(1,2-HOPO) and one or more diluents. In some embodiments, the diluents include, but are not limited to, mannitol, compressible sugar, coprocessed microcrystalline cellulose and guar gum, coprocessed lactose monohydrate and povidone, microcrystalline cellulose, and lactose monohydrate. In some embodiments, the composition can include 10% diluent by weight. In some embodiments, the composition can include 70% diluent by weight. In some embodiments, the composition can include between 10% and 70% diluent by weight. In some embodiments, the composition can include mannitol at a concentration of 2 mg/ml. In some embodiments, the composition can include compressible sugar at a concentration of 2 mg/ml.

In some embodiments, a formulation can comprise a pharmaceutically suitable composition of 3,4,3-L1(1,2-HOPO) and one or more binders. In some embodiments, the binders include, but are not limited to, povidone, HPMC, hypromellose, and pregelatinized starch. In some embodiments, the composition can include 10% binder by weight. In some embodiments, the composition can include 70% binder by weight. In some embodiments, the composition can include between 10% and 70% binder by weight.

In some embodiments, the composition can include povidone at a concentration of 2 mg/ml. In some embodiments, the composition can include hypromellose at a concentration of 2 mg/ml. In some embodiments, the composition can include pregelatinized starch at a concentration of 2 mg/ml.

In some embodiments, a formulation can comprise a pharmaceutically suitable composition of 3,4,3-L1(1,2-HOPO) and one or more disintegrants. In some embodiments, the disintegrants include, but are not limited to, croscarmellose sodium, sodium starch glycolate, and crospovidone. In some embodiments, the composition can include 2% disintegrant by weight. In some embodiments, the composition can include 8% disintegrant by weight. In some embodiments, the composition can include between 2% and 8% disintegrant by weight.

In some embodiments, the composition can include croscarmellose sodium at a concentration of 2 mg/ml. In some embodiments, the composition can include sodium starch glycolate at a concentration of 2 mg/ml. In some embodiments, the composition can include crospovidone at a concentration of 2 mg/ml.

In some embodiments, a formulation can comprise a pharmaceutically suitable composition of 3,4,3-L1(1,2-HOPO) and one or more lubricants and glidants. In some embodiments, the lubricants and glidants include, but are not limited to, colloidal silicon dioxide and magnesium stearate. In some embodiments, the composition can include 0.2% lubricant and glidant by weight. In some embodiments, the composition can include 20% lubricant and glidant by weight. In some embodiments, the composition can include between 0.2% and 20% lubricant and glidant by weight.

In some embodiments, the composition can include colloidal silicon dioxide at a concentration of 2 mg/ml. In some embodiments, the composition can include magnesium stearate at a concentration of 2 mg/ml.

In some embodiments, a formulation can comprise a pharmaceutically suitable composition of 3,4,3-L1(1,2-HOPO) and one or more other excipients. In some embodiments, the other excipients include, but are not limited to, microcrystalline cellulose and carboxymethyl cellulose, microcrystalline cellulose and guar gum, hydrogenated vegetable oil, type 1, co-processed lactose monohydrate, povidone and crospovidone, co-processed microcrystalline cellulose and carboxymethyl cellulose, maltodextrin, sodium citrate, and sodium chloride.

In some embodiments, the composition can include hydrogenated vegetable oil type 1 at a concentration of 2 mg/ml. In some embodiments, the composition can include sodium citrate at a concentration of 0.008 M. In some embodiments, the composition can include sodium chloride at a concentration of 0.14 M.

The 1,2-HOPO and 3,2-HOPO chelating agents suitable for use in the present invention are taught in U.S. Pat. No. 4,698,431 ("Hydroxypyridonate Chelating Agents"), U.S. Pat. No. 5,634,901 ("3-Hydroxy-2(1H)-pyridonate Chelating Agents"), and U.S. Pat. No. 5,892,029 ("3-Hydroxy-2 (1H)-pyridonate Chelating Agents"), all of which are hereby incorporated by reference.

Suitable 1,2-HOPO chelating agent include, but are not limited to, molecules defined by the structure:

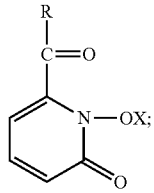

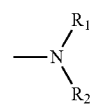

wherein R is a hydroxy group or where $R_1$ and $R_2$ are selected from the group consisting of H, —$CH_3$, —$CH_2CH_3$ and —$CH_2\varphi$, and X is either hydrogen, an alkali metal ion, or a quaternary ammonium ion.

Suitable 1,2-HOPO chelating agent include, but are not limited to, molecules incorporating a plurality of HOPO-type structures, including:

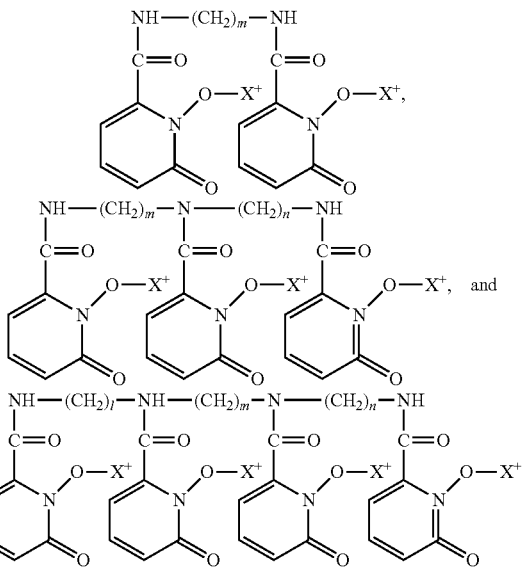

wherein 1, m and n are integers between one and twenty. In a particular embodiment of the invention, m is three. In a particular embodiment of the invention, m is three and n is four. In a particular embodiment of the invention, 1 and n are three, and m is four.

Suitable 1,2-HOPO and 3,2-HOPO chelating agents include, but are not limited to, a chelating agent comprised of a plurality of chelating functional units joined by one or more linking members, said chelating functional units independently selected from the group consisting of

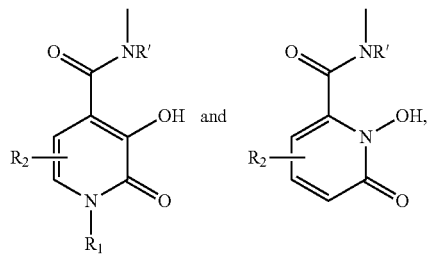

in which at least one of said plurality of chelating functional units on said chelating agent is

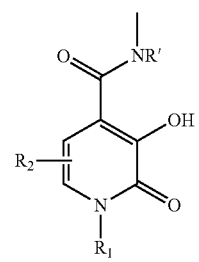

wherein $R_1$ and $R_2$ are independently selected from the group consisting of hydrogen, $C_{1-4}$ aliphatic hydrocarbon groups, and $C_{1-4}$ aliphatic hydrocarbon groups substituted by a single halide, hydroxy, carboxy, acrylamido group or an aryl group, and R' is a member selected from the group consisting of a bond to a linking member, a hydrogen atom, $C_{1-8}$ aliphatic hydrocarbon groups, aryl groups, and $C_{1-8}$ aliphatic hydrocarbon groups substituted by amino, carboxy, or hydroxy groups.

Suitable 3,2-HOPO chelating agents include, but are not limited to, a chelating agent having the structure:

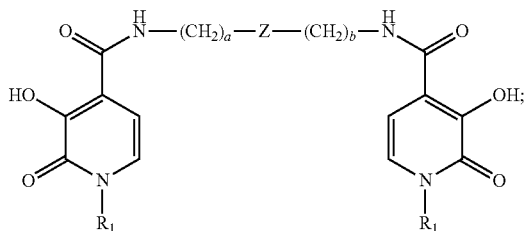

wherein $R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group; Z is a member selected from the group consisting of O, NH, N-alkyl, and N-aryl; a is 2-4; and b is 2-4.

Figure 1:
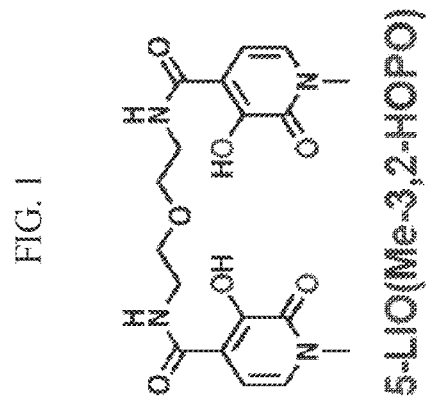
FIG. 1 shows the structures of 5-LIO(Me-3,2-HOPO) ("5LIO") and 3,4,3-L1(1,2-HOPO) ("343L1").
Figure 2:
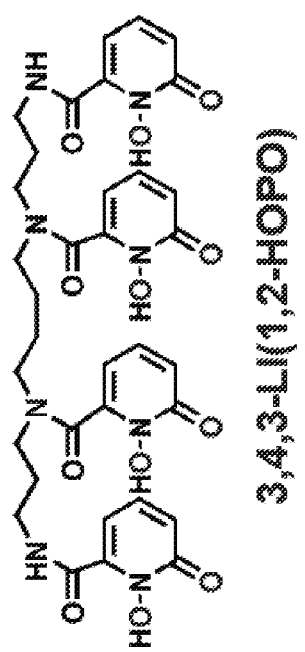
FIG. 2 shows the structure of diethylenetriamine pentaacetic acid (DTPA).

A suitable 1,2-HOPO and a suitable 3,2-HOPO are shown in FIG. 1.

The methods for synthesizing the 1,2-HOPO and 3,2-HOPO chelating agents are taught in U.S. Pat. Nos. 4,698,431; 5,634,901; and 5,892,029, all of which are hereby incorporated by reference.

The chelating agents are capable of binding or chelating, or capable of forming stable complexes with actinides and/or lanthanides, such as the cations of Eu, Pu, Np, Th, Am, and/or Cf, such as of $^{152}Eu(III)$, $^{241}Am(III)$, $^{238}Pu(IV)$, $^{237}Np(IV)$, $^{237}Np(V)$, and $^{233}U(VI)$.

Embodiments provided herein include prodrugs of the chealtors. Such prodrugs are in general functional derivatives of the compounds that are readily convertible in vivo into the required compound. Thus, in the methods, the term "administering" shall encompass the treatment of the various disorders described with the compound specifically disclosed or with a compound which may not be specifically disclosed, but which converts to the specified compound in vivo after administration to a subject in need thereof. Conventional procedures for the selection and preparation of suitable prodrug derivatives are described, for example, in Wermuth, "Designing Prodrugs and Bioprecursors," in Wermuth, ed., The Practice of Medicinal Chemistry, 2nd Ed., pp. 561-586 (Academic Press 2003). Prodrugs include esters that hydrolyze in vivo (for example in the human body) to produce a compound of this invention or a salt thereof. Suitable ester groups include, without limitation, those derived from pharmaceutically acceptable aliphatic carboxylic acids, particularly alkanoic, alkenoic, cycloalkanoic and alkanedioic acids, in which each alkyl or alkenyl moiety preferably has no more than six carbon atoms. Illustrative esters include formates, acetates, propionates, butyrates, acrylates, citrates, succinates, and ethylsuccinates.

Methods of Use

In some embodiments, a method for treating a subject for a heavy metal exposure is provided. The method comprises administering a therapeutically effective amount of a pharmaceutical formulation comprising a 1,2-HOPO chelating agent to a subject that has an excess amount of one or more of heavy metals, actinides and/or lanthanides, or a mixture thereof. Additional options for therapies are also provided in U.S. Pat. Pub. No. 20120214843, the entirety of which is hereby incorporated by reference. Methods of treatment can include treating a subject in need by administering a therapeutically effective amount of one or more pharmaceutical compositions comprising a chelating agent (as provided herein) to a subject in need of such treatment. In some embodiments the subject has been exposed to, have been in contact with, or contaminated by one or more known or unknown actinides and/or lanthanides, or a mixture thereof.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a chelating agent" includes a plurality of such chelating agents, and so forth.

The invention having been described, the following examples are offered to illustrate the subject invention by way of illustration, not by way of limitation.

EXAMPLES

Example 1-3,4,3-L1(1,2-HOPO)-Excipient Compatibility Study

Summary

The objective of the analytical study described in this report was to evaluate the interactions between 3,4,3-L1(1,2-HOPO) and selected pharmaceutical excipients under 25° C./60% RH and 40° C./75% RH conditions over eight weeks. Physical appearance and potency of the different samples were assessed at T=0, 2, 4, and 8 weeks through visual observations and high performance liquid chromatography (HPLC) analysis.

The HPLC system suitability and linearity were verified at each time point and were within the protocol requirements.

Among the 14 compounds tested, 4 excipients (pregelatinized starch, compressible sugar, providone, and hydrogenated vegetable oil) resulted in a decrease in 3,4,3-L1(1,2-HOPO) purity or in an increase of specific impurity content. These results will be taken into consideration for further investigation on the bioavailability enhancement of 3,4,3-L1(1,2-HOPO).

1. Purpose of Study

The purpose of this study was to provide data that can be used to support research efforts. It was not conducted in accordance with U.S. Food and Drug Administration (FDA) "Good Laboratory Practice for Nonclinical Laboratory Studies" (GLP) regulations, as described in 21 CFR Part 58. However, the study was planned, performed, recorded, and reported in accordance with standard practices to ensure data quality and integrity.

2. Objective of Study

The objective of this study was to evaluate the interactions between 3,4,3-L1(1,2-HOPO) and selected pharmaceutical excipients under 25° C./60% RH and 40° C./75% RH conditions over eight weeks, including:
 a. Mannitol
 b. Lactose Monohydrate
 c. Compressible sugar
 d. Microcrystalline Cellulose
 e. Hypromellose
 f. Povidone
 g. Pregelatinized Starch
 h. Croscarmellose Sodium
 i. Sodium Starch Glycolate
 j. Crospovidone
 k. Colloidal silicon dioxide
 l. Magnesium stearate
 m. Hydrogenated Vegetable Oil, Type 1
 n. Polysorbate 80 (PS), NF (Spectrum Chemicals, Cat #PO138)

3. Experimental Design

The stability of 3,4,3-L1(1,2-HOPO) was tested according to the conditions listed below in TABLE 1.1. All test samples were stored throughout the study in 40 mL clear USP Type 1 glass vials (28 mm OD×95 mm height; 24 mm screw cap), wrapped in aluminum foil.

TABLE 1.1

CONDITIONS FOR TESTING STABILITY OF STABILITY OF 3,4,3-LI(1,2-HOPO)

| Condition | Test Time Points | | | | |
|---|---|---|---|---|---|
| | T = 0 | 2 weeks | 4 weeks | 8 weeks | Extra Samples |
| 40° C./75% RH | X | X | X | X | 2 vials |
| 25° C./60% RH | | X | X | X | 2 vials |

X test represents:
1. Visual Observation (color and physical form)
2. Assay and Chromatographic Purity TABLE 1.2 shows the list of excipients, and various drug-excipient ratios that were used in the study.

TABLE 1.2

LIST OF EXCIPIENTS AND VARIOUS DRUG-EXCIPIENT RATIOS USED IN THE STUDY

| Sample No. | Excipient Name* | Category | API-Excipient Ratio** | Quantity to be Filled in each Vial (mg) API | Quantity to be Filled in each Vial (mg) Excipient | No. of Vials to be filled |
|---|---|---|---|---|---|---|
| 1 | Mannitol (MA) | Diluent | 1:1 | 50 | 50 | 11 |
| 2 | Lactose monohydrate (LM) | Diluent | 1:1 | 50 | 50 | 11 |
| 3 | Compressible sugar (CS) | Diluent | 1:1 | 50 | 50 | 11 |
| 4 | Microcrystalline Cellulose (MCC) | Diluent | 1:1 | 50 | 50 | 11 |
| 5 | Hypromellose (HYP) | Binder | 1:1 | 50 | 50 | 11 |
| 6 | Povidone (PVP) | Binder | 1:1 | 50 | 50 | 11 |
| 7 | Pregelatinized Starch (PGS) | Binder | 1:1 | 50 | 50 | 11 |
| 8 | Croscarmellose sodium (CCS) | Disintegrant | 1:1 | 50 | 50 | 11 |
| 9 | Sodium Starch Glycolate (SSG) | Disintegrant | 1:1 | 50 | 50 | 11 |
| 10 | Crospovidone (CPVP) | Disintegrant | 1:1 | 50 | 50 | 11 |
| 11 | Colloidal silicon dioxide (CSD) | Lubricant/Glidant | 1:0.2 | 50 | 10 | 11 |
| 12 | Magnesium Stearate (MGS) | Lubricant/Glidant | 1:0.2 | 50 | 10 | 11 |
| 13 | Hydrogenated Vegetable Oil (HVO) | Lubricant/Glidant | 1:0.2 | 50 | 10 | 11 |

TABLE 1.2-continued

LIST OF EXCIPIENTS AND VARIOUS DRUG-
EXCIPIENT RATIOS USED IN THE STUDY

| Sample No. | Excipient Name* | Category | API-Excipient Ratio** | Quantity to be Filled in each Vial (mg) API | Quantity to be Filled in each Vial (mg) Excipient | No. of Vials to be filled |
|---|---|---|---|---|---|---|
| 14 | Polysorbate 80 (PS) | Permeation Enhancer | 1:0.2 | 50 | 10 | 11 |
| 15 | Control: 3,4,3-LI(1,2-HOPO) (API) | API | 1:0 | 50 | 0 | 11 |

*These excipients are generally used in the development of chewable tablets, orally dispersible tablets (ODT), and mouth dissolving tablets.
**For placebo preparations of each combination, the specified amount of excipient was weighed separately into one vial per condition, to the exception of the API control.

4. Materials And Methods
   a. Test and Control Articles
Test Article: 3,4,3-L1(1,2-HOPO)
Manufacturer: Ash Stevens, Inc. (Detroit, Mich.)
Lot Number: ML-11-276
Physical Description: Pale yellow solid
Storage Conditions: Refrigerated 2-8° C. protected from light.
Materials:

| | |
|---|---|
| Purified Water | HPLC Grade - Supplier: Ricca |
| Hydrochloric acid | ACS Grade - Supplier: EMD |
| Sodium hydroxide | ACS Grade - Supplier: BDH |
| Formic Acid | HPLC Grade - Supplier: EMD |
| Acetonitrile | HPLC Grade - Supplier: Fischer |
| HPLC Column | Agilent, Eclipse XDB-C18, 4.6 × 150 mm, 5 μm |
| Hypromellose, Substitution Type 2910, 50 mPa · s, USP | Spectrum Chemicals, Cat# HY122 |
| Mannitol, USP | Spectrum Chemicals, Cat# MA165 |
| Lactose Monohydrate, Powder, NF | Spectrum Chemicals, Cat# LA106 |
| Microcrystalline Cellulose, NF | Spectrum Chemicals, Cat# C1679 |
| Compressible sugar, NF | Domino Specialty Ingredients |
| Povidone K-29/32, USP | Plasdone K29/32, ISP Technologies |
| Pregelatinized Starch, NF (Starch 1500) | Colorcon, Inc |
| Croscarmellose sodium, NF | Spectrum Chemicals, Cat# C1366 |
| Sodium Starch Glycolate, Type-A, pH 5.5 to 7.5, NF | Spectrum Chemicals, Cat# S1962 |
| Crospovidone, NF | Polyplasdone, ISP Technologies |
| Colloidal silicon dioxide, NF | Spectrum Chemicals, Cat# S1510 |
| Magnesium stearate, NF | Spectrum Chemicals, Cat# MA130 |
| Hydrogenated Vegetable Oil, Type 1, NF | Lubritab, JRS Pharma |
| Polysorbate 80, NF | Spectrum Chemicals, Cat# PO138 |

Test Samples: Each test mixture was prepared by weighing the desired quantity of 3,4,3-L1(1,2-HOPO) and excipient (both screened through sieve #40) into vials. Both ingredients were first mixed using a clean glass rod and then vortexed. At each time interval, one vial was withdrawn from each drug-excipient series along with the corresponding placebo preparation and tested as described below.
   b. Sample Characterization
Visual Observation: For each sample solution, visual observation consisted in recording color and physical form.
   c. Chromatographic Assay and Purity Assessment
Standard Stock Solutions: For each standard stock solutions, the test article was weighed (200 mg) and dissolved by sonication into 30 mL of diluent (water:acetonitrile=90%: 10%). After equilibration at room temperature, the volume of the standard solution was adjusted to 50 mL. Standard stock solutions were prepared in duplicates, working standard solutions were prepared by dilution of each stock with the diluent to the desired concentrations.
Calibration Standards: With each experiment, 5 calibration standard solutions at different concentrations were prepared from stock solutions using the diluent. Concentrations of the calibration standards were between 1.6 and 2.4 mg/mL. The calibration standard solutions were chromatographed to demonstrate the linearity of the calibration curve over the concentration range.
Chromatographic Purity: For test article purity evaluation, one of the calibration standard solutions prepared above was used.
Sample Preparation: For each sample, 25 mL of diluent was added to the sample vial to reach a final concentration of 2 mg/mL of 3,4,3-L1(1,2-HOPO). The vials were then mechanically shaken for 15 minutes, followed by centrifugation of the sample solutions (10,000 rpm, 10 min), and the supernatants were used for the assay.
Placebo Preparation: 25 mL of diluent was added to each of the placebo vial. The vials were then mechanically shaken for 15 minutes, followed by centrifugation of the sample solutions (10,000 rpm, 10 min), and the supernatants were used for the assay.
Analytical Method:
Instrument: Waters Alliance 2695 liquid chromatography system
Column: Agilent, Eclipse XDB-C18, 4.6×150 mm, 5 μm.
Mobile Phase A: 0.05% formic acid in 95% H2O: 5% ACN
Mobile Phase B: 0.05% formic acid in acetonitrile (ACN)

TABLE 1.3

GRADIENT CONDITIONS

| Time (min) | A % | B % |
|---|---|---|
| 0.00 | 100 | 0 |
| 30.00 | 60 | 40 |
| 40.00 | 0 | 100 |
| 41.00 | 100 | 0 |
| 50.10 | 100 | 0 |

Column Temperature: 25° C.
Flow Rate: 1.0 mL/min.
Injection Volume: 10 μL
Detection: 250 nm
Run Time: 50 min
Diluent: 9:1 $H_2O$:ACN Analysis Sequence:

TABLE 1.4

ANALYSIS SEQUENCE

| Sample Name | #of Injections |
|---|---|
| Diluent | 1 |
| Standard Solution (System Suitability) | 6 |
| Diluent | 1 |
| Linearity Solution - 1 through 5 | 1 (for each concentration) |
| Diluent | 1 |
| Samples (Not more than twelve (12) injections) | Each sample 1 injection |
| Bracketing Standard (Standard Solution) | 1 |
| Excipient Placebos | 1 (for each placebo) |
| At the end of the samples, inject bracketing | 1 |

Suitability Requirements: There should be no interference from the diluent/blank at the retention times of 3,4,3-L1 (1,2-HOPO) peaks. The relative standard deviation (% RSD) for five replicate system suitability injections should be below 2.0%. The response factor of the second standard should be within 95-105%. The correlation coefficient ($R_2$) of the system linearity standards should be higher than 0.990.

5. Results
   a. System Suitability

System suitability and linearity results are summarized in TABLE 1.5 to TABLE 1.8 and FIG. 23 to FIG. 26 for all time points (T=0 (FIG. 23), 2 (FIG. 24), 4 (FIG. 25), and 8 (FIG. 26) weeks). All system suitability and linearity results were within the protocol requirements. The prepared calibration standard curves were found to be linear, and the correlation coefficients are included in the tables, together with calibration curves.

TABLE 1.5

SYSTEM SUITABILITY FOR 3,4,3-LI(1,2-HOPO) AT T = 0

| Standard Details | Weight taken (mg) | Std. Dilution (ml) | ml Taken | Dilution Vol (ml) | % Purity |
|---|---|---|---|---|---|
| | 200.77 | 50 | 5 | 10 | 100 |

| S.No. | Bracketing std Area | Recovery |
|---|---|---|
| 1 | 8631074 | 100.5 |
| 2 | 8633151 | 100.5 |
| 3 | 8428130 | 98.2 |

| Details | 343LI Peak Area |
|---|---|
| Standard-1 | 8535609 |
| Standard-2 | 8541521 |
| Standard-3 | 8596940 |
| Standard-4 | 8652568 |
| Standard-5 | 8592901 |
| Standard-6 | 8600027 |
| Average | 8586594 |
| SD | 43153 |
| % RSD | 0.50 |

| Linearity Samples | Concentration (mg/mL) | Peak Area |
|---|---|---|
| Linearity Standard 1 | 1.61 | 6730552 |
| Linearity Standard 2 | 1.81 | 7645145 |
| Linearity Standard 3 | 2.01 | 8534785 |

TABLE 1.5-continued

SYSTEM SUITABILITY FOR 3,4,3-LI(1,2-HOPO) AT T = 0

| Linearity Samples | Concentration (mg/mL) | Peak Area |
|---|---|---|
| Linearity Standard 4 | 2.21 | 9344601 |
| Linearity Standard 5 | 2.41 | 10267523 |
| Slope | | 4369875 |
| Intercept | | −268877 |
| R squared | | 1.000 |

TABLE 1.6

SYSTEM SUITABILITY FOR 3,4,3-LI(1,2-HOPO) AT T = 2 WEEKS

| Standard Details | Weight taken (mg) | Std. Dilution (ml) | ml Taken | Dilution Vol (ml) | % Purity |
|---|---|---|---|---|---|
| | 202.86 | 50 | 5 | 10 | 100 |

| S.No. | Bracketing std Area | Recovery |
|---|---|---|
| 1 | 8643151 | 101.1 |
| 2 | 8678578 | 101.5 |
| 3 | 8670629 | 101.4 |
| 4 | 8538994 | 99.9 |

| Details | 3LIO Peak Area |
|---|---|
| Standard-1 | 8425238 |
| Standard-2 | 8547444 |
| Standard-3 | 8562554 |
| Standard-4 | 8579837 |
| Standard-5 | 8570076 |
| Standard-6 | 8605815 |
| Average | 8548494 |
| SD | 63442 |
| % RSD | 0.74 |

| Linearity Samples | Concentration (mg/mL) | Peak Area |
|---|---|---|
| Linearity Standard 1 | 1.62 | 6791128 |
| Linearity Standard 2 | 1.83 | 7701103 |
| Linearity Standard 3 | 2.03 | 8624832 |
| Linearity Standard 4 | 2.23 | 9455860 |
| Linearity Standard 5 | 2.43 | 10369590 |
| Slope | | 4393020 |
| Intercept | | −323178 |
| R squared | | 1.000 |

TABLE 1.7

SYSTEM SUITABILITY FOR 3,4,3-LI(1,2-HOPO) AT T = 4 WEEKS

| Standard Details | Weight taken (mg) | Std. Dilution (ml) | ml Taken | Dilution Vol (ml) | % Purity |
|---|---|---|---|---|---|
| | 200.09 | 50 | 5 | 10 | 100 |

| S.No. | Bracketing std Area | Recovery |
|---|---|---|
| 1 | 8546199 | 100.6 |
| 2 | 8567449 | 100.9 |
| 3 | 8531088 | 100.4 |
| 4 | 8526160 | 100.4 |

TABLE 1.7-continued

SYSTEM SUITABILITY FOR 3,4,3-LI(1,2-HOPO) AT T = 4 WEEKS

| Details | 3LIO Peak Area | |
|---|---|---|
| Standard-1 | 8375801 | |
| Standard-2 | 8504122 | |
| Standard-3 | 8521310 | |
| Standard-4 | 8494189 | |
| Standard-5 | 8518087 | |
| Standard-6 | 8548076 | |
| Average | 8493598 | |
| SD | 60536 | |
| % RSD | 0.71 | |

| Linearity Samples | Concentration (mg/mL) | Peak Area |
|---|---|---|
| Linearity Standard 1 | 1.60 | 6756483 |
| Linearity Standard 2 | 1.80 | 7708440 |
| Linearity Standard 3 | 2.00 | 8594007 |
| Linearity Standard 4 | 2.20 | 9472736 |
| Linearity Standard 5 | 2.40 | 10304210 |
| Slope | | 4427882 |
| Intercept | | −292575 |
| R squared | | 0.999 |

TABLE 1.8

SYSTEM SUITABILITY FOR 3,4,3-LI(1,2-HOPO) AT T = 8 WEEKS

| Standard Details | Weight taken (mg) | Std. Dilution (ml) | ml Taken | Dilution Vol (ml) | % Purity |
|---|---|---|---|---|---|
| | 200.34 | 50 | 5 | 10 | 100 |

| S.No. | Bracketing std Area | Recovery |
|---|---|---|
| 1 | 8523708 | 100.7 |
| 2 | 8507536 | 100.6 |
| 3 | 8521355 | 100.7 |
| 4 | 8376145 | 99.0 |

| Details | 3LIO Peak Area | |
|---|---|---|
| Standard-1 | 8344005 | |
| Standard-2 | 8430555 | |
| Standard-3 | 8506911 | |
| Standard-4 | 8531787 | |
| Standard-5 | 8408894 | |
| Standard-6 | 8540557 | |
| Average | 8460452 | |
| SD | 78455 | |
| % RSD | 0.93 | |

| Linearity Samples | Concentration (mg/mL) | Peak Area |
|---|---|---|
| Linearity Standard 1 | 1.60 | 6688971 |
| Linearity Standard 2 | 1.80 | 770585 |
| Linearity Standard 3 | 2.00 | 8553209 |
| Linearity Standard 4 | 2.20 | 9394501 |
| Linearity Standard 5 | 2.40 | 10326009 |
| Slope | | 4474090 |
| Intercept | | −429817 |
| R squared | | 0.999 | b. Stability Determination

Results of the compatibility study are summarized in TABLE 1.9 to TABLE 1.23. The test article 3,4,3-L1(1,2-HOPO) was stable over 8 weeks under the described conditions (25° C./60% RH and 40° C./75% RH) in the control samples. Most excipient-API mixtures displayed similar stability, to the exception of the mixtures including pregelatinized starch (TABLE 1.15) and hydrogenated vegetable oil (TABLE 1.21) that resulted in apparent decrease of 3,4,3-L1(1,2-HOPO) HPLC purity. In addition an increase in specific purities was observed for the excipient-API mixtures containing pregelatinized starch (TABLE 1.15), compressible sugar (TABLE 1.11), providone (TABLE 1.14), and hydrogenated vegetable oil (TABLE 1.21).

TABLE 1.9

3,4,3-LI(1,2-HOPO)-MANNITOL COMPATIBILITY

| Test | Initial (T = 0) | 40° C./75% RH | | | 25° C./60% RH | | |
|---|---|---|---|---|---|---|---|
| | | 2 Weeks | 4 weeks | 8 Weeks | 2 Weeks | 4 Weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area. n = I) | | | | | | | |
| 3LIO Purity | 98.77 | 98.73 | 98.67 | 98.50 | 98.77 | 98.80 | 98.57 |
| Total Impurities | 1.23 | 1.27 | 1.33 | 1.50 | 1.23 | 1.20 | 1.43 |

TABLE 1.9-continued 3,4,3-LI(1,2-HOPO)-MANNITOL COMPATIBILITY

| Unknown Impurities | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown | 0.24 | — | 0.24 | 0.03 | 0.24 | 0.04 | 0.24 | 0.05 | 0.25 | 0.03 | 0.24 | 0.03 | 0.24 | 0.03 |
| Unknown | 0.58 | 0.03 | 0.58 | 0.06 | 0.58 | 0.08 | 0.58 | 0.08 | 0.58 | 0.02 | 0.58 | 0.04 | 0.58 | 0.03 |
| Unknown | 0.59 | 0.04 | 0.59 | 0.05 | 0.6 | 0.06 | 0.59 | 0.06 | 0.59 | 0.03 | 0.6 | 0.04 | 0.59 | 0.03 |
| Unknown | 0.62 | 0.03 | 0.62 | 0.05 | 0.62 | 0.06 | 0.62 | 0.06 | 0.62 | 0.03 | 0.62 | 0.04 | 0.62 | 0.04 |
| Unknown | 0.81 | — | 0.81 | 0.02 | 0.81 | 0.02 | 0.81 | 0.02 | — | — | — | — | — | — |
| Unknown | 0.87 | 0.09 | 0.87 | 0.14 | 0.87 | 0.15 | 0.87 | 0.16 | 0.87 | 0.09 | 0.87 | 0.12 | 0.87 | 0.1 |
| Unknown | 0.89 | 0.04 | 0.89 | 0.03 | 0.89 | 0.02 | 0.89 | 0.02 | 0.89 | 0.05 | 0.89 | 0.03 | 0.89 | 0.03 |
| Unknown | 1.03 | 0.2 | 1.03 | 0.06 | 1.02 | 0.04 | 1.03 | 0.09 | 1.03 | 0.05 | 1.02 | 0.04 | 1.03 | 0.07 |
| Unknown | 1.11 | 0.04 | 1.11 | 0.05 | 1.11 | 0.05 | 1.11 | 0.06 | 1.11 | 0.05 | 1.11 | 0.05 | 1.11 | 0.05 |
| Unknown | 1.27 | 0.3 | 1.27 | 0.28 | 1.27 | 0.23 | 1.27 | 0.36 | 1.27 | 0.36 | 1.27 | 0.24 | 1.27 | 0.5 |
| Unknown | 1.3 | 0.23 | 1.3 | 0.24 | 1.3 | 0.27 | 1.3 | 0.21 | 1.3 | 0.21 | 1.3 | 0.26 | 1.3 | 0.18 |
| Unknown | 1.39 | 0.06 | 1.39 | 0.06 | 1.39 | 0.05 | 1.39 | 0.04 | 1.4 | 0.05 | 1.39 | 0.05 | 1.39 | 0.06 |
| Unknown | 1.41 | 0.03 | 1.41 | 0.02 | 1.41 | 0.01 | 1.41 | 0.01 | 1.41 | 0.06 | 1.41 | 0.02 | 1.41 | 0.02 |
| Unknown | 1.46 | 0.11 | 1.46 | 0.08 | 1.46 | 0.07 | 1.46 | 0.07 | 1.47 | 0.08 | 1.46 | 0.06 | 1.46 | 0.08 |
| Unknown | 1.72 | — | — | — | 1.72 | 0.07 | 1.73 | 0.08 | — | — | 1.72 | 0.07 | 1.73 | 0.03 |
| Unknown | 2.31 | 0.04 | 2.31 | 0.04 | 2.3 | 0.04 | 2.31 | 0.06 | 2.32 | 0.05 | 2.3 | 0.05 | 2.31 | 0.09 |
| Unknown | 2.6 | — | 2.6 | 0.04 | 2.59 | 0.03 | 2.6 | 0.04 | 2.61 | 0.04 | 2.59 | 0.04 | 2.6 | 0.06 |
| Unknown | 2.8 | — | 2.8 | 0.03 | 2.79 | 0.03 | 2.8 | 0.03 | 2.82 | 0.03 | 2.79 | 0.03 | 2.8 | 0.04 |

TABLE 1.10

3,4,3-LI(1,2-HOPO)-LACTOSE MONOHYDRATE COMPATIBILITY

| Test | Initial (T = 0) | 40° C./75% RH | | | 25° C./60% RH | | |
|---|---|---|---|---|---|---|---|
| | | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area. n = I) | | | | | | | |
| 3LIO Purity | 98.79 | 98.64 | 98.65 | 98.45 | 98.74 | 98.72 | 98.45 |
| Total Impurities | 1.21 | 1.36 | 1.35 | 1.55 | 1.26 | 1.28 | 1.55 |

| Unknown Impurities | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown | 0.24 | — | 0.24 | 0.13 | 0.24 | 0.04 | 0.24 | 0.05 | 0.25 | 0.03 | 0.24 | 0.03 | 0.24 | 0.03 |
| Unknown | 0.58 | 0.05 | 0.58 | 0.09 | 0.58 | 0.07 | 0.58 | 0.08 | 0.57 | 0.05 | 0.58 | 0.06 | 0.58 | 0.05 |
| Unknown | 0.59 | 0.05 | 0.59 | 0.07 | 0.6 | 0.06 | 0.59 | 0.06 | 0.59 | 0.05 | 0.6 | 0.05 | 0.59 | 0.05 |
| Unknown | 0.62 | 0.04 | 0.62 | 0.08 | 0.62 | 0.06 | 0.62 | 0.07 | 0.62 | 0.04 | 0.62 | 0.05 | 0.62 | 0.05 |
| Unknown | 0.81 | — | 0.81 | 0.03 | 0.81 | 0.02 | 0.81 | 0.02 | — | — | — | — | — | — |
| Unknown | 0.87 | 0.12 | 0.87 | 0.12 | 0.87 | 0.15 | 0.87 | 0.15 | 0.87 | 0.13 | 0.87 | 0.14 | 0.87 | 0.13 |
| Unknown | 0.89 | 0.03 | 0.89 | 0.13 | 0.89 | 0.02 | 0.89 | 0.02 | 0.89 | 0.04 | 0.89 | 0.02 | 0.89 | 0.02 |
| Unknown | 1.03 | 0.19 | 1.02 | 0.07 | 1.03 | 0.04 | 1.03 | 0.08 | 1.03 | 0.08 | 1.02 | 0.04 | 1.03 | 0.07 |
| Unknown | 1.11 | 0.04 | 1.11 | 0.05 | 1.11 | 0.06 | 1.11 | 0.05 | 1.11 | 0.05 | 1.11 | 0.05 | 1.11 | 0.05 |
| Unknown | 1.27 | 0.23 | 1.27 | 0.34 | 1.27 | 0.26 | 1.27 | 0.41 | 1.27 | 0.31 | 1.27 | 0.27 | 1.27 | 0.52 |
| Unknown | 1.3 | 0.23 | 1.3 | 0.08 | 1.3 | 0.27 | 1.3 | 0.2 | 1.3 | 0.22 | 1.3 | 0.26 | 1.3 | 0.19 |
| Unknown | 1.39 | 0.05 | 1.39 | 0.03 | 1.39 | 0.05 | 1.39 | 0.06 | 1.4 | 0.04 | 1.39 | 0.05 | 1.39 | 0.05 |
| Unknown | 1.41 | 0.01 | 1.41 | 0.01 | 1.41 | 0.01 | 1.41 | 0.01 | 1.41 | 0.02 | 1.41 | 0.01 | 1.41 | 0.01 |
| Unknown | 1.46 | 0.13 | 1.46 | 0.06 | 1.46 | 0.07 | 1.46 | 0.08 | 1.47 | 0.06 | 1.46 | 0.07 | 1.46 | 0.1 |
| Unknown | 1.72 | — | — | — | 1.72 | 0.07 | 1.73 | 0.07 | — | — | 1.72 | 0.06 | 1.73 | 0.03 |
| Unknown | 2.31 | 0.03 | 2.31 | 0.03 | 2.3 | 0.04 | 2.31 | 0.07 | 2.32 | 0.05 | 2.3 | 0.04 | 2.31 | 0.08 |
| Unknown | 2.6 | — | 2.6 | 0.03 | 2.59 | 0.03 | 2.6 | 0.04 | 2.61 | 0.04 | 2.59 | 0.03 | 2.6 | 0.05 |
| Unknown | 2.8 | — | 2.8 | 0.03 | 2.79 | 0.02 | 2.8 | 0.03 | 2.82 | 0.03 | 2.79 | 0.03 | 2.8 | 0.04 |

TABLE 1.11

| | | 40° C./75% RH | | | | 25° C./60% RH | | | |
|---|---|---|---|---|---|---|---|---|---|
| Test | Initial (T = 0) | | 2 Weeks | 4 weeks | 8 Weeks | 2 Weeks | 4 Weeks | 8 Weeks | |

3,4,3-LI(1,2-HOPO)-COMPRESSIBLE SUGAR COMPATIBILITY

| Test | Initial (T = 0) | 2 Weeks | 4 weeks | 8 Weeks | 2 Weeks | 4 Weeks | 8 Weeks |
|---|---|---|---|---|---|---|---|
| Visual Observation | Pale yellow powder | Brown pasty material | Brown pasty material | Brown pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area. n = 1) | | | | | | | |
| 3LIO Purity | 98.77 | 98.24 | 98.27 | 98.42 | 98.69 | 98.73 | 98.49 |
| Total Impurities | 1.23 | 1.76 | 1.73 | 1.58 | 1.31 | 1.27 | 1.51 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.09 | 0.24 | 0.01 | 0.24 | 0.06 | 0.25 | 0.03 | 0.24 | 0.03 | 0.24 | 0.03 |
| Unknown | 0.45 | — | 0.45 | 0.41 | 0.45 | 0.37 | — | — | — | — | — | — | — | — |
| Unknown | 0.58 | 0.06 | 0.57 | 0.09 | 0.58 | 0.1 | 0.58 | 0.08 | 0.57 | 0.05 | 0.58 | 0.06 | 0.58 | 0.06 |
| Unknown | 0.59 | 0.05 | 0.59 | 0.08 | 0.6 | 0.08 | 0.59 | 0.07 | 0.59 | 0.05 | 0.6 | 0.05 | 0.59 | 0.05 |
| Unknown | 0.62 | 0.05 | 0.62 | 0.07 | 0.62 | 0.08 | 0.62 | 0.07 | 0.62 | 0.04 | 0.62 | 0.05 | 0.62 | 0.05 |
| Unknown | 0.81 | — | 0.81 | 0.02 | 0.81 | 0.03 | 0.81 | 0.02 | — | — | — | — | — | — |
| Unknown | 0.87 | 0.11 | 0.87 | 0.14 | 0.87 | 0.13 | 0.87 | 0.15 | 0.87 | 0.12 | 0.87 | 0.14 | 0.87 | 0.14 |
| Unknown | 0.89 | 0.03 | 0.89 | 0.07 | 0.89 | 0.1 | 0.89 | 0.02 | 0.89 | 0.04 | 0.89 | 0.02 | 0.89 | 0.02 |
| Unknown | 1.03 | 0.19 | 1.03 | 0.08 | 1.02 | 0.04 | 1.03 | 0.18 | 1.03 | 0.06 | 1.02 | 0.03 | 1.03 | 0.09 |
| Unknown | 1.11 | 0.04 | 1.11 | 0.05 | 1.11 | 0.06 | 1.11 | 0.06 | 1.11 | 0.05 | 1.11 | 0.05 | 1.11 | 0.05 |
| Unknown | 1.27 | 0.24 | 1.27 | 0.32 | 1.27 | 0.28 | 1.27 | 0.38 | 1.27 | 0.37 | 1.27 | 0.27 | 1.27 | 0.44 |
| Unknown | 1.3 | 0.23 | 1.3 | 0.12 | 1.3 | 0.08 | 1.3 | 0.18 | 1.3 | 0.22 | 1.3 | 0.25 | 1.3 | 0.22 |
| Unknown | 1.39 | 0.06 | 1.39 | 0.03 | 1.39 | 0.03 | 1.39 | 0.04 | 1.4 | 0.04 | 1.39 | 0.05 | 1.39 | 0.05 |
| Unknown | 1.4 | 0.01 | 1.41 | 0.01 | 1.41 | 0.01 | 1.41 | 0.01 | 1.41 | 0.02 | 1.41 | 0.01 | 1.41 | 0.01 |
| Unknown | 1.46 | 0.14 | 1.46 | 0.11 | 1.46 | 0.08 | 1.46 | 0.06 | 1.47 | 0.09 | 1.46 | 0.07 | 1.46 | 0.09 |
| Unknown | 1.72 | — | — | — | 1.72 | 0.09 | 1.73 | 0.07 | — | — | 1.72 | 0.05 | 1.73 | 0.04 |
| Unknown | 2.31 | 0.04 | 2.31 | 0.04 | 2.3 | 0.03 | 2.31 | 0.07 | 2.32 | 0.04 | 2.3 | 0.04 | 2.31 | 0.08 |
| Unknown | 2.6 | — | 2.6 | 0.03 | 2.59 | 0.03 | 2.6 | 0.04 | 2.61 | 0.05 | 2.59 | 0.04 | 2.6 | 0.05 |
| Unknown | 2.8 | — | 2.8 | 0.03 | 2.79 | 0.02 | 2.8 | 0.03 | 2.82 | 0.03 | 2.79 | 0.03 | 2.8 | 0.04 |

TABLE 1.12

3,4,3-LI(1,2-HOPO)-MICROCRYSTALLINE CELLULOSE COMPATIBILITY

| Test | Initial (T = 0) | 40° C./75% RH | | | 25° C./60% RH | | |
|---|---|---|---|---|---|---|---|
| | | 2 Weeks | 4 weeks | 8 Weeks | 2 Weeks | 4 Weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area. n = 1) | | | | | | | |
| 3LIO Purity | 98.79 | 98.43 | 98.53 | 98.42 | 98.64 | 98.73 | 98.48 |
| Total Impurities | 1.21 | 1.57 | 1.47 | 1.58 | 1.36 | 1.27 | 1.52 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.17 | 0.24 | 0.04 | 0.24 | 0.05 | 0.25 | 0.04 | 0.24 | 0.04 | 0.24 | 0.03 |
| Unknown | 0.58 | 0.06 | 0.58 | 0.1 | 0.58 | 0.08 | 0.58 | 0.08 | 0.57 | 0.05 | 0.58 | 0.07 | 0.58 | 0.06 |
| Unknown | 0.59 | 0.05 | 0.59 | 0.08 | 0.6 | 0.05 | 0.58 | 0.06 | 0.59 | 0.05 | 0.6 | 0.05 | 0.59 | 0.05 |
| Unknown | 0.62 | 0.05 | 0.62 | 0.09 | 0.62 | 0.06 | 0.62 | 0.06 | 0.62 | 0.04 | 0.60 | 0.05 | 0.62 | 0.05 |
| Unknown | 0.81 | — | 0.81 | 0.05 | 0.81 | 0.02 | 0.81 | 0.02 | — | — | — | — | — | — |
| Unknown | 0.87 | 0.12 | 0.87 | 0.12 | 0.87 | 0.15 | 0.87 | 0.14 | 0.87 | 0.11 | 0.87 | 0.15 | 0.87 | 0.14 |
| Unknown | 0.89 | 0.03 | 0.89 | 0.27 | 0.89 | 0.03 | 0.89 | 0.02 | 0.89 | 0.04 | 0.89 | 0.02 | 0.89 | 0.02 |
| Unknown | 1.03 | 0.18 | 1.03 | 0.05 | 1.03 | 0.03 | 1.03 | 0.1 | 1.03 | 0.07 | 1.03 | 0.06 | 1.03 | 0.08 |
| Unknown | 1.11 | 0.04 | 1.13 | 0.07 | 1.11 | 0.06 | 1.11 | 0.06 | 1.11 | 0.05 | 1.11 | 0.05 | 1.11 | 0.05 |
| Unknown | 1.27 | 0.21 | 1.27 | 0.27 | 1.27 | 0.32 | 1.27 | 0.44 | 1.27 | 0.43 | 1.27 | 0.24 | 1.27 | 0.5 |

TABLE 1.12-continued

3,4,3-LI(1,2-HOPO)-MICROCRYSTALLINE CELLULOSE COMPATIBILITY

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown | 1.3 | 0.25 | 1.3 | 0.09 | 1.3 | 0.25 | 1.3 | 0.18 | 1.3 | 0.18 | 1.3 | 0.26 | 1.3 | 0.21 |
| Unknown | 1.39 | 0.05 | 1.39 | 0.03 | 1.39 | 0.06 | 1.39 | 0.05 | 1.39 | 0.06 | 1.39 | 0.04 | 1.39 | 0.04 |
| Unknown | 1.41 | 0.01 | 1.41 | 0.01 | 1.41 | 0.02 | 1.41 | 0.01 | 1.41 | 0.03 | 1.41 | 0.01 | 1.41 | 0.01 |
| Unknown | 1.46 | 0.12 | 1.46 | 0.07 | 1.46 | 0.11 | 1.46 | 0.09 | 1.47 | 0.09 | 1.47 | 0.06 | 1.46 | 0.08 |
| Unknown | 1.72 | — | — | — | 1.72 | 0.07 | 1.73 | 0.06 | — | — | 1.72 | 0.07 | 1.73 | 0.03 |
| Unknown | 2.31 | 0.04 | 2.31 | 0.03 | 2.3 | 0.05 | 2.31 | 0.07 | 2.32 | 0.06 | 2.3 | 0.04 | 2.31 | 0.08 |
| Unknown | 2.6 | — | 2.6 | 0.03 | 2.59 | 0.05 | 2.6 | 0.04 | 2.61 | 0.05 | 2.59 | 0.04 | 2.6 | 0.05 |
| Unknown | 2.8 | — | 2.8 | 0.03 | 2.79 | 0.03 | 2.8 | 0.03 | 2.81 | 0.03 | 2.79 | 0.03 | 2.8 | 0.04 |

TABLE 1.13

3,4,3-LI(1,2-HOPO)-HYPROMELLOSE COMPATIBILITY

| | | 40° C./75% RH | | | 25° C./60% RH | | |
|---|---|---|---|---|---|---|---|
| Test | Initial (T = 0) | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 96.75 | 98.39 | 98.53 | 98.39 | 98.69 | 98.69 | 98.34 |
| Total Impurities | 1.25 | 1.61 | 1.47 | 1.61 | 1.31 | 1.31 | 1.66 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.16 | 0.24 | 0.04 | 0.24 | 0.06 | 0.24 | 0.03 | 0.24 | 0.03 | 0.24 | 0.03 |
| Unknown | 0.58 | 0.05 | 0.58 | 0.1 | 0.58 | 0.08 | 0.58 | 0.09 | 0.57 | 0.05 | 0.58 | 0.07 | 0.58 | 0.06 |
| Unknown | 0.59 | 0.05 | 0.59 | 0.08 | 0.6 | 0.06 | 0.59 | 0.07 | 0.59 | 0.05 | 0.6 | 0.05 | 0.59 | 0.05 |
| Unknown | 0.62 | 0.04 | 0.62 | 0.08 | 0.62 | 0.06 | 0.62 | 0.08 | 0.62 | 0.04 | 0.62 | 0.05 | 0.62 | 0.05 |
| Unknown | 0.81 | — | 0.81 | 0.05 | 0.81 | 0.02 | 0.81 | 0.02 | — | — | — | — | — | — |
| Unknown | 0.87 | 0.09 | 0.87 | 0.09 | 0.87 | 0.15 | 0.87 | 0.15 | 0.87 | 0.12 | 0.87 | 0.14 | 0.87 | 0.13 |
| Unknown | 0.89 | 0.03 | 0.89 | 0.23 | 0.89 | 0.03 | 0.89 | 0.03 | 0.89 | 0.03 | 0.89 | 0.02 | 0.89 | 0.02 |
| Unknown | 1.03 | 0.19 | 1.03 | 0.05 | 1.02 | 0.03 | 1.03 | 0.09 | 1.03 | 0.08 | 1.02 | 0.04 | 1.03 | 0.08 |
| Unknown | 1.11 | 0.04 | 1.13 | 0.08 | 1.11 | 0.05 | 1.11 | 0.07 | 1.11 | 0.05 | 1.11 | 0.05 | 1.11 | 0.05 |
| Unknown | 1.27 | 0.29 | 1.27 | 0.37 | 1.27 | 0.32 | 1.27 | 0.43 | 1.27 | 0.36 | 1.27 | 0.27 | 1.27 | 0.59 |
| Unknown | 1.3 | 0.2 | 1.3 | 0.1 | 1.3 | 0.24 | 1.3 | 0.11 | 1.3 | 0.22 | 1.3 | 0.26 | 1.3 | 0.19 |
| Unknown | 1.39 | 0.06 | 1.39 | 0.05 | 1.39 | 0.08 | 1.39 | 0.09 | 1.39 | 0.05 | 1.39 | 0.05 | 1.39 | 0.05 |
| Unknown | 1.41 | 0.01 | 1.41 | 0.01 | 1.41 | 0.01 | 1.4 | 0.01 | 1.41 | 0.02 | 1.41 | 0.01 | 1.41 | 0.01 |
| Unknown | 1.46 | 0.18 | 1.46 | 0.09 | 1.46 | 0.12 | 1.46 | 0.12 | 1.47 | 0.1 | 1.46 | 0.09 | 1.46 | 0.15 |
| Unknown | 1.72 | — | — | — | 1.72 | 0.07 | 1.73 | 0.08 | — | — | 1.72 | 0.06 | 1.73 | 0.03 |
| Unknown | 2.31 | 0.03 | 2.31 | 0.03 | 2.3 | 0.03 | 2.31 | 0.06 | 2.32 | 0.05 | 2.3 | 0.03 | 2.31 | 0.07 |
| Unknown | 2.6 | — | 2.6 | 0.03 | 2.59 | 0.04 | 2.6 | 0.04 | 2.61 | 0.04 | 2.59 | 0.04 | 2.6 | 0.06 |
| Unknown | 2.8 | — | 2.8 | 0.03 | 2.79 | 0.03 | 2.8 | 0.03 | 2.81 | 0.03 | 2.79 | 0.03 | 2.8 | 0.04 |

TABLE 1.14

3,4,3-LI(1,2-HOPO)-POVIDONE COMPATIBILITY

| | | 40° C./75% RH | | | 25° C./60% RH | | |
|---|---|---|---|---|---|---|---|
| Test | Initial (T = O) | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 98.77 | 98.63 | 98.60 | 98.27 | 98.62 | 98.60 | 98.40 |
| Total Impurities | 1.23 | 1.37 | 1.40 | 1.73 | 1.38 | 1.40 | 1.60 |

| | RRT | % w/w | RRT | % w/w | RRT | %w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.08 | 0.24 | 0.04 | 0.24 | 0.05 | 0.24 | 0.03 | 0.24 | 0.04 | 0.24 | 0.03 |
| Unknown | 0.58 | 0.05 | 0.58 | 0.08 | 0.58 | 0.07 | 0.58 | 0.08 | 0.57 | 0.04 | 0.58 | 0.07 | 0.58 | 0.06 |
| Unknown | 0.59 | 0.05 | 0.59 | 0.07 | 0.6 | 0.05 | 0.59 | 0.06 | 0.59 | 0.05 | 0.6 | 0.05 | 0.59 | 0.05 |
| Unknown | 0.62 | 0.04 | 0.62 | 0.07 | 0.62 | 0.06 | 0.62 | 0.07 | 0.62 | 0.04 | 0.62 | 0.06 | 0.62 | 0.05 |
| Unknown | 0.81 | — | 0.81 | 0.03 | 0.81 | 0.02 | 0.81 | 0.02 | — | — | — | — | — | — |
| Unknown | 0.87 | 0.1 | 0.87 | 0.11 | 0.87 | 0.14 | 0.87 | 0.15 | 0.87 | 0.12 | 0.87 | 0.15 | 0.87 | 0.14 |
| Unknown | 0.89 | 0.03 | 0.89 | 0.1 | 0.89 | 0.03 | 0.89 | 0.02 | 0.89 | 0.04 | 0.89 | 0.03 | 0.89 | 0.02 |
| Unknown | 1.03 | 0.18 | 1.02 | 0.07 | 1.03 | 0.03 | 1.03 | 0.11 | 1.02 | 0.08 | 1.03 | 0.04 | 1.03 | 0.07 |
| Unknown | 1.11 | 0.03 | 1.11 | 0.06 | 1.11 | 0.05 | 1.11 | 0.06 | 1.11 | 0.05 | 1.11 | 0.05 | 1.11 | 0.05 |
| Unknown | 1.27 | 0.27 | 1.27 | 0.37 | 1.27 | 0.3 | 1.27 | 0.51 | 1.27 | 0.43 | 1.27 | 0.27 | 1.27 | 0.54 |
| Unknown | 1.3 | 0.23 | 1.3 | 0.09 | 1.3 | 0.25 | 1.3 | 0.17 | 1.3 | 0.18 | 1.3 | 0.29 | 1.3 | 0.19 |
| Unknown | 1.39 | 0.06 | 1.39 | 0.04 | 1.39 | 0.08 | 1.39 | 0.1 | 1.39 | 0.08 | 1.39 | 0.06 | 1.39 | 0.07 |
| Unknown | 1.41 | 0.01 | 1.41 | 0.01 | 1.41 | 0.01 | 1.4 | 0.01 | 1.41 | 0.03 | 1.41 | 0.01 | 1.41 | 0.01 |
| Unknown | 1.46 | 0.14 | 1.46 | 0.09 | 1.46 | 0.1 | 1.46 | 0.14 | 1.47 | 0.1 | 1.46 | 0.1 | 1.46 | 0.11 |
| Unknown | 1.72 | — | — | — | 1.72 | 0.05 | 1.73 | 0.05 | — | — | 1.72 | 0.09 | 1.73 | 0.03 |
| Unknown | 2.31 | 0.03 | 2.31 | 0.04 | 2.3 | 0.03 | 2.31 | 0.06 | 2.32 | 0.04 | 2.3 | 0.04 | 2.31 | 0.07 |
| Unknown | 2.6 | — | 2.6 | 0.03 | 2.59 | 0.04 | 2.6 | 0.05 | 2.61 | 0.05 | 2.59 | 0.03 | 2.6 | 0.06 |
| Unknown | 2.8 | — | 2.8 | 0.03 | 2.79 | 0.03 | 2.8 | 0.03 | 2.81 | 0.03 | 2.79 | 0.03 | 2.8 | 0.04 |

TABLE 1.15

3,4,3-LI(1,2-HOPO)-PREGELATINIZED STARCH COMPATIBILITY

| | | 40° C./75% RH | | | 25° C./60% RH | | |
|---|---|---|---|---|---|---|---|
| Test | Initial (T = O) | 2 Weeks | 4 Weeks | 8 Weeks | 2 Weeks | 4 Weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 98.78 | 98.55 | 98.55 | 97.56 | 98.66 | 98.69 | 98.32 |
| Total Impurities | 1.22 | 1.45 | 1.45 | 2.44 | 1.34 | 1.31 | 1.68 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.11 | 0.24 | 0.05 | 0.24 | 0.36 | 0.24 | 0.03 | 0.24 | 0.03 | 0.24 | 0.03 |
| Unknown | 0.58 | 0.04 | 0.58 | 0.09 | 0.58 | 0.07 | 0.58 | 0.12 | 0.57 | 0.04 | 0.58 | 0.07 | 0.58 | 0.06 |
| Unknown | 0.59 | 0.05 | 0.59 | 0.07 | 0.6 | 0.06 | 0.59 | 0.16 | 0.59 | 0.04 | 0.6 | 0.05 | 0.59 | 0.05 |
| Unknown | 0.62 | 0.04 | 0.62 | 0.07 | 0.62 | 0.06 | 0.62 | 0.22 | 0.62 | 0.04 | 0.62 | 0.05 | 0.62 | 0.05 |
| Unknown | 0.81 | — | 0.81 | 0.03 | 0.81 | 0.02 | 0.81 | 0.07 | — | — | — | — | — | — |

TABLE 1.15-continued 3,4,3-LI(1,2-HOPO)-PREGELATINIZED STARCH COMPATIBILITY

| Unknown | 0.87 | 0.08 | 0.87 | 0.12 | 0.87 | 0.15 | 0.87 | 0.18 | 0.87 | 0.13 | 0.87 | 0.14 | 0.87 | 0.13 |
|---|---|---|---|---|---|---|---|---|---|---|---|---|---|---|
| Unknown | 0.89 | 0.03 | 0.89 | 0.12 | 0.89 | 0.04 | 0.89 | 0.52 | 0.89 | 0.04 | 0.89 | 0.02 | 0.89 | 0.02 |
| Unknown | 0.91 | — | — | — | — | — | 0.91 | 0.18 | — | — | — | — | — | — |
| Unknown | 0.95 | — | — | — | — | — | 0.95 | 0.07 | — | — | — | — | — | — |
| Unknown | 1.03 | 0.19 | 1.02 | 0.07 | 1.03 | 0.03 | 1.03 | 0.05 | 1.02 | 0.08 | 1.02 | 0.04 | 1.03 | 0.09 |
| Unknown | 1.11 | 0.04 | 1.11 | 0.05 | 1.11 | 0.06 | 1.12 | 0.06 | 1.11 | 0.05 | 1.11 | 0.05 | 1.11 | 0.05 |
| Unknown | 1.27 | 0.28 | 1.27 | 0.41 | 1.27 | 0.32 | 1.27 | 0.19 | 1.27 | 0.38 | 1.27 | 0.27 | 1.27 | 0.61 |
| Unknown | 1.3 | 0.19 | 1.3 | 0.09 | 1.3 | 0.25 | 1.3 | 0.01 | 1.3 | 0.21 | 1.3 | 0.26 | 1.3 | 0.17 |
| Unknown | 1.39 | 0.08 | 1.39 | 0.05 | 1.39 | 0.08 | 1.39 | 0.03 | 1.39 | 0.7 | 1.39 | 0.06 | 1.39 | 0.08 |
| Unknown | 1.41 | 0.02 | 1.41 | 0.01 | 1.41 | 0.02 | 1.41 | 0 | 1.41 | 0.02 | 1.41 | 0.01 | 1.41 | 0.02 |
| Unknown | 1.46 | 0.14 | 1.46 | 0.06 | 1.46 | 0.08 | 1.46 | 0.06 | 1.46 | 0.09 | 1.46 | 0.08 | 1.46 | 0.12 |
| Unknown | 1.72 | — | — | — | 1.72 | 0.07 | 1.73 | 0.07 | — | — | 1.72 | 0.07 | 1.73 | 0.02 |
| Unknown | 2.31 | 0.04 | 2.31 | 0.04 | 2.3 | 0.04 | 2.31 | 0.03 | 2.32 | 0.04 | 2.3 | 0.04 | 2.31 | 0.08 |
| Unknown | 2.6 | — | 2.6 | 0.03 | 2.59 | 0.04 | 2.6 | 0.02 | 2.6 | 0.05 | 2.59 | 0.03 | 2.6 | 0.06 |
| Unknown | 2.8 | — | 2.8 | 0.03 | 2.79 | 0.03 | 2.82 | 0.03 | 2.81 | 0.03 | 2.79 | 0.03 | 2.8 | 0.04 |

TABLE 1.16

3,4,3-L1(1,2-HOPO)-CROSCARMELLOSE SODIUM COMPATIBILITY

| Test | Initial (T = O) | 40° C./75% RH | | | 25° C./60% RH | | |
|---|---|---|---|---|---|---|---|
| | | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 98.75 | 98.77 | 98.69 | 98.43 | 98.77 | 98.74 | 98.58 |
| Total Impurities | 1.25 | 1.23 | 1.31 | 1.57 | 1.23 | 1.26 | 1.42 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.06 | 0.24 | 0.04 | 0.24 | 0.05 | 0.24 | 0.03 | 0.24 | 0.04 | 0.24 | 0.04 |
| Unknown | 0.59 | 0.02 | 0.58 | 0.07 | 0.58 | 0.08 | 0.58 | 0.08 | 0.58 | 0.05 | 0.58 | 0.07 | 0.58 | 0.06 |
| Unknown | 0.6 | 0.02 | 0.59 | 0.05 | 0.6 | 0.05 | 0.59 | 0.06 | 0.59 | 0.04 | 0.6 | 0.05 | 0.59 | 0.05 |
| Unknown | 0.63 | 0.02 | 0.62 | 0.06 | 0.62 | 0.05 | 0.62 | 0.06 | 0.62 | 0.04 | 0.62 | 0.05 | 0.62 | 0.05 |
| Unknown | 0.81 | — | 0.81 | 0.02 | 0.81 | 0.02 | 0.81 | 0.02 | — | — | — | — | — | — |
| Unknown | 0.87 | 0.07 | 0.87 | 0.13 | 0.87 | 0.15 | 0.87 | 0.16 | 0.87 | 0.13 | 0.87 | 0.15 | 0.87 | 0.15 |
| Unknown | 0.89 | 0.03 | 0.89 | 0.04 | 0.89 | 0.02 | 0.89 | 0.02 | 0.89 | 0.03 | 0.89 | 0.02 | 0.89 | 0.02 |
| Unknown | 1.03 | 0.21 | 1.03 | 0.08 | 1.02 | 0.04 | 1.03 | 0.11 | 1.03 | 0.08 | 1.03 | 0.04 | 1.03 | 0.09 |
| Unknown | 1.11 | 0.05 | 1.11 | 0.05 | 1.11 | 0.06 | 1.11 | 0.07 | 1.11 | 0.05 | 1.11 | 0.06 | 1.11 | 0.06 |
| Unknown | 1.26 | 0.31 | 1.27 | 0.31 | 1.27 | 0.23 | 1.27 | 0.35 | 1.27 | 0.29 | 1.27 | 0.2 | 1.27 | 0.35 |
| Unknown | 1.29 | 0.2 | 1.3 | 0.11 | 1.3 | 0.26 | 1.3 | 0.23 | 1.3 | 0.26 | 1.3 | 0.29 | 1.3 | 0.22 |
| Unknown | 1.38 | 0.08 | 1.39 | 0.03 | 1.39 | 0.04 | 1.39 | 0.04 | 1.39 | 0.03 | 1.39 | 0.03 | 1.39 | 0.03 |
| Unknown | 1.4 | 0.04 | 1.41 | 0.01 | 1.41 | 0.01 | 1.41 | 0.01 | 1.41 | 0.02 | 1.41 | 0.01 | 1.41 | 0.01 |
| Unknown | 1.45 | 0.14 | 1.46 | 0.09 | 1.46 | 0.08 | 1.46 | 0.08 | 1.47 | 0.05 | 1.46 | 0.06 | 1.46 | 0.07 |
| Unknown | 1.72 | — | — | — | 1.72 | 0.06 | 1.73 | 0.08 | — | — | 1.72 | 0.09 | 1.73 | 0.06 |
| Unknown | 2.29 | 0.05 | 2.31 | 0.05 | 2.3 | 0.04 | 2.31 | 0.07 | 2.32 | 0.05 | 2.3 | 0.05 | 2.31 | 0.08 |
| Unknown | 2.6 | — | 2.6 | 0.03 | 2.59 | 0.03 | 2.6 | 0.04 | 2.61 | 0.04 | 2.59 | 0.03 | 2.6 | 0.04 |
| Unknown | 2.8 | — | 2.8 | 0.03 | 2.79 | 0.03 | 2.8 | 0.03 | 2.81 | 0.03 | 2.79 | 0.02 | 2.8 | 0.03 |

TABLE 1.17

3,4,3-LI(1,2-HOPO)-SODIUM STARCH GLYCOLATE COMPATIBILITY

| | | 40° C./75% RH | | | | 25°C./60% RH | | |
|---|---|---|---|---|---|---|---|---|
| Test | Initial (T = O) | 2 Weeks | 4 weeks | 8 Weeks | | 2 Weeks | 4 weeks | 8 Weeks |
| Visual Observation | Pale yellow powder | Pale yellow pasty material | Pale yellow pasty material | Pale yellow pasty material | | Pale yellow powder | Pale yellow powder | Pale yellow powder |
| Identification by HPLC (3LIO) | RT matches with standard | RT matches with standard | RT matches with standard | RT matches with standard | | RT matches with standard | RT matches with standard | RT matches with standard |
| Related Substances (% Area, n = 1) | | | | | | | | |
| 3LIO Purity | 98.77 | 98.79 | 98.69 | 98.53 | | 98.81 | 98.77 | 98.55 |
| Total Impurities | 1.23 | 1.21 | 1.31 | 1.47 | | 1.19 | 1.23 | 1.45 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.07 | 0.24 | 0.1 | 0.24 | 0.06 | 0.24 | 0.03 | 0.24 | 0.04 | 0.24 | 0.04 |
| Unknown | 0.58 | 0.05 | 0.58 | 0.07 | 0.58 | 0.09 | 0.58 | 0.07 | 0.57 | 0.05 | 0.58 | 0.06 | 0.58 | 0.06 |
| Unknown | 0.59 | 0.04 | 0.59 | 0.06 | 0.6 | 0.06 | 0.59 | 0.05 | 0.59 | 0.04 | 0.6 | 0.04 | 0.59 | 0.04 |
| Unknown | 0.62 | 0.03 | 0.62 | 0.06 | 0.62 | 0.06 | 0.62 | 0.05 | 0.62 | 0.04 | 0.62 | 0.04 | 0.62 | 0.05 |
| Unknown | 0.81 | — | 0.81 | 0.02 | 0.81 | 0.03 | 0.81 | 0.02 | — | — | — | — | — | — |
| Unknown | 0.87 | 0.12 | 0.87 | 0.14 | 0.87 | 0.15 | 0.87 | 0.16 | 0.87 | 0.13 | 0.87 | 0.15 | 0.87 | 0.15 |
| Unknown | 0.89 | 0.03 | 0.89 | 0.07 | 0.89 | 0.12 | 0.89 | 0.02 | 0.89 | 0.03 | 0.89 | 0.02 | 0.89 | 0.02 |
| Unknown | 1.03 | 0.21 | 1.03 | 0.08 | 1.02 | 0.05 | 1.03 | 0.08 | 1.03 | 0.08 | 1.02 | 0.04 | 1.03 | 0.09 |
| Unknown | 1.11 | 0.04 | 1.11 | 0.05 | 1.11 | 0.07 | 1.11 | 0.07 | 1.11 | 0.05 | 1.11 | 0.06 | 1.11 | 0.06 |
| Unknown | 1.27 | 0.25 | 1.27 | 0.3 | 1.27 | 0.24 | 1.27 | 0.37 | 1.27 | 0.32 | 1.27 | 0.23 | 1.27 | 0.39 |
| Unknown | 1.3 | 0.25 | 1.3 | 0.11 | 1.3 | 0.1 | 1.3 | 0.2 | 1.3 | 0.25 | 1.3 | 0.27 | 1.3 | 0.23 |
| Unknown | 1.39 | 0.05 | 1.39 | 0.03 | 1.39 | 0.03 | 1.39 | 0.04 | 1.39 | 0.03 | 1.39 | 0.03 | 1.39 | 0.04 |
| Unknown | 1.41 | 0.01 | 1.41 | 0.01 | 1.41 | 0 | 1.41 | 0.01 | 1.41 | 0.02 | 1.41 | 0.01 | 1.41 | 0.01 |
| Unknown | 1.46 | 0.11 | 1.46 | 0.07 | 1.46 | 0.06 | 1.46 | 0.07 | 1.47 | 0.04 | 1.46 | 0.06 | 1.46 | 0.07 |
| Unknown | 1.72 | — | — | — | 1.72 | 0.08 | 1.72 | 0.09 | — | — | 1.72 | 0.07 | 1.73 | 0.06 |
| Unknown | 2.31 | 0.04 | 2.31 | 0.04 | 2.3 | 0.03 | 2.31 | 0.06 | 2.32 | 0.04 | 2.3 | 0.04 | 2.31 | 0.07 |
| Unknown | 2.6 | — | 2.6 | 0.03 | 2.59 | 0.02 | 2.6 | 0.03 | 2.61 | 0.03 | 2.59 | 0.03 | 2.6 | 0.04 |
| Unknown | 2.8 | — | 2.8 | 0.03 | 2.79 | 0.02 | 2.8 | 0.03 | 2.81 | 0.02 | 2.79 | 0.03 | 2.8 | 0.03 |

TABLE 1.18

3,4,3-LI( 1,2-HOPO)-CROSPOVIDONE COMPATIBILITY

| | | 40° C./75% RH | | | | 25° C./60% RH | | |
|---|---|---|---|---|---|---|---|---|
| Test | Initial (T = O) | 2 Weeks | 4 weeks | 8 Weeks | | 2 Weeks | 4 weeks | 8 Weeks |
| Visual Observation | Pale yellow powder | Pale yellow pasty material | Pale yellow pasty material | Pale yellow pasty material | | Pale yellow powder | Pale yellow powder | Pale yellow powder |
| Identification by HPLC (3LIO) | RT matches with standard | RT matches with standard | RTmatches with standard | RT matches with standard | | RT matches with standard | RT matches with standard | RT matches with standard |
| Related Substances (% Area, n = 1) | | | | | | | | |
| 3LIO Purity | 98.74 | 98.49 | 98.57 | 98.47 | | 98.74 | 98.74 | 98.52 |
| Total Impurities | 1.26 | 1.51 | 1.43 | 1.53 | | 1.26 | 1.26 | 1.48 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.14 | 0.24 | 0.04 | 0.24 | 0.05 | 0.24 | 0.03 | 0.24 | 0.04 | 0.24 | 0.04 |
| Unknown | 0.58 | 0.05 | 0.58 | 0.1 | 0.58 | 0.08 | 0.58 | 0.09 | 0.58 | 0.05 | 0.58 | 0.07 | 0.58 | 0.07 |
| Unknown | 0.59 | 0.04 | 0.59 | 0.08 | 0.6 | 0.06 | 0.59 | 0.07 | 0.59 | 0.05 | 0.6 | 0.05 | 0.59 | 0.05 |
| Unknown | 0.62 | 0.04 | 0.62 | 0.08 | 0.62 | 0.05 | 0.62 | 0.07 | 0.62 | 0.06 | 0.62 | 0.05 | 0.62 | 0.06 |
| Unknown | 0.81 | — | 0.81 | 0.06 | 0.81 | 0.02 | 0.81 | 0.02 | — | — | — | — | — | — |

TABLE 1.18-continued 3,4,3-LI( 1,2-HOPO)-CROSPOVIDONE COMPATIBILITY

| Unknown | 0.87 | 0.1  | 0.87 | 0.13 | 0.87 | 0.16 | 0.87 | 0.17 | 0.87 | 0.14 | 0.87 | 0.15 | 0.87 | 0.15 |
|---------|------|------|------|------|------|------|------|------|------|------|------|------|------|------|
| Unknown | 0.89 | 0.03 | 0.89 | 0.24 | 0.89 | 0.03 | 0.89 | 0.04 | 0.89 | 0.03 | 0.89 | 0.03 | 0.89 | 0.02 |
| Unknown | 1.03 | 0.2  | 1.02 | 0.06 | 1.03 | 0.03 | 1.03 | 0.11 | 1.03 | 0.08 | 1.03 | 0.05 | 1.03 | 0.07 |
| Unknown | 1.11 | 0.04 | 1.13 | 0.1  | 1.11 | 0.06 | 1.11 | 0.05 | 1.11 | 0.05 | 1.11 | 0.06 | 1.11 | 0.06 |
| Unknown | 1.27 | 0.31 | 1.27 | 0.25 | 1.27 | 0.28 | 1.27 | 0.32 | 1.27 | 0.31 | 1.27 | 0.22 | 1.27 | 0.39 |
| Unknown | 1.3  | 0.19 | 1.3  | 0.11 | 1.3  | 0.25 | 1.3  | 0.24 | 1.3  | 0.23 | 1.3  | 0.26 | 1.3  | 0.24 |
| Unknown | 1.39 | 0.09 | 1.39 | 0.04 | 1.39 | 0.08 | 1.39 | 0.05 | 1.39 | 0.05 | 1.39 | 0.04 | 1.39 | 0.05 |
| Unknown | 1.41 | 0.02 | 1.41 | 0    | 1.41 | 0.01 | 1.41 | 0    | 1.41 | 0.01 | 1.41 | 0.01 | 1.41 | 0.01 |
| Unknown | 1.46 | 0.12 | 1.46 | 0.06 | 1.46 | 0.09 | 1.46 | 0.06 | 1.46 | 0.07 | 1.46 | 0.06 | 1.46 | 0.08 |
| Unknown | 1.72 | —    | —    | —    | 1.72 | 0.09 | 1.72 | 0.11 | —    | —    | 1.72 | 0.08 | 1.73 | 0.07 |
| Unknown | 2.31 | 0.04 | 2.31 | 0.03 | 2.3  | 0.03 | 2.31 | 0.06 | 2.32 | 0.04 | 2.3  | 0.03 | 2.31 | 0.07 |
| Unknown | 2.6  | —    | 2.6  | 0.03 | 2.59 | 0.04 | 2.6  | 0.03 | 2.6  | 0.04 | 2.59 | 0.03 | 2.6  | 0.04 |
| Unknown | 2.8  | —    | 2.8  | 0.03 | 2.79 | 0.03 | 2.8  | 0.02 | 2.81 | 0.03 | 2.79 | 0.03 | 2.8  | 0.03 |

TABLE 1.19

3,4,3-LI(1,2-HOPO)-COLLOIDAL SILICON DIOXIDE COMPATIBILITY

| Test | Initial (T = O) | 40° C./75% RH | | | 25° C./60% RH | | |
|------|----|------|------|------|------|------|------|
| | | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 98.77 | 98.57 | 98.52 | 98.39 | 98.70 | 98.65 | 98.29 |
| Total Impurities | 1.23 | 1.43 | 1.48 | 1.61 | 1.30 | 1.35 | 1.71 |

| | RRT | % w/w | RRT | % w/w | RRT | % w/w | RRT | %w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | —    | 0.24 | 0.14 | 0.24 | 0.04 | 0.24 | 0.06 | 0.24 | 0.03 | 0.24 | 0.03 | 0.24 | 0.04 |
| Unknown | 0.58 | 0.06 | 0.58 | 0.09 | 0.58 | 0.07 | 0.58 | 0.09 | 0.58 | 0.05 | 0.58 | 0.06 | 0.58 | 0.06 |
| Unknown | 0.59 | 0.04 | 0.59 | 0.08 | 0.6  | 0.06 | 0.59 | 0.06 | 0.59 | 0.04 | 0.6  | 0.05 | 0.59 | 0.05 |
| Unknown | 0.62 | 0.04 | 0.62 | 0.07 | 0.62 | 0.06 | 0.62 | 0.07 | 0.62 | 0.04 | 0.62 | 0.05 | 0.62 | 0.05 |
| Unknown | 0.81 | —    | 0.81 | 0.03 | 0.81 | 0.02 | 0.81 | 0.02 | —    | —    | —    | —    | —    | —    |
| Unknown | 0.87 | 0.11 | 0.87 | 0.12 | 0.87 | 0.15 | 0.87 | 0.16 | 0.87 | 0.12 | 0.87 | 0.13 | 0.87 | 0.13 |
| Unknown | 0.89 | 0.03 | 0.89 | 0.15 | 0.89 | 0.03 | 0.89 | 0.03 | 0.89 | 0.03 | 0.89 | 0.03 | 0.89 | 0.02 |
| Unknown | 1.03 | 0.2  | 1.03 | 0.06 | 1.02 | 0.03 | 1.03 | 0.11 | 1.02 | 0.07 | 1.02 | 0.04 | 1.02 | 0.07 |
| Unknown | 1.11 | 0.04 | 1.11 | 0.05 | 1.11 | 0.05 | 1.11 | 0.06 | 1.11 | 0.05 | 1.11 | 0.05 | 1.11 | 0.05 |
| Unknown | 1.27 | 0.25 | 1.27 | 0.39 | 1.27 | 0.34 | 1.27 | 0.41 | 1.27 | 0.4  | 1.27 | 0.34 | 1.27 | 0.66 |
| Unknown | 1.3  | 0.23 | 1.3  | 0.06 | 1.3  | 0.25 | 1.3  | 0.19 | 1.3  | 0.2  | 1.3  | 0.23 | 1.3  | 0.17 |
| Unknown | 1.39 | 0.07 | 1.39 | 0.03 | 1.39 | 0.09 | 1.39 | 0.07 | 1.39 | 0.05 | 1.39 | 0.07 | 1.39 | 0.08 |
| Unknown | 1.41 | 0.01 | 1.41 | 0.01 | 1.41 | 0.02 | 1.41 | 0.01 | 1.41 | 0.03 | 1.41 | 0.02 | 1.41 | 0.02 |
| Unknown | 1.46 | 0.12 | 1.46 | 0.06 | 1.46 | 0.1  | 1.46 | 0.08 | 1.46 | 0.07 | 1.46 | 0.1  | 1.46 | 0.12 |
| Unknown | 1.72 | —    | —    | —    | 1.72 | 0.06 | 1.72 | 0.08 | —    | —    | 1.72 | 0.04 | 1.73 | 0.02 |
| Unknown | 2.31 | 0.04 | 2.31 | 0.04 | 2.3  | 0.04 | 2.31 | 0.06 | 2.32 | 0.04 | 2.3  | 0.05 | 2.31 | 0.08 |
| Unknown | 2.6  | —    | 2.6  | 0.03 | 2.59 | 0.04 | 2.6  | 0.04 | 2.6  | 0.05 | 2.59 | 0.05 | 2.6  | 0.07 |
| Unknown | 2.8  | —    | 2.8  | 0.03 | 2.79 | 0.03 | 2.8  | 0.02 | 2.81 | 0.02 | 2.79 | 0.03 | 2.8  | 0.04 |

TABLE 1.20

3,4,3-LI(1,2-HOPO)-MAGNESIUM STEARATE COMPATIBILITY

| Test | Initial (T = O) | 40° C./75% RH | | | 25° C./60% RH | | |
|---|---|---|---|---|---|---|---|
| | | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3LIO) | RT matches with standard | RT matches with standard | RT matches with standard | RT matches with standard | RT matches with standard | RT matches with standard | RT matches with standard |
| Related Substances (% Area, n = 1) | | | | | | | |
| 3LIO Purity | 98.75 | 98.67 | 98.41 | 98.47 | 98.68 | 98.70 | 98.37 |
| Total Impurities | 1.25 | 1.33 | 1.59 | 1.53 | 1.32 | 1.30 | 1.63 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.04 | 0.24 | 0.15 | 0.24 | 0.06 | 0.24 | 0.03 | 0.24 | 0.03 | 0.24 | 0.04 |
| Unknown | 0.58 | 0.06 | 0.58 | 0.06 | 0.58 | 0.1 | 0.58 | 0.09 | 0.58 | 0.05 | 0.58 | 0.06 | 0.58 | 0.06 |
| Unknown | 0.59 | 0.05 | 0.59 | 0.05 | 0.6 | 0.08 | 0.59 | 0.06 | 0.59 | 0.04 | 0.6 | 0.05 | 0.59 | 0.05 |
| Unknown | 0.62 | 0.04 | 0.62 | 0.05 | 0.62 | 0.08 | 0.62 | 0.08 | 0.62 | 0.04 | 0.62 | 0.05 | 0.62 | 0.05 |
| Unknown | 0.81 | — | 0.81 | 0.02 | 0.81 | 0.03 | 0.81 | 0.02 | — | — | — | — | — | — |
| Unknown | 0.87 | 0.11 | 0.87 | 0.14 | 0.87 | 0.13 | 0.87 | 0.16 | 0.87 | 0.13 | 0.87 | 0.13 | 0.87 | 0.14 |
| Unknown | 0.89 | 0.03 | 0.89 | 0.03 | 0.89 | 0.21 | 0.89 | 0.03 | 0.89 | 0.03 | 0.89 | 0.02 | 0.89 | 0.02 |
| Unknown | 1.03 | 0.21 | 1.03 | 0.07 | 1.02 | 0.03 | 1.03 | 0.1 | 1.02 | 0.08 | 1.02 | 0.03 | 1.03 | 0.08 |
| Unknown | 1.11 | 0.04 | 1.13 | 0.05 | 1.12 | 0.07 | 1.11 | 0.06 | 1.11 | 0.05 | 1.11 | 0.05 | 1.11 | 0.05 |
| Unknown | 1.27 | 0.27 | 1.27 | 0.32 | 1.27 | 0.35 | 1.27 | 0.34 | 1.27 | 0.34 | 1.27 | 0.32 | 1.27 | 0.52 |
| Unknown | 1.3 | 0.21 | 1.3 | 0.23 | 1.3 | 0.06 | 1.3 | 0.18 | 1.3 | 0.23 | 1.3 | 0.22 | 1.3 | 0.2 |
| Unknown | 1.39 | 0.07 | 1.39 | 0.06 | 1.39 | 0.06 | 1.39 | 0.06 | 1.39 | 0.07 | 1.39 | 0.07 | 1.39 | 0.09 |
| Unknown | 1.41 | 0.01 | 1.41 | 0.02 | 1.41 | 0.01 | 1.41 | 0.01 | 1.41 | 0.02 | 1.41 | 0.02 | 1.41 | 0.01 |
| Unknown | 1.46 | 0.13 | 1.46 | 0.06 | 1.46 | 0.08 | 1.46 | 0.06 | 1.46 | 0.07 | 1.46 | 0.09 | 1.46 | 0.11 |
| Unknown | 1.72 | — | — | — | 1.72 | 0.06 | 1.72 | 0.1 | — | — | 1.72 | 0.03 | 1.73 | 0.04 |
| Unknown | 2.31 | 0.04 | 2.31 | 0.06 | 2.3 | 0.03 | 2.31 | 0.06 | 2.32 | 0.05 | 2.3 | 0.04 | 2.31 | 0.07 |
| Unknown | 2.6 | — | 2.6 | 0.05 | 2.59 | 0.03 | 2.6 | 0.03 | 2.6 | 0.05 | 2.59 | 0.06 | 2.6 | 0.05 |
| Unknown | 2.8 | — | 2.8 | 0.04 | 2.79 | 0.02 | 2.8 | 0.02 | 2.81 | 0.03 | 2.79 | 0.03 | 2.8 | 0.03 |

TABLE 1.21

3,4,3-LI(1,2-HOPO)-HYDROGENATED VEGETABLE OIL COMPATIBILITY

| Test | Initial (T = 0) | 40° C./75% RH | | | 25° C./60% RH | | |
|---|---|---|---|---|---|---|---|
| | | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3L1O) | RT matches with standard | RT matches with standard | RT matches with standard | RT matches with standard | RT matches with standard | RT matches with standard | RT matches with standard |
| Related Substances (% Area, n = 1) | | | | | | | |
| 3L1O Purity | 98.73 | 98.58 | 98.37 | 96.98 | 98.71 | 98.65 | 98.39 |
| Total Impurities | 1.27 | 1.42 | 1.63 | 3.02 | 1.29 | 1.35 | 1.61 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.14 | 0.24 | 0.24 | 0.24 | 0.48 | 0.24 | 0.03 | 0.24 | 0.04 | 0.24 | 0.04 |
| Unknown | 0.58 | 0.05 | 0.58 | 0.1 | 0.58 | 0.14 | 0.58 | 0.24 | 0.58 | 0.06 | 0.58 | 0.07 | 0.58 | 0.07 |
| Unknown | 0.59 | 0.04 | 0.59 | 0.08 | 0.6 | 0.1 | 0.59 | 0.17 | 0.59 | 0.05 | 0.6 | 0.05 | 0.59 | 0.05 |
| Unknown | 0.62 | 0.04 | 0.62 | 0.08 | 0.62 | 0.12 | 0.62 | 0.2 | 0.62 | 0.05 | 0.62 | 0.05 | 0.62 | 0.05 |
| Unknown | 0.81 | — | 0.81 | 0.03 | 0.81 | 0.05 | 0.81 | 0.12 | — | — | — | — | — | — |

TABLE 1.21-continued 3,4,3-LI(1,2-HOPO)-HYDROGENATED VEGETABLE OIL COMPATIBILITY

| | | 40° C./75% RH | | | | | | 25° C./60% RH | | | | | |
|---|---|---|---|---|---|---|---|---|---|---|---|---|---|
| Test | Initial (T = 0) | | 2 Weeks | | 4 weeks | | 8 Weeks | | 2 Weeks | | 4 weeks | | 8 Weeks | |
| Unknown | 0.87 | 0.1 | 0.87 | 0.12 | 0.87 | 0.12 | 0.87 | 0.2 | 0.87 | 0.14 | 0.87 | 0.14 | 0.87 | 0.14 |
| Unknown | 0.89 | 0.03 | 0.89 | 0.14 | 0.89 | 0.28 | 0.89 | 0.71 | 0.89 | 0.03 | 0.89 | 0.02 | 0.89 | 0.02 |
| Unknown | 0.91 | — | — | — | — | — | 0.91 | 0.24 | — | — | — | — | — | — |
| Unknown | 0.95 | — | — | — | — | — | 0.95 | 0.17 | — | — | — | — | — | — |
| Unknown | 1.03 | 0.2 | 1.02 | 0.05 | 1.02 | 0.02 | 1.03 | 0.04 | 1.03 | 0.07 | 1.02 | 0.03 | 1.03 | 0.08 |
| Unknown | 1.11 | 0.03 | 1.11 | 0.06 | 1.12 | 0.09 | 1.12 | 0.14 | 1.11 | 0.05 | 1.11 | 0.05 | 1.11 | 0.06 |
| Unknown | 1.27 | 0.31 | 1.27 | 0.35 | 1.27 | 0.17 | 1.27 | 0.06 | 1.27 | 0.29 | 1.27 | 0.29 | 1.27 | 0.5 |
| Unknown | 1.3 | 0.2 | 1.3 | 0.07 | 1.3 | 0.04 | 1.3 | 0.01 | 1.3 | 0.24 | 1.3 | 0.24 | 1.3 | 0.2 |
| Unknown | 1.39 | 0.09 | 1.39 | 0.03 | 1.39 | 0.04 | 1.39 | 0.05 | 1.39 | 0.08 | 1.39 | 0.1 | 1.39 | 0.08 |
| Unknown | 1.41 | 0.02 | 1.41 | 0.01 | 1.41 | 0 | 1.41 | 0 | 1.41 | 0.02 | 1.41 | 0.2 | 1.41 | 0.01 |
| Unknown | 1.46 | 0.11 | 1.46 | 0.06 | 1.46 | 0.08 | 1.46 | 0.07 | 1.46 | 0.07 | 1.46 | 0.09 | 1.46 | 0.11 |
| Unknown | 1.72 | — | — | — | 1.72 | 0.07 | 1.72 | 0.07 | — | — | 1.72 | 0.05 | 1.73 | 0.04 |
| Unknown | 2.31 | 0.04 | 2.31 | 0.04 | 2.3 | 0.03 | 2.31 | 0.02 | 2.31 | 0.04 | 2.3 | 0.05 | 2.31 | 0.08 |
| Unknown | 2.6 | — | 2.6 | 0.03 | 2.59 | 0.03 | 2.59 | 0.02 | 2.6 | 0.03 | 2.59 | 0.05 | 2.6 | 0.06 |
| Unknown | 2.8 | — | 2.8 | 0.03 | 2.79 | 0.02 | 2.8 | 0.02 | 2.81 | 0.03 | 2.79 | 0.03 | 2.8 | 0.04 |

TABLE 1.22

3,4,3-LI(1,2-HOPO)-POLYSORBATE 80 COMPATIBILITY

| | | 40° C./75% RH | | | 25° C./60% RH | | |
|---|---|---|---|---|---|---|---|
| Test | Initial (T = 0) | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3L1O) | RT matches with standard | RT matches with standard | RT matches with standard | RT matches with standard | RT matches with standard | RT matches with standard | RT matches with standard |
| Related Substances (% Area, n = 1) | | | | | | | |
| 3L1O Purity | 98.76 | 98.63 | 98.43 | 98.14 | 98.57 | 98.54 | 98.46 |
| Total Impurities | 1.24 | 1.37 | 1.57 | 1.86 | 1.43 | 1.46 | 1.54 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.05 | 0.24 | 0.19 | 0.24 | 0.14 | 0.24 | 0.03 | 0.24 | 0.03 | 0.24 | 0.05 |
| Unknown | 0.58 | 0.05 | 0.58 | 0.07 | 0.58 | 0.16 | 0.58 | 0.13 | 0.58 | 0.05 | 0.58 | 0.07 | 0.58 | 0.07 |
| Unknown | 0.59 | 0.04 | 0.59 | 0.05 | 0.6 | 0.14 | 0.59 | 0.1 | 0.59 | 0.05 | 0.6 | 0.05 | 0.59 | 0.06 |
| Unknown | 0.62 | 0.04 | 0.62 | 0.06 | 0.62 | 0.12 | 0.62 | 0.11 | 0.62 | 0.04 | 0.62 | 0.05 | 0.62 | 0.06 |
| Unknown | 0.81 | — | 0.81 | 0.02 | 0.81 | 0.07 | 0.81 | 0.06 | — | — | — | — | — | — |
| Unknown | 0.87 | 0.12 | 0.87 | 0.13 | 0.87 | 0.14 | 0.87 | 0.19 | 0.87 | 0.11 | 0.87 | 0.15 | 0.87 | 0.14 |
| Unknown | 0.89 | 0.03 | 0.89 | 0.04 | 0.89 | 0.19 | 0.89 | 0.22 | 0.89 | 0.03 | 0.89 | 0.06 | 0.89 | 0.04 |
| Unknown | 0.91 | — | — | — | — | — | 0.91 | 0.07 | — | — | — | — | — | — |
| Unknown | 1.03 | 0.19 | 1.02 | 0.07 | 1.03 | 0.04 | 1.02 | 0.09 | 1.02 | 0.08 | 1.02 | 0.03 | 1.03 | 0.08 |
| Unknown | 1.11 | 0.04 | 1.11 | 0.06 | 1.12 | 0.12 | 1.12 | 0.08 | 1.11 | 0.05 | 1.11 | 0.05 | 1.11 | 0.06 |
| Unknown | 1.27 | 0.24 | 1.27 | 0.35 | 1.27 | 0.1 | 1.27 | 0.38 | 1.27 | 0.45 | 1.27 | 0.32 | 1.27 | 0.45 |
| Unknown | 1.3 | 0.24 | 1.3 | 0.19 | 1.3 | 0.04 | 1.3 | 0.02 | 1.3 | 0.19 | 1.3 | 0.27 | 1.3 | 0.18 |
| Unknown | 1.39 | 0.08 | 1.39 | 0.07 | 1.39 | 0.04 | 1.39 | 0.04 | 1.39 | 0.08 | 1.39 | 0.08 | 1.39 | 0.06 |
| Unknown | 1.41 | 0.01 | 1.41 | 0.02 | 1.41 | 0 | 1.41 | 0 | 1.41 | 0.04 | 1.41 | 0.02 | 1.41 | 0.01 |
| Unknown | 1.46 | 0.11 | 1.46 | 0.08 | 1.46 | 0.05 | 1.46 | 0.06 | 1.46 | 0.11 | 1.46 | 0.1 | 1.46 | 0.08 |
| Unknown | 1.72 | — | — | — | 1.72 | 0.14 | 1.73 | 0.15 | — | — | 1.72 | 0.06 | 1.73 | 0.07 |
| Unknown | 2.31 | 0.04 | 2.31 | 0.05 | 2.3 | 0.02 | 2.31 | 0.03 | 2.31 | 0.05 | 2.3 | 0.04 | 2.31 | 0.06 |
| Unknown | 2.6 | — | 2.6 | 0.04 | 2.59 | 0.01 | 2.6 | 0.01 | 2.6 | 0.05 | 2.59 | 0.04 | 2.6 | 0.04 |
| Unknown | 2.8 | — | 2.8 | 0.03 | 2.79 | 0.01 | 2.8 | 0.01 | 2.8 | 0.03 | 2.79 | 0.03 | 2.8 | 0.03 |

TABLE 1.23

| | | 3,4,3-LI(1,2-HOPO) CONTROL | | | | | |
|---|---|---|---|---|---|---|---|
| | | 40° C./75% RH | | | 25° C./60% RH | | |
| Test | Initial (T = 0) | 2 Weeks | 4 weeks | 8 Weeks | 2 Weeks | 4 weeks | 8 Weeks |
| Visual Observation | Pale yellow powder | Pale yellow pasty material | Pale yellow pasty material | Pale yellow pasty material | Pale yellow powder | Pale yellow powder | Pale yellow powder |
| Identification by HPLC (3L1O) | RT matches with standard | RT matches with standard | RT matches with standard | RT matches with standard | RT matches with standard | RT matches with standard | RT matches with standard |
| Related Substances (% Area, n = 1) | | | | | | | |
| 3L1O Purity | 98.73 | 98.62 | 98.63 | 97.49 | 98.67 | 98.66 | 98.47 |
| Total Impurities | 1.27 | 1.38 | 1.37 | 2.51 | 1.33 | 1.34 | 1.53 |

| | RRT | % w/w | RRT | % w/w | RRT | % w/w | RRT | % w/w | RRT | % w/w | RRT | % w/w | RRT | % w/w |
|---|---|---|---|---|---|---|---|---|---|---|---|---|---|---|
| Unknown Impurities | | | | | | | | | | | | | | |
| Unknown | 0.24 | — | 0.24 | 0.06 | 0.24 | 0.05 | 0.24 | 0.34 | 0.24 | 0.03 | 0.24 | 0.03 | 0.24 | 0.04 |
| Unknown | 0.58 | 0.05 | 0.58 | 0.07 | 0.58 | 0.09 | 0.58 | 0.2 | 0.58 | 0.05 | 0.58 | 0.07 | 0.58 | 0.07 |
| Unknown | 0.59 | 0.04 | 0.59 | 0.06 | 0.6 | 0.06 | 0.59 | 0.16 | 0.59 | 0.05 | 0.6 | 0.05 | 0.59 | 0.05 |
| Unknown | 0.62 | 0.04 | 0.62 | 0.06 | 0.62 | 0.07 | 0.62 | 0.18 | 0.62 | 0.05 | 0.62 | 0.05 | 0.62 | 0.06 |
| Unknown | 0.81 | — | 0.81 | 0.02 | 0.81 | 0.02 | 0.81 | 0.05 | — | — | — | — | — | — |
| Unknown | 0.87 | 0.1 | 0.87 | 0.13 | 0.87 | 0.16 | 0.87 | 0.18 | 0.87 | 0.12 | 0.87 | 0.14 | 0.87 | 0.15 |
| Unknown | 0.89 | 0.02 | 0.89 | 0.07 | 0.89 | 0.03 | 0.89 | 0.32 | 0.89 | 0.03 | 0.89 | 0.02 | 0.89 | 0.02 |
| Unknown | 0.91 | — | — | — | — | — | 0.91 | 0.11 | — | — | — | — | — | — |
| Unknown | 0.95 | — | — | — | — | — | 0.95 | 0.04 | — | — | — | — | — | — |
| Unknown | 1.03 | 0.21 | 1.02 | 0.07 | 1.02 | 0.03 | 1.02 | 0.09 | 1.02 | 0.08 | 1.03 | 0.04 | 1.03 | 0.08 |
| Unknown | 1.11 | 0.04 | 1.11 | 0.06 | 1.11 | 0.06 | 1.12 | 0.05 | 1.11 | 0.05 | 1.11 | 0.05 | 1.11 | 0.05 |
| Unknown | 1.27 | 0.29 | 1.27 | 0.36 | 1.27 | 0.26 | 1.27 | 0.4 | 1.27 | 0.36 | 1.27 | 0.28 | 1.27 | 0.41 |
| Unknown | 1.3 | 0.21 | 1.3 | 0.16 | 1.3 | 0.2 | 1.31 | 0.01 | 1.3 | 0.22 | 1.3 | 0.26 | 1.3 | 0.23 |
| Unknown | 1.39 | 0.09 | 1.39 | 0.05 | 1.39 | 0.74 | 1.39 | 0.08 | 1.39 | 0.07 | 1.39 | 0.07 | 1.39 | 0.07 |
| Unknown | 1.41 | 0.01 | 1.41 | 0.01 | 1.41 | 0.01 | 1.41 | 0 | 1.41 | 0.03 | 1.41 | 0.01 | 1.41 | 0.01 |
| Unknown | 1.46 | 0.11 | 1.46 | 0.07 | 1.46 | 0.08 | 1.46 | 0.12 | 1.46 | 0.08 | 1.46 | 0.09 | 1.46 | 0.09 |
| Unknown | 1.72 | — | — | — | 1.72 | 0.09 | 1.72 | 0.1 | — | — | 1.72 | 0.05 | 1.73 | 0.06 |
| Unknown | 2.31 | 0.05 | 2.31 | 0.05 | 2.3 | 0.04 | 2.31 | 0.03 | 2.31 | 0.05 | 2.3 | 0.05 | 2.31 | 0.07 |
| Unknown | 2.59 | — | 2.59 | 0.04 | 2.59 | 0.03 | 2.6 | 0.02 | 2.6 | 0.04 | 2.59 | 0.04 | 2.6 | 0.05 |
| Unknown | 2.8 | — | 2.8 | 0.03 | 2.79 | 0.02 | 2.8 | 0.02 | 2.8 | 0.03 | 2.79 | 0.03 | 2.8 | 0.03 |

6. Conclusion

A series of commonly used pharmaceutical excipients were tested for interactions and compatibility with 3,4,3-L1 (1,2-HOPO). Among those 14 compounds tested, 4 excipients (pregelatinized starch, compressible sugar, providone, and hydrogenated vegetable oil) resulted in a decrease in 3,4,3-L1(1,2-HOPO) purity or in an increase of specific impurity content. Those 4 excipients should be avoided in future formulations of 3,4,3-L1(1,2-HOPO).

Example 2—Feasibility of Developing Oral Formulations for 3,4,3-L1(1,2-HOPO)

Summary

The feasibility of developing oral formulations for 3,4,3-L1(1,2-HOPO) was evaluated. Four oral dosage forms were investigated: (i) powder in bottle, (ii) dispersible/dissolvable granules, (iii) chewable tablets, and (iv) conventional immediate release tablets. Based on the studies performed, nine formulation prototypes that showed immediate drug release behavior and required physical properties were identified and selected for API verification, gastric fluid dissolution, and related substance testing following defined liquid chromatography methods. Among these selected compositions, two are powder in bottle formulations, two are granule formulations, three are chewable tablet formulations, and two are conventional tablet formulations. The respective compositions of these prototype formulations are summarized and tabulated in TABLE 2.1. All assays confirmed that these prototypes are suitable for further development. The stability of these formulations will be evaluated prior to a first-in-human trial for 3,4,3-L1(1,2-HOPO). These stability studies will also include capsules containing the powder in bottle composition A2, which may be the optimal dosage form for adjusting does levels in clinical settings.

TABLE 2.1

COMPOSITIONS OF PROTOTYPE FORMULATIONS

| Ingredients Dosage Form → | Powder in | | Granules | | Chewable Tables | | | Conventional Tables | |
|---|---|---|---|---|---|---|---|---|---|
| | A2 | A11 | G11 | G12 | C11 | C13 | C21 | T50 | T51 |
| Intra-Granular Materials (for granules and conventional tablets) | | | | | | | | | |
| 3,4,3-L1(1,2-HOPO) | 1.000 | 1.000 | 1.000 | 1.000 | 0.500 | 0.500 | 0.500 | 0.500 | 0.500 |
| Sodium Oleate | 0.092 | 0.092 | 0.092 | 0.092 | 0.046 | 0.046 | 0.046 | 0.046 | 0.046 |
| Microcrystalliine Cellulose and Carboxymethyl Cellulose NF (Avivel RC-591) | — | 1.000 | — | — | — | — | — | — | — |
| Croscarmellose Sodium, NF (Ac-Di-Sol) | — | — | 0.075 | 0.075 | 0.075 | — | 0.075 | 0.084 | 0.092 |
| Microcrystalliine Cellulose and guar gum, NF (Avivel | — | — | 1.833 | — | 1.854 | — | 0.927 | — | — |
| Lactose Monohydrate, NF (Pharmatose 300 M) | — | — | 1.533 | — | — | — | — | — | — |
| Lactose Monohydrate, Povidone and Crospovidone, NF (Ludipress) | — | — | — | — | — | 1.929 | — | — | — |
| Mannitol, USP (Mannogem) | — | — | — | — | — | — | 0.9227 | — | — |
| Magensium sterate, NF (HyQual) | — | — | — | — | 0.025 | 0.025 | 0.025 | — | — |
| Microcrystalliine Cellulose and guar gum, NF (Avivel | — | — | — | — | — | — | — | 0.410 | 0.501 |
| Colloidal silicone dioxide, NF (Cab-O-Sil M5P) | — | — | — | — | — | — | — | 0.005 | 0.006 |
| Purified water USP | — | — | Q.S. | Q.S. | — | — | — | — | — |
| Magensium sterate, NF (HyQual) | — | — | — | — | — | — | — | — | — |
| Extra Granular Materials (for granules and conventional tablets) | | | | | | | | | |
| Hvnromellose.50 cps | — | — | — | 0.300 | — | — | — | — | — |
| Magnesium sterate, NF (HyQual) | — | — | — | — | — | — | — | 0.005 | 0.006 |
| Unit weight (g) | 1.092 | 2.0962 | 3.000 | 3.000 | 2.500 | 2.500 | 2.500 | 1.050 | 1.151 |

1. Purpose of Study

The purpose of this study was to provide data that can be used to support research efforts. It was not conducted in accordance with U.S. Food and Drug Administration (FDA) "Good Laboratory Practice for Nonclinical Laboratory Studies" (GLP) regulations, as described in 21 CFR Part 58. However, the study was planned, performed, recorded, and reported in accordance with standard practices to ensure data quality and integrity.

2. Objective of Study

The objective of this study was to develop prototype oral formulations of the active pharmaceutical ingredient 3,4,3-L1(1,2-HOPO). The clinical dose of 3,4,3-L1(1,2-HOPO) is expected to be in the range of 1-2 grams per unit. In order to retain the flexibility of dosing lower and higher dose strengths in clinical evaluation, several oral formulations were included in the development work, including:
  Powder in bottle (PIB)
  Orally dispersible/dissolvable granules
  Chewable tablets
  Conventional oral tablets 3. Experimental Design Suitable excipients were selected based on the results of drug-excipient compatibility studies (3,4,3-L1(1,2-HOPO)—Excipient Compatibility Study; EXAMPLE 1), and evaluated for feasibility of developing the selected formulations. All test formulations contained sodium oleate as a permeation enhancer, based on pharmacokinetic results established in parallel. In addition to 3,4,3-L1(1,2-HOPO), diluents, and the permeation enhancer, other formulation components were also probed for each prototype formulation. A typical formulation matrix is shown in TABLE 2.2.

TABLE 2.2

FORMULATION MATRIX

| Formulation Component | Typical Composition | | | |
|---|---|---|---|---|
| | 1 | 2 | 3 | 4 |
| API (20-80%) | 3,4,3-LI(1,2-HOPO) | | | |
| Permeation enhancer (1-10%) | Sodium Oleate<br>Note: Oleic acid is being used in oral drug products (max potency: 598 mg). The sodium salt of oleic acid has not been reported in approved oral drug products, however, literature reports support its use as a permeation enhancer for oral applications.<br>References: http://www.accessdata.fda.gov/scripts/cder/iig/index.cfm; Pharm. Res. 25, 8, (2008). | | | |
| Diluent (10-70%) | Coprocessed Microcrystalline Cellulose and guar Gum (Example: Avicel CE-15 from FMC Biopolymer) | Coprocessed Lactose Monohydrate and Povidone (Example: Ludipress from BASF) | Microcrystalline Cellulose, NF (Example: Avicel PH 101/Avicel PH 102 from FMC Biopolymer) | Lactose Monohydrate, NF (Pharmatose 350 M/SuperTab 11SD from DMV - Fonterra) |
| Binders (1-6%) | PVP/HPMC | PVP/HPMC | PVP/HPMC | PVP/HPMC |
| Disintegrants (2-8%) | Croscarmellose Sodium, Crospovidone, Sodium Starch Glycolate | | | |
| Lubricants & glidants (0.2-20%) | Colloidal Silicon Dioxide, Magnesium stearate | | | |

Suitable formulation methodologies such as direct compression, dry compaction, and/or wet granulation processes were evaluated. Selected prototype compositions were tested for various physicochemical properties as shown in TABLE 2.3.

TABLE 2.3

PHYSICOCHEMICAL PROPERTIES TESTED

| Sample No. | Dosage Form | Evaluation | |
|---|---|---|---|
| | | Granular Properties | Tables Properties |
| 1 | Powder in bottle | 1. Appearance | Not Applicable |
| | | 2. Fines to Course ration | |
| 2 | Orally dispersible/ dissolvable granules | 3. Loss on drying | |
| | | 4. Flow nature | |
| | | 5. Bulk and tapped densities | |
| | | 6. Dispersibility in water | |
| | | 7. Dissolution assay | |
| | | 8. Interference assay | |
| | | 9. Filter adsorption assay | |
| 3 | Chewable tables | 1. Appearance | 1. Appearance. |
| | | 2. Flow nature | 2. Weight |
| 4 | Conventional oral tables | 3. Compressibility index | 3. Thickness. |
| | | | 4. Hardness |
| | | | 5. Friability |
| | | | 6. Disintegration Time |
| | | | 7. Dissolution assay |
| | | | 8. Interference assay |
| | | | 9. Filter adsorption assay |

4. Materials And Methods a. Test and Control Articles

Test Article: 3,4,3-L1(1,2-HOPO)
Manufacturer: Ash Stevens, Inc. (Detroit, Mich.)
Lot Number: ML-11-276
Physical Description: Pale yellow solid
Storage Conditions: Refrigerated 2-8° C. protected from light.
Analytical Materials:

| | |
|---|---|
| Purified Water, USP | HPLC Grade - Supplier: Ricca Chemical Inc. |
| Trifluoroacetic acid | ACS Grade - Supplier: Sigma Aldrich |
| Formic Acid | HPLC Grade - Supplier: EMD Chemicals |
| Acetonitrile | HPLC Grade - Supplier: Fischer Scientific |
| HPLC Column | Agilent, Eclipse XDB-C18, 4.6 × 150 mm, 5 μm |

Formulation Components:
  Croscarmellose Sodium, NF, Ph. Eur., JP (Ac-Di-Sol)
  FMC Biopolymer, Lot #TN13825327
  Crospovidone, NF, Ph. Eur., JPE (Kollidone-CLM)
  BASF, Lot #10204988Q0
  Sodium Starch Glycolate, NF
  Spectrum Chemicals, Lot #1BC0437
  Lactose Monohydrate, USP/NF, Ph. Eur., JP (SuperTab 11SD)
  DFE Pharma, Lot #10697993/5731011
  Lactose Monohydrate, USP/NF, Ph. Eur., JP (Pharmatose 300M)
  DFE Pharma, Lot #10601833/9445861
  Co-Processed Lactose monohydrate, povidone and crospovidone, NF (Ludipress)
  BASF, Lot #05266375L0
  Microcrystalline cellulose, NF (Avicel PH102)
  FMC Biopolymer, Lot #P212824001
  Co-Processed microcrystalline cellulose and guar gum, GRAS (Avicel CE-15)
  FMC Biopolymer, Lot #RH10821854
  Co-Processed microcrystalline cellulose and Carboxymethyl Cellulose, NF (Avicel RC-591)
  FMC Biopolymer, Lot #DN008820108
  Povidone, USP (Plasdone K-29/32)
  ISP Technologies, Lot #052304677
  Mannitol, USP (Mannogem)
  SPI Pharma, Lot #12000076G
  Maltodextrin, NF (Glucidex IT 19)
  Grain Processing Corporation, Lot #3084
  Colloidal Silicon Dioxide (Cab-O-Sil MSP)
  Cabot, Lot #3367714
  Hypromellose, USP, 50 mPa·S
  Spectrum Chemicals, Lot #1BJ2114
  Sodium Oleate
  Tokyo Chemical Industries Co. Ltd., Lot #3CSSIBI
  Magnesium stearate, NF (HyQual)
  Mallinckrodt, Lot #0912000002

A Prototype Preparation and Physico-Chemical Characterization

TABLE 2.4

PROTOTYPE PREPARATION AND PHYSICO-CHEMICAL CHARACTERIZATION

| | |
|---|---|
| Powder in Bottle, 1000 mg: | The API and other excipients, except sodium oleate, were passed through sieve #30 and mixed with sodium oleate (screened through mesh #40) following a geometrical addition approach. The blends were packed in glass vials (protected from light), labeled, and evaluated for the following properties: appearance, flow nature, bulk density, fines to coarse ratio, and dispersibility in water. Selected blends were evaluated for dissolution in simulated gastric fluid without enzymes, API content verification, and related substances. |
| Granules, 1000 mg: | Granules were prepared by wet granulation process, involving the following steps: (1) Sieving of the API and excipients through sieve #30. (2) Preparation of granulation fluid solution in trials where binder such as povidone and hypromellose otherwise water is used as granulating fluid. (3) Mix API and excipients geometrically using plastic spatula. (4) Granulate the blend in stainless steel vessel using plastic spatula. (5) Pass the wet granules through sieve #14 and allow it to dry in hot air oven at 60° C. until the LOD reaches below 2%. (6) Pass the dried granules though sieve #14. (7) Sieve the extragranular materials through screen #20, and blend geometrically using plastic spatula. Lubricate the granules if necessary using magnesium stearate. The granules were packed in aluminum pouches (protected from light), labeled, and evaluated for the following properties: appearance, flow nature, fines to coarse ratio, dispersibility in water, and texture. Selected formulations were evaluated for dissolution in simulated gastric fluid without enzymes, API content verification, and related substances. |
| Chewable Tablets, 500 mg: | The chewable tablets were prepared by direct compression process, involving the following steps: (1) Sieving of the API and excipients (except sodium oleate and magnesium stearate) through sieve #30. (2) Mixing of excipients and API manually. (3) Sieving of sodium oleate, and magnesium stearate through mesh #40. (4) Mixing of sieved sodium oleate with the API-excipient(s) blend. (5) Lubrication of the powder blend with sieved magnesium stearate. (6) Evaluation of the physical blends for appearance, flow nature, and compressibility. (7) Compression of the powder blends into tablets using suitable tooling. The tablets were packaged in aluminum pouches (protected from light), labeled, and evaluated for the following properties: appearance, size, hardness, friability, thickness, disintegration time. Selected tablets were evaluated for dissolution in simulated gastric fluid without enzymes, API content verification, and related substances. |
| Conventional Tablets, 500 mg: | Formulation of tablets by direct compression (DC) involved the following steps: (1) Sieving of the API and intragranular excipients (except magnesium stearate) through sieve #30. (2) Mixing of excipients and API manually. (3) Sieving of magnesium stearate through mesh #40. (4) Lubrication of the powder blend with sieved magnesium stearate. (5) Evaluation of the physical blend for appearance, flow nature, and compressibility. (6) Compression of the powder blend into tablets using suitable tooling. Formulation of tablets by wet granulation (WG) involved the following steps: (1) Sieving of the API and intra-granular excipients through sieve #30. (2) Mixing of intragranular excipients and API manually. (3) Wet granulation of the powder blend using purified water. (4) Drying of the wet granules at 60° C. until the loss on drying reaches <2.0%. (5) Screening of the dried granules through mesh #14. (6) Sieving of magnesium stearate through mesh #40. (7) Lubrication of the granules with sieved magnesium stearate. (8) Evaluation of the physical blend for appearance, flow nature, and compressibility. (9) Compression of the powder blend into tablets using suitable tooling. The tablets were packaged in glass vials (protected from light), labeled, and evaluated for the following properties: appearance, size, hardness, friability, thickness, disintegration time Selected tablets were evaluated for dissolution in simulated gastric fluid without enzymes, API content verification, and related substances. | c. Sample Preparation for Solution Assays

| | |
|---|---|
| API Content Verification: | For powder in bottle, granules, and chewable tablets crushed with a pestle and mortar, an amount of blend equivalent to 50 mg of 3,4,3-LI(1,2-HOPO) was weighed |

TABLE 2.4-continued

PROTOTYPE PREPARATION AND PHYSICO-CHEMICAL CHARACTERIZATION

| | |
|---|---|
| | and transferred accurately into a clean dry 100 mL volumetric flask. About 50 mL of diluent was added, mixed well and made up to the 100 mL mark. The flask was sonicated for about 30 minutes in ice water. For immediate release tablets, 5 tablets were added to a clean dry 1000 mL volumetric flask. About 500 mL of diluent was added, mixed well and sonicated for 90 minutes in ice water with intermittent shaking. The volume was made up to 1000 mL mark and further sonicated under ice for about 30 minutes. In all cases, the sample solution was filtered through a 0.45μ Nylon syringe filter and the filtrate was used for assay. The 3,4,3-LI(1,2-HOPO) concentration in the sample solution was about 0.5 mg/mL. Note: Throughout the sample preparation and storage, the flasks were covered with aluminum foil. The samples were placed at 5° C. in the HPLC auto-sampler just after preparation to avoid any degradation, and the run time was increased to 12 minutes to allow for column equilibration. |
| Dissolution Testing: | The dissolution testing was performed in 900 mL of simulated gastric fluid without enzymes maintained at 37 ± 0.5° C. using USP Apparatus II (Paddle) at 50 rpm. For each prototype formulation, a unit dose was added to each of 6 dissolution vessels. Aliquots of 5 mL of sample were manually withdrawn and filtered through a 0.45μ Nylon syringe filter at required time intervals. Aliquots of 5 mL of dissolution medium were replaced after sampling at each respective time point. The 3,4,3-LI(1,2-HOPO) concentration in the sample solution was about 1.1 mg/mL. Note: Throughout the sample preparation, the dissolution vessels were covered with aluminum foil. The samples were placed at 5° C. in the HPLC autosampler just after preparation to avoid any degradation, and the run time was increased to 12 minutes to allow for column equilibration. |
| Related Substances: | For powder in bottle and granule prototype formulations, one unit dose was transferred into a clean dry 250 mL volumetric flask. For tablet formulations, two tablets were crushed and transferred into a clean dry 250 mL volumetric flask. In all cases, about 200 mL of diluent was added to the flask, which was shaken in a wrist action shaker till a complete uniform dispersion was obtained (about 40 minutes). The volume was made up to the mark with diluent and mixed well. The sample solution was filtered using a 0.45μ Nylon syringe filter. Aliquots of 1 mL of the filtrate were diluted to 4 mL in a scintillation vial and chromatographed. The 3,4,3-LI(1,2-HOPO) concentration in the sample solution was about 1.0 mg/mL. Note: Throughout the sample preparation and storage, the flasks were covered with aluminum foil. |
| a. Chromatographic Assay and Purity Assessment | |
| Standard Stock Solutions: | For each standard stock solutions, the test article was weighed (200 mg) and dissolved by sonication into 30 mL of diluent (water:acetonitrile = 90%:10%). After equilibration at room temperature, the volume of the standard solution was adjusted to 50 mL. Standard stock solutions were prepared in duplicates, working standard solutions were prepared by dilution of each stock with the diluent to the desired concentrations. |
| Calibration Standards: | With each experiment, 5 calibration standard solutions at different concentrations were prepared from stock solutions using the diluent. Concentrations of the calibration standards were between 0.2 and 2.0 mg/mL. The calibration standard solutions were chromatographed to demonstrate the linearity of the calibration curve over the concentration range. |

Analytical Method I for Related Substance Assay (TABLE 2.5):

This method was previously established and validated (see 3,4,3-L1(1,2-HOPO)—Excipient Compatibility Study; EXAMPLE 1). Suitability was therefore not re-evaluated as part of this study.

Instrument: Waters Alliance 2695 liquid chromatography system

Detector: 2487 Waters Dual Wavelength Detector

Column: Agilent, Eclipse XDB-C18, 4.6×150 mm, 5

Mobile Phase A: 0.05% formic acid in 95% H2O: 5% ACN

Mobile Phase B: 0.05% formic acid in acetonitrile (ACN)

Column Temperature: 25° C.

Flow Rate: 1.0 mL/min.

Injection Volume: 20 μL

Detection: 250 nm

Run Time: 50 min

Diluent: 9:1 $H_2O$:ACN

TABLE 2.5

GRADIENT CONDITIONS

| Time (min) | A % | B % |
|---|---|---|
| 0.00 | 100 | 0 |
| 30.00 | 60 | 40 |
| 40.00 | 0 | 100 |
| 41.00 | 100 | 0 |
| 50.10 | 100 | 0 |

Analytical Method I for Related Substance Assay (TABLE 2.6):

This method was previously established and validated (see 3,4,3-L1(1,2-HOPO)—Excipient Compatibility Study; EXAMPLE 1). Suitability was therefore not re-evaluated as part of this study.

Instrument: Waters Alliance 2695 liquid chromatography system

Detector: 2487 Waters Dual Wavelength Detector

Column: Agilent, Eclipse XDB-C18, 4.6×150 mm, 5 μm.

Mobile Phase A: 0.05% formic acid in 95% H2O: 5% ACN

Mobile Phase B: 0.05% formic acid in acetonitrile (ACN)

Column Temperature: 25° C.

Flow Rate: 1.0 mL/min.

Injection Volume: 20 μL

Detection: 250 nm

Run Time: 50 min

Diluent: 9:1 $H_2O$:ACN

TABLE 2.6

GRADIENT CONDITIONS

| Time (min) | A % | B % |
|---|---|---|
| 0.00 | 100 | 0 |
| 30.00 | 60 | 40 |
| 40.00 | 0 | 100 |
| 41.00 | 100 | 0 |
| 50.10 | 100 | 0 |

Analytical Method II for API Content and Dissolution Assays (TABLE 2.7 and TABLE 2.8):

TABLE 2.7

| | |
|---|---|
| Instrument: | Waters Alliance 2695 liquid chromatography system |
| Detector: | 2487 Waters Dual Wavelength Detector |
| Column: | Waters, Symmetry C18, 2.1 × 150 mm, 5 μm. |
| Mobile Phase A: | 0.1% trifluoroacetic acid in H2O |
| Mobile Phase B: | 0.1% trifluoroacetic acid in ACN |
| Column Temperature: | 30° C. |
| Flow Rate: | 0.5 mL/min. |
| Injection Volume: | 10 μL |
| Detection: | 250 nm |
| Run Time: | 10 min |
| Diluent: | 9:1 H2O:ACN or simulated gastric fluid without enzymes, USP |

TABLE 2.8

GRADIENT CONDITIONS

| Time (min) | A % | B % |
|---|---|---|
| 0.00 | 90 | 10 |
| 3.5 | 58 | 42 |
| 4.5 | 58 | 42 |
| 5.0 | 2 | 98 |
| 6.5 | 2 | 98 |
| 7.0 | 90 | 10 |
| 10.0 | 90 | 10 |

Method II—Suitability Requirements: There should be no interference from the diluent/blank at the retention times of 3,4,3-L1(1,2-HOPO) peaks. The relative standard deviation (% RSD) for five replicate system suitability injections should be below 2.0%. The response factor of recovery check standards should be within 95-105%.

Figure 3:
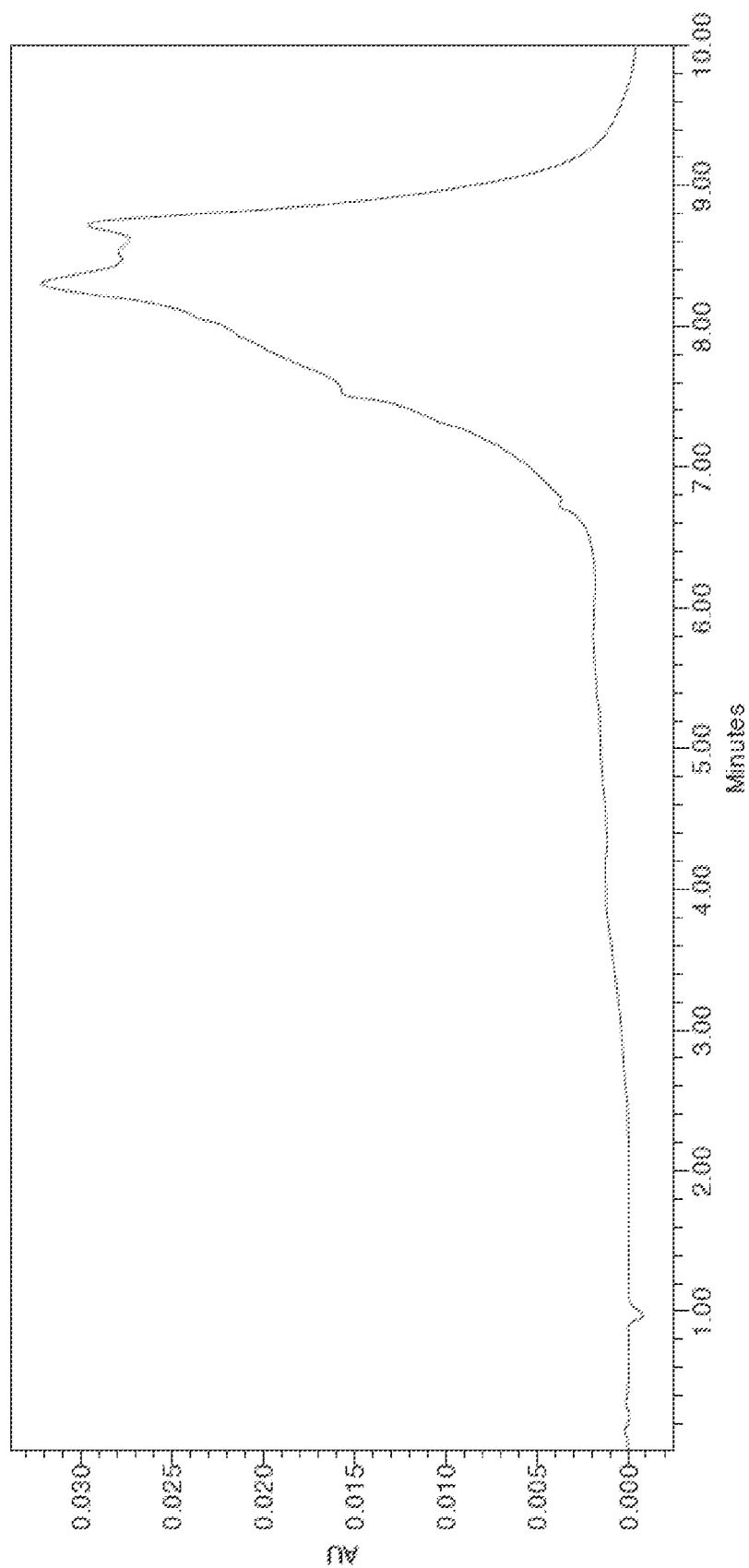
FIG. 3 shows an embodiment of a chromatogram of API verification assay diluent (9:1 water:ACN).
Figure 4:
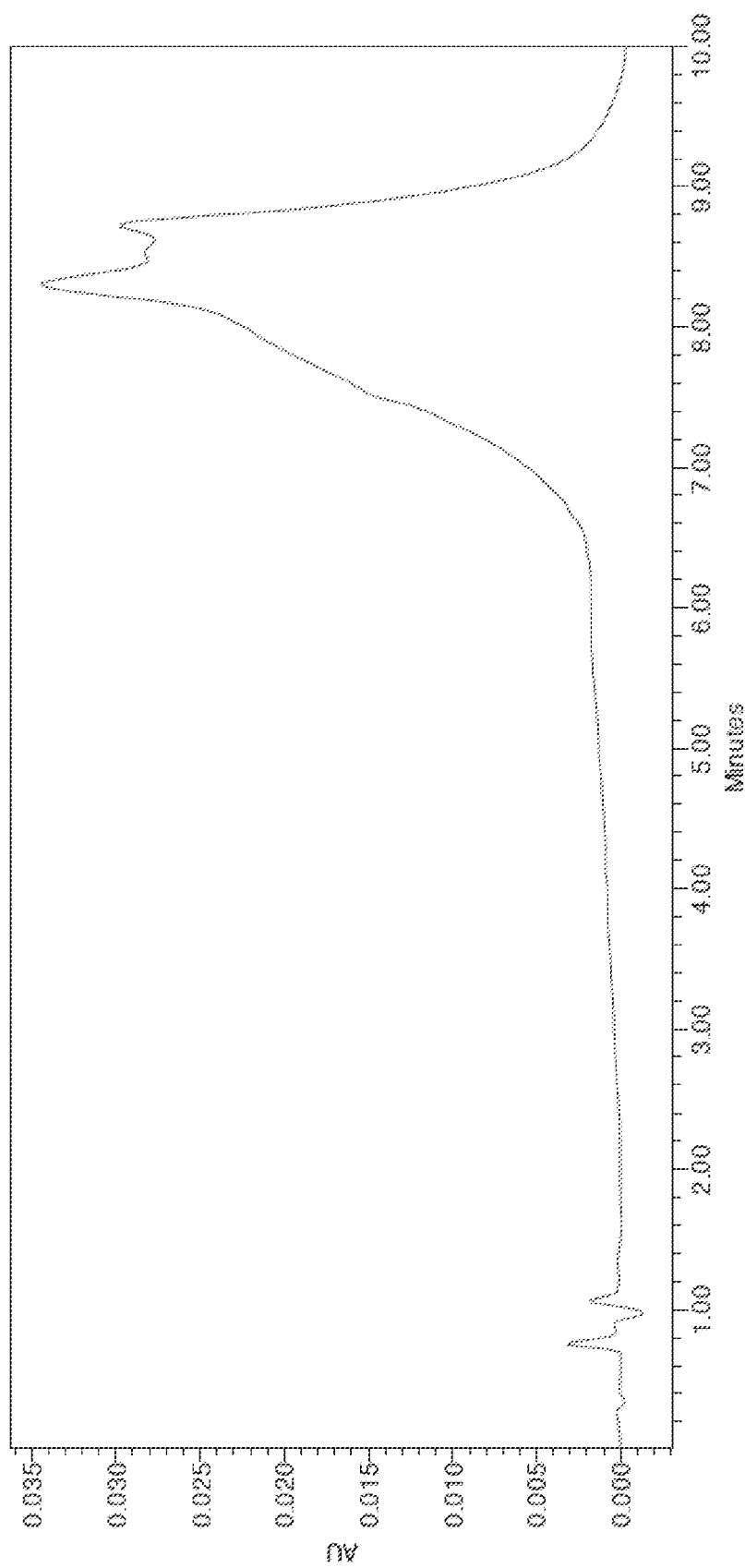
FIG. 4 shows an embodiment of a chromatogram of dissolution assay diluent (SGF without enzyme, USP).
Figure 5:
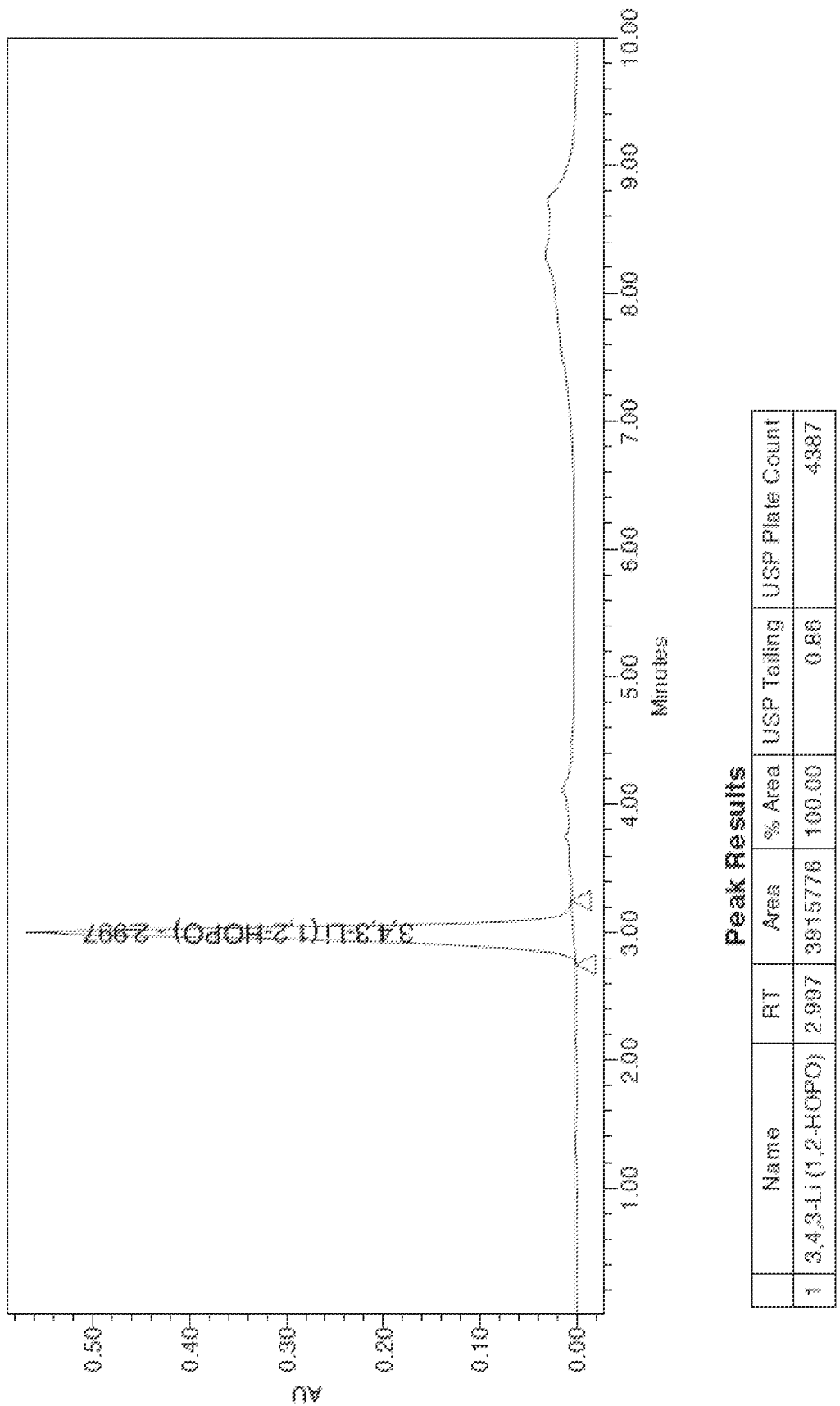
FIG. 5 shows an embodiment of a chromatogram of 3,4,3-L1(1,2-HOPO) 0.5 mg/ml in API verification assay diluent.
Figure 6:
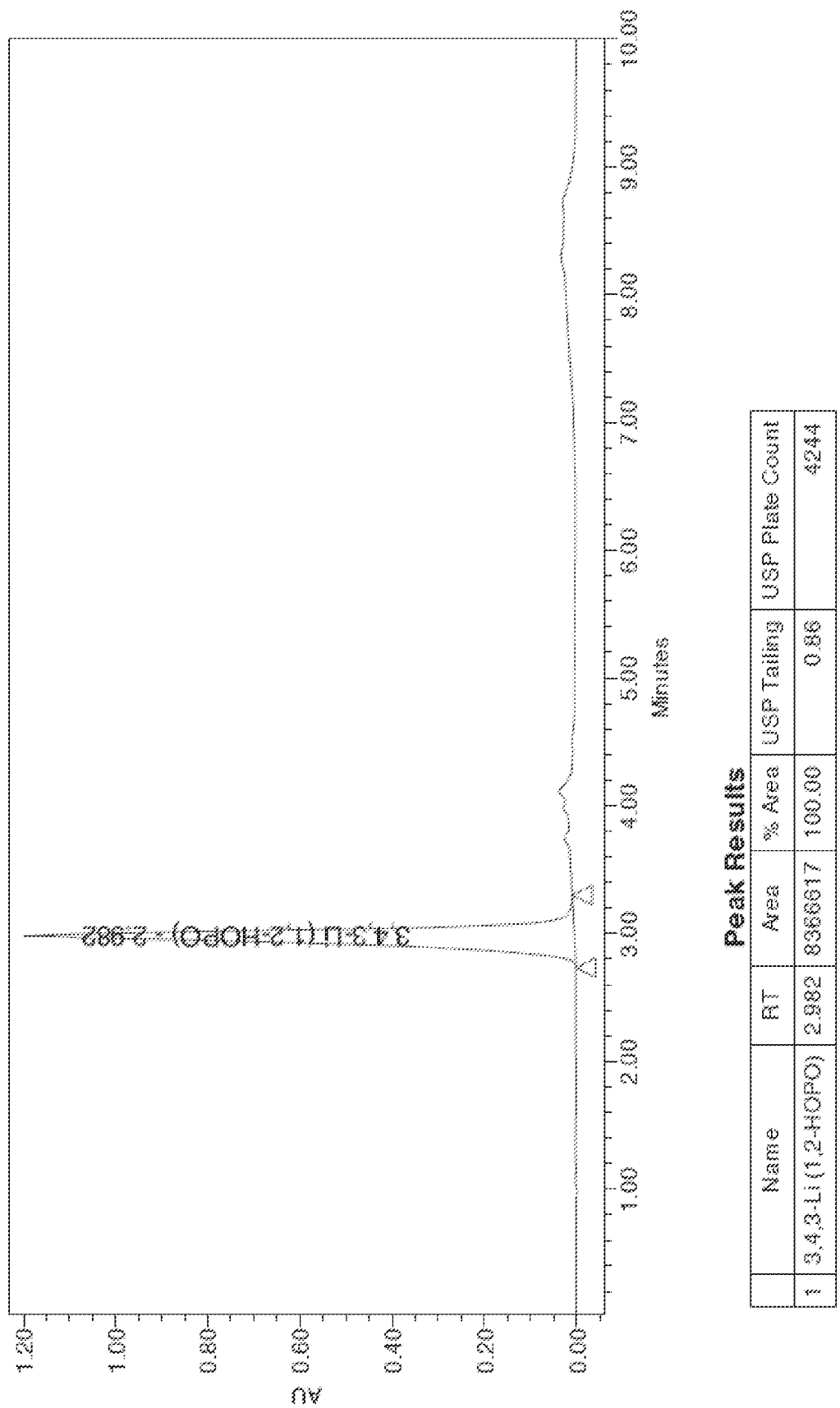
FIG. 6 shows an embodiment of a chromatogram of 3,4,3-L1(1,2-HOPO) 1.1 mg/ml in dissolution assay diluent.

Method II—Diluent Interference: There was no interference observed from the API verification assay diluent (9:1 water:ACN) and dissolution diluent (Simulated gastric fluid without enzymes, USP) at the retention times of 3,4,3-L1(1,2-HOPO). The chromatograms of API verification assay diluent and dissolution assay diluent are shown in FIG. 3 and FIG. 4, respectively. The chromatograms of 3,4,3-L1(1,2-HOPO) in API verification assay diluent and dissolution assay diluent are shown in FIG. 5 and FIG. 6, respectively.

Method II—System Suitability: The RSDs of the five standard injections were found to be less than 2.0% for both verification and dissolution assays. The recoveries of the check standards were found to be between 98.0% and 102% for both verification and dissolution assays. The results of the system suitability evaluation are shown in TABLE 2.9 and TABLE 2.10.

TABLE 2.9

3,4,3-LI(1,2-HOPO) VERIFICATION ASSAY - SYSTEM SUITABILITY EVALUATION

| Details | Weight (mg)/Concentration (mg/mL) | 3,4,3-Li(1,2-HOPO) Peak Area |
|---|---|---|
| Standard inj#1 | 25.36/0.51 | 3915776 |
| Standard inj#2 | | 3983634 |
| Standard inj#3 | | 3980352 |
| Standard inj#4 | | 3989295 |
| Standard inj#5 | | 4001175 |
| Average | | 3974046 |
| SD | | 33524.63 |
| % RSD | | 0.84 |
| Limit | | % RSD NMT 2.0 |
| Result | | Pass |
| Check Standard inj#1 | 24.75/0.50 | 3826628 |
| Check Standard inj#2 | | 3910821 |
| Average | | 3868725 |
| Check Standard Recovery % | | 100.3 |
| Limit | | % Recovery 98.0-102.0 |
| Result | | Pass |

TABLE 2.10

3,4,3-LI(1,2-HOPO) DISSOLUTION ASSAY - SYSTEM SUITABILITY EVALUATION

| Details | Weight (mg)/Concentration (mg/mL) | 3,4,3-Li(1,2-HOPO) Peak Area |
|---|---|---|
| Standard inj#1 | 28.02/1.12 | 8366617 |
| Standard inj#2 | | 8587201 |
| Standard inj#3 | | 8666099 |
| Standard inj#4 | | 8676613 |
| Standard inj#5 | | 8630739 |
| Average | | 8585454 |
| SD | | 127236.98 |
| % RSD | | 1.48 |
| Limit | | % RSD NMT 2.0 |
| Result | | Pass |
| Check Standard inj#1 | 27.30/1.09 | 8264625 |
| Check Standard inj#2 | | 8401828 |
| Average | | 8333227 |
| Check Standard Recovery % | | 100.4 |
| Limit | | % Recovery 98.0-102.0 |
| Result | | Pass |

Method II—Filter Adsorption: As filtration is an unavoidable step in the drug product sample preparation, the filters listed in TABLE 2.11 were evaluated for the adsorption of 3,4,3-L1(1,2-HOPO):

TABLE 2.11

FILTERS EVALUATED

| Verification Assay | Dissolution Assay |
|---|---|
| 0.45μ Nylon Syringe Filter | 10μ Dissolution Sample Inline- Filter |
| 0.2μ PTFE Syringe Filter | 35μ Dissolution Sample Inline- Filter |
| 0.2μ PVDF Syringe Filter | 70μ Dissolution Sample Inline- Filter |

The respective standard solution was filtered through each of the above filter and the recovery was calculated for the filtered and unfiltered solution. The results for the recovery of filtered and un filtered solution were found to be within 98.0-102.0%, which indicates, there is no significant adsorption of 3,4,3-L1(1,2-HOPO) with the above studied filters, therefore, any of the above filters may be selected for the sample preparation. The results of the filter study are shown below in TABLE 2.12.

TABLE 2.12

3,4,3-LI(1,2-HOPO) - FILTER ADSORPTION EVALUATION

| | Verification Assay | | | Dissolution Assay | |
|---|---|---|---|---|---|
| Filter | Peak Area | % Recovery* | Filter | Peak Area | % Recovery* |
| 0.45µ Nylon | 3865675 | 100.6 | 10µ Filter | 8669826 | 99.8 |
| 0.2µ PTFE | 3878512 | 101.0 | 35µ Filter | 8575232 | 98.7 |
| 0.2µ PVDF | 3842269 | 100.0 | 70µ Filter | 8637276 | 99.5 |
| Un-Filtered | 386492 | 100.6 | Un-Filtered | 8653392 | 99.6 |

5. Results a. Powder in Bottle (PIB) Dosage Forms

Powder in bottle (PIB) is one of the most convenient dosage form used in early stage clinical development because of its ease of use. In comparison with capsules, PIB can carry large dose and fill weights. TABLE 2.13 shows the compositions of PIB evaluated. The reason for evaluating each composition is also described. The target was to identify a suitable composition that can form uniform dispersion when diluted with water, and also exhibit immediate drug release characteristics. TABLE 2.14 describes the corresponding properties of the evaluated formulations.

TABLE 2.13

3,4,3-LI(1,2-HOPO) POWDER IN BOTTLE (PIB) FORMULATION COMPOSITIONS

| | | Formulation ID (Unit Quantity in g) | | | | | | | | | | |
|---|---|---|---|---|---|---|---|---|---|---|---|---|
| Ingredients ↓ | Objective → | A1 API Ctrl | A2 API + PE | A3 Use of Providone as dispersibility enhancer | A4 | A5 | A6 Use of Hypromellos as dispersibility enhancer | A7 | A8 | A9 Use of Avicel as dispersibility enhancer | A10 | A11 |
| 3,4,3-Li(1,2-HOPO) | | 1.000 | 1.000 | 1.000 | 1.000 | 1.000 | 1.000 | 1.000 | 1.000 | 1.000 | 1.000 | 1.000 |
| Sodium Oleate | | | 0.092 | 0.092 | 0.092 | 0.092 | 0.092 | 0.092 | 0.092 | 0.092 | 0.092 | 0.092 |
| Providone, USP (Plasdone K-29/32) | | | | 0.250 | 0.500 | 1.000 | | | | | | |
| Hypromellose, 50 cps, USP | | | | | | | 0.250 | 0.500 | 1.000 | | | |
| Microcrystalline Cellulose and Carboxymethyl Cellulose, NF (Avivel RC-591) | | | | | | | | | | 0.250 | 0.500 | 1.000 |
| Unite Weight (g) | | 1.000 | 1.092 | 1.342 | 1.592 | 2.092 | 1.342 | 1.592 | 2.092 | 1.342 | 1.592 | 2.092 |

TABLE 2.14

3,4,3-LI(1,2-HOPO) POWDER IN BOTTLE (PIB) FORMULATION PROPERTIES

| | Formulation ID and Physico-Chemical Properties | | | | | | | | | | |
|---|---|---|---|---|---|---|---|---|---|---|---|
| Parameters | A1 | A2 | A3 | A4 | A5 | A6 | A7 | A8 | A9 | A10 | A11 |
| Appearance | Off-white color uniform blend | | | | | | | | | | |
| Flow of blend/granules through Funnel (Flodex orifice dia. In mm) | 10 | 10 | 14 | 14 | 16 | 12 | 14 | 14 | 12 | 14 | 16 |
| Bulk Density (g/mL) | 0.51 | 0.53 | — | — | — | — | — | — | — | — | 0.42 |
| Fines (% passed through mesh #40) | 61 | 63 | — | — | — | — | — | — | — | — | 68 |
| Dispersibility in 10 mL water | | | Formation of sticky mass | | | | | | Formation of uniform dispersion | Formation of uniform dispersion | |

The API 3,4,3-L1(1,2-HOPO) and all other compositions except A9 to A11 formed a sticky mass when reconstituted in water. This behavior was considerably reduced after incorporation of Avicel RC-591 (a co-processed excipient of Microcrystalline Cellulose and Carboxymethyl Cellulose). Composition A11 prepared using a 1:1 drug:excipient ratio formed a uniform dispersion and was therefore evaluated using the API content verification assay and the dissolution in simulated gastric fluid without enzymes assay. Both assays were also performed with composition A2 (API+ permeation enhancer sodium oleate blend) for comparison, as described further in this report.

b. Orally Dispersible/Dissolvable Granules

Orally Dispersible/Dissolvable Granules are similar to commercially available "Sprinkles" where the granules of 3,4,3-L1(1,2-HOPO) can be directly transferred into the mouth from individually packed pouches/sachets and swallowed with or without water. TABLE 2.15 shows various compositions of orally dispersible/dissolvable granules evaluated. The reason for evaluating each composition is also described.

TABLE 2.15

3,4,3-LI(1,2-HOPO) DISPERSIBLE/DISSOLVABLE GRANULE FORMULATION COMPOSITIONS

| Ingredients ↓ | Effect of → | G1 | G2 | G3 | G4 | G5 | G6 | G7 | G8 | G9 | G10 | G11* | G12* |
|---|---|---|---|---|---|---|---|---|---|---|---|---|---|
| | | Diluents without Sodium Oleate | | | Diluents with Sodium Oleate | | | PVP on Gritty feel | | HPMC on gritty feel | | Milled API | Milled API |
| Intra-Granular Materials | | | | | | | | | | | | | |
| 3,4,3-Li(1,2-HOPO) | | 1.000 | 1.000 | 1.000 | 1.000 | 1.000 | 1.000 | 1.000 | 1.000 | 1.000 | 1.000 | 1.000 | 1.000 |
| Sodium Oleate | | — | — | — | 0.092 | 0.092 | 0.092 | 0.092 | 0.092 | 0.092 | 0.092 | 0.092 | 0.092 |
| Croscarmellose Sodium, NF (Ac-Di-Sol) | | 0.075 | 0.075 | 0.075 | 0.075 | 0.075 | 0.075 | 0.075 | 0.075 | 0.075 | 0.075 | 0.075 | 0.075 |
| Microcrystalline Cellulose and guar gum, NF (Avicel CE-15) | | 1.910 | — | — | 1.833 | — | — | 1.821 | — | 1.821 | — | 1.833 | — |
| Lactose Monohydrate, NF (Pharmatose 300 M) | | — | 1.910 | — | — | 1.833 | — | — | 1.821 | — | 1.821 | — | 1.533 |
| Mannitol, USP (Mannogem) | | — | — | 1.910 | — | — | 1.833 | — | — | — | — | — | — |
| Povidone, USP (Plasdone K-29/32) | | — | — | — | — | — | — | 0.012 | 0.012 | — | — | — | — |
| Purified Water, USP | | Q.S. | Q.S. | Q.S. | Q.S. | Q.S. | Q.S. | Q.S. | Q.S. | Q.S. | Q.S. | Q.S. | Q.S. |
| Extra-Granular Materials | | | | | | | | | | | | | |
| Magensium sterate, NF (HyQual) | | 0.015 | 0.015 | 0.015 | — | — | — | — | — | — | — | — | — |
| Hypromellose, 50 cps | | — | — | — | — | — | — | — | — | 0.012 | 0.012 | — | 0.300 |
| Unit Weight (g) | | 3.000 | 3.000 | 3.000 | 3.000 | 3.000 | 3.000 | 3.000 | 3.000 | 3.000 | 3.000 | 3.000 | 3.000 |

The target was to identify a suitable composition that can impart smooth feel in the mouth, and also exhibit immediate drug release characteristics. TABLE 2.16 describes the corresponding properties of the evaluated formulations.

TABLE 2.16

3,4,3-LI(1,2-HOPO) DISPERSIBLE/DISSOLVABLE GRANULE FORMULATION PROPERTIES

| Parameters | G1 | G2 | G3 | G4 | G5 | G6 | G7 | G8 | G9 | G10 | G11* | G12* |
|---|---|---|---|---|---|---|---|---|---|---|---|---|
| Flow of blend/granules through Funnel (Flodex orifice dia. In mm) | 10 | 12 | 12 | 12 | 12 | 10 | 12 | 12 | 12 | 12 | 14 | 14 |
| Dispersibility in 10 mL water | Uniform Dispersion | | | API settled at the bottom of the beaker | | | | | | | Uniform Dispersion | |
| Files (% passed through mesh #40) | 28 | 32 | 48 | 26 | 34 | 46 | 23 | 30 | 23 | 28 | 23 | 29 |

TABLE 2.16-continued 3,4,3-LI(1,2-HOPO) DISPERSIBLE/DISSOLVABLE GRANULE FORMULATION PROPERTIES

| Parameters | Formulation ID and Physico-Chemical Properties | | | | | | | | | | | |
|---|---|---|---|---|---|---|---|---|---|---|---|---|
|  | G1 | G2 | G3 | G4 | G5 | G6 | G7 | G8 | G9 | G10 | G11* | G12* |
| Texture of granules when wetted with water | | | | | Gritty | | | | | | Smooth | Slight gritty. Turns smooth over time |

Among various compositions evaluated, G11, which was formulated using co-processed microcrystalline cellulose (Avicel CE-15) showed smooth feel when wetted with water. Composition G12, which was formulated using Lactose monohydrate (Pharmatose 300 M), was also showed smooth feel after few minutes of wetting. Based on these observations, compositions G11 and G12 were further tested for the API verification assay and the dissolution in simulated gastric fluid without enzymes assay. The results are described further in this report.

c. Chewable Tablets

Chewable tablets are formulated for use in the mouth. They are usually uncoated, and are formulated to provide a release and absorption of the active ingredient(s) in the mouth/buccal cavity or from stomach. TABLE 2.17 shows the various chewable tablet compositions evaluated. The target was to identify a suitable composition that can be formulated by direct compression process, and shows immediate drug release characteristics. TABLE 2.18 describes the corresponding properties of the evaluated formulations.

Compositions C13 and C21 showed satisfactory physical properties (absence of segregation, friability, and disintegration). These compositions were, together with Composition C11, further tested for the API verification assay and the dissolution in simulated gastric fluid without enzymes assay. The results are described further in this report.

TABLE 2.17

3,4,3-LI(1,2-HOPO) CHEWABLE TABLET COMPOSITIONS

| Ingredients ↓ | Formulation ID (Unit Quantity in g) | | | | | | | | | | | |
|---|---|---|---|---|---|---|---|---|---|---|---|---|
|  | C1 | C2 | C3 | C4 | C5 | C6 | C7 | C8 | C9 | C10 | C11 | C12 |
| 3,4,3-LI(1,2-HOPO) | 1.000 | 1.000 | 1.000 | 1.000 | 1.000 | 0.500 | 0.500 | 1.000 | 0.500 | 1.000 | 0.500 | 0.500 |
| Sodium Oleate | — | — | — | — | — | — | — | — | — | — | 0.046 | — |
| Croscarmellos Sodium, NF (Ac-Di-Sol) | 0.075 | 0.075 | — | 0.075 | 0.075 | — | — | 0.075 | 0.075 | 0.076 | 0.075 | — |
| Microcrystalline Cellulose and guar gum, FN (Avicel CE-15) | 1.400 | — | — | — | 0.350 | — | — | 1.400 | 1.900 | — | 1.854 | — |
| Lactose Monohydrate, Povidone and Crospovidone, NF (Ludipress) | — | 1.400 | — | — | — | — | — | — | — | — | — | 1.975 |
| Lactos Monohydrate, NF (SuperTab 11 SD) | — | — | 1.475 | — | 1.050 | 1.480 | 0.490 | — | — | 0.350 | — | — |
| Mannitol, USP (Mannogem) | — | — | — | 1.400 | — | — | — | — | — | — | — | — |
| Maltodextrin, NF | — | — | — | — | — | — | — | — | — | — | — | — |
| Magensium sterate, NF (HyQual) | 0.025 | 0.025 | 0.025 | 0.025 | 0.025 | 0.020 | 0.010 | 0.025 | 0.025 | 0.025 | 0.025 | 0.025 |
| Unit Total Weight (g) | 2.500 | 2.500 | 2.500 | 2.500 | 2.500 | 2.500 | 1.000 | 2.500 | 2.500 | 2.500 | 2.500 | 2.500 |

|  | C13 | C14 | C15 | C16 | C17 | C18 | C19 | C20 | C21 | C11A | C13A | C21A |
|---|---|---|---|---|---|---|---|---|---|---|---|---|
| 3,4,3-LI(1,2-HOPO) | 0.500 | 0.500 | 0.500 | 0.500 | 1.000 | 0.500 | 0.500 | 0.500 | 0.500 | 0.500 | 0.500 | 0.500 |
| Sodium Oleate | 0.046 | — | — | — | — | — | 0.046 | — | 0.046 | 0.005 | 0.005 | 0.005 |
| Croscarmellos Sodium, NF (Ac-Di-Sol) | — | 0.075 | 0.075 | 0.075 | 0.075 | 0.075 | 0.075 | 0.075 | 0.075 | 0.008 | — | 0.008 |
| Microcrystalline Cellulose and guargum, FN (Avicel CE-15) | — | — | — | — | — | — | — | 0.950 | 0.927 | 0.185 | — | 0.093 |

TABLE 2.17-continued 3,4,3-LI(1,2-HOPO) CHEWABLE TABLET COMPOSITIONS

Formulation ID (Unit Quantity in g)

| Ingredients ↓ | C1 | C2 | C3 | C4 | C5 | C6 | C7 | C8 | C9 | C10 | C11 | C12 |
|---|---|---|---|---|---|---|---|---|---|---|---|---|
| Lactose Monohydrate, Povidone and Crospovidone, NF (Ludipress) | 1.929 | — | — | — | — | — | — | — | — | — | 0.193 | — |
| Lactos Monohydrate, NF (SuperTab 11 SD) | — | 1.900 | — | — | — | — | — | — | — | — | — | — |
| Mannitol, USP (Mannogem) | — | — | 1.900 | — | — | — | — | 0.950 | 0.927 | — | — | 0.093 |
| Maltodextrin, NF | — | — | — | 1.900 | 1.100 | 1.600 | 1.554 | — | — | — | — | — |
| Magensium sterate, NF (HyQual) | 0.025 | 0.025 | 0.025 | 0.025 | 0.025 | 0.025 | 0.025 | 0.025 | 0.025 | 0.003 | 0.003 | 0.003 |
| Unit Total Weight (g) | 2.500 | 2.500 | 2.500 | 2.500 | 2.200 | 2.200 | 2.200 | 2.500 | 2.500 | 0.250 | 0.250 | 0.250 |

TABLE 2.18

3,4,3-LI(1,2-HOPO) CHEWABLE TABLET PROPERTIES

Formulation ID and Properties

| Parameters ↓ | C1 | C2 | C3 | C4 | C5 | C6 |
|---|---|---|---|---|---|---|
| Visual signs of segregation* | — | Segregation | Segregation | Segregation | Segregation | Segregation |
| Flow of blend/granules through funnel | Free flow | Free flow | Free flow | Free flow | Free flow | Free flow |
| Tablet tool size | 20 mm Round beveled edge | 20 mm Round beveled edge | 20 mm Round beveled edge | 20 mm Round beveled edge | 20 mm Round beveled edge | 20 mm Round beveled edge |
| Hardness (kp) | 6-7 | 7 | 11 | 6-7 | 8 | 8 |
| Friability (%) | Fail** | Fail** | Fail** | Fail** | Fail** | Fail** |
| Thickness (mm) | — | — | — | — | — | — |
| Disintegration time (min) | — | — | — | — | — | — |

| | C13 | C14 | C15 | C16 | C17 | C18 |
|---|---|---|---|---|---|---|
| Visual signs of segregation | NA | Segregation | Segregation | Segregation | Segregation | Segregation |
| Flow of blend/granules flow through funnel | Free flow | Free flow | Free flow | Free flow | Free flow | Free flow |
| Tablet tool size | 20 mm Round beveled edge | 20 mm Round beveled edge | 20 mm Round beveled edge | 20 mm Round beveled edge | 20 mm Round beveled edge | 20 mm Round beveled edge |
| Hardness (kp) | 22 | 17 | 18 | NA | NA | NA |
| Friability (%) | 0.57 | Fail** | Fail** | Fail** | Fail** | Fail** |
| Thickness (mm) | 6.23 | NA | NA | NA | NA | NA |
| Disintegration time (min) | 4 | NA | NA | NA | NA | NA |

TABLE 2.18-continued

| Parameters ↓ | C7 | C8 | C9 | C10 | C11 | C12 |
|---|---|---|---|---|---|---|
| Visual signs of segregation* | Segregation | NA | — | Segregation | Segregation | — |
| Flow of blend/granules through funnel | Free flow | Free flow | Free flow | Free flow | Free flow | Free flow |
| Tablet tool size | 16 mm Round beveled edge | 20 mm Round beveled edge | 20 mm Round beveled edge | 20 mm Round beveled edge | 20 mm Round beveled edge | 20 mm Round beveled edge |
| Hardness (kp) | 10 | 17 | 20 | 17 | 20 | 22 |
| Friability (%) | Fail** | Fail** | 0.35 | Fail** | 0.23 | 0.56 |
| Thickness (mm) | — | — | NA | NA | 6.43 | NA |
| Disintegration time (min) | — | — | >25 (gel) | NA | >25 | 5 |

| Parameters ↓ | C19 | C20 | C21 | C11A[x] | C13A[x] | C21A[x] |
|---|---|---|---|---|---|---|
| Visual signs of segregation | Segregation | NA | NA | NA | Segregation | NA |
| Flow of blend/granules flow through funnel | Free flow | Free flow | Free flow | Free flow | Free flow | Free flow |
| Tablet tool size | 20 mm Round beveled edge | 20 mm Round beveled edge | 20 mm Round beveled edge | 20 mm Round beveled edge | 20 mm Round beveled edge | 20 mm Round beveled edge |
| Hardness (kp) | NA | 23 | 25 | 9 | 12 | 11 |
| Friability (%) | Fail** | 0.38 | 0.27 | 0.004 | 0.04 | 0.008 |
| Thickness (mm) | NA | NA | 6.39 | 3.92 | 3.75 | 3.86 |
| Disintegration time (min) | NA | 5 | 5 | 15 | 10 | 10 |

*3,4,3-LI(1,2-HOPO) is brown, allowing visual monitoring of segregation after blending with excipients, Segregation is not ideal as it may result in content uniformity issues.
**>1.00% loss of tablet weight when rotated 100 times in friability tester.
[x]Smaller tablets with 50 mg API load.

d. Conventional Tablets

Various compositions and processes (Direct compression & Wet granulation) were evaluated to formulate conventional tablets with 1000, 750 and/or 500 mg drug load. The target was to identify a suitable composition that shows immediate drug release characteristics. Tables 2.19-2.22 show various tablet compositions and processes evaluated. The tablets were evaluated for various physical properties, and the results are summarized in TABLE 2.19-TABLE 2.22.

Tablet compositions T44, T45, T50, and T51 showed ideal tablets properties (compressibility, friability, hardness, and disintegration). Compositions T44 and T45 were prepared by wet granulation process, and Compositions 50 and 51 were prepared by direct compression. As direct compression is generally a preferred process based drug stability, manufacturing time, and cost aspects, Compositions T50 and T51 were considered ideal, and their verification assay and dissolution in simulated gastric fluid without enzymes were tested. The results are shown further in this report.

TABLE 2.19

3,4,3-LI(1,2-HOPO) CONVENTIONAL TABLET COMPOSITIONS AND PROPERTIES (COMPOSITION T1-T12)

| Ingredients ↓ Process → | ID → | T1 DC | T2 DC | T3 DC | T4 DC | T5 DC | T6 DC | T7 DC | T8 DC | T9 DC | T10 DC | T11 DC | T12 DC |
|---|---|---|---|---|---|---|---|---|---|---|---|---|---|
| Intra-Granular Materials ||||||||||||||
| 3,4,3-L1(1,2-HOPO) | | 1.000 | 1.000 | 1.000 | 1.000 | 1.000 | 0.500 | 0.500 | 1.000 | 0.500 | 1.000 | 0.500 | 0.500 |
| Sodium Oleate | | — | — | — | — | — | — | — | — | — | — | — | — |
| Croscarmellos Sodium, NF (Ac-Di-Sol) | | — | 0.075 | — | — | 0.075 | 0.075 | 0.075 | — | 0.075 | — | — | 0.075 |
| Crosspovidone, NF (Kollidone-CL M) | | — | — | 0.075 | — | — | — | — | — | — | 0.075 | — | — |
| Sodium starch glycolate, NF | | — | — | — | 0.075 | — | — | — | — | — | — | 0.075 | — |
| Microcrystalline Cellulose, FN (Avicel PH 102) | | — | — | — | 0.200 | — | — | — | — | — | — | — | 0.200 |
| Lactose Monohydrate, NF (SuperTab 11 SD) | | — | — | — | — | — | 0.200 | — | — | — | — | — | — |
| Mannitol, USP (Mannogem) | | — | — | — | — | — | — | 0.200 | — | — | — | — | — |
| Magensium sterate, NF (HyQual) | | 0.010 | 0.011 | 0.011 | 0.011 | — | — | — | 0.010 | 0.011 | 0.011 | 0.011 | — |
| Colloidal silicone dioxide, NF (Cab-O-Sil M5P) | | — | — | — | — | — | — | — | — | — | — | — | — |
| Purified Water, USP | | — | — | — | — | — | — | — | — | — | — | — | — |
| Extra-Granular Materials ||||||||||||||
| Croscarmellos Sodium, NF (Ac-Di-Sol) | | — | — | — | — | — | — | — | — | — | — | — | — |
| Colloidal silicone dioxide, NF (Cab-O-Sil M5P) | | — | — | — | — | — | — | — | — | — | — | — | — |
| Magensium sterate, NF (HyQual) | | — | — | — | — | — | — | — | — | — | — | — | — |
| Unit Total Weight (g) | | 1.010 | 1.086 | 1.086 | 1.086 | 1.275 | 1275 | 1.275 | 1.010 | 1.086 | 1.086 | 1.086 | 1.275 |
| Physical Properties ||||||||||||||
| Flow of blend/ granules flow through Funnel | | No rat hole |||||||||||
| Tablet Tooling/ Dimension (mm) | | | 10 × 20 | | 8.1 × 19.1 | | 10 × 20 | | | 8.1 × 19.1 | | | 10 × 20 |
| Hardness (kp) | | — | — | — | — | — | — | — | — | — | — | — | — |
| Friability (%) | | — | — | — | — | — | — | — | — | — | — | — | — |
| Thickness (mm) | | — | — | — | — | — | — | — | — | — | — | — | — |
| Disintegration time (min) | | — | — | — | — | — | — | — | — | — | — | — | — |
| Observations | | Chipping and capping observed during compression |||||||||||

TABLE 2.20

3,4,3-LI(1,2-HOPO) CONVENTIONAL TABLET COMPOSITIONS AND PROPERTIES (COMPOSITION T13-T25)

| Ingredients ↓ Process → | ID → | T13 DC | T14 DC | T15 DC | T16 DC | T17 DC | T18 DC | T19 DC | T20 DC | T21 DC | T22 WG | T23 WG | T24 WG | T25 WG |
|---|---|---|---|---|---|---|---|---|---|---|---|---|---|---|
| Intra-Granular Materials |||||||||||||||
| 3,4,3-LI(1,2-HOPO) | | 1.000 | 1.000 | 1.000 | 1.000 | 1.000 | 1.000 | 1.000 | 1.000 | 1.000 | 1.000 | 1.000 | 1.000 | 1.000 |
| Sodium Oleate | | — | — | — | — | — | — | — | — | — | — | — | — | — |
| Croscarmellos Sodium, NF (Ac-Di-Sol) | | 0.075 | 0.075 | — | 0.075 | — | — | 0.075 | 0.075 | 0.075 | 0.075 | 0.075 | 0.075 | 0.075 |
| Crosspovidone, NF (Kollidone-CL M) | | — | — | — | — | 0.075 | — | — | — | — | — | — | — | — |

TABLE 2.20-continued 3,4,3-LI(1,2-HOPO) CONVENTIONAL TABLET COMPOSITIONS AND PROPERTIES (COMPOSITION T13-T25)

| Ingredients ↓   ID → Process → | T13 DC | T14 DC | T15 DC | T16 DC | T17 DC | T18 DC | T19 DC | T20 DC | T21 DC | T22 WG | T23 WG | T24 WG | T25 WG |
|---|---|---|---|---|---|---|---|---|---|---|---|---|---|
| Sodium starch glycolate, NF | — | — | — | — | — | 0.075 | — | — | — | — | — | — | — |
| Microcrystalline Cellulose, FN (Avicel PH 102) | — | — | — | — | — | — | 0.200 | — | — | — | 0.200 | — | — |
| Lactos Monohydrate, NF (SuperTab 11 SD) | 0.200 | — | — | — | — | — | — | 0.200 | — | — | — | 0.200 | — |
| Mannitol, USP (Mannogem) | — | 0.200 | — | — | — | — | — | — | 0.200 | — | — | — | 0.200 |
| Magensium sterate, NF (HyQual) | — | — | 0.010 | 0.011 | 0.011 | 0.011 | 0.013 | 0.013 | 0.013 | — | — | — | — |
| Colloidal silicone dioxide, NF (Cab-O-Sil M5P) | — | — | 0.020 | 0.022 | 0.022 | 0.022 | 0.026 | 0.026 | 0.026 | — | — | — | — |
| Purified Water, USP | — | — | — | — | — | — | — | — | — | Q.S. | Q.S. | Q.S. | Q.S. |
| Extra-Granular Materials | | | | | | | | | | | | | |
| Croscarmellos Sodium, NF (Ac-Di-Sol) | — | — | — | — | — | — | — | — | — | — | — | — | — |
| Colloidal silicone dioxide, NF (Cab-O-Sil M5P) | — | — | — | — | — | — | — | — | — | — | — | — | — |
| Magensium sterate, NF (HyQual) | — | — | — | — | — | — | — | — | — | 0.011 | 0.013 | 0.013 | 0.013 |
| Unit Total Weight (g) | 1.275 | 1.275 | 1.030 | 1108 | 1.108 | 1.108 | 1.314 | 1.314 | 1.314 | 1.086 | 1.288 | 1.288 | 1.288 |
| Physical Properties | | | | | | | | | | | | | |
| Flow of blend/ granules flow through Funnel | No rat hole | | | | | | | | | | | | |
| Tablet Tooling/ Dimension (mm) | 10 × 20 | 8.1 × 19.1 | 10 × 20, modified oval tooling | | | | | | | | | | |
| Hardness (kp) | — | — | — | — | — | — | — | — | — | — | — | — | — |
| Friability (%) | — | — | — | — | — | — | — | — | — | — | — | — | — |
| Thickness (mm) | — | — | — | — | — | — | — | — | — | — | — | — | — |
| Disintegration time (min) | — | — | — | — | — | — | — | — | — | — | 27 | — | — |
| Observations | Except for T23, all compositions showed chipping during compression | | | | | | | | | | | | |

TABLE 2.21

3,4,3-LI(1,2-HOPO) CONVENTIONAL TABLET COMPOSITIONS AND PROPERTIES (COMPOSITION T26-T38)

| Ingredients ↓   ID → Process → | T26 WG | T27 WG | T28 WG | T29 WG | T30 WG | T31 WG | T32 WG | T33 DC | T34 DC | T35 DC | T36 DC | T37 DC | T38 DC |
|---|---|---|---|---|---|---|---|---|---|---|---|---|---|
| Intra-Granular Material | | | | | | | | | | | | | |
| 3,4,3-LI(1,2-HOPO) | 1.000 | 1.000 | 1.000 | 1.000 | 1.000 | 0.500 | 0.750 | 0.500 | 0.750 | 0.750 | 0.500 | 0.500 | 0.500 |
| Sodium Oleate | — | — | — | — | — | — | — | — | — | — | — | — | — |
| Croscarmellos Sodium, NF (Ac-Di-Sol) | 0.040 | 0.040 | 0.040 | 0.040 | 0.040 | 0.040 | 0.040 | 0.075 | 0.075 | 0.075 | 0.050 | 0.050 | 0.040 |
| Crosspovidone, NF (Kollidone-CL M) | — | — | — | — | — | — | — | — | — | — | — | — | — |
| Sodium starch glycolate, NF | — | — | — | — | — | — | — | — | — | — | — | — | — |
| Microcrystalline Cellulose, FN (Avicel PH 102) | 0.270 | 0.270 | 0.217 | — | — | 0.712 | 0.462 | 0.712 | 0.462 | 0.313 | 0.209 | 0.308 | — |
| Lactose Monohydrate, NF (SuperTab 11 SD) | — | — | — | 0.217 | — | — | — | — | — | — | — | — | 0.209 |
| Mannitol, USP (Mannogem) | — | — | — | — | 0.217 | — | — | — | — | — | — | — | — |
| Magensium sterate, NF (HyQual) | | | | | | | | | | | | | |

TABLE 2.21-continued 3,4,3-LI(1,2-HOPO) CONVENTIONAL TABLET COMPOSITIONS AND PROPERTIES (COMPOSITION T26-T38)

| Ingredients ID → <br> ↓ Process → | T26 WG | T27 WG | T28 WG | T29 WG | T30 WG | T31 WG | T32 WG | T33 DC | T34 DC | T35 DC | T36 DC | T37 DC | T38 DC |
|---|---|---|---|---|---|---|---|---|---|---|---|---|---|
| Colloidal silicone dioxide, NF (Cab-O-Sil M5P) | — | — | 0.052 | 0.052 | 0.052 | — | — | 0.013 | 0.013 | 0.012 | 0.004 | 0.004 | 0.009 |
| Purified Water, USP | Q.S. | Q.S. | Q.S. | Q.S. | Q.S. | Q.S. | Q.S. | — | — | — | — | — | — |
| Extra-Granular Materials | | | | | | | | | | | | | |
| Croscarmellos Sodium, NF (Ac-Di-Sol) | 0.035 | 0.035 | 0.035 | 0.035 | 0.035 | 0.035 | 0.035 | — | — | — | — | — | — |
| Colloidal silicone dioxide, NF (Cab-O-Sil M5P) | — | 0.026 | 0.026 | 0.026 | 0.026 | — | — | — | — | — | — | — | — |
| Magensium sterate, NF (HyQual) | 0.013 | 0.013 | 0.014 | 0.014 | 0.014 | 0.013 | 0.013 | 0.013 | 0.013 | 0.012 | 0.004 | 0.004 | 0.004 |
| Unit Total Weight (g) | 1.358 | 1.384 | 1.384 | 1.384 | 1.384 | 1.300 | 1.300 | 1.313 | 1.313 | 1.162 | 0.766 | 0.866 | 0.761 |
| Physical Properties | | | | | | | | | | | | | |
| Flow of blend/granules flow through Funnel | | | | | | No rat hole | | | | | | | |
| Tablet Tooling/Dimension (mm) | | | | | | 10 × 20 | | | | | | 8.1 × 19.1 | |
| Hardness (kp) | 14-16 | 14-16 | 14-16 | NA | NA | 14-18 | 14-17 | 14-17 | 14-17 | 14-16 | 8.0-11.0 | 13-15 | NA |
| Friability (%) | 0.18 | 0.19 | 0.18 | NA | NA | 0.19 | 0.22 | 0.21 | 0.20 | 0.16 | 0.14 | 0.16 | NA |
| Thickness (mm) | 8.65 | 8.73 | 8.69 | NA | NA | 8.92 | 8.54 | 8.97 | 8.48 | 6.96 | 5.49 | 5.63 | NA |
| Disintegration time (min) | 26 | 27 | 26 | NA | NA | 4 | 10 | 3 | 8 | 6 | 9 | 8 | NA |
| Observations | | Slow disintegration | | Chipping | | | Good tablets but do not contain sodium oleate | | | | | | Chipping |

TABLE 2.22

3,4,3-LI(1,2-HOPO) CONVENTIONAL TABLET
COMPOSITIONS AND PROPERTIES (COMPOSITION T39-T51)

| Ingredients | T39 | T40 | T41 | T42 | T43 | T44 | T45 | T46 | T47 | T48 | T49 | T50 | T51 |
|---|---|---|---|---|---|---|---|---|---|---|---|---|---|
| | DC | WG | WG | WG | WG | WG | WG | WG | WG | DC | DC | DC | DC |
| | | | | | | | Process | | | | | | |
| | | | | | | | ID | | | | | | |
| | | | | | | Intra-Granular Materials | | | | | | | |
| 3,4,3-LI(1,2-HOPO) | 0.500 | 0.500 | 0.500 | 0.750 | 1.000 | 0.750 | 0.500 | 0.500 | 0.750 | 0.500 | 0.750 | 0.500 | 0.500 |
| Sodium Oleate | — | — | — | — | — | 0.069 | 0.046 | 0.046 | 0.069 | 0.046 | 0.069 | 0.046 | 0.046 |
| Croscarmellos Sodium, NF (Ac-Di-Sol) | 0.040 | 0.040 | 0.040 | 0.075 | 0.040 | 0.040 | 0.040 | 0.040 | 0.040 | 0.075 | 0.075 | 0.084 | 0.092 |
| Crosspovidone, NF (Kollidone-CL M) | — | — | — | — | — | — | — | — | — | — | — | — | — |
| Sodium starch glycolate, NF | — | — | — | — | — | — | — | — | — | — | — | — | — |
| Microcrystalline Cellulose, FN (Avicel PH 102) | — | — | — | — | 0.200 | 0.313 | 0.308 | — | — | — | 0.313 | 0.410 | 0.501 |
| Lactose Monohydrate, NF (SuperTab 11 SD) | 0.308 | 0.209 | 0.308 | 0.313 | — | — | — | 0.308 | 0.313 | 0.308 | — | — | — |
| Mannitol, USP (Mannogem) | — | — | — | — | — | — | — | — | — | — | — | — | — |
| Magensium sterate, NF (HyQual) | — | — | — | — | — | — | — | — | — | — | — | — | — |
| Colloidal silicone dioxide, NF (Cab-O-Sil M5P) | 0.009 | 0.009 | 0.009 | 0.012 | — | — | — | — | — | 0.005 | 0.006 | 0.005 | 0.006 |
| Purified Water, USP | — | — | — | — | — | 0.080 | 0.090 | 0.060 | 0.070 | — | — | — | — |
| | | | | | Extra-Granular Materials | | | | | | | | |
| Croscarmellos Sodium NF (Ac-Di-Sol) | — | — | — | — | 0.035 | 0.035 | 0.035 | 0.035 | 0.035 | — | — | — | — |
| Colloidal silicone dioxide, NF (Cab-O-Sil M5P) | — | — | — | — | — | — | — | — | — | — | — | — | — |
| Magensium sterate, NF (HyQual) | 0.004 | 0.004 | 0.004 | 0.006 | 0.013 | 0.015 | 0.009 | 0.009 | 0.012 | 0.005 | 0.006 | 0.005 | 0.006 |
| Unit Total Weight (g) | 0.861 | 0.761 | 0.861 | 1.156 | 1.380 | 1.302 | 1.028 | 0.998 | 1.289 | 0.938 | 1.219 | 1.050 | 1.151 |
| | | | | | Physical Properties | | | | | | | | |
| Flow of blend/granules flow through Funnel | | | | | No rat hole | | | | | No rat hole, 14 mm orifice | | | |
| Tablet Tooling/ Dimension (mm) | | 8.1 × 19.1 | | 11.0-13.0 | 10 × 20 | | 8.1 × 19.1 | | 10 × 20 | 9.2 × 18.9 | 10 × 20 | 9.2 × 18.9 | |
| | | | | | | | | | | | Modified oval | | |
| Hardness (kp) | NA | 8.0-11.0 | 8.0-11 | 11.0-13.0 | — | 13-6 | 13-6 | — | — | 12.0-16.0 | 14-18 | 15-18 | 18-20 |
| Friability (%) | NA | .014 | .014 | .019 | — | .018 | .015 | — | — | .011 | .009 | 0.12 | 0.13 |
| Thickness (mm) | NA | 5.42 | 5.82 | 6.72 | — | 6.82 | 6.15 | — | — | 5.99 | 7.48 | 7.72 | 7.96 |
| Disintegration time (min) | NA | 11 | 10 | 14 | — | 11 | 13 | — | — | 9 | 11 | 6 | 4 |
| Observations | Chipping | Good but no sodium oleate | | | Chipping | Good tablets | | Chipping | Chipping | Good (slow dissolution) | | Good tablets | | e. Selected Prototypes: Appearance and API Verification Assay

Figure 7:
FIG. 7 shows the appearance and packaging of embodiments of powder in bottle compositions A2 (left) and A11 (right).
Figure 8:
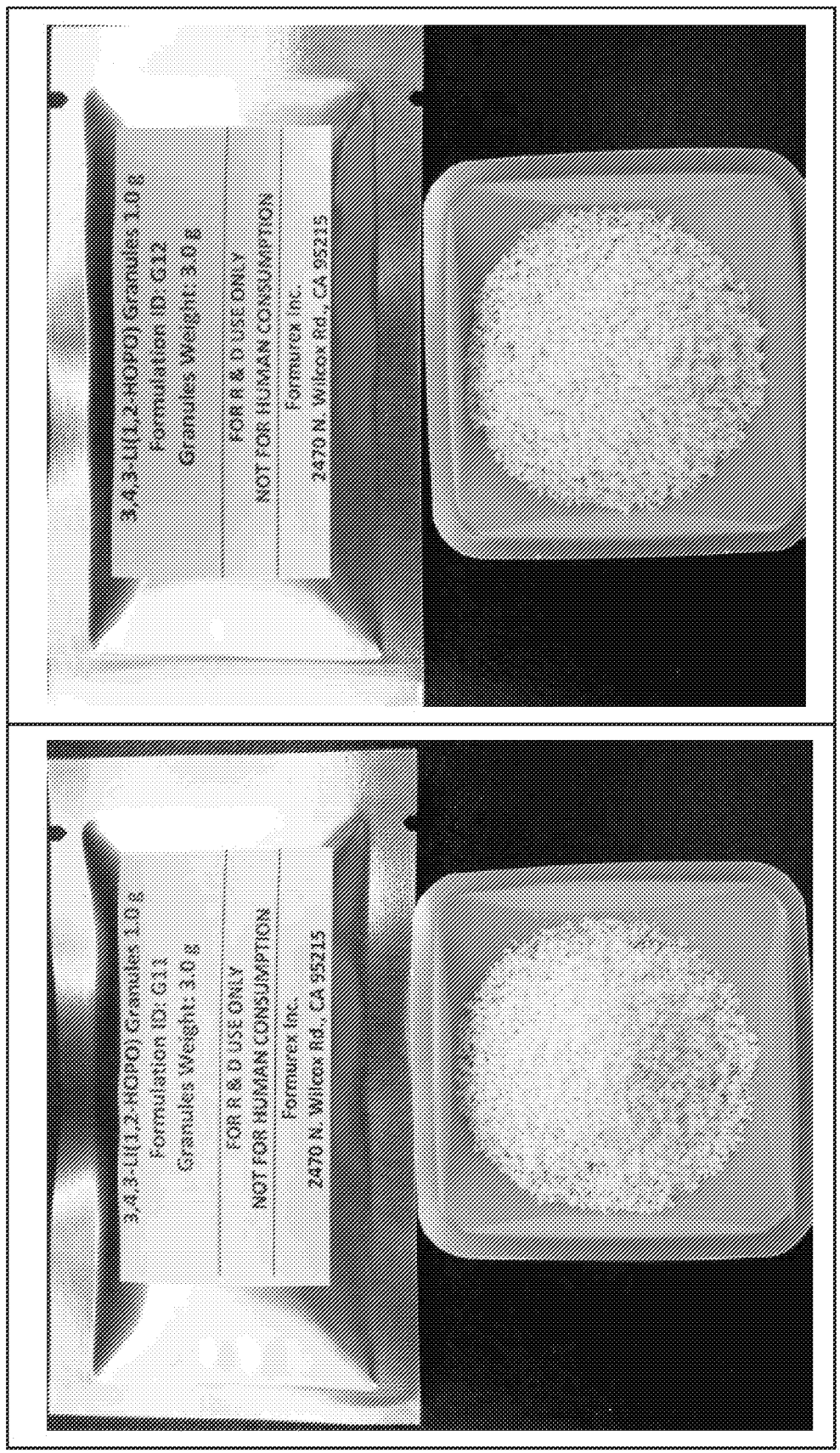
FIG. 8 shows the appearance and packaging of embodiments of granule compositions G11 (left) and G12 (right).
Figure 9:
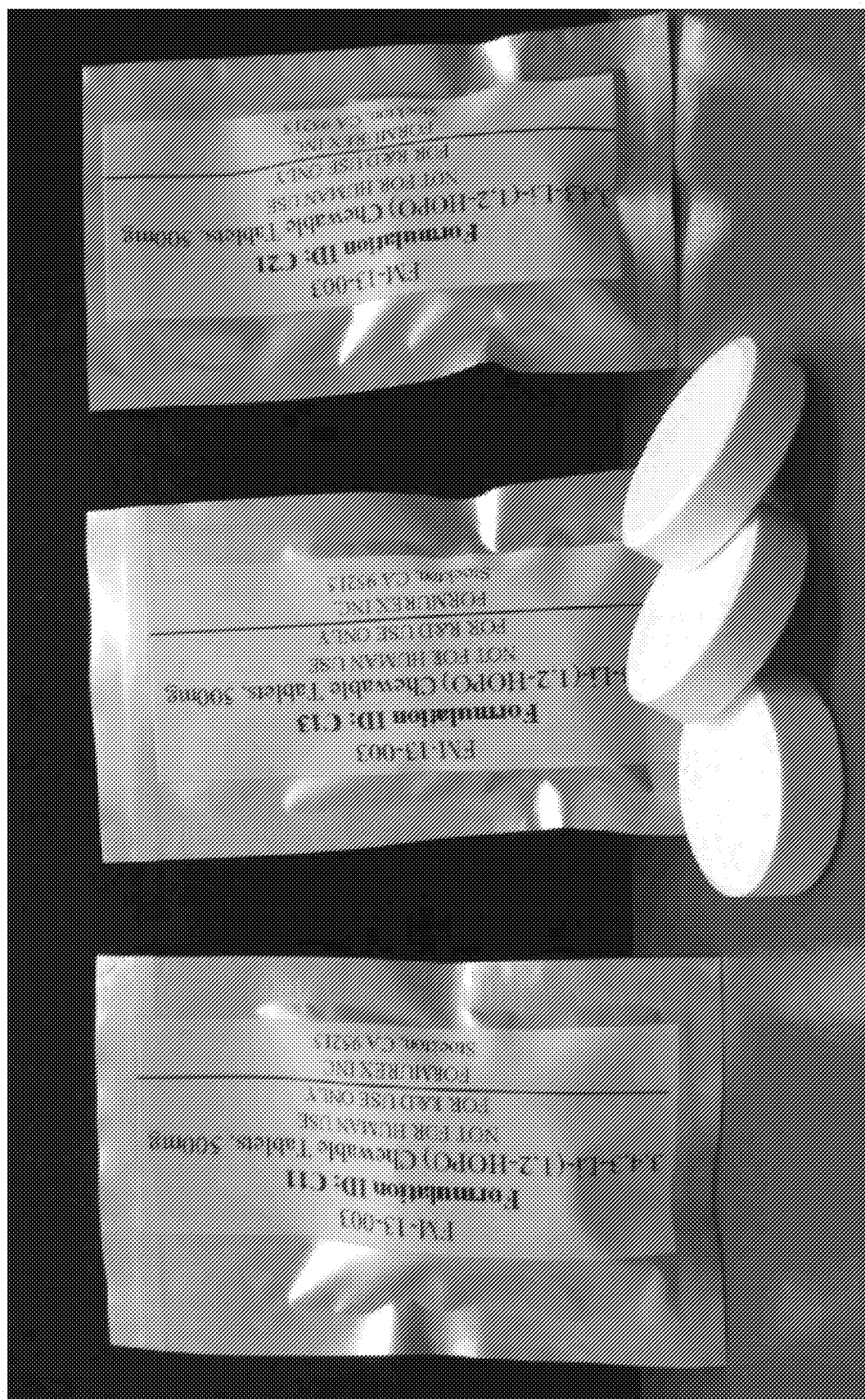
FIG. 9 shows the appearance and packaging of embodiments of chewable tablet compositions C11 (left), C13 (center) and C21 (right).
Figure 10:
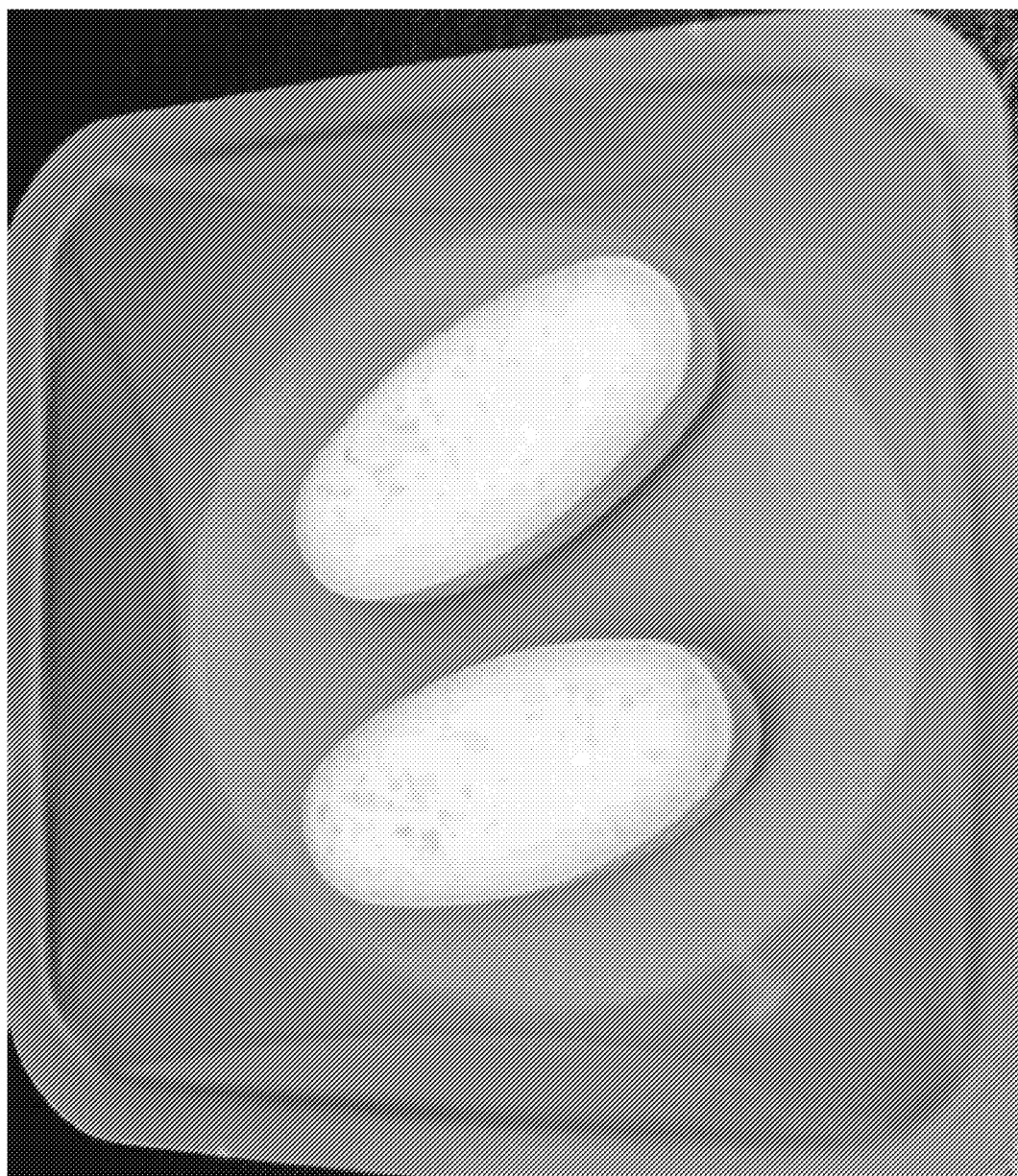
FIG. 10 shows the appearance and packaging of embodiments of tablet compositions T50 (left) and T51 (right).

Based on the development studies performed, nine formulation prototypes that showed immediate drug release behavior and required physical properties were identified and selected for further testing: Powder in bottle compositions A2 and A11, granule compositions G11 and G12, chewable tablet compositions C11, C13, and C21, and immediate release tablet compositions T50 and T51. The appearance and packaging of selected powder in bottle formulation prototypes A2 and A11 are shown in FIG. 7 (left) and FIG. 7 (right), respectively. The appearance and packaging of selected granule formulation prototypes G11 and G12 are shown in FIG. 8 (left) and FIG. 8 (right), respectively. The appearance and packaging of selected chewable tablet formulation prototypes C11, C13 and C21 are shown in FIG. 9 (left), FIG. 9 (center) and FIG. 9 (right), respectively. The appearance and packaging of selected tablet formulation prototypes T50 and T51 are shown in FIG. 10 (left) and FIG. 10 (right), respectively.

These selected prototype formulations were assayed for their content of 3,4,3-L1(1,2-HOPO) as per the methods outlined for the content verification assay. In general, all the tested formulations were found to contain 90-110% of the label claim of 3,4,3-L1(1,2-HOPO). TABLE 2.23 lists the verification assay values obtained for each of them.

TABLE 2.23

API CONTENT VERIFICATION ASSAY FOR SELECTED PROTOTYPE FORMULATIONS

| Formulation ID | Prototype formulation | Verification Assay (% W/W)* |
|---|---|---|
| A2 | Powder in bottle | 101.2 |
| A11 |  | 104.1 |
| G11 | Dispersible/dissolvable | 105.0 |
| G12 | granules | 106.5 |
| C11 | Chewable tablets | 104.5 |
| C13 |  | 107.2 |
| C21 |  | 103.0 |
| T50 | Convention tablets | 105.7 |
| T51 |  | 104.6 |

*Values were calculated based on bulk drug substance (API) as a standard and assuming purity to be 100%

In the sample preparation from chewable tablets, the tablets were ground in a mortar and pestle due to the fact that the tablet matrix material gels up upon exposure to the diluent thereby, hindering complete extraction into the assay medium upon either shaking (by a wrist action shaker) or sonication. The grinding of the tablet matrix aids in complete extraction of the analyte. Extraction from the intact dosage form in the other prototype formulations is complete as observed from the values in TABLE 2.23.

f. Selected Prototypes: Dissolution Assay

Gastric fluid dissolution testing of the prototype formulations was carried out detailed in the methods section. In general, more than 80% of the API was released within 45 minutes of dissolution testing in all the formulations tested. The results of the studies are listed in TABLE 2.24-TABLE 2.27.

TABLE 2.24

GASTRIC FLUID DISSOLUTION RESULTS FOR POWER IN BOTTLE PROTOTYPES

| Time point(s) | 10 min | 15 min | 30 min | 45 min | Inf.* |
|---|---|---|---|---|---|
| Formulation ID# A-2 | | | | | |
| Unit#1 | 96.35 | 99.51 | 100.08 | 101.20 | 100.40 |
| Unit#2 | 91.21 | 97.08 | 99.42 | 99.03 | 98.67 |
| Unit#3 | 98.12 | 100.67 | 100.81 | 100.62 | 99.68 |
| Average | 95.2 | 99.1 | 100.1 | 100.3 | 99.6 |
| SD | 3.59 | 1.83 | 0.70 | 1.12 | 0.87 |
| RSD | 3.77 | 1.85 | 0.69 | 1.12 | 0.87 |
| Formulation ID# A-11 | | | | | |
| Unit#1 | 93.09 | 96.02 | 97.03 | 97.12 | 103.54 |
| Unit#2 | 92.84 | 96.18 | 98.04 | 97.83 | 103.28 |
| Unit#3 | 93.60 | 96.30 | 98.34 | 98.53 | 103.60 |
| Average | 93.2 | 96.2 | 97.8 | 97.8 | 103.5 |
| SD | 0.39 | 0.14 | 0.69 | 0.71 | 0.17 |
| RSD | 0.41 | 0.15 | 0.70 | 0.72 | 0.16 |

*Infinity (Inf.) timepoint: 15 min at 250 rpm after 45 min

TABLE 2.25

GASTRIC FLUID DISSOLUTION RESULTS FOR GRANULE PROTOTYPES

| Time point(s) | 10 min | 15 min | 30 min | 45 min | Inf.* |
|---|---|---|---|---|---|
| Formulation ID# G-11 | | | | | |
| Unit#1 | 103.04 | 102.07 | 101.56 | 101.45 | 103.07 |
| Unit#2 | 107.16 | 107.18 | 108.27 | 108.87 | 110.31 |
| Unit#3 | 106.80 | 106.72 | 106.61 | 107.31 | 107.83 |
| Average | 105.7 | 105.3 | 105.5 | 105.9 | 107.1 |
| SD | 2.28 | 2.83 | 3.49 | 3.91 | 3.68 |
| RSD | 2.16 | 2.68 | 3.31 | 3.70 | 3.44 |
| Formulation ID# G-12 | | | | | |
| Unit#1 | 79.94 | 90.14 | 101.72 | 102.63 | 103.11 |
| Unit#2 | 81.51 | 90.79 | 103.73 | 104.71 | 105.25 |
| Unit#3 | 81.44 | 90.19 | 102.27 | 103.58 | 104.20 |
| Average | 81.0 | 90.4 | 102.6 | 103.6 | 104.2 |
| SD | 0.89 | 0.36 | 1.04 | 1.04 | 1.07 |
| RSD | 1.10 | 0.40 | 1.01 | 1.00 | 1.03 |

*Infinitiy (Inf.) timepoint: 15 min at 250 rpm after 45 min

TABLE 2.26

GASTRIC FLUID DISSOLUTION RESULTS FOR CHEWABLE TABLET PROTOTYPES

| Time point(s) | 10 min | 15 min | 30 min | 45 min | Inf.* |
|---|---|---|---|---|---|
| Formulation ID# C-11 | | | | | |
| Tablet#1 | 26.88 | 35.09 | 95.33 | 94.51 | 97.06 |
| Tablet#2 | 13.01 | 21.69 | 69.36 | 102.36 | 103.69 |
| Tablet#3 | 15.69 | 27.93 | 71.94 | 98.38 | 99.91 |
| Average | 18.5 | 28.2 | 78.9 | 98.4 | 100.2 |
| SD | 7.36 | 6.71 | 14.31 | 3.93 | 3.33 |
| RSD | 39.71 | 23.75 | 18.14 | 3.99 | 3.32 |
| Formulation ID# C-13 | | | | | |
| Tablet#1 | 42.55 | 55.99 | 94.99 | 100.92 | 101.97 |
| Tablet#2 | 42.24 | 62.84 | 101.29 | 104.19 | 104.13 |
| Tablet#3 | 36.48 | 63.54 | 98.46 | 102.78 | 103.25 |
| Average | 40.4 | 60.8 | 98.2 | 102.6 | 103.1 |
| SD | 3.42 | 4.17 | 3.16 | 1.64 | 1.09 |
| RSD | 8.45 | 6.86 | 3.21 | 1.60 | 1.05 |
| Formulation ID# C-21 | | | | | |
| Tablet#1 | 42.39 | 75.87 | 100.65 | 101.37 | 101.29 |
| Tablet#2 | 56.86 | 85.14 | 102.60 | 101.68 | 101.83 |

TABLE 2.26-continued

GASTRIC FLUID DISSOLUTION RESULTS FOR CHEWABLE TABLET PROTOTYPES

| Time point(s) | 10 min | 15 min | 30 min | 45 min | Inf.* |
|---|---|---|---|---|---|
| Tablet#3 | 52.38 | 81.93 | 98.88 | 100.23 | 99.93 |
| Average | 50.5 | 81.0 | 100.7 | 101.1 | 101.0 |
| SD | 7.41 | 4.71 | 1.86 | 0.76 | 0.98 |
| RSD | 14.65 | 5.81 | 1.85 | 0.76 | 0.97 |

*Infinitiy (Inf.) timepoint: 15 min at 250 rpm after 45 min

TABLE 2.27

GASTRIC FLUID DISSOLUTION RESULTS FOR CONVENTIONAL TABLET PROTOTYPES

| Time point(s) | 10 min | 15 min | 30 min | 45 min | Inf.* |
|---|---|---|---|---|---|
| Formulation ID# T-50 | | | | | |
| Tablet#1 | 67.91 | 77.18 | 82.05 | 85.01 | 104.25 |
| Tablet#2 | 55.87 | 70.15 | 83.97 | 86.63 | 105.11 |
| Tablet#3 | 50.18 | 62.85 | 76.36 | 80.11 | 015.18 |
| Average | 58.0 | 70.1 | 80.8 | 83.9 | 104.8 |
| SD | 9.05 | 7.17 | 3.96 | 3.39 | 0.52 |
| RSD | 15.61 | 10.23 | 4.90 | 4.05 | 0.49 |
| Formulation ID# T-51 | | | | | |
| Tablet#1 | 91.44 | 92.95 | 94.53 | 96.45 | 103.04 |
| Tablet#2 | 83.54 | 87.30 | 90.26 | 91.48 | 102.25 |
| Tablet#3 | 81.76 | 87.69 | 90.42 | 92.24 | 104.70 |
| Average | 85.6 | 89.3 | 91.7 | 93.4 | 103.3 |
| SD | 5.15 | 3.16 | 2.42 | 2.68 | 1.25 |
| RSD | 6.02 | 3.53 | 2.64 | 2.87 | 1.21 |

*Infinitiy (Inf.) timepoint: 15 min at 250 rpm after 45 min g. Selected Prototypes: Related Substance Assay The related substances, estimated as area (%) from the chromatograms, and the chromatographic purity of 3,4,3-LI(1,2-HOPO) in selected prototype formulations are listed in TABLE 2.28. For all tested compositions, the amount of related substances found in the prototype formulations is comparable to that present in the drug substance used as control.

TABLE 2.28

CHROMATOGRAPHIC API PURITY AND RELATED SUBSTANCES PRESENT IN PROTOTYPE FORMULATIONS

| | | Chromatographic Purity of 3,4,3-LI(1,2-HOPO) and Related Substances | | | | | | |
|---|---|---|---|---|---|---|---|---|
| Name of Peak | RRT | Drug Substance Control | Powder in Bottle | | Granules | | Immediate Release Tablets | Chewable Tables |
| | | | A2 | A11 | G11 | G12 | T51 | C21 |
| 3,4,3-LI (1,2-HOPO) | — | 97.45 | 97.71 | 97.64 | 97.70 | 97.69 | 97.72 | 97.71 |
| Unknown | 0.59 | 0.01 | 0.03 | 0.02 | 0.02 | 0.02 | 0.01 | 0.01 |
| Unknown | 0.61 | 0.01 | 0.04 | 0.03 | 0.03 | 0.03 | 0.03 | 0.03 |
| Unknown | 0.62 | 0.01 | 0.04 | 0.03 | 0.03 | 0.03 | 0.02 | 0.03 |
| Unknown | 0.87 | 0.11 | 0.16 | 0.14 | 0.15 | 0.17 | 0.15 | 0.14 |
| Unknown | 0.89 | 0.13 | 0.07 | 0.08 | 0.07 | 0.11 | 0.08 | 0.09 |
| Unknown | 1.02 | 0.08 | 0.07 | 0.07 | 0.08 | 0.06 | 0.09 | 0.07 |
| Unknown | 1.11 | 0.04 | 0.06 | 0.05 | 0.05 | 0.04 | 0.05 | 0.04 |
| Unknown | 1.27 | 0.17 | 0.16 | 0.18 | 0.17 | 0.17 | 0.18 | 0.19 |
| Unknown | 1.30 | 0.10 | 0.13 | 0.09 | 0.11 | 0.13 | 0.12 | 0.11 |
| Unknown | 1.39 | 0.20 | 0.13 | 0.13 | 0.13 | 0.13 | 0.13 | 0.13 |
| Unknown | 1.40 | 0.04 | 0.02 | 0.02 | 0.02 | 0.01 | 0.01 | 0.02 |
| Unknown | 1.46 | 0.60 | 0.46 | 0.49 | 0.50 | 0.47 | 0.49 | 0.52 |
| Unknown | 1.74 | 0.15 | 0.12 | 0.14 | 0.13 | 0.12 | 0.12 | 0.13 |
| Unknown | 1.89 | 0.18 | 0.14 | 0.16 | 0.14 | 0.14 | 0.14 | 0.14 |
| Unknown | 2.17 | 0.33 | 0.27 | 0.32 | 0.28 | 0.27 | 0.27 | 0.28 |
| Unknown | 2.30 | 0.05 | 0.06 | 0.07 | 0.06 | 0.06 | 0.05 | 0.06 |
| Unknown | 2.58 | 0.25 | 0.23 | 0.24 | 0.23 | 0.22 | 0.22 | 0.22 |
| Unknown | 2.79 | 0.11 | 0.11 | 0.12 | 0.10 | 0.10 | 0.10 | 0.10 |
| Unknown | 0.59 | 0.01 | 0.03 | 0.02 | 0.02 | 0.02 | 0.01 | 0.01 |
| Unknown | 0.61 | 0.01 | 0.04 | 0.03 | 0.03 | 0.03 | 0.03 | 0.03 |
| Unknown | 0.62 | 0.01 | 0.04 | 0.03 | 0.03 | 0.03 | 0.02 | 0.03 |

6. Conclusion

The feasibility of developing oral formulations for 3,4,3-L1(1,2-HOPO) was evaluated. Four oral dosage forms were investigated: (i) powder in bottle, (ii) dispersible/dissolvable granules, (iii) chewable tablets, and (iv) conventional immediate release tablets. Based on the studies performed, nine formulation prototypes that showed immediate drug release behavior and required physical properties were identified and selected for API verification, gastric fluid dissolution, and related substance testing following defined liquid chromatography methods. Among these selected compositions, two are powder in bottle formulations, two are granule formulations, three are chewable tablet formulations, and two are conventional tablet formulations. All assays confirmed that these prototypes are suitable for further development. The stability of these formulations will be evaluated prior to a first-in-human trial for 3,4,3-L1(1,2-HOPO). These stability studies will also include capsules containing the powder in bottle composition A2, which may be the optimal dosage form for adjusting does levels in clinical settings.

Example 3—Evaluation of Stability of Prototype Oral Formulations of the Active Pharmaceutical Ingredient 3,4,3-L1(1,2-HOPO)

Summary

The objective of this study was to evaluate the stability of prototype oral formulations of the active pharmaceutical ingredient 3,4,3-L1(1,2-HOPO) under 25° C./60% RH and 40° C./75% RH storage conditions over six months. The clinical dose of 3,4,3-L1(1,2-HOPO) is expected to be in the range of 1-2 grams per unit. In order to retain the flexibility of dosing lower and higher dose strengths in clinical evaluation, several oral formulations were included in this work:

Powder for Reconstitution (500 mg)
Immediate Release Tablets (500 mg)
Chewable Tablets (500 mg)
Capsules (500 mg)
Capsules (100 mg)
Placebo Capsules (size 00)
Placebo Capsules (size 4)

The following is a summary of observations and trends observed in the stability study of 3,4,3-L1(1,2-HOPO) prototype formulations.

There was no change in physical appearance of the prototype formulations and placebos upon storage at 25° C./60% RH and at 40° C./75% RH for 6 months.

The moisture content increased slightly in powder for reconstitution prototype formulation stored at 40° C./75% RH. In all the other formulations including the placebos the moisture content is comparable to the values observed in T0 samples.

The hardness of the chewable and immediate release tablets decreased slightly upon storage when compared to their values at T0.

Development of a rancid odor upon storage at 25° C./60% RH and at 40° C./75% RH was observed in all prototype formulations except in powder for reconstitution. The development of rancid odor was also observed in the placebos for 3,4,3-L1(1,2-HOPO) capsules when stored at 25° C./60% RH and at 40° C./75% RH.

No major changes in the dissolution profiles of the prototype formulations were noted in the stability study samples. The dissolution of 3,4,3-L1(1,2-HOPO) from chewable tablets and immediate release tablets appear to be slightly faster in the stability study samples than what was observed in T0 samples. All the samples tested released more than 85% of the label claim for 3,4,3-L1(1,2-HOPO) in 45 minutes.

Assay, % Label claim of 3,4,3-L1(1,2-HOPO)) in prototype dosage form was found to be between 90-110% in all the stability study samples analyzed as well as the T0 samples.

Chromatographic purity measured for prototype formulations in the stability study varied slightly in the samples upon storage at 25° C./60% RH and at 40° C./75% RH when compared to that observed at T0.

1. Purpose of Study

The purpose of this study was to provide data that can be used to support research efforts. It was not conducted in accordance with U.S. Food and Drug Administration (FDA) "Good Laboratory Practice for Nonclinical Laboratory Studies" (GLP) regulations, as described in 21 CFR Part 58. However, the study was planned, performed, recorded, and reported in accordance with standard practices to ensure data quality and integrity.

2. Objective of Study

The objective of this study was to evaluate the stability of prototype oral formulations of the active pharmaceutical ingredient)3,4,3-L1(1,2-HOPO) under 25° C./60% RH and 40° C./75% RH storage conditions over six months. The clinical dose of 3,4,3-L1(1,2-HOPO) is expected to be in the range of 1-2 grams per unit. In order to retain the flexibility of dosing lower and higher dose strengths in clinical evaluation, several oral formulations were included in this work:

Powder for Reconstitution (500 mg)

Immediate Release Tablets (500 mg)

Chewable Tablets (500 mg)

Capsules (500 mg)

Capsules (100 mg)

Placebo Capsules (size 00)

Placebo Capsules (size 4)

3. Experimental Design

Prototype formulations were selected based on the results of a previous formulation development study (3,4,3-L1(1,2-HOPO)—Formulation Development; EXAMPLE 2), and are presented below in TABLE 3.1 and TABLE 3.2.

All prototype formulations and placebo capsules were staged in this stability study under 25±2° C./60±5% RH or 40±2° C./75±5% RH storage conditions for 6 months, with sampling at 1, 3, 6 months and at T0 (initial). TABLE 3.3 shows the packaging configuration for all the prototype formulations.

A variety of tests were applied to each sample at each sampling time point, as detailed in TABLE 3.4.

TABLE 3.1

COMPOSITION OF PROTOTYPE FORMULATIONS
OF 3,4,3-LI(1,2-HOPO)

| | Quantity in unit dosage form (mg) | | | | |
|---|---|---|---|---|---|
| Ingredients | Prototype Powder for Reconstitution Formulation ID #A11 | Immediate Release Tablets Formulation ID #T51 | Chewable Tablets Formulation ID #C21 | Capsules (500 mg) 3,4,3-LI(1,2-HOPO) Blend Lot #FLBN-20131029-1-00 gelatin capsule | Capsules (100 mg) 3,4,3-LI(1,2-HOPO) Blend Lot #FLBN-20131029-1-4 gelatin capsule |
| 3,4,3-LI-(1,2-HOPO) | 500.0 | 500.0 | 500.0 | 500.0 | 100.0 |
| Sodium Oleate | 46.0 | 46.0 | 46.0 | 55.6 | 11.1 |
| Microcrystalline Cellulose and Carboxymethyl Cellulose, NF (Avicel RC-591) | 500.0 | — | — | — | — |
| Croscarmellos Sodium, NF (AC-Di-Sol) | — | 92.0 | 75.0 | — | — |
| Microcrystalline Cellulose NF (Avicel PH 102) | — | 501.0 | — | — | — |
| Colloidal silicon dioxide, (CAB-O-Sil-M5 P) | — | 6.0 | — | — | — |
| Coprocessed Microcrystalline Cellulose and Guar gum, (Avicel CE-15) | — | — | 927.0 | — | — |
| Mannitol, (Mannogem Granular 2080) | — | — | 927.0 | — | — |
| Magnesium Stearate, NF (HyQual) | — | 6.0 | 25.0 | — | — |
| Unit Weight (mg) | 1046.0 | 1151.0 | 2500.0 | 555.6 | 111.1 |

TABLE 3.2

COMPOSITION OF PLACEBO FORMULATIONS

| | Quantity in unit dosage form (mg) | |
|---|---|---|
| Ingredients | Placebo for 3,4,3-LI(1,2-HOPO) Capsules, 500 mg Lot #FLBN-20140619-1-00 gelatin capsule | Placebo for 3,4,3-LI(1,2-HOPO) Capsules, 100 mg Lot #FLBN-20140619-2-4 gelatin capsule |
| Sodium Alginate, NF | 350.0 | 70.0 |
| Microcrystalline Cellulose and Guar Gum (Coprocessed) | 150.0 | 30.0 |
| Sodium Oleate | 55.6 | 11.1 |
| Unite Weight (mg) | 555.6 | 111.1 |

TABLE 3.3

PACKAGING CONFIGURATION OF PROTOTYPE FORMULATIONS
OF 3,4,3-LI (1,2-HOPO)

| Prototype Formulation | Packaging Configuration |
|---|---|
| Powder for reconstitution | 1 unit in induction heat-sealed pharmaceutical grade white round HDPE bottles (1 oz). Closure/Cap: Polypropylene 24 mm SecRx Ribbed side Text top. |
| Immediate release tablets | 20 tablets in induction heat-sealed white HDPE bottle (40/50 cc) with rayon coil and Sorb-IT desiccant canister 1 G. Closure/Cap: Polypropylene 33 mm White Saf- Cap IIIA (CRC). |

TABLE 3.3-continued

PACKAGING CONFIGURATION OF PROTOTYPE FORMULATIONS OF 3,4,3-LI (1,2-HOPO)

| Prototype Formulation | Packaging Configuration |
|---|---|
| Chewable Tablets | 20 tablets in induction heat-sealed white HDPE bottle (150 cc) with rayon coil and Sorb-IT desiccant canister 1 G. Closure/Cap: Polypropylene 38 mm White Saf- Cap IIIA (CRC). |
| Capsules (Size 00) | 20 capsules in induction heat-sealed white HDPE bottle (40/50 cc) with rayon coil. Closure/Cap: Polypropylene 33 mm White Saf- Cap IIIA (CRC). |
| Capsules (Size 4) | 20 capsules in induction heat-sealed white HDPE bottle (25 cc) with rayon coil. Closure/Cap: Polypropylene 28 mm White Saf- Cap IIIA (CRC). |
| Placebo Capsules (Size 00) | 20 capsules in induction heat-sealed white HDPE bottle (40/50 cc) with rayon coil. Closure/Cap: Polypropylene 33 mm White Saf- Cap IIIA (CRC). |
| Placebo Capsules (Size 4) | 20 capsules in induction heat-sealed white HDPE bottle (25 cc) with rayon coil. Closure/Cap: Polypropylene 28 mm White Saf- Cap IIIA (CRC). |

TABLE 3.4

TESTS PERFORMED ON THE PROTOTYPE FORMULATIONS OF 3,4,3-LI(1,2-HOPO)

| Prototypes | Physical Tests | | | | | |
|---|---|---|---|---|---|---|
| | Appearance and Organoleptic property | Moisture Content | Hardness | Dissolution | Assay | Chromatographic purity |
| Powder for Reconstitution | X | X | — | X | X | X |
| Immediate Release Tablets | X | X | X | X | X | X |
| Chewable Tablets | X | X | X | X | X | X |
| Capsules (00) | X | X | — | X | X | X |
| Capsules (4) | X | X | — | X | X | X |
| Placebo Capsules (00) | X | X | — | — | — | — |
| Placebo Capsules (4) | X | X | — | — | — | — |

4. Materials and Methods
 a. Test Formulation Articles and Materials
Test Article: 3,4,3-L1(1,2-HOPO)
Manufacturer: Ash Stevens, Inc. (Detroit, Mich.)
Lot Number: ML-11-276
Physical Description: Pale yellow solid
Storage Conditions: Refrigerated 2-8° C. protected from light.
Permeability Enhancer: Sodium Oleate
Manufacturer: Sigma Aldrich (St Louis, Mo.)
Lot Number: SLBH3379V
Physical Description: White powder
Storage Conditions: Refrigerated 2-8° C. protected from light.
Formulation Articles:
 3,4,3-L1(1,2-HOPO) Capsules, 500 mg Lot #FLBN-20140206-2
 3,4,3-L1(1,2-HOPO) Capsules, 100 mg Lot #FLBN-20140211-1
 3,4,3-L1(1,2-HOPO) Powder for Reconstitution, 500 mg Lot #FLBN-20140206-1
 3,4,3-L1(1,2-HOPO) Immediate Release Tablets, 500 mg Lot #FLBN-20140211-3
 3,4,3-L1(1,2-HOPO) Chewable Tablets, 500 mg Lot #FLBN-20140211-2

Packaging Materials:
 Bottles: 25 cc White HDPE bottle (Package All)
 Closure/Cap: Polypropylene 28 mm White Saf-Cap IIIA (CRC) (Package All)
 Bottles: 40/50 cc White HDPE bottle (Package All)
 Closure/Cap: Polypropylene 33 mm White Saf-Cap IIIA (CRC) (Package All)
 Bottles: 150 cc White HDPE bottle (Package All)
 Closure/Cap: Polypropylene 38 mm White Saf-Cap IIIA (CRC) (Package All)
 Bottles: HDPE 1 oz Pharmaceutical Round White bottles (Drug Plastic and Glass Company Inc)
 Closure/Cap: Polypropylene 24 mm SecuRx Ribbed Side Text top (Drug Plastic and Glass Company Inc)
 Rayon Coil 12 Grain (Mfg: Carolina Absorbent Cotton)
 Sorb-IT® 1 g, desiccant canister containing silica gel (Mfg: Sud Chemie)
Analytical Materials:
Solvents HPLC Grade—Supplier: Fischer Scientific
Chemicals ACS Grade or equivalent
HPLC Column Agilent, Eclipse XDB-C18, 4.6×150 mm, 5 μm
 b. Direct Physical Test Methods
Appearance: The color and appearance of the prototype dosage forms were observed and recorded.

Organoleptic The smell emanating from the freshly opened package of the Property: prototype formulations was noted.

Hardness: Hardness of the tablet samples were measured with a calibrated hardness tester and recorded.

c. Moisture Content (by KF) Test Method

Sample Preparation: Moisture content of the prototype formulations was measured using a calibrated Karl Fisher coulometric titrator. For determination of moisture content in powder for reconstitution samples, 2 units were emptied into a scintillation vial and the powder sample was used for the determination as is. For determination of moisture content in tablet samples (immediate release and chewable), 2 tablets were crushed in a clean dry glass pestle and mortar and the powder sample was used for analysis. For determination of moisture content in capsule samples, 2 units were emptied into a scintillation vial and the powder sample was used for the determination as is.

Analysis Procedure: An empty vial with crimp cap was weighed (W1). About 30 mg of powder sample was accurately weighed and transferred to the empty vial and weighed (W2). About 4 mL of methanol (Drysolv®) was added to the sample in the vial. The gross weight of the vial was noted (W3). The sample was agitated on a vortex mixer for about 2 minutes and a 3 mL aliquot was withdrawn into a syringe. The syringe was weighed (S1). The entire content of the syringe was added to the KF titrator and the empty syringe was weighed (S2). The weight of the sample added (S1-S2) was entered in the KF titrator. Note: The KF Titrator was calibrated 0.1% water standard before use, and a blank water determination was performed using methanol (Drysolv®). Water content was calculated as:

(Water content of Sample×Weight of sample ($W3-W1$))−(Water content of blank×Weight of methanol ($W3-W2$))=Net powder weight ($W2-W1$)

d. Solution Assay and Content Uniformity

Chromatographic Method: Assay for 3,4,3-L1(1,2-HOPO) in capsules, powder for reconstitution, immediate release tablets, and chewable tablet samples were performed by the following chromatographic method.

Note: Due to the ability of 3,4,3-L1(1,2-HOPO) to scavenge trace metals in acidic conditions, the HPLC system was passivated by multiple injections of the standard solution until the % RSD of the last five injections reached less than 2%.

Column: Waters, Symmetry C18, 2.1×150 mm, 5 µm.
Mobile Phase A: 0.1% Trifluroacetic acid in Water
Mobile Phase B: 0.1% Trifluroacetic acid in Acetonitrile
Column Temperature: 30° C.
Flow Rate: 0.5 mL/min.
Injection Volume: 10 µL
Detection: UV at 250 nm
Run Time: 12 min
Diluent (Assay): 9:1 Water: Acetonitrile
Diluent (Dissolution): Simulated Gastric Fluid without enzymes

TABLE 3.5

| GRADIENT CONDITIONS Gradient Program: | | |
| --- | --- | --- |
| Time (min) | A % | B % |
| 0.0 | 90 | 10 |
| 3.5 | 58 | 42 |
| 4.5 | 58 | 42 |
| 5.0 | 2 | 98 |
| 6.5 | 2 | 98 |
| 7.0 | 90 | 10 |
| 12.0 | 90 | 10 |

System Suitability: No Interference from the diluent/placebo components at the retention time of 3,4,3-L1(1,2-HOPO) peak. The % RSD for the five replicate system suitability injections is not more than 2.0%. The check standard recovery is within 95-105%. Note: Throughout the sample preparation and storage, the flasks were covered with aluminum foil.

Standard Preparation: About 25 mg of 3,4,3-L1(1,2-HOPO) was transferred to a 50 mL volumetric flask. About 30 mL of diluent was added to the flask, and mixed well. The volume was made up to the mark and sonicated. The temperature of the sonication bath was kept low with the addition of ice. Similarly, another standard was prepared as check standard.

Sample Preparation: 3,4,3-L1(1,2-HOPO) Powder for Reconstitution, 500 mg. Powder for reconstitution from 5 units was filled into in a glass vial. About 104.6 mg of powder sample (equivalent to 50 mg of 3,4,3-L1(1,2-HOPO)) was accurately weighed and transferred to a clean and dry 100 mL volumetric flask covered with aluminum foil. About 50 mL of diluent was added, mixed well and made up to the mark. The flasks were sonicated for 30 minutes on ice-cold water. The samples were filtered using a 0.45µ Nylon syringe filter and the filtrate used for assay. The samples were stored at 5° C. in the HPLC autosampler just after preparation. The 3,4,3-L1(1,2-HOPO) concentration in each sample solution was about 0.5 mg/mL.

3,4,3-L1(1,2-HOPO) Immediate Release Tablets, 500 mg. Five (5) immediate release tablets were added to a dry 1000 mL volumetric flask covered with aluminum foil. About 500 mL of diluent was added, mixed well and made up to the mark. The flasks were sonicated for 90 minutes on ice-cold water. The samples were filtered using 0.45µ Nylon syringe filter. 2 mL of the filtrate was diluted to 10 mL with diluent and used for assay. The samples were stored at 5° C. in the HPLC autosampler just after preparation. The 3,4,3-L1(1,2-HOPO) concentration in each sample solution was about 0.5 mg/mL.

3,4,3-L1(1,2-HOPO) Chewable Tablets, 500 mg. Five (5) chewable tablets were powdered with a pestle and mortar. About 250 mg of powdered sample (50 mg equivalent of 3,4,3-L1(1,2-HOPO)) was weighed accurately and transferred to a clean and dry 100 mL volumetric flask covered with aluminum foil. About 50 mL of diluent was added and mixed well. The volume was made up to 100 mL. Each sample was sonicated for about 30 min on ice-cold water. Samples were then filtered through a 0.45µ Nylon syringe filter and the filtrates used for assay. The samples were stored at 5° C. in the HPLC autosampler just after preparation. The 3,4,3-L1(1,2-HOPO) concentration in each sample solution was about 0.5 mg/mL.

3,4,3-L1(1,2-HOPO) Capsules, 500 mg. Five (5) capsules were emptied in a glass vial. About 55.6 mg of powder (50 mg equivalent of 3,4,3-L1(1,2-HOPO)) was weighed in a dry 100 mL volumetric flask covered with aluminum foil. About 50 mL of diluent was added, and the volume was adjusted to 100 mL after mixing. Each sample was sonicated for about 30 min on ice-cold water. Samples were then filtered through a 0.45μ Nylon syringe filter and the filtrates used for assay. The samples were stored at 5° C. in the HPLC autosampler just after preparation. The 3,4,3-L1(1,2-HOPO) concentration in each sample solution was about 0.5 mg/mL.

3,4,3-L1 (1,2-HOPO) Capsules, 100 mg. Five (5) capsules were emptied in a glass vial. About 55.6 mg of powder (50 mg equivalent of 3,4,3-L1 (1,2-HOPO)) was weighed in a dry 100 mL volumetric flask covered with aluminum foil. About 50 mL of diluent was added, and the volume was adjusted to 100 mL after mixing. Each sample was sonicated for about 30 min on ice-cold water. Samples were then filtered through a 0.45μ Nylon syringe filter and the filtrates used for assay. The samples were stored at 5° C. in the HPLC autosampler just after preparation. The 3,4,3-L1(1,2-HOPO) concentration in each sample solution was about 0.5 mg/mL.

Calculation:

$$\text{Assay (\% Label Claim)} = \frac{Aspl \times Astd \times Wstd \times 50 \times Vspl}{\text{Sample Wt.} \times DF \times P \times 100 \times \text{Averag Wt.} \times 1 \times 100 LC}$$

Aspl=Peak area of sample solution
Astd=Average peak area of 5 injections of working standard solution
Wstd=Weight of 3,4,3-L1(1,2-HOPO) used as standard in mg
Vspl=Volume of sample solution in mL
DF=Dilution factor (for immediate release tablets DF=5, for other prototypes DF=1)
P=Purity factor of standard material
LC=Label Claim (Theoretical amount of 3,4,3-L1(1,2-HOPO) per unit dose in mg)

e. Dissolution Testing

Chromatographic Unit doses of 3,4,3-L1(1,2-HOPO) powder for reconstitution,
Method: immediate release tablets, chewable tablets, and capsules were transferred to each dissolution vessel and dissolution testing was performed using the following conditions:
Apparatus: USP Apparatus II (Paddle)
Temperature: 37±0.5° C.
Stirring Speed: 50 RPM
Dissolution Medium: 900 mL of Simulated Gastric Fluid (without enzymes)
Medium Sampling: 5 mL at 10, 15, 30, 45 minutes and Infinity (15 minutes at 250 rpm after 45 minute time point) with media replacement.
The samples were filtered through 0.45 μl nylon syringe filter and stored at 5° C. in the HPLC autosampler just after withdrawal.
Throughout the dissolution testing, vessels were covered with aluminum foil. The capsule prototype formulations were introduced into the dissolution vessel with the help of a sinker.
The dissolution samples were analyzed by the following HPLC method.
Column: Waters, Symmetry C18, 2.1×150 mm, 5 μm.
Mobile Phase A: 0.1% Trifluroacetic acid in Water Mobile Phase B: 0.1% Trifluroacetic acid in Acetonitrile Column Temperature: 30° C.
Sample Temperature: 5° C.
Flow Rate: 0.5 mL/min.
Injection Volume: 10 μL (50 μL for 100 mg capsule dissolution study only)
Detection: UV at 250 nm
Run Time: 12 min
Diluent (Assay): 9:1 Water: Acetonitrile
Diluent (Dissolution): Simulated Gastric Fluid without enzymes

TABLE 3.6

GRADIENT CONDITIONS
Gradient Program:

| Time (min) | A % | B % |
|---|---|---|
| 0.0 | 90 | 10 |
| 3.5 | 58 | 42 |
| 4.5 | 58 | 42 |
| 5.0 | 2 | 98 |
| 6.5 | 2 | 98 |
| 7.0 | 90 | 10 |
| 12.0 | 90 | 10 |

System Suitability: No Interference from the diluent/placebo components at the retention time of 3,4,3-L1(1,2-HOPO) peak.
The % RSD for the five replicate system suitability injections is not more than 2.0%.
The check standard recovery is within 95-105%.

Standard Preparation: 0.1 mg/mL 3,4,3-L1(1,2-HOPO). About 25 mg of 3,4,3-L1(1,2-HOPO) was accurately weighed and transferred to a 250 mL volumetric flask. About 200 mL of diluent was added, and mixed well. The volume of the standard was made up to the mark. The solution was sonicated in ice-cold water till complete dissolution of the standard. Similarly, another standard was prepared as check standard. These set of standards were used in dissolution testing of formulations with 100 mg dose strength.

0.5 mg/mL 3,4,3-L1(1,2-HOPO). About 25 mg of 3,4,3-L1(1,2-HOPO) was accurately weighed and transferred to a 50 mL volumetric flask. About 30 mL of diluent was added, and mixed well. The volume of the standard was made up to the mark. The solution was sonicated in ice-cold water till complete dissolution of the standard. Similarly, another standard was prepared as check standard. These set of standards were used in dissolution testing of formulations with 500 mg dose strength.

Calculation:

$$\% \text{ Dissolved}_n = \frac{Aspl \times Astd \times Wstd Vstd \times 900 LC \times P \times 100 + 5900 \times n = 1n - n - 1\% \text{ Dissolved}}{}$$

Aspl=Peak area of sample solution
Astd=Average peak area of five injections of working standard solution for assay
Wstd=Weight of 3,4,3-L1(1,2-HOPO) used as standard in mg
Vstd=Volume of standard solution in mL
Vspl=Volume of sample solution in mL
DF=Dilution factor (for immediate release tablets DF=5, for other prototypes DF=1)
P=Purity factor of standard material
LC=Label Claim (Theoretical amount of 3,4,3-L1(1,2-HOPO) per unit dose in mg)

f. Chromatographic Purity Assessment

Chromatographic To determine the chromatographic purity of 3,4,3-L1(1,2-HOPO)

Method:
in prototype formulations the following HPLC method was used.

Column: Agilent Eclipse XDB-C18, 4.6×150 mm, 5 μm

Mobile Phase A: 0.05% Formic acid in 95:5 Water: Acetonitrile

Mobile Phase B: 0.05% Formic acid in Acetonitrile

Column Temperature: 25° C.

Flow Rate: 1.0 mL/min.

Injection Volume: 20 μL

Detection: UV at 250 nm

Run Time: 50 min

Diluent (Assay): 9:1 Water: Acetonitrile

Diluent (Dissolution): Simulated Gastric Fluid without enzymes

TABLE 3.7

GRADIENT CONDITIONS
Gradient Program:

| Time (min) | A % | B % |
|---|---|---|
| 0.0 | 100 | 0 |
| 30.0 | 60 | 40 |
| 40.0 | 0 | 100 |
| 41.0 | 100 | 0 |
| 50.0 | 100 | 0 |

System Suitability: No Interference from the diluent/placebo components at the retention time of 3,4,3-L1(1,2-HOPO) peak.

The % RSD for the five replicate system suitability injections is not more than 2.0%.

The check standard recovery is within 95-105%.

Standard Stock About 50 mg of 3,4,3-L1(1,2-HOPO) was accurately weighed and

Solutions: transferred into a 25 mL clear volumetric flask wrapped with aluminium foil. 20 mL of diluent was added for complete dissolution, the standard was diluted to volume with diluent and mixed well. Similarly, another stock was prepared as check standard stock.

Calibration Standards: Five mL of the standard stock solution was pipetted to a labeled 10 mL clear volumetric flask wrapped with aluminum foil. The stock was diluted to volume with diluent and mixed well. The concentration of 3,4,3-L1(1,2-HOPO) in the standard solution was about 1.0 mg/mL. Similarly a check standard solution was prepared from the check standard stock.

Sample Preparation: 3,4,3-L1(1,2-HOPO) Powder for Reconstitution, 500 mg. Two unit doses of powder for reconstitution prototype formulation were transferred to a clean dry 250 mL volumetric flask. About 200 mL of diluent was added to the sample, and shaken on a wrist action shaker until a complete uniform dispersion was obtained (about 40 minutes). The volume was made up to the mark with diluent and mixed well. The sample solution was filtered using a 0.45p, nylon syringe filter. 1 mL of the filtrate was diluted to 4 mL in a scintillation vial with the diluent and analyzed by HPLC. The 3,4,3-L1(1,2-HOPO) concentration in the sample solution is about 1.0 mg/mL.

3,4,3-L1(1,2-HOPO) Immediate Release Tablets, 500 mg. Two prototype immediate release tablets were transferred to a clean dry 250 mL volumetric flask. About 200 mL of diluent was added to the sample, and shaken on a wrist action shaker till a complete uniform dispersion was obtained (about 40 minutes). The volume was made up to the mark with diluent and mixed well. The sample solution was filtered using a 0.45μ nylon syringe filter. 1 mL of the filtrate was diluted to 4 mL in a scintillation vial with the diluent and analyzed by HPLC. The 3,4,3-L1(1,2-HOPO) concentration in the sample solution is about 1.0 mg/mL.

3,4,3-L1(1,2-HOPO) Chewable Tablets, 500 mg. Two prototype chewable tablets were broken into few pieces in a pestle and mortar and was transferred to a clean dry 250 mL volumetric flask. About 200 mL of diluent was added to the sample, and shaken on a wrist action shaker till a complete uniform dispersion was obtained (about 40 minutes). The volume was made up to the mark with diluent and mixed well. The sample solution was filtered using a 0.45μ nylon syringe filter. 1 mL of the filtrate was diluted to 4 mL in a scintillation vial with the diluent and analyzed by HPLC. 3,4,3-L1(1,2-HOPO) concentration in the sample solution is about 1.0 mg/mL.

3,4,3-L1(1,2-HOPO) Capsules, 500 mg. Two prototype capsules were opened and the contents added to a clean dry 250 mL volumetric flask. About 200 mL of diluent was added to the sample, and shaken on a wrist action shaker till a complete uniform dispersion was obtained (about 40 minutes). The volume was made up to the mark with diluent and mixed well. The sample solution was filtered using a 0.45μ nylon syringe filter. 1 mL of the filtrate was diluted to 4 mL in a scintillation vial with the diluent and analyzed by HPLC. The 3,4,3-L1 (1,2-HOPO) concentration in the sample solution is about 1.0 mg/mL.

3,4,3-L1 (1,2-HOPO) Capsules, 100 mg. Two prototype capsules were opened and the contents added to a clean dry 50 mL volumetric flask. About 40 mL of diluent was added to the sample, and shaken on a wrist action shaker till a complete uniform dispersion was obtained (about 40 minutes). The volume was made up to the mark with diluent and mixed well. The sample solution was filtered using a 0.45μ nylon syringe filter. 1 mL of the filtrate was diluted to 4 mL in a scintillation vial with the diluent and analyzed by HPLC. The 3,4,3-L1 (1,2-HOPO) concentration in the sample solution is about 1.0 mg/mL.

Note: Throughout sample preparation and storage, the flasks were covered with aluminum foil.

Blank Preparation: Blank samples were prepared with placebos of the prototype formulations using a similar preparation method as for the samples.

Reporting: The chromatographic purity of 3,4,3-L1(1,2-HOPO) was reported as HPLC area (%). All unknown peaks from the samples with area ≥0.03% were integrated. Peaks in sample chromatograms common to diluent, and blank preparations were disregarded.

5. Results

Results of all tests performed on the prototype formulations are summarized in TABLE 3.8-TABLE 3.12, with each TABLE showing the results for a particular assay.

TABLE 3.8

OBSERVATIONS OF PHYSICAL APPEARANCE, MOISTURE CONTENT, AND ORGANOLEPTIC PROPERTY OF 3,4,3-LI(1,2-HOPO) PROTOTYPE FORMULATIONS UPON STORAGE AT 25° C./60% RH AND AT 40° C./75% RH

3,4,3-LI (1,2-HOPO) Capsules, 500 mg (FLBN-20140206-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Physical Appearance | Size '00' capsules filled with off-white colored powder | Size '00' capsules filled with off-white colored powder | Size '00' capsules filled with off-white colored powder | Size '00' capsules filled with off-white colored powder | Size '00' capsules filled with off-white colored powder | Size '00' capsules filled with off-white colored powder | Size '00' capsules filled with off-white colored powder |
| Moisture Content % w/w | 3.39 | 3.86 | 3.88 | 4.17 | 3.66 | 3.38 | 3.46 |
| Organoleptic property (smell) | None | Rancid smell in product and bottle | Rancid smell in product and bottle | Rancid smell in product and bottle | Rancid smell in product and bottle | Rancid smell in product and bottle | Rancid smell in product and bottle |

3,4,3-LI (1,2-HOPO) Capsules, 100 mg (FLBN-20140211-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Physical Appearance | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder |
| Moisture Content % w/w | 3.53 | 4.32 | 4.68 | 4.38 | 3.90 | 3.95 | 3.62 |
| Organoleptic property (smell) | None | Rancid smell in product and bottle | Rancid smell in product and bottle | Rancid smell in product and bottle | Rancid smell in product and bottle | Rancid smell in product and bottle | Rancid smell in product and bottle |

3,4,3-LI (1,2-HOPO) Powder for Reconstitution, 500 mg (FLBN-20140206-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Physical Appearance | Off-white colored powder | Off-white colored powder | Off-white colored powder | Off-white colored powder | Off-white colored powder | Off-white colored powder | Off-white colored powder |
| Moisture Content % w/w | 2.32 | 3.42 | 4.89 | 5.92 | 2.73 | 2.78 | 3.18 |
| Organoleptic property (smell) | None | None | None | None | None | None | None |

3,4,3-LI (1,2-HOPO) Chewable Tablets, 500 mg (FLBN-20140211-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Physical Appearance | Off-white colored, round flat bevel edged uncoated tablets | Off-white colored, round flat bevel edged uncoated tablets | Off-white colored, round flat bevel edged uncoated tablets | Off-white colored, round flat bevel edged uncoated tablets | Off-white colored, round flat bevel edged uncoated tablets | Off-white colored, round flat bevel edged uncoated tablets | Off-white colored, round flat bevel edged uncoated tablets |
| Hardness (kp) | 15.4 ± 0.4* | 9.1 ± 0.15 | 9.1 ± 0.55 | 8.4 ± 0.06 | 9.7 ± 0.06 | 9.9 ± 0.20 | 9.2 ± 0.50 |
| Moisture Content % w/w | 2.16 | 2.18 | 1.87 | 1.61 | 2.28 | 2.00 | 1.81 |

TABLE 3.8-continued

OBSERVATIONS OF PHYSICAL APPEARANCE, MOISTURE CONTENT, AND ORGANOLEPTIC PROPERTY OF 3,4,3-LI(1,2-HOPO) PROTOTYPE FORMULATIONS UPON STORAGE AT 25° C./60% RH AND AT 40° C./75% RH

| | | | | | | | |
|---|---|---|---|---|---|---|---|
| Organoleptic property (smell) | None | None | Rancid smell in product and bottle | Rancid smell in product and bottle | None | Rancid smell in product and bottle | Rancid smell in product and bottle |

3,4,3-LI (1,2-HOPO) Immediate Release Tablets, 500 mg (FLBN-20140211-3)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Physical Appearance | Off-white colored, oval shaped uncoated tablets | Off-white colored, oval shaped uncoated tablets | Off-white colored, oval shaped uncoated tablets | Off-white colored, oval shaped uncoated tablets | Off-white colored, oval shaped uncoated tablets | Off-white colored, oval shaped uncoated tablets | Off-white colored, oval shaped uncoated tablets |
| Hardness (kp) | 17.0 ± 0.3* | 12.5 ± 0.51 | 13.9 ± 0.42 | 13.8 ± 0.78 | 15.3 ± 0.72 | 13.7 ± 0.75 | 14.7 ± 1.82 |
| Moisture Content % w/w | 3.55 | 3.73 | 3.89 | 3.9 | 3.76 | 3.35 | 3.80 |
| Organoleptic property (smell) | None | None | Slight rancid smell in product and bottle | Rancid smell in product and bottle | None | Slight rancid smell in product and bottle | Rancid smell in product and bottle |

TABLE 3.9

DISSOLUTION TESTING OF 3,4,3-LI(1,2-HOPO) PROTOTYPE FORMULATIONS STORAGE AT 25°C./60% RH AND AT 40°C./75% RH 3,4,3-LI (1,2-HOPO) Capsules, 500 mg (FLBN-20140206-2)

| | | Storage Condition | | | | | |
|---|---|---|---|---|---|---|---|
| | | 40° C./75% RH | | | 25° C./60% RH | | |
| Sampling Time (mins) | T0 % Dissolved | 1 Month % Dissolved | 3 Month % Dissolved | 6 Month % Dissolved | 1 Month % Dissolved | 3 Month % Dissolved | 6 Month % Dissolved |
| 10 | 44.0 | 51.8 | 52.7 | 46.7 | 49.6 | 62.8 | 41.9 |
| 15 | 58.6 | 61.9 | 68.0 | 61.6 | 63.9 | 77.4 | 57.7 |
| 30 | 83.7 | 87.1 | 92.9 | 86.0 | 89.2 | 98.9 | 84.9 |
| 45 | 95.8 | 96.6 | 100.3 | 94.6 | 97.5 | 105.3 | 96.1 |
| Inf | 99.6 | 98.5 | 100.9 | 96.5 | 98.4 | 103.7 | 98.8 |
| SD | SD | SD | SD | SD | SD | SD | SD |
| | 5.5 | 5.3 | 7.1 | 4.6 | 5.2 | 5.5 | 7.3 |
| | 5.5 | 3.7 | 6.5 | 4.4 | 5.0 | 6.5 | 5.8 |
| | 4.5 | 3.2 | 4.7 | 3.7 | 3.6 | 5.4 | 5.9 |
| | 3.7 | 2.2 | 2.2 | 1.0 | 1.1 | 3.0 | 3.9 |
| | 2.8 | 2.3 | 1.7 | 1.8 | 0.6 | 2.7 | 2.8 |

3,4,3-LI (1,2-HOPO) Capsules, 100 mg (FLBN-20140211-1)

| | | Storage Condition | | | | | |
|---|---|---|---|---|---|---|---|
| | | 40° C./75% RH | | | 25° C./60% RH | | |
| Sampling Time (mins) | T0 % Dissolved | 1 Month % Dissolved | 3 Month % Dissolved | 6 Month % Dissolved | 1 Month % Dissolved | 3 Month % Dissolved | 6 Month % Dissolved |
| 10 | 73.0 | 80.8 | 74.9 | 70.6 | 65.2 | 78.4 | 66.7 |
| 15 | 87.6 | 95.8 | 85.9 | 88.0 | 84.8 | 92.4 | 81.9 |
| 30 | 101.2 | 104.0 | 98.3 | 97.6 | 95.2 | 102.2 | 101.8 |

TABLE 3.9-continued

DISSOLUTION TESTING OF 3,4,3-LI(1,2-HOPO) PROTOTYPE
FORMULATIONS STORAGE AT 25°C./60% RH AND AT 40°C./75% RH

|   | | | | | | | |
|---|---|---|---|---|---|---|---|
| 45  | 100.7 | 105.0 | 98.7 | 99.0 | 95.9 | 100.5 | 102.2 |
| Inf | 100.3 | 104.2 | 98.9 | 97.6 | 96.4 | 96.8  | 100.4 |
|     | SD    | SD    | SD   | SD   | SD   | SD    | SD    |
|     | 17.4  | 11.7  | 13.6 | 9.3  | 15.5 | 16.2  | 11.2  |
|     | 11.3  | 9.8   | 12.1 | 10.8 | 12.2 | 9.6   | 9.6   |
|     | 2.3   | 4.5   | 5.7  | 4.3  | 3.7  | 1.9   | 3.5   |
|     | 2.9   | 4.1   | 3.8  | 2.8  | 4.5  | 4.4   | 2.7   |
|     | 2.7   | 3.3   | 5.1  | 1.6  | 3.6  | 3.6   | 5.0   |

3,4,3-LI (1,2-HOPO) Powder for Reconstitution, 500 mg (FLBN-20140206-1)

| | | Storage Condition | | | | | |
|---|---|---|---|---|---|---|---|
| | | 40° C./75% RH | | | 25° C./60% RH | | |
| Sampling Time (mins) | T0 % Dissolved | 1 Month % Dissolved | 3 Month % Dissolved | 6 Month % Dissolved | 1 Month % Dissolved | 3 Month % Dissolved | 6 Month % Dissolved |
| 10  | 99.0 | 100.4 | 98.5  | 96.6 | 97.1 | 97.3 | 96.7 |
| 15  | 99.7 | 100.2 | 99.2  | 96.9 | 97.7 | 97.6 | 96.5 |
| 30  | 99.2 | 100.0 | 99.5  | 97.8 | 97.8 | 98.5 | 96.6 |
| 45  | 99.6 | 101.1 | 99.2  | 97.4 | 97.6 | 97.1 | 96.9 |
| Inf | 99.9 | 101.4 | 100.3 | 97.1 | 97.8 | 96.8 | 97.3 |
|     | SD   | SD    | SD    | SD   | SD   | SD   | SD   |
|     | 2.7  | 1.2   | 1.4   | 1.9  | 1.1  | 1.6  | 2.4  |
|     | 2.8  | 1.1   | 2.1   | 1.7  | 0.8  | 1.6  | 2.2  |
|     | 2.3  | 1.3   | 1.9   | 2.0  | 1.3  | 1.9  | 2.6  |
|     | 2.3  | 1.4   | 1.9   | 1.9  | 1.3  | 1.8  | 2.4  |
|     | 2.6  | 1.3   | 1.6   | 1.9  | 0.9  | 1.8  | 2.2  |

3,4,3-LI (1,2-HOPO) Chewable Tablets, 500 mg (FLBN-20140211-2)

| | | Storage Condition | | | | | |
|---|---|---|---|---|---|---|---|
| | | 40° C./75% RH | | | 25° C./60% RH | | |
| Sampling Time (mins) | T0 % Dissolved | 1 Month % Dissolved | 3 Month % Dissolved | 6 Month % Dissolved | 1 Month % Dissolved | 3 Month % Dissolved | 6 Month % Dissolved |
| 10  | 85.7  | 99.0 | 79.4 | 99.7   | 97.4  | 80.4  | 99.7  |
| 15  | 97.6  | 99.3 | 84.0 | 101.4  | 100.5 | 89.8  | 101.4 |
| 30  | 100.3 | 99.3 | 88.6 | 102.2  | 100.4 | 95.1  | 101.8 |
| 45  | 98.3  | 98.9 | 91.2 | 102.1  | 100.4 | 96.3  | 102.1 |
| Inf | 100.9 | 99.3 | 98.6 | 85.7*  | 100.0 | 102.5 | 102.1 |
|     | SD    | SD   | SD   | SD     | SD    | SD    | SD    |
|     | 3.3   | 0.6  | 3.4  | 1.3    | 2.6   | 5.8   | 3.1   |
|     | 2.2   | 1.0  | 2.4  | 1.3    | 0.7   | 2.7   | 0.5   |
|     | 1.2   | 0.8  | 1.9  | 1.0    | 1.1   | 1.6   | 0.9   |
|     | 1.1   | 0.6  | 1.6  | 1.0    | 0.9   | 0.7   | 1.0   |
|     | 1.2   | 0.9  | 1.0  | 40.9   | 1.0   | 0.9   | 0.7   |

3,4,3-LI (1,2-HOPO) Immediate Release Tablets, 500 mg (FLBN-20140211-3)

| | | Storage Condition | | | | | |
|---|---|---|---|---|---|---|---|
| | | 40° C./75% RH | | | 25° C./60% RH | | |
| Sampling Time (mins) | T0 % Dissolved | 1 Month % Dissolved | 3 Month % Dissolved | 6 Month % Dissolved | 1 Month % Dissolved | 3 Month % Dissolved | 6 Month % Dissolved |
| 10  | 33.2  | 50.2  | 49.0  | 39.6  | 52.6  | 41.4  | 39.8  |
| 15  | 49.3  | 63.3  | 67.3  | 61.8  | 66.8  | 60.7  | 61.2  |
| 30  | 77.0  | 81.0  | 83.7  | 81.5  | 81.3  | 86.5  | 83.8  |
| 45  | 86.7  | 85.4  | 89.6  | 85.2  | 86.6  | 91.3  | 88.8  |
| Inf | 104.9 | 101.0 | 108.6 | 101.5 | 100.6 | 107.1 | 101.8 |
|     | SD    | SD    | SD    | SD    | SD    | SD    | SD    |
|     | 11.2  | 15.5  | 8.0   | 11.6  | 11.7  | 15.4  | 11.6  |
|     | 12.6  | 12.2  | 7.9   | 10.1  | 8.9   | 14.0  | 9.2   |
|     | 13.8  | 6.6   | 9.2   | 8.5   | 8.0   | 6.0   | 9.9   |
|     | 6.3   | 4.4   | 7.6   | 7.7   | 7.4   | 6.1   | 8.5   |
|     | 2.4   | 1.9   | 2.9   | 2.5   | 2.8   | 2.1   | 2.0   |

*First dissolution testing sample at infinity timepoint did not show peak at correct RT.

TABLE 3.10

ASSAY OF 3,4,3-LI(1,2-HOPO) PROTOTYPE FORMULATIONS STORED AT 25° C./60% RH AND AT 40° C./75% RH 3,4,3-LI (1,2-HOPO) Capsules, 500 mg (FLBN-20140206-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Assay (% LC) | 103.9 | 103.5 | 99.7 | 102.8 | 102.1 | 101.3 | 100.8 |

3,4,3-LI (1,2-HOPO) Capsules 100 mg (FLBN-20140211-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Assay (% LC) | 101.2 | 100.8 | 95.5 | 90.5 | 101.0 | 99.4 | 96.9 |

3,4,3-LI (1,2-HOPO) Powder for Reconstitution, 500 mg (FLBN-20140206-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Assay (% LC) | 107.7 | 102.4 | 101.1 | 101.7 | 106.4 | 107.0 | 101.9 |

3,4,3-LI (1,2-HOPO) Capsules 500 mg (FLBN-20140211-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Assay (% LC) | 104.6 | 102.2 | 103.2 | 101.7 | 104 | 103.1 | 102.5 |

3,4,3-LI (1,2-HOPO) Capsules 500 mg (FLBN-20140211-3)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Assay (% LC) | 107.0 | 103.6 | 102.7 | 105.9 | 104.7 | 103.6 | 102.6 |

TABLE 3.11

CHROMATOGRAPHIC PURITY OF 3,4,3-LI(1,2-HOPO) IN PROTOTYPE FORMULATION STABILITY SAMPLES STORED AT 25° C./60% RH AND AT 40° C./75% RH 3,4,3-LI (1,2-HOPO) Capsules, 500 mg (FLBN-20140206-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Chromatographic Purity (area %) | 96.80 | 98.65 | 96.29 | 98.30 | 98.57 | 96.17 | 98.30 |

TABLE 3.11-continued

CHROMATOGRAPHIC PURITY OF 3,4,3-LI(1,2-HOPO) IN PROTOTYPE FORMULATION STABILITY SAMPLES STORED AT 25° C./60% RH AND AT 40° C./75% RH 3,4,3-LI (1,2-HOPO) Capsules, 100 mg (FLBN-20140211-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Chromatographic Purity (area %) | 96.94 | 98.58 | 96.38 | 98.50 | 98.63 | 96.12 | 98.07 |

3,4,3-LI (1,2-HOPO) Powder for Reconstitution, 500 mg (FLBN-20140206-1)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Chromatographic Purity (area %) | 96.58 | 98.66 | 96.02 | 98.08 | 98.67 | 95.94 | 97.82 |

3,4,3-LI (1,2-HOPO) Capsules, 500 mg (FLBN-20140211-2)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Chromatographic Purity (area %) | 96.81 | 98.67 | 96.18 | 98.40 | 98.63 | 96.03 | 98.11 |

3,4,3-LI (1,2-HOPO) Capsules, 500 mg (FLBN-20140211-3)

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Chromatographic Purity (area %) | 96.73 | 98.65 | 96.40 | 98.37 | 98.67 | 96.05 | 98.46 |

TABLE 3.12

OBSERVATIONS OF PHYSICAL APPEARANCE, MOISTURE CONTENT, AND ORGANOLEPTIC PROPERTY OF PLACEBO CAPSULES FOR 3,4,3-LI(1,2-HOPO) PROTOTYPE FORMULATIONS UPON STORAGE AT 25° C./60% RH AND AT 40° C./75% RH

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |

Placebo for 3,4,3-LI (1,2-HOPO) Capsules, 500 mg (FLBN-20140619-1 - 00 size capsules)

| | | | | | | | |
|---|---|---|---|---|---|---|---|
| Physical Appearance | Size '00' capsules filled with off-shite colored powder | Size '00' capsules filled with off-white colored powder | Size '00' capsules filled with off-white colored powder | Size '00' capsules filled with off-white colored powder | Size '00' capsules filled with off-white colored powder | Size '00' capsules filled with off-white colored powder | Size '00' capsules filled with off-white colored powder |

TABLE 3.12-continued

OBSERVATIONS OF PHYSICAL APPEARANCE, MOISTURE CONTENT,
AND ORGANOLEPTIC PROPERTY OF PLACEBO CAPSULES FOR
3,4,3-LI(1,2-HOPO) PROTOTYPE FORMULATIONS UPON STORAGE
AT 25° C./60% RH AND AT 40° C./75% RH

| | | Storage Condition | | | | | |
|---|---|---|---|---|---|---|---|
| | | 40° C./75% RH | | | 25° C./60% RH | | |
| Test | T0 | 1 Month | 3 Month | 6 Month | 1 Month | 3 Month | 6 Month |
| Moisture Content % w/w | 5.19 | 5.53 | 6.45 | 6.07 | 5.36 | 5.18 | 5.02 |
| Organoleptic property (smell) | None | Rancid smell in product and bottle | Rancid smell in product and bottle | Rancid smell in product and bottle | Slight rancid smell in product and bottle | Rancid smell in product and bottle | Rancid smell in product and bottle |
| Placebo for 3,4,3-LI (1,2-HOPO) Capsules, 500 mg (FLBN-20140619-2 - size 4 capsules) | | | | | | | |
| Physical Appearance | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder | Size 4 capsules filled with off-white colored powder |
| Moisture Content % w/w | 5.19 | 5.65 | 6.34 | 6.28 | 5.48 | 5.21 | 6.05 |
| Organoleptic property (smell) | None | Rancid smell in product and bottle | Rancid smell in product and bottle | Rancid smell in product and bottle | Slight rancid smell in product and bottle | Rancid smell in product and bottle | Rancid smell in product and bottle |

6. Conclusion

The following is a summary of observations and trends observed in the stability study of 3,4,3-L1(1,2-HOPO) prototype formulations.
  There was no change in physical appearance of the prototype formulations and placebos upon storage at 25° C./60% RH and at 40° C./75% RH for 6 months.
  The moisture content increased slightly in powder for reconstitution prototype formulation stored at 40° C./75% RH. In all the other formulations including the placebos the moisture content is comparable to the values observed in T0 samples.
  The hardness of the chewable and immediate release tablets decreased slightly upon storage when compared to their values at T0.
  Development of a rancid odor upon storage at 25° C./60% RH and at 40° C./75% RH was observed in all prototype formulations except in powder for reconstitution. The development of rancid odor was also observed in the placebos for 3,4,3-L1(1,2-HOPO) capsules when stored at 25° C./60% RH and at 40° C./75% RH.
  No major changes in the dissolution profiles of the prototype formulations were noted in the stability study samples. The dissolution of 3,4,3-L1(1,2-HOPO) from chewable tablets and immediate release tablets appear to be slightly faster in the stability study samples than what was observed in T0 samples. A11 the samples tested released more than 85% of the label claim for 3,4,3-L1(1,2-HOPO) in 45 minutes.
  Assay, % Label claim of 3,4,3-L1(1,2-HOPO)) in prototype dosage form was found to be between 90-110% in all the stability study samples analyzed as well as the T0 samples.
  Chromatographic purity measured for prototype formulations in the stability study varied slightly in the samples upon storage at 25° C./60% RH and at 40° C./75% RH when compared to that observed at T0.

Example 4—Efficacy of Repeated 3,4,3-L1(1,2-HOPO) Treatment for Removing an Intravenous Dose of $^{238}$Pu from the Body of Female and Male Swiss-Webster Mice Summary The objective of this study was to characterize the efficacy of 3,4,3-L1(1,2-HOPO) at enhancing elimination from an internal plutonium burden in female and male Swiss-Webster mice administered a soluble citrate complex of $^{238}$Pu and treated multiple times, starting at 24 hours after the exposure. Efficacy was evaluated by comparing the tissue contents, urinary and fecal excretions of $^{238}$Pu in treated animals versus untreated animals.

The medical countermeasure 3,4,3-L1(1,2-HOPO) was administered parenterally (ip) or orally (po) via consecutive injections or gavages (six daily or twelve twice daily) starting at 24 hours post contamination at the following four selected doses: 30 μmol/kg ip, 150 μmol/kg po, 300 μmol/kg po, and 600 μmol/kg po (equivalent to respective approximate human doses range of 2.5, 12.5, 25, and 50 mol/kg, using the accepted conversion system of mouse doses into human equivalent doses—HED—based on body surface area). Oral doses also included the permeability enhancer selected during formulation development work.

Repeated parenteral and oral treatments with 3,4,3-L1(1, 2-HOPO) resulted in enhanced elimination rates and reductions in total body burden and distinct tissue content even when the first treatment dose was delayed until 24 hours post-contamination. In the first cohorts euthanized at seven days, the $^{238}$Pu elimination resulting from the twice-daily dosing schemes was not as good as the corresponding once daily dosing scheme with an equivalent total daily amount of API (i.e, once-daily doses of 300 and 600 mol/kg were better than twice-daily doses of 150 and 300 mol/kg)), when compared with saline controls. Extending the dosing regimen from a single dose to six once-daily doses allowed for more sustained elimination rates for groups treated with 3,4,3-L1(1,2-HOPO), in comparison to saline-administered controls. At 11 days post-contamination, maximum decorporation efficacy was observed after the six once-daily parenteral doses of 3,4,3-L1(1,2-HOPO). The $^{238}$Pu elimination enhancement after multiple oral treatments was still dose-dependent, as reductions in body and tissue content were slightly greater after 6 daily doses at 600 mol/kg than after the corresponding dosing regimen at 300 μmol/kg. Nevertheless, oral treatment with 300 μmol/kg resulted in significant $^{238}$Pu full body and tissue content reduction in comparison with saline-treated controls, with a decorporation efficacy equivalent to that of parenteral treatment with DTPA. Finally, differences were noted in excretion paths: $^{238}$Pu elimination occurred predominantly through feces for 3,4,3-L1(1,2-HOPO)-treated mice and through urine for DTPA-treated mice, with a lower feces to urine $^{238}$Pu ratio in females, as compared with males.

The results of this study confirmed the efficacious dose level for oral treatment administration: When formulated with sodium oleate and orally administered daily for six consecutive days, 300-600 μmol/kg dose levels of 3,4,3-L1 (1,2-HOPO) produced significant decorporation efficacy of soluble $^{238}$Pu in mice.

In this regimen-optimization study, the medical countermeasure 3,4,3-L1(1,2-HOPO) was administered parenterally (ip) or orally (po) via consecutive injections or gavages (six daily or twelve twice daily) starting at 24 hours post contamination at the following four selected doses: 30 mol/kg ip, 150 μmol/kg po, 300 μmol/kg po, and 600 μmol/kg po (equivalent to respective approximate human doses range of 2.5, 12.5, 25, and 50 μmol/kg, using the accepted conversion system of mouse doses into human equivalent doses—HED—based on body surface area). Currently, the "clinical oral dose" for this product from preliminary work ranges from 10 to 150 μmol/kg when administered once orally at 24 hours after internalization of the isotope. The selected doses correspond to the lowest doses resulting in almost maximum decorporation efficacy when administered once at 24 hours post-exposure. These doses had not resulted in any obvious toxicity in prior experiments.

Experimental Design

Challenge isotope: $^{238}$Pu

Challenge dose: 25 nCi (i.e., approximately 0.8 μCi/kg)

Route of contamination: Intravenous (iv) tail-vein

Route of treatment: Intraperitoneal Injection (ip) or Oral (po)

Frequency of treatment: Multiple (once- or twice-daily for 6 days) doses, starting 24 hr postcontamination Treatment dose calculation: Dose calculations (mg/kg or μmol/kg) for the decorporation agent were based on the individual body weight measured after contamination.

Study Duration: 11 days, in-life

TABLE 4.1

EXPERIMENTAL DESIGN
Study Design for 3,4,3-LI(1,2-HOPO) Multiple Dosing Starting at 24 Hours Post Exposure with Intravenous $^{238}$Pu-Citrate in Swiss-Webster Mice.[a]

| Randomization Group | Total Number of Animals | Animals Culled for Necropsy at D-7[b] (1 day-recovery) | Animals Culled for Necropsy at D-11[b] (5 day-recovery) | Animals Culled for Necropsy at H-1[c] (standard mice) | Treatment Dose Level (API, μmol/kg) | Treatment Dose Concentration (mg/mL)[d] | Treatment Time* | Dose of Challenge Agent per Animal (nCI) |
|---|---|---|---|---|---|---|---|---|
| Control ip (6×) | 9F/9M | — | 8F/8M | 1F/1M | NA | NA | 6 daily (D 1 to D 6) | 25 |
| DTPA[f] ip (6 × 30) | 9F/9M | — | 8F/8M | 1F/1M | 30 | 2.09 | 6 daily (D 1 to D 6) | 25 |
| HOPO ip (6 × 30) | 9F/9M | — | 8F/8M | 1F/1M | 30 | 3.15 | 6 daily (D 1 to D 6) | 25 |
| Control po (6×) | 13F/13M | 4F/4M | 8F/8M | 1F/1M | NA | NA | 6 × 2 daily (D 1 to D 6) | 25 |
| Control po (12×) | 4F/4M | 4F/4M | — | — | NA | NA | 6 daily (D 1 to D 6) | 25 |
| HOPO[g] po (6 × 300) | 13F/13M | 4F/4M | 8F/8M | 1F/1M | 300 | 31.50 | 6 daily (D 1 to D 6) | 25 |
| HOPO[g] po (12 × 150) | 4F/4M | 4F/4M | — | — | 150 | 15.75 | 6 × 2 daily (D 1 to D 6) | 25 |
| HOPO[g] po (6 × 600) | 13F/13M | 4F/4M | 8F/8M | 1F/1M | 600 | 64.00 | 6 daily (D 1 to D 6) | 25 |
| HOPO[g] po (12 × 300) | 4F/4M | 4F/4M | — | — | 300 | 31.50 | 6 × 2 daily (D 1 to D 6) | 25 |

[a]Contamination event defined as Day 0 (D-0) and treatment dosing started on Day 1 (D-1), 24 hrs post-contamination. Contamination achieved by intravenous injection in a warmed lateral tail vein of 0.2 mL of the challenge isotope ($^{238}$Pu) in 0.008M sodium citrate and 0.14M sodium chloride, pH 4. Treatments and control vehicle administered by intraperitoneal injection (ip) or oral gavage (po).
[b]Whole animal and tissue challenge isotope content determined at two unique timepoints (D-7, D-11) post treatment administration. Excreta collected daily post contamination until necropsy.
[c]Day 0 culling of one animal from each 5-day recovery group included to determine the mean challenge isotope burden and baseline tissue and carcass values as % of injected dose (% ID) at 1 hour post isotope administration.
[d]Based on a molecular weight of 750.71 g/mol for 3,4,3-LI(1,2-HOPO) (0.7507 mg/μmol) and 497.4 g/mol for Ca-DTPA (04974 mg/μmol), and corresponding to a 0.25 mL dose volume for a 35 g mouse.
[e]Two dosing regimen investigated: size daily doses starting at 24 h post-exposure and twelve twice-daily doses starting at 24 h post-exposure. Doses explored in the second arm corresponded to half of the doses explored in the first arm, to mimic a fractionated dosing regimen.
[f]Sterile solutions of Ca-DTPA and Zn-DTPA in water assembled from commercial pentetic acid, calcium carbonate, zinc oxide, and sodium hydroxide, with pH adjusted at ~7.4 Ca-DTPA is given for the first dose; Zn-DTPA is administered for the subsequent 5 doses to follow FDA recommendations.
[g]All 3,4,3-LI(1,2-HOPO) oral formulations included the permeability enhancer sodium oleate (1:10, w:w), as defined by previous formulation development work.

Objective of Study

The objective of this study was to characterize the efficacy of 3,4,3-L1(1,2-HOPO) at enhancing elimination from an internal plutonium burden in female and male Swiss-Webster mice administered a soluble citrate complex of $^{238}$Pu and treated multiple times, starting at 24 hours after the exposure. Efficacy was evaluated by comparing the tissue contents, urinary and fecal excretions of $^{238}$Pu in treated animals versus untreated animals.

5. Materials And Methods a. Challenge Agent

Challenge Agent: Pu-$^{238}$

Supplier: Eckert & Ziegler (Valencia, Calif.)

Original Stock: Pu-$^{238}$ nitrate in 4M HNO3

Lot Number: 118521

Injection solution: 0.008M sodium citrate, 0.14M sodium chloride, pH 4

Activity: 0.100 μCi/mL

Radiochemical purity (%): 99.938
Storage Conditions: filter-sterilized, −18° C. protected from light.
  b. Test and Control Articles
Test Article: 3,4,3-L1(1,2-HOPO)
Manufacturer: Ash Stevens, Inc. (Detroit, Mich.)
Lot Number: ML-11-276
Physical Description: Pale yellow solid
Storage Conditions: Refrigerated 2-8° C. protected from light.
Test Article Excipient: Sodium oleate
Manufacturer: Tokyo Chemical Industry, Inc. (Tokyo, Japan)
Lot Number: W76EC
Physical Description: White powder
Storage Conditions: Room temperature (15-30° C.), protected from light.
Test Article Vehicle: Sterile saline for injection, USP
Manufacturer: Baxter (Deerfield, Ill.)
Lot Number: C880088
Physical Description: Clear, colorless, aqueous solution
Storage Conditions: 15-30° C. (room temperature); clear viaflex container.
Control Article: DTPA
Manufacturer: Sigma-Aldrich
Lot Number: SLBB4940V
Physical Description: White powder
Storage Conditions: Refrigerated 2-8° C. protected from light (amber vial).
Control Article: Calcium carbonate
Manufacturer: Sigma-Aldrich
Lot Number: MKBJ9544V
Physical Description: White powder
Storage Conditions: Refrigerated 2-8° C. protected from light (amber vial).
Control Article: Zinc oxide
Manufacturer: Sigma-Aldrich
Lot Number: BCBM0343V
Physical Description: White powder
Storage Conditions: Refrigerated 2-8° C. protected from light (opaque plastic bottle).
Control Article Vehicle: Sterile water
Manufacturer: BBraun Medical Inc.
Lot Number: J3N588
Physical Description: Clear, colorless solution
Storage Conditions: 15-30° C. (room temperature); clear viaflex container.
pH Adjustment Solution: 1N Sodium hydroxide
Manufacturer: Sigma-Aldrich
Lot Number: BCBH1222V
Physical Description: Clear, colorless, aqueous solution
Storage Conditions: Refrigerated 2-8° C. protected from light (opaque plastic bottle).
  c. Dose Formulations
Preparation: The test article did not come into contact with metals (e.g., no stainless steel spatulas, syringe needles, or amber vials). Test article and control dose formulations were prepared within 1 day of dose administration, by weighing out the appropriate amount of test article, dispersing in vehicle. For ip solutions, the test article was used alone, while for oral suspensions, a mixture of test article and excipient (90:10, w:w) was used. The pH was adjusted to 7.0-7.4 for ip administration and 5.0-5.5 for oral administration with sterile NaOH. Dose formulations were prepared at room temperature and filter-sterilized.
Storage: 2-8° C.; refrigerated; protected from light.
Characterization: The concentration of each test article formulation was verified by high-performance liquid chromatography-mass spectrometry.
Test Article Handling: Test, reference, and control article formulations were handled with the use of eye protection, gloves, and a protective laboratory coat.
Correct Dose Assurance: The test article was weighed with calibrated balances. The administration of each dose formulation was properly documented, and the amount administered to each animal recorded.
  d. Test System
Animals:
Species: Mouse
Strain: Swiss-Webster
Supplier: Simonsen Laboratories, CA
Sex: Female and Male
Number of Animals: 90F and 90M assigned to test (78F/78M+12F/12M extra)
Age at First Dose: F: 11-12 weeks; M: 11-12 weeks
Weight at First Dose: F: 28.8±1.6 g, M: 31.5±1.3 g
  Both female and male animals were fasted for ca. 16 hrs prior to treatment, which explains the low average weight at first dose.
Animal Care: General procedures for animal care and housing were in accordance with the National Research Council (NRC) Guide for the Care and Use of Laboratory Animals (1996) and the Animal Welfare Standards Incorporated in 9 CFR Part 3, 1991.
Acclimation: Mice were acclimated for three to five days before the start of the study. The general appearance of the animals was evaluated by the research staff.
Housing: Individual in each cage
Cages: Metabolism plastic (Tecniplast)
Light Cycle: 12 hr light/12 hr dark
Temperature: 68-77° F.
Humidity: 30-70%
Ventilation: 10-15 room volumes per hour, with no recirculation of air.
Food: Purina Certified Rodent Chow #5002 (pellets, stock cages), Picolab Certified Rodent Meal #5053 (powder, metabolism cages), or equivalent, ad libitum.
Water: Water (Purified, Reverse Osmosis) was provided ad libitum.
Bedding: Not applicable.
Enrichment: Red plastic igloo.
Animal Assignment:
Day: On day of contamination.
Randomization: Randomly assigned to treatment groups.
Identification: Individually identified by tail ink mark.
Welfare of the Animals: Every effort was made to minimize, if not eliminate, pain and suffering in all animals in this study. Moribund animals and animals experiencing undue pain and suffering were euthanized at the discretion of the research staff e. Experimental Procedures (In-Life Evaluations and Euthanasia)

Contamination: Single administration by intravenous (iv) tail-vein injection (0.2 mL injection volume) under isoflurane anesthesia. Three standard 0.2 mL injections were performed into polyethylene bottles and pre-loaded with aliquots of concentrated nitric acid on each injection day. Six female and six male mice were culled for necropsy 1 hr post-contamination and were used as standards. All standards were processed and counted together with the final samples to allow verification of the contamination dose.

Dose Administration: Single administration by intraperitoneal injection (ip) or oral gavage (po) under isoflurane anesthesia.

Mortality/Morbidity: Assessed at least once daily.

Clinical Observations: Recorded once daily (4 hr post-dose on day of treatment), or more often as clinical signs warranted. Animals were examined for any altered clinical signs, including gross motor and behavioral activity, and observable changes in appearance.

Body weights: Day 1, prior to dose administration.

Euthanasia: Mice were sacrificed by cervical dislocation, frozen, and dissected partially thawed to limit blood loss.

Sample Processing: Liver, kidneys, and abdominal tissue remainder (ATR, including intact gastrointestinal (GI) tract, reproductive organs, spleen, urinary bladder, abdominal fat) were collected for analysis. The skeleton was defleshed after the burning cycle by rinsing soft tissue off with water. All bone samples and remaining soft tissues were collected and digested with 6N HNO3 for analysis. Urine and fecal pellets were collected daily from the designated tubes in each metabolism cage.

Method of Analysis: All samples were dried at 100° C., followed by controlled high temperature burning at 575° C. The resulting ashes were chemically treated with concentrated nitric acid. A defined aliquot of these acidified solutions or of the urine solutions was then transferred (at a minimum volume, to ensure a maximum sample:cocktail ratio of 1:5) and homogenized with 1N nitric acid and scintillation cocktail into a 20-mL scintillation vial for liquid scintillation analysis.

Statistical Analysis: When comparing values between groups in this study, the term "significant" is used in the statistical sense, indicating $P<0.01$ or $P<0.05$ by one-way analysis of variance (ANOVA) followed by adequate post hoc analysis. The Dunnett's multiple comparison test was used to compare the groups of animals treated with the chelating agent to the corresponding control group that was administered saline, while the Tukey's honestly significant difference multiple comparison test was used to perform pair wise comparisons between all the groups treated with the chelating agent. Both tests were performed twice, at the 95% and 99% confidence interval levels. All statistical analyses were performed using GraphPad Prism 5 (GraphPad Software, Inc., San Diego, Calif., USA).

f. Control of Bias

While evaluating the responses of the animals and conducting the analyses, the technical staff was aware of the treatment history of each animal and sample. Based on the relatively objective endpoints to be examined, however, bias is not expected to have influenced the results of the study.

6. Results

The in-life portion of the study was accomplished without incident. The average radiochemical recovery in the female arms was 90.6% and 88.5% for the 7-day and 11-day necropsy cohorts, respectively. The average radiochemical recovery in the male arms was 85.7% and 86.5% for the 7-day and 11-day necropsy cohorts, respectively.

No adverse effect was noted for the groups of animals treated with parenteral or oral 3,4,3-L1(1,2-HOPO) at all dose level. All female and male animals in all dose groups appeared healthy and survived until their respective scheduled necropsy, except for one female mouse that was found dead in its cage at 4 hours after its first treatment (in the once-daily 30 μmol/kg parenteral 3,4,3-L1(1,2-HOPO) treatment group with necropsy scheduled on day 11). A large blood clot on the left abdominal cavity wall was found during necropsy, and internal bleeding due to failed dose administration was the probable cause of death. This mouse was not included for average dose calculations in the corresponding group. A few anomalies were noted during sample collection and processing, with no significant impact on the outcome of the study: urine samples were spilled for two female mice on a single day collection (on day 8 for one female mouse in the 300 μmol/kg oral treatment group with necropsy scheduled on day 11, and on day 7 for one female mouse in the 600 μmol/kg treatment group with necropsy scheduled on day 11).

a. Female Excretion Data Analysis

Figure 11A:
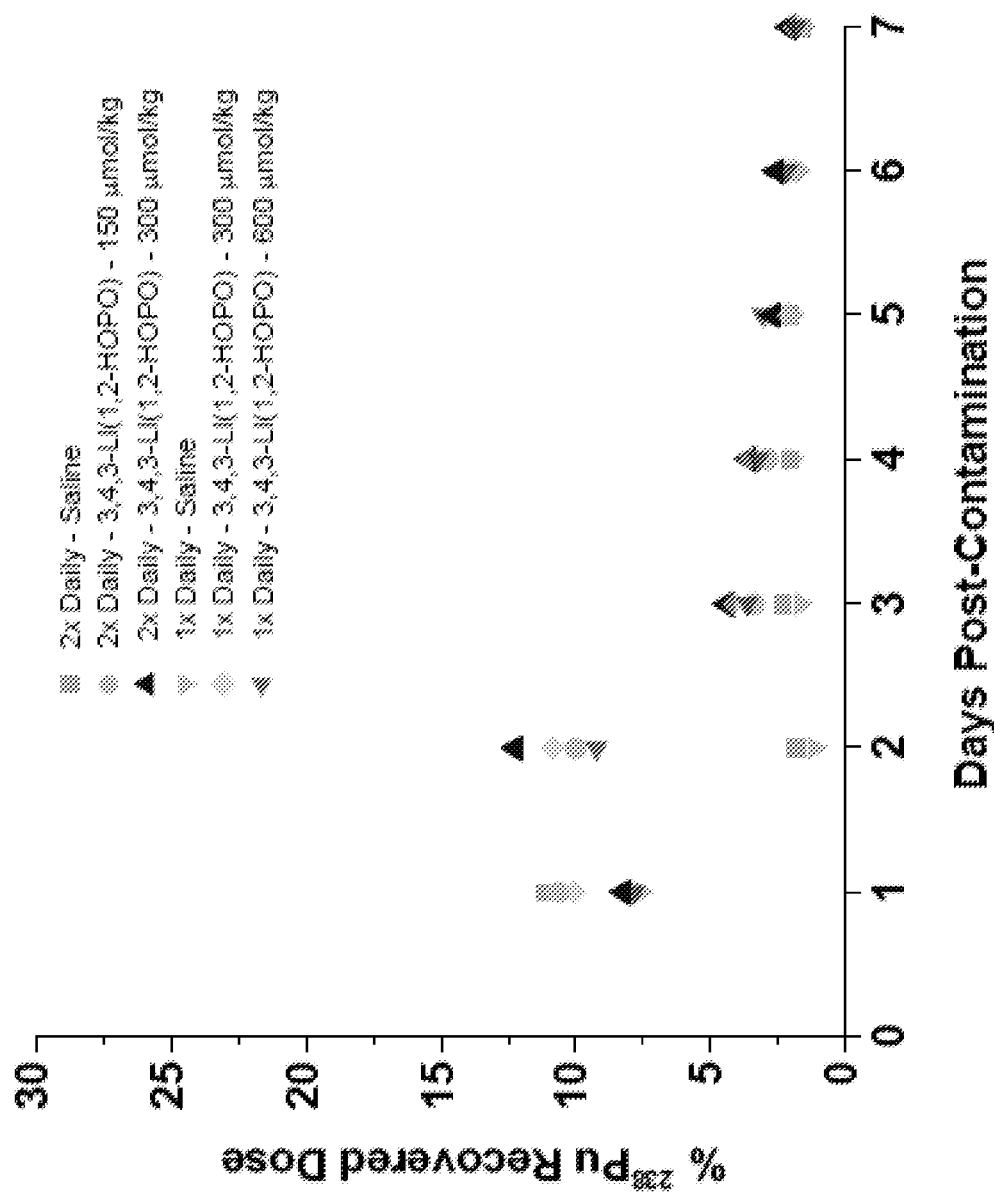
FIG. 11A shows the daily fecal excretion rate at necropsy of young adult female Swiss-Webster mice injected i.v. with $^{238}$Pu-citrate. 3,4,3-L1(1,2-HOPO) treatment was administered p.o. twice-daily or once-daily for 6 days, starting at 24 hours post-exposure and mice were euthanized at 7 days.
Figure 11B:
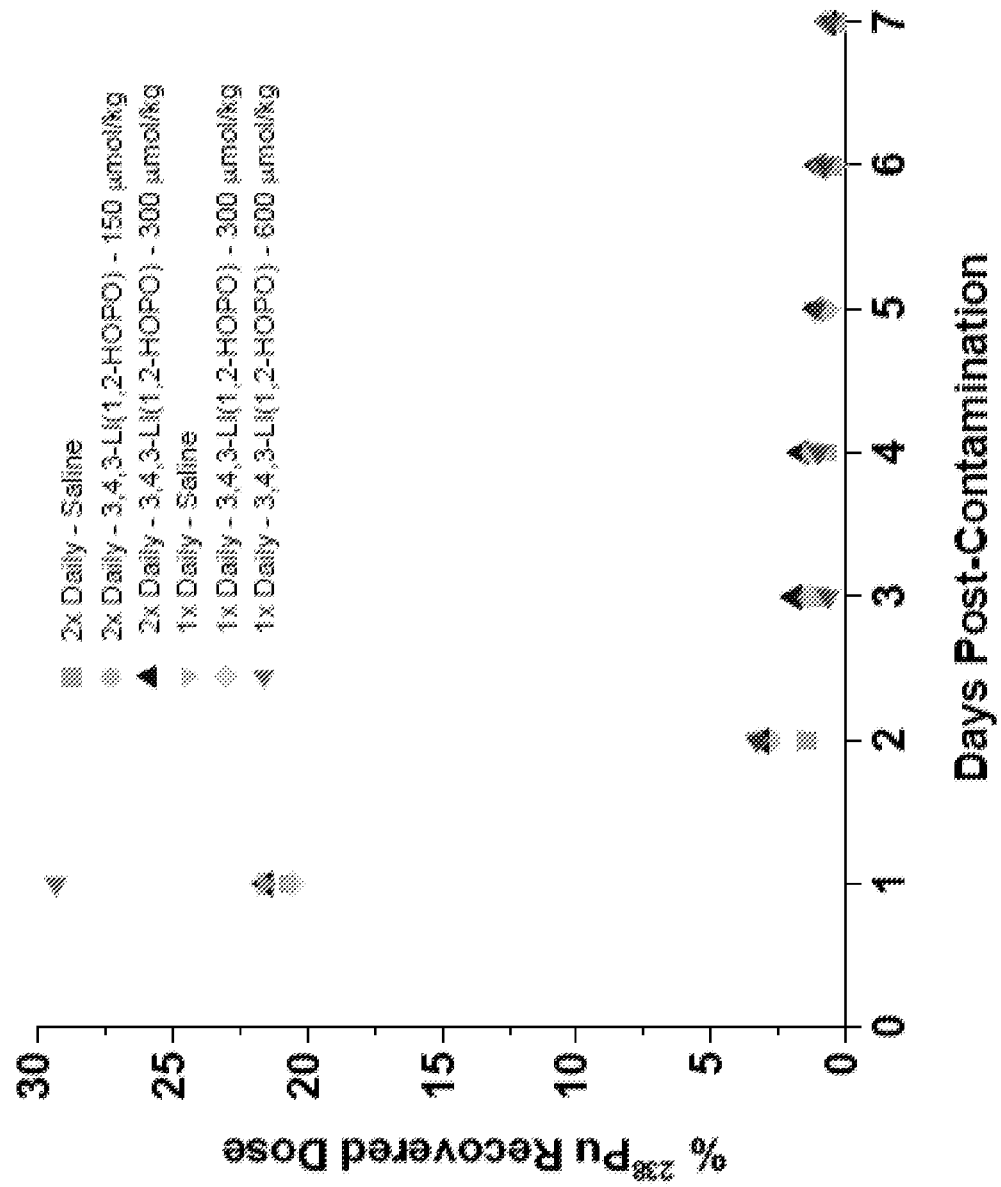
FIG. 11B shows the daily urinary excretion rate at necropsy of young adult female Swiss-Webster mice injected i.v. with $^{238}$Pu-citrate. 3,4,3-L1(1,2-HOPO) treatment was administered p.o. twice-daily or once-daily for 6 days, starting at 24 hours post-exposure and mice were euthanized at 7 days.
Figure 11C:
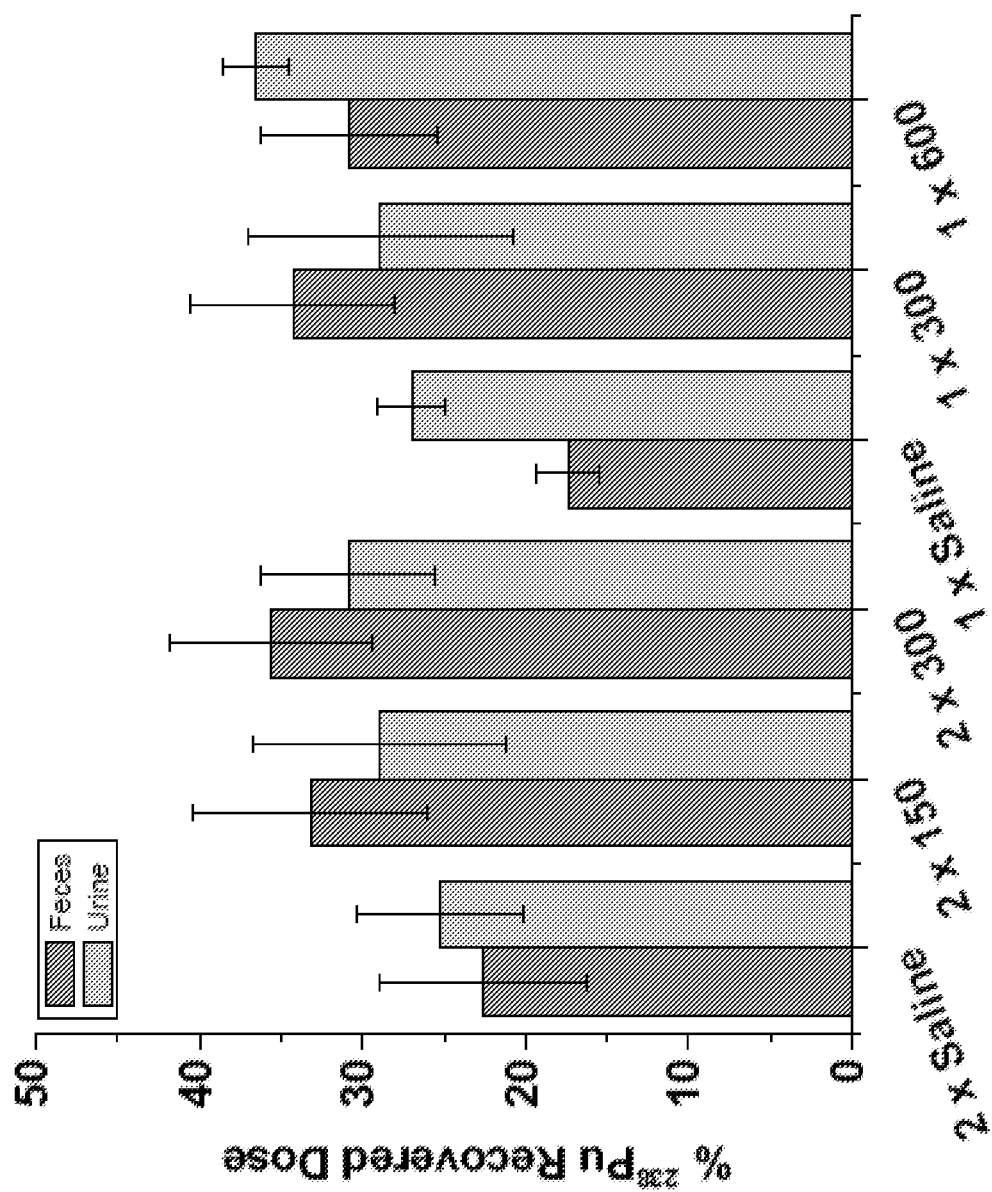
FIG. 11C shows the cumulative excretion at necropsy on day 7 for FIG. 11A and FIG. 11B.

FIG. 11A shows the daily fecal elimination of $^{238}$Pu and FIG. 11B shows the daily urinary elimination of $^{238}$Pu for all treatment groups with scheduled necropsy at 7 days post-contamination. FIG. 12A shows the daily fecal elimination of $^{238}$Pu and FIG. 12B shows the daily urinary elimination of $^{238}$Pu for all treatment groups with scheduled necropsy at 11 days post-contamination. The cumulative urinary and fecal $^{238}$Pu elimination at the different scheduled necropsy times (7 days and 11 days days post-contamination, respectively) are shown graphically for all experimental groups in FIG. 11C and FIG. 12C, and numerically in TABLE 4.2A; all results are expressed as a fraction of the total recovered $^{238}$Pu dose.

Statistical analysis was not conducted on the daily collections, but was conducted on the cumulative fecal, urinary, and combined excretion data at the two scheduled necropsy times. Oral treatment with 3,4,3-L1(1,2-HOPO) twice-daily at 150 and 300 μmol/kg or once-daily at 300 and 600 μmol/kg resulted in significant $^{238}$Pu elimination enhancement at 7-days postcontamination, and the groups treated with the higher twice-daily 300 μmol/kg and once-daily 300 and 600 mol/kg 3,4,3-L1(1,2-HOPO) dose levels also displayed significantly enhanced fecal excretion at the 7-day time point. At the 11-day necropsy time point, all treatment regimens showed significant combined excretion enhancement. However, only the 30 μmol/kg parenteral and 600 μmol/kg oral treatments resulted in significant elimination enhancement through both urine and feces. Daily treatment seemed to enhance urinary excretion compared to single treatment (see previous reports) for 3,4,3-L1(1,2-HOPO).

TABLE 4.2A $^{238}$PU EXCRETION IN FEMALE MICE: AVERAGE PERCENT RECOVERED DOSE

| Female 7-Day Necropsy Group Treatment | Total Urine Avg (Std Dev) | Total Feces Avg (Std Dev) | Total Excretion Avg (Std Dev) |
|---|---|---|---|
| Saline; 2 doses PO | 25.25 5.14 | 22.64 6.27 | 47.89 2.26 |
| 343 (150 µmol/kg); 2 doses PO | 29.02 7.68 | 33.16 7.23 | 62.18 2.34** |
| 343 (300 µmol/kg); 2 doses PO | 30.90 5.36 | 35.68 6.22* | 66.57 5.97** |
| Saline; 1 dose PO | 27.01 2.10 | 17.42 1.96 | 44.43 3.70 |
| 343 (300 µmol/kg); 1 dose PO | 28.92 8.11 | 34.34 6.28* | 63.26 3.59** |
| 343 (600 µmol/kg); 1 dose PO | 36.57 2.01 | 30.80 5.38* | 67.37 5.09** |
| Saline; IP | 21.83 5.36 | 28.48 6.60 | 50.32 4.90 |
| DTPA (30 µmol/kg); IP | 41.93 3.73** | 30.20 3.51 | 72.13 2.48** |
| 343 (30 µmol/kg); IP | 37.57 3.48** | 41.80 3.66** | 79.37 1.92** |
| Saline; PO | 28.01 2.86 | 23.10 3.40 | 51.11 4.00 |
| 343 (300 µmol/kg); PO | 34.27 5.86 | 37.63 6.15** | 71.89 2.36** |
| 343 (600 µmol/kg); PO | 38.52 3.33** | 34.70 2.96** | 73.22 3.10** |

AVG (SD):
*P < 0.05,
**p < 0.01 against corresponding saline control group

TABLE 4.2B $^{238}$PU EXCRETION IN FEMALE MICE: PERCENT INCREASE IN EXCRETION

| Female 7-Day Necropsy | Total Urine | Total Feces | Total Excretion |
|---|---|---|---|
| 343 (150 µmol/kg); 2 doses PO | 114.93 | 146.48 | 129.85 |
| 343 (300 µmol/kg); 2 doses PO | 122.37 | 157.58 | 139.02 |
| 343 (300 µmol/kg); 1 dose PO | 107.09 | 197.06 | 142.38 |
| 343 (600 µmol/kg); 1 dose PO | 135.42 | 176.75 | 151.63 |
| DTPA (30 µmol/kg); IP | 192.03 | 106.02 | 143.34 |
| 343 (30 µmol/kg); IP | 172.05 | 146.77 | 157.74 |
| 343 (300 µmol/kg); PO | 122.35 | 162.86 | 140.66 |
| 343 (600 µmol/kg); PO | 137.53 | 150.20 | 143.25 |

FIG. 13A and FIG. 13B show the cumulative urinary, fecal, and combined elimination of $^{238}$Pu of all treated groups relative to controls for day 7 and day 11, respectively, and TABLE 4.2B summarizes the percentage of urinary, fecal, and combined excretion enhancement over the untreated control groups. Total excretion rates were better after 6 daily oral treatments with 600 µmol/kg 3,4,3-L1(1, 2-HOPO) than after parenteral DTPA, resulting in up to 143% increase in total excretion compared to the control groups at 11 days post-contamination. Finally fractionation of the dose seemed to reduce efficacy since twice daily doses at 150 and 300 µmol/kg resulted in a lesser $^{238}$Pu elimination enhancement than the corresponding once-daily 300 and 600 mol/kg dose levels.

b. Female Tissue Data Analysis

The full body, skeleton, and liver contents of $^{238}$Pu at the 7-day (FIG. 14A) and 11-day (FIG. 14B) necropsy time points are shown graphically for all experimental groups in and numerically in TABLE 4.3A; all results are expressed as a fraction of the total recovered $^{238}$Pu dose. All analyzed tissues showed large reductions in tissue content of $^{238}$Pu for the groups treated with DTPA or 3,4,3-L1(1,2-HOPO), compared to the corresponding saline control group, at all dosing regimens. All groups treated with 3,4,3-L1(1,2-HOPO) showed significant reductions in full body content of $^{238}$Pu compared to the saline control groups and groups treated with 3,4,3-L1(1,2-HOPO) at 300 and 600 µmol/kg once-daily showed significant reductions in liver, kidney, GI tract, soft tissue, and skeleton content. Finally, oral treatment with once-daily 300 µmol/kg 3,4,3-L1(1,2-HOPO) resulted in a decorporation efficacy equivalent to that of parenteral treatment with DTPA.

TABLE 4.3B shows the percentage tissue content reduction compared to the corresponding untreated control group (for significant reductions). All treated group displayed significant reductions, with up to 45% decrease in body burden compared to the control groups at 11 days postcontamination after once-daily oral treatment with 600 µmol/kg 3,4,3-L1(1,2-HOPO). Data related to percent recovered dose from the female arm are shown in TABLE 4.6.

TABLE 4.3A $^{238}$PU RETENTION IN FEMALE MICE: AVERAGE PERCENT RECOVERED DOSE

| Group Treatment | Kidney Avg (Std Dev) | Liver Avg (Std Dev) | GI Tract Avg (Std Dev) | Soft Tissue Avg (Std Dev) | Total Bone Avg (Std Dev) | Total Body Avg (Std Dev) |
|---|---|---|---|---|---|---|
| Female 7-Day Necropsy | | | | | | |
| Saline; 2 doses PO | 0.41 0.19 | 18.71 4.33 | 1.86 0.49 | 2.04 0.43 | 29.09 5.07 | 52.11 2.26 |
| 343 (150 µmol/kg); 2 doses PO | 0.23 0.06 | 12.83 4.08 | 1.20 0.16* | 1.64 0.10 | 21.92 3.68 | 37.82 2.34** |

TABLE 4.3A-continued $^{238}$PU RETENTION IN FEMALE MICE: AVERAGE PERCENT RECOVERED DOSE

| Group Treatment | Kidney Avg | (Std Dev) | Liver Avg | (Std Dev) | GI Tract Avg | (Std Dev) | Soft Tissue Avg | (Std Dev) | Total Bone Avg | (Std Dev) | Total Body Avg | (Std Dev) |
|---|---|---|---|---|---|---|---|---|---|---|---|---|
| 343 (300 µmol/kg); 2 doses PO | 0.18 | 0.09 | 6.85 | 1.80** | 1.25 | 0.11* | 1.62 | 0.27 | 23.54 | 4.89 | 33.43 | 5.97** |
| Saline; 1 dose PO | 0.33 | 0.05 | 16.59 | 4.36 | 1.35 | 0.22 | 2.32 | 0.10 | 34.97 | 6.96 | 55.57 | 3.70 |
| 343 (300 µmol/kg); 1 dose PO | 0.26 | 0.13 | 10.22 | 5.60 | 1.20 | 0.17 | 1.74 | 0.25* | 23.31 | 3.89* | 36.74 | 3.59** |
| 343 (600 µmol/kg); 1 dose PO | 0.23 | 0.03 | 12.48 | 4.33 | 1.24 | 0.26 | 1.62 | 0.35* | 17.06 | 1.56** | 32.63 | 5.09** |
| Female 11-Day Necropsy | | | | | | | | | | | | |
| Saline; IP | 0.26 | 0.05 | 12.04 | 3.89 | 1.34 | 0.33 | 2.85 | 0.27 | 33.19 | 6.89 | 49.68 | 4.90 |
| DTPA (30 µmol/kg); IP | 0.13 | 0.04** | 4.14 | 1.15** | 0.54 | 0.10** | 1.66 | 0.33** | 21.40 | 2.88** | 27.87 | 2.48** |
| 343 (30 µmol/kg); IP | 0.11 | 0.04** | 2.79 | 1.31** | 0.59 | 0.10** | 1.40 | 0.31** | 15.74 | 2.31** | 20.63 | 1.92** |
| Saline; PO | 0.27 | 0.06 | 13.39 | 4.54 | 1.37 | 0.35 | 2.67 | 0.60 | 31.19 | 5.67 | 48.89 | 4.00 |
| 343 (300 µmol/kg); 1 dose PO | 0.17 | 0.06* | 6.02 | 1.71** | 1.02 | 0.21* | 2.06 | 0.38* | 18.85 | 2.91** | 28.11 | 2.36** |
| 343 (600 µmol/kg); 1 dose PO | 0.14 | 0.04** | 5.60 | 1.86** | 0.83 | 0.22** | 2.01 | 0.36* | 18.20 | 2.47** | 26.78 | 3.10** |

AVG (SD):
*P < 0.05,
**p < 0.01 against corresponding saline control group

TABLE 4.3B $^{238}$PU RETENTION IN FEMALE MICE: PERCENT TISSUE REDUCTION

| | Kidney | Liver | GI Tract | Soft Tissue | Total Bone | Total Body |
|---|---|---|---|---|---|---|
| Female 7-Day Necropsy | | | | | | |
| 343 (150 µmol/kg); 2 doses PO | 43.29 | 31.41 | 35.66 | 19.55 | 24.67 | 27.43 |
| 343 (300 µmol/kg); 2 doses PO | 56.34 | 63.39 | 33.06 | 20.76 | 19.10 | 35.85 |
| 343 (300 µmol/kg); 1 doses PO | 20.17 | 38.39 | 11.06 | 25.25 | 33.33 | 33.88 |
| 343 (600 µmol/kg); 1 dose PO | 29.85 | 24.79 | 8.30 | 30.25 | 51.23 | 41.28 |
| Female 11-Day Necropsy | | | | | | |
| DTPA (30 µmol/kg); IP | 51.24 | 65.62 | 59.99 | 41.56 | 35.51 | 43.90 |
| 343 (30 µmol/kg); IP | 58.43 | 76.81 | 55.96 | 50.90 | 52.58 | 58.48 |
| 343 (300 µmol/kg); 1 dose PO | 37.82 | 55.06 | 25.61 | 22.98 | 39.58 | 42.51 |
| 343 (600 µmol/kg); 1 dose PO | 48.77 | 58.17 | 39.39 | 24.63 | 41.64 | 45.22 | c. Male Excretion Data Analysis

FIG. 15A shows the daily fecal elimination of $^{238}$Pu and FIG. 15B shows the daily urinary elimination of $^{238}$Pu for all treatment groups with scheduled necropsy at 7 days post-contamination. FIG. 16A shows the daily fecal elimination of $^{238}$Pu and FIG. 16B shows the daily urinary elimination of $^{238}$Pu for all treatment groups with scheduled necropsy at 11 days post-contamination. The cumulative urinary and fecal $^{238}$Pu elimination at the different scheduled necropsy times (7 days and 11 days days post-contamination, respectively) are shown graphically for all experimental groups in FIG. 15C and FIG. 16C, and numerically in TABLE 4.4A; all results are expressed as a fraction of the total recovered $^{238}$Pu dose. Oral treatment with 3,4,3-L1(1,2-HOPO) twice-daily at 150 and 300 μmol/kg or once-daily at 300 and 600 μmol/kg resulted in significant $^{238}$Pu elimination enhancement and in significantly enhanced fecal excretion at 7-days post-contamination. At the 11-day necropsy time point, all treatment regimens showed significant combined excretion and fecal excretion enhancement. However, no 3,4,3-L1(1, 2-HOPO) oral treatments resulted in significant elimination enhancement through the urine.

dose seemed to reduce efficacy at the lower dose level since twice-daily doses at 150 μmol/kg resulted in a lesser $^{238}$Pu elimination enhancement than the corresponding once-daily 300 μmol/kg dose levels. However, twice-daily doses at 300 μmol/kg or once-daily 300 μmol/kg doses resulted in equivalent $^{238}$Pu elimination enhancement. One difference that seemed to arise during fractionation is a change in the $^{238}$Pu urine:feces ratio: urine elimination was higher after fractionated doses (twice-daily regimens) than after the corresponding once-daily dosing regimen, which may indicate saturation in the hepatic clearance capacity.

d. Male Tissue Data Analysis

The full body, skeleton, and liver contents of $^{238}$Pu at the 7-day (FIG. 18A) and 11-day (FIG. 18B) necropsy time points are shown graphically for all experimental groups in and numerically in TABLE 4.5A; all results are expressed as

TABLE 4.4A $^{238}$PU EXCRETION IN MALE MICE: AVERAGE PERCENT RECOVERED DOSE

| Female 7-Day Necropsy Group Treatment | Total Urine Avg | (Std Dev) | Total Feces Avg | (Std Dev) | Total Excretion Avg | (Std Dev) |
|---|---|---|---|---|---|---|
| Saline; 2 doses PO | 18.49 | 5.27 | 17.33 | 2.35 | 35.82 | 3.96 |
| 343 (150 μmol/kg); 2 doses PO | 23.32 | 1.76 | 30.26 | 7.91** | 53.58 | 6.28** |
| 343 (300 μmol/kg); 2 doses PO | 25.57 | 4.05 | 34.14 | 1.36** | 59.71 | 3.55** |
| Saline; 1 dose PO | 21.81 | 4.30 | 17.76 | 2.24 | 39.57 | 5.24 |
| 343 (300 μmol/kg); 1 dose PO | 24.00 | 3.84 | 40.12 | 0.55** | 64.11 | 4.18** |
| 343 (600 μmol/kg); 1 dose PO | 25.13 | 4.69 | 40.53 | 3.79** | 65.66 | 4.35** |
| Saline; IP | 21.95 | 5.69 | 25.53 | 6.65 | 47.48 | 4.63 |
| DTPA (30 μmol/kg); IP | 35.09 | 10.80** | 35.89 | 10.92** | 70.98 | 3.80** |
| 343 (30 μmol/kg); IP | 31.65 | 6.02* | 48.24 | 7.04** | 79.89 | 2.67** |
| Saline; PO | 23.98 | 3.74 | 22.36 | 3.15 | 46.34 | 1.92 |
| 343 (300 μmol/kg); PO | 25.84 | 3.90 | 40.33 | 4.98** | 66.17 | 5.80* |
| 343 (600 μmol/kg); PO | 27.43 | 8.25 | 44.91 | 8.39** | 72.33 | 5.15** |

AVG (SD):
*P < 0.05,
**p < 0.01 against corresponding saline control group

TABLE 4.4B

238PU EXCRETION IN MALE MICE: PERCENT INCREASE IN EXCRETION

| Female 7-Day Necropsy | Total Urine | Total Feces | Total Excretion |
|---|---|---|---|
| 343 (150 μmol/kg); 2 doses PO | 126.15 | 174.63 | 149.61 |
| 343 (300 μmol/kg); 2 doses PO | 138.32 | 197.01 | 166.71 |
| 343 (300 μmol/kg); 1 dose PO | 110.04 | 225.83 | 162.02 |
| 343 (600 μmol/kg); 1 dose PO | 115.25 | 228.14 | 165.93 |
| DTPA (30 μmol/kg); IP | 159.88 | 140.57 | 149.50 |
| 343 (30 μmol/kg); IP | 144.22 | 188.96 | 168.28 |
| 343 (300 μmol/kg); PO | 107.78 | 180.35 | 142.80 |
| 343 (600 μmol/kg); PO | 114.39 | 200.32 | 156.10 |

FIG. 17A and FIG. 17B shows the cumulative urinary, fecal, and combined elimination of $^{238}$Pu of all treated groups relative to controls for day 7 and day 11, respectively, and TABLE 4.4B summarizes the percentage of urinary, fecal, and combined excretion enhancement over the untreated control groups. Total excretion rates were better after 6 daily oral treatments with 600 μmol/kg 3,4,3-L1(1, 2-HOPO) than after parenteral DTPA, resulting in up to 156% increase in total excretion compared to the control groups at 11 days post-contamination. Fractionation of the a fraction of the total recovered $^{238}$Pu dose. A11 analyzed tissues showed large reductions in tissue content of $^{238}$Pu for the groups treated with DTPA or 3,4,3-L1(1,2-HOPO), compared to the corresponding saline control group, at all dosing regimens. A11 groups treated with 3,4,3-L1(1,2-HOPO) showed significant reductions in full body content of $^{238}$Pu compared to the saline control groups and groups treated with 3,4,3-L1(1,2-HOPO) at 300 and 600 μmol/kg once-daily showed significant reductions in liver, kidney, GI tract, soft tissue, and skeleton content. Finally, oral treatment with once-daily 300 and 600 μmol/kg 3,4,3-L1(1,2-HOPO) resulted in a decorporation efficacy equivalent to that of parenteral treatment with DTPA.

TABLE 4.5B shows the percentage tissue content reduction compared to the corresponding untreated control group (for significant reductions). A11 treated group displayed significant reductions, with up to 48% decrease in body burden compared to the control groups at 11 days postcontamination after once-daily oral treatment with 600 μmol/kg 3,4,3-L1(1,2-HOPO). Data related to percent recovered dose from the male arm are shown in TABLE 4.7.

In general the decrease in tissue burdens follows similar patterns for male and female animals.

TABLE 4.5A $^{238}$PU RETENTION IN MALE MICE: AVERAGE PERCENT RECOVERED DOSE

| Group Treatment | Kidney Avg | (Std Dev) | Liver Avg | (Std Dev) | GI Tract Avg | (Std Dev) | Soft Tissue Avg | (Std Dev) | Total Bone Avg | (Std Dev) | Total Body Avg | (Std Dev) |
|---|---|---|---|---|---|---|---|---|---|---|---|---|
| Female 7-Day Necropsy | | | | | | | | | | | | |
| Saline; 2 doses PO | 0.30 | 0.06 | 26.12 | 6.58 | 1.42 | 0.24 | 3.00 | 0.23 | 33.34 | 8.74 | 64.18 | 3.96 |
| 343 (150 µmol/kg); 2 doses PO | 0.31 | 0.09 | 21.40 | 7.47 | 1.67 | 0.35 | 3.16 | 0.33 | 19.87 | 3.20** | 46.42 | 6.28** |
| 343 (300 µmol/kg); 2 doses PO | 0.18 | 0.03 | 15.12 | 2.09* | 1.45 | 0.09 | 2.41 | 0.37 | 21.12 | 3.82* | 40.29 | 3.55** |
| Saline; 1 dose PO | 0.28 | 0.03 | 22.44 | 3.19 | 1.57 | 0.39 | 2.68 | 0.51 | 33.46 | 4.85 | 60.43 | 5.24 |
| 343 (300 µmol/kg); 1 dose PO | 0.17 | 0.04* | 12.68 | 2.54* | 1.23 | 0.15 | 1.75 | 0.40* | 20.06 | 1.56** | 35.89 | 4.18** |
| 343 (600 µmol/kg); dose PO | 0.25 | 0.11 | 12.44 | 4.56* | 1.63 | 0.55 | 2.22 | 0.30 | 17.81 | 1.61* | 34.34 | 4.35** |
| Female 11-Day Necropsy | | | | | | | | | | | | |
| Saline; IP | 0.33 | 0.14 | 16.77 | 4.63 | 1.97 | 0.62 | 3.55 | 0.32 | 29.90 | 4.83 | 52.52 | 4.63 |
| DTPA (30 µmol/kg); IP | 0.17 | 0.05** | 4.78 | 0.75** | 0.76 | 0.43** | 2.05 | 0.51** | 21.26 | 2.83** | 29.02 | 3.80** |
| 343 (30 µmol/kg); IP | 0.12 | 0.03** | 2.42 | 0.39** | 0.53 | 0.10** | 1.14 | 0.20** | 15.90 | 2.88** | 20.11 | 2.67** |
| Saline; PO | 0.27 | 0.07 | 18.32 | 3.19 | 1.47 | 0.38 | 2.84 | 0.75 | 30.13 | 4.73 | 53.66 | 1.92 |
| 343 (300 µmol/kg); 1 dose PO | 0.15 | 0.03** | 9.46 | 3.05** | 1.03 | 0.10 | 2.20 | 0.38 | 20.99 | 3.98* | 33.83 | 5.80** |
| 343 (600 µmol/kg); 1 dose PO | 0.19 | 0.07 | 6.78 | 3.25** | 0.75 | 0.20** | 1.93 | 0.38** | 18.02 | 3.37* | 27.67 | 5.15** |

AVG (SD):
*P < 0.05,
**p < 0.01 against corresponding saline control group

TABLE 4.5B $^{238}$PU RETENTION IN MALE MICE: PERCENT TISSUE REDUCTION

| Female 7-Day Necropsy | Kidney | Liver | GI Tract | Soft Tissue | Total Bone | Total Body |
|---|---|---|---|---|---|---|
| 343 (150 µmol/kg); 2 doses PO | −4.19 | 18.09 | −17.71 | −5.31 | 40.39 | 27.68 |
| 343 (300 µmol/kg); 2 doses PO | 39.84 | 42.11 | −2.24 | 19.73 | 36.64 | 37.23 |
| 343 (300 µmol/kg); 1 dose PO | 40.67 | 43.47 | 21.76 | 34.62 | 40.06 | 40.61 |
| 343 (600 µmol/kg); 1 dose PO | 11.13 | 44.57 | −3.93 | 17.40 | 46.78 | 43.17 |

| Female 11-Day Necropsy | Kidney | Liver | GI Trace | Soft Tissue | Total Bone | Total Body |
|---|---|---|---|---|---|---|
| DTPA (30 µmol/kg); IP | 47.89 | 71.51 | 61.32 | 42.09 | 28.92 | 44.74 |
| 343 (30 µmol/kg); IP | 65.35 | 85.55 | 72.95 | 67.92 | 46.83 | 61.72 |
| 343 (300 µmol/kg); 1 dose PO | 45.60 | 48.32 | 30.01 | 22.51 | 30.34 | 36.96 |
| 343 (600 µmol/kg); 1 dose PO | 32.19 | 62.99 | 49.06 | 32.01 | 40.18 | 48.44 |

7. Conclusions

Repeated parenteral and oral treatments with 3,4,3-L1(1,2-HOPO) resulted in enhanced elimination rates and reductions in total body burden and distinct tissue content even when the first treatment dose was delayed until 24 hours post-contamination. In the first cohorts euthanized at seven days, the $^{238}$Pu elimination resulting from the twice-daily dosing schemes was not as good as the corresponding once daily dosing scheme with an equivalent total daily amount of API (i.e, once-daily doses of 300 and 600 mol/kg were better than twice-daily doses of 150 and 300 µmol/kg), when compared with saline controls. Extending the dosing regimen from a single dose to six once-daily doses allowed for more sustained elimination rates for groups treated with 3,4,3-L1(1,2-HOPO), in comparison to saline-administered controls. At 11 days post-contamination, maximum decorporation efficacy was observed after the six once-daily parenteral doses of 3,4,3-L1(1,2-HOPO). The $^{238}$Pu elimination enhancement after multiple oral treatments was still dose-dependent, as reductions in body and tissue content were slightly greater after 6 daily doses at 600 µmol/kg than after the corresponding dosing regimen at 300 mol/kg. Nevertheless, oral treatment with 300 µmol/kg resulted in significant $^{238}$Pu full body and tissue content reduction in comparison with saline-treated controls, with a decorporation efficacy equivalent to that of parenteral treatment with DTPA. Finally, differences were noted in excretion paths: $^{238}$Pu elimination occurred predominantly through feces for 3,4,3-L1(1,2-HOPO)-treated mice and through urine for DTPA-treated mice, with a lower feces to urine $^{238}$Pu ratio in females, as compared with males.

The results of this study confirmed the efficacious dose level for oral treatment administration: When formulated with sodium oleate and orally administered daily for six consecutive days, 300-600 µmol/kg dose levels of 3,4,3-L1(1,2-HOPO) produced significant decorporation efficacy of soluble $^{238}$Pu in mice.

a. Percent Recovered Dose for Female Arm

TABLE 4.6

PERCENT RECOVERED DOSE FEMALE ARM

% Recovered Dose-Female Animals-D-7 Necropsy

| Animal ID | Kidney | Liver | ART | SOFT | SKEL | Combined Body | Total Urine | Total Feces | Combined Excreta |
|---|---|---|---|---|---|---|---|---|---|
| A1 | 0.28% | 21.55% | 1.51% | 1.98% | 28.36% | 53.67% | 28.69% | 17.63% | 46.33% |
| A2 | 0.35% | 12.41% | 2.59% | 2.61% | 36.46% | 54.41% | 24.40% | 21.19% | 45.59% |
| A3 | 0.68% | 19.26% | 1.65% | 2.03% | 26.27% | 49.89% | 18.32% | 31.79% | 50.11% |
| A4 | 0.32% | 21.60% | 1.71% | 1.56% | 25.29% | 50.47% | 29.58% | 19.95% | 49.53% |
| B1 | 0.27% | 8.04% | 1.01% | 1.63% | 23.83% | 34.79% | 27.84% | 37.37% | 65.21% |
| B2 | 0.15% | 11.52% | 1.36% | 1.69% | 24.03% | 38.75% | 35.60% | 25.66% | 61.25% |
| B3 | 0.24% | 14.05% | 1.12% | 1.50% | 23.40% | 40.32% | 18.65% | 41.03% | 59.68% |
| B4 | 0.27% | 17.71% | 1.30% | 1.75% | 16.40% | 37.43% | 33.98% | 28.59% | 62.57% |
| C1 | 0.17% | 5.50% | 1.12% | 1.54% | 28.04% | 36.37% | 23.02% | 40.61% | 63.63% |
| C2 | 0.31% | 9.28% | 1.21% | 2.00% | 26.98% | 39.78% | 33.48% | 26.74% | 60.22% |
| C3 | 0.14% | 7.15% | 1.29% | 1.36% | 21.55% | 31.50% | 32.25% | 36.25% | 68.50% |
| C4 | 0.09% | 5.47% | 1.37% | 1.57% | 17.57% | 26.07% | 34.83% | 39.09% | 73.93% |
| D1 | 0.28% | 12.55% | 1.24% | 2.47% | 44.52% | 61.05% | 23.99% | 14.96% | 38.95% |
| D2 | 0.38% | 19.94% | 1.59% | 2.27% | 30.07% | 54.24% | 27.81% | 17.95% | 45.76% |
| D3 | 0.37% | 20.77% | 1.10% | 2.26% | 29.53% | 54.04% | 28.84% | 17.12% | 45.96% |
| D4 | 0.30% | 13.12% | 1.49% | 2.28% | 35.76% | 52.94% | 27.39% | 19.67% | 47.06% |
| E1 | 0.24% | 15.03% | 1.20% | 1.61% | 18.05% | 36.12% | 38.49% | 25.39% | 63.88% |
| E2 | 0.28% | 5.40% | 0.98% | 2.12% | 27.21% | 35.98% | 29.16% | 34.86% | 64.02% |
| E3 | 0.43% | 15.12% | 1.39% | 1.63% | 23.15% | 41.72% | 18.65% | 39.63% | 58.28% |
| E4 | 0.12% | 5.35% | 1.24% | 1.58% | 24.86% | 33.15% | 29.39% | 37.46% | 66.85% |
| F1 | 0.21% | 15.19% | 1.16% | 1.55% | 17.48% | 35.58% | 35.51% | 28.91% | 64.42% |
| F2 | 0.22% | 6.77% | 1.24% | 1.38% | 15.65% | 25.26% | 37.41% | 37.33% | 74.74% |
| F3 | 0.22% | 11.56% | 0.98% | 1.41% | 19.07% | 33.24% | 34.43% | 32.34% | 66.76% |
| F4 | 0.28% | 16.40% | 1.59% | 2.13% | 16.03% | 36.43% | 38.95% | 24.62% | 63.57% |

% Recovered Dose-Female Animals-D-11 Necropsy

| Animal ID | Kidney | Liver | GI Tract | Soft Tissue | Total Bone | Combined Body | Total Urine | Total Feces | Combined Excreta |
|---|---|---|---|---|---|---|---|---|---|
| G1 | 0.25% | 10.04% | 1.01% | 3.07% | 31.33% | 45.70% | 19.94% | 34.35% | 54.30% |
| G2 | 0.34% | 10.95% | 1.11% | 3.01% | 34.72% | 50.12% | 16.92% | 32.96% | 49.88% |
| G3 | 0.23% | 9.30% | 1.51% | 2.66% | 36.12% | 49.83% | 29.84% | 20.33% | 50.17% |
| G4 | 0.24% | 15.11% | 1.07% | 2.75% | 36.09% | 55.26% | 23.37% | 21.37% | 44.74% |
| G5 | 0.29% | 8.39% | 1.16% | 2.81% | 38.03% | 50.69% | 12.78% | 36.53% | 49.31% |
| G6 | 0.21% | 14.16% | 1.76% | 2.33% | 22.35% | 40.80% | 25.37% | 33.83% | 59.20% |
| G7 | 0.31% | 19.50% | 1.87% | 3.04% | 24.29% | 49.01% | 25.31% | 25.68% | 50.99% |
| G8 | 0.21% | 8.84% | 1.26% | 3.12% | 42.62% | 56.05% | 21.14% | 22.81% | 43.95% |
| H1 | 0.10% | 5.20% | 0.42% | 1.19% | 18.19% | 25.11% | 47.30% | 27.59% | 74.89% |
| H2 | 0.17% | 5.39% | 0.69% | 1.76% | 17.88% | 25.89% | 41.13% | 32.98% | 74.11% |
| H3 | 0.11% | 4.97% | 0.55% | 2.17% | 21.46% | 29.26% | 38.93% | 31.81% | 70.74% |
| H4 | 0.09% | 3.06% | 0.41% | 1.23% | 20.16% | 24.94% | 44.88% | 30.18% | 75.06% |
| H5 | 0.10% | 3.14% | 0.54% | 1.58% | 21.81% | 27.17% | 39.65% | 33.18% | 72.83% |
| H6 | 0.17% | 3.33% | 0.60% | 1.77% | 25.40% | 31.27% | 37.66% | 31.07% | 68.73% |
| H7 | 0.09% | 2.77% | 0.48% | 1.93% | 25.54% | 30.80% | 46.47% | 22.73% | 69.20% |
| H8 | 0.18% | 5.25% | 0.62% | 1.69% | 20.80% | 28.53% | 39.42% | 32.06% | 71.47% |
| I1 | 0.09% | 4.74% | 0.65% | 1.29% | 11.21% | 17.98% | 43.75% | 38.27% | 82.02% |
| I2 | 1.35% | 36.77% | 1.84% | 3.31% | 32.22% | 75.50% | 10.74% | 13.76% | 24.50% |

TABLE 4.6-continued

PERCENT RECOVERED DOSE FEMALE ARM

| | | | | | | | | | |
|---|---|---|---|---|---|---|---|---|---|
| I3 | 0.13% | 4.16% | 0.77% | 0.99% | 14.80% | 20.85% | 37.58% | 41.57% | 79.15% |
| I4 | 0.08% | 1.79% | 0.48% | 1.29% | 15.63% | 19.27% | 34.92% | 45.81% | 80.73% |
| I5 | 0.18% | 1.96% | 0.55% | 1.94% | 16.61% | 21.23% | 39.21% | 39.56% | 78.77% |
| I6 | 0.08% | 2.48% | 0.52% | 1.49% | 16.38% | 20.95% | 33.32% | 45.73% | 79.05% |
| I7 | 0.14% | 3.25% | 0.62% | 1.62% | 18.50% | 24.13% | 38.85% | 37.01% | 75.87% |
| I8 | 0.05% | 1.16% | 0.54% | 1.17% | 17.05% | 19.99% | 35.33% | 44.68% | 80.01% |
| K1 | 0.24% | 14.85% | 1.05% | 2.30% | 29.96% | 48.40% | 30.69% | 20.91% | 51.60% |
| K2 | 0.29% | 16.00% | 0.95% | 2.26% | 35.21% | 54.71% | 28.99% | 16.29% | 45.29% |
| K3 | 0.24% | 12.20% | 1.52% | 2.41% | 34.03% | 50.40% | 24.41% | 25.19% | 49.60% |
| K4 | 0.24% | 10.83% | 1.08% | 2.68% | 37.18% | 52.00% | 26.06% | 21.94% | 48.00% |
| K5 | 0.34% | 15.48% | 1.78% | 3.89% | 21.14% | 42.63% | 32.97% | 24.40% | 57.37% |
| K6 | 0.23% | 21.50% | 1.78% | 1.99% | 25.45% | 50.94% | 25.32% | 23.74% | 49.06% |
| K7 | 0.37% | 9.14% | 1.65% | 3.06% | 30.05% | 44.28% | 28.32% | 27.41% | 55.72% |
| K8 | 0.23% | 7.11% | 1.14% | 2.75% | 36.52% | 47.75% | 27.30% | 24.95% | 52.25% |
| L1 | 0.13% | 8.54% | 0.97% | 1.66% | 13.83% | 25.13% | 38.64% | 36.23% | 74.87% |
| L2 | 0.11% | 3.78% | 0.80% | 1.55% | 18.64% | 24.87% | 23.93% | 51.20% | 75.13% |
| L3 | 0.25% | 4.98% | 1.10% | 2.66% | 18.99% | 27.98% | 41.45% | 30.57% | 72.02% |
| L4 | 0.16% | 7.97% | 0.99% | 2.10% | 15.53% | 26.74% | 40.10% | 33.16% | 73.26% |
| L5 | 0.26% | 5.01% | 0.95% | 2.26% | 21.88% | 30.36% | 29.89% | 39.74% | 69.64% |
| L6 | 0.14% | 6.46% | 1.50% | 1.73% | 21.46% | 31.29% | 31.40% | 37.31% | 68.71% |
| L7 | 0.12% | 4.53% | 0.96% | 2.18% | 21.52% | 29.30% | 33.61% | 37.09% | 70.70% |
| L8 | 0.20% | 6.86% | 0.87% | 2.32% | 18.92% | 29.18% | 35.12% | 35.70% | 70.82% |
| M1 | 0.20% | 4.50% | 0.80% | 2.21% | 19.89% | 27.61% | 44.11% | 28.28% | 72.39% |
| M2 | 0.14% | 3.03% | 0.70% | 2.05% | 17.79% | 23.71% | 38.93% | 37.36% | 76.29% |
| M3 | 0.15% | 5.22% | 0.91% | 2.16% | 12.72% | 21.16% | 42.60% | 36.24% | 78.84% |
| M4 | 0.10% | 3.96% | 0.68% | 2.59% | 18.57% | 25.90% | 37.79% | 36.31% | 74.10% |
| M5 | 0.11% | 5.73% | 0.50% | 1.56% | 20.43% | 28.33% | 35.45% | 36.22% | 71.67% |
| M6 | 0.14% | 8.43% | 1.19% | 1.94% | 17.82% | 29.52% | 37.97% | 32.51% | 70.48% |
| M7 | 0.10% | 7.92% | 0.81% | 1.48% | 20.28% | 30.59% | 34.47% | 34.94% | 69.41% |
| M8 | 0.16% | 6.01% | 1.03% | 2.11% | 18.12% | 27.44% | 36.82% | 35.74% | 72.56% |

| Animal ID | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|
| % Recovered Dose-Female Animals-Urine per Day-Day 7 Necropsy | | | | | | | | | | | |
| A1 | 23.84% | 1.24% | 1.15% | 0.56% | 0.66% | 0.65% | 0.59% | | | | |
| A2 | 19.79% | 1.29% | 0.90% | 0.96% | 0.83% | 0.45% | 0.18% | | | | |
| A3 | 14.67% | 1.14% | 0.76% | 0.56% | 0.62% | 0.39% | 0.17% | | | | |
| A4 | 24.46% | 1.88% | 1.02% | 0.52% | 1.06% | 0.38% | 0.26% | | | | |
| B1 | 19.78% | 3.55% | 1.42% | 0.90% | 1.07% | 0.62% | 0.50% | | | | |
| B2 | 27.69% | 2.63% | 1.68% | 0.97% | 0.75% | 1.18% | 0.70% | | | | |
| B3 | 10.97% | 3.07% | 1.64% | 0.97% | 0.60% | 0.82% | 0.58% | | | | |
| B4 | 27.78% | 1.94% | 1.73% | 1.01% | 0.54% | 0.45% | 0.54% | | | | |
| C1 | 13.09% | 3.34% | 1.81% | 1.57% | 1.35% | 1.27% | 0.59% | | | | |
| C2 | 23.04% | 3.31% | 2.36% | 1.99% | 1.01% | 1.19% | 0.58% | | | | |
| C3 | 23.78% | 3.11% | 1.62% | 1.35% | 1.12% | 0.82% | 0.46% | | | | |
| C4 | 26.41% | 2.69% | 1.73% | 1.57% | 0.77% | 0.84% | 0.83% | | | | |
| D1 | 17.83% | 1.80% | 1.23% | 1.23% | 0.70% | 0.37% | 0.82% | | | | |
| D2 | 22.27% | 1.98% | 1.21% | 1.06% | 0.45% | 0.43% | 0.43% | | | | |
| D3 | 23.54% | 1.69% | 1.12% | 1.18% | 0.57% | 0.34% | 0.40% | | | | |
| D4 | 22.78% | 0.67% | 0.79% | 1.88% | 0.78% | 0.32% | 0.17% | | | | |
| E1 | 31.95% | 2.40% | 1.37% | 0.87% | 0.59% | 0.80% | 0.51% | | | | |
| E2 | 18.66% | 4.44% | 1.55% | 1.14% | 1.04% | 1.36% | 0.97% | | | | |
| E3 | 10.76% | 2.89% | 1.26% | 1.30% | 1.12% | 0.74% | 0.59% | | | | |
| E4 | 20.85% | 3.41% | 1.25% | 1.61% | 0.81% | 0.71% | 0.76% | | | | |
| F1 | 29.58% | 2.53% | 0.61% | 0.61% | 0.85% | 0.83% | 0.50% | | | | |
| F2 | 29.11% | 3.79% | 0.83% | 1.24% | 1.14% | 0.76% | 0.54% | | | | |
| F3 | 26.72% | 3.72% | 0.55% | 0.90% | 1.38% | 0.71% | 0.45% | | | | |
| F4 | 31.93% | 3.08% | 0.48% | 1.15% | 1.12% | 0.58% | 0.62% | | | | |
| % Recovered Dose-Female Animals-Urine per Day-Day 11 Necropsy | | | | | | | | | | | |
| G1 | 16.14% | 1.10% | 0.52% | 0.25% | 0.28% | 0.14% | 0.29% | 0.21% | 0.36% | 0.36% | 0.29% |
| G2 | 11.27% | 2.14% | 0.55% | 0.40% | 0.58% | 0.31% | 0.36% | 0.10% | 0.52% | 0.36% | 0.33% |
| G3 | 23.25% | 1.53% | 0.90% | 0.55% | 0.35% | 0.80% | 0.78% | 0.41% | 0.62% | 0.23% | 0.40% |
| G4 | 19.62% | 1.20% | 0.40% | 0.36% | 0.16% | 0.06% | 0.20% | 0.23% | 0.52% | 0.47% | 0.15% |
| G5 | 8.76% | 0.85% | 0.37% | 0.74% | 0.42% | 0.12% | 0.31% | 0.39% | 0.25% | 0.28% | 0.31% |
| G6 | 21.13% | 1.55% | 0.82% | 0.22% | 0.14% | 0.21% | 0.18% | 0.25% | 0.28% | 0.22% | 0.36% |
| G7 | 20.25% | 0.95% | 0.44% | 1.24% | 0.48% | 0.11% | 0.29% | 0.38% | 0.25% | 0.51% | 0.41% |
| G8 | 15.55% | 1.73% | 0.80% | 0.36% | 0.44% | 0.32% | 0.31% | 0.28% | 0.61% | 0.21% | 0.53% |
| H1 | 25.13% | 7.36% | 4.29% | 2.85% | 2.01% | 1.66% | 1.58% | 0.73% | 0.82% | 0.55% | 0.22% |
| H2 | 23.80% | 5.15% | 3.95% | 2.27% | 1.90% | 1.23% | 1.25% | 0.39% | 0.29% | 0.63% | 0.26% |
| H3 | 11.11% | 9.04% | 5.05% | 4.68% | 2.73% | 2.20% | 1.35% | 0.78% | 1.10% | 0.48% | 0.41% |
| H4 | 25.15% | 7.39% | 4.23% | 2.55% | 1.76% | 1.23% | 1.05% | 0.48% | 0.45% | 0.19% | 0.39% |
| H5 | 19.98% | 6.78% | 4.17% | 3.02% | 1.78% | 1.29% | 1.16% | 0.48% | 0.55% | 0.28% | 0.15% |
| H6 | 19.64% | 5.76% | 3.53% | 2.51% | 2.10% | 1.30% | 1.28% | 0.50% | 0.49% | 0.50% | 0.05% |
| H7 | 25.03% | 7.99% | 3.93% | 3.39% | 2.58% | 1.06% | 0.51% | 0.53% | 0.66% | 0.38% | 0.41% |
| H8 | 19.18% | 6.96% | 5.61% | 2.43% | 1.71% | 1.18% | 1.06% | 0.28% | 0.40% | 0.19% | 0.42% |

TABLE 4.6-continued

PERCENT RECOVERED DOSE FEMALE ARM

| | | | | | | | | | | | |
|---|---|---|---|---|---|---|---|---|---|---|---|
| I1 | 33.65% | 4.07% | 1.90% | 0.50% | 0.52% | 0.58% | 0.48% | 0.36% | 0.73% | 0.57% | 0.39% |
| I2 | 10.74% | | | | | | | | | | |
| I3 | 28.43% | 2.82% | 1.82% | 1.07% | 0.53% | 0.31% | 0.64% | 0.32% | 0.82% | 0.56% | 0.26% |
| I4 | 26.88% | 2.99% | 1.27% | 0.86% | 0.75% | 0.50% | 0.43% | 0.44% | 0.15% | 0.47% | 0.18% |
| I5 | 22.35% | 9.50% | 2.19% | 1.12% | 0.97% | 0.67% | 0.62% | 0.55% | 0.49% | 0.55% | 0.19% |
| I6 | 22.70% | 4.20% | 2.65% | 1.22% | 0.46% | 0.38% | 0.26% | 0.40% | 0.15% | 0.35% | 0.55% |
| I7 | 24.00% | 5.49% | 3.17% | 1.43% | 1.23% | 0.59% | 0.68% | 0.46% | 0.50% | 0.58% | 0.72% |
| I8 | 25.06% | 4.48% | 1.99% | 0.88% | 0.75% | 0.28% | 0.37% | 0.42% | 0.42% | 0.24% | 0.44% |
| K1 | 27.03% | 1.50% | 0.79% | 0.32% | 0.22% | 0.00% | 0.17% | 0.17% | 0.37% | 0.08% | 0.04% |
| K2 | 25.13% | 1.93% | 0.34% | 0.25% | 0.26% | 0.09% | 0.19% | 0.21% | 0.25% | 0.20% | 0.13% |
| K3 | 19.76% | 1.65% | 0.42% | 0.30% | 0.16% | 0.33% | 0.26% | 0.38% | 0.67% | 0.17% | 0.29% |
| K4 | 22.71% | 1.38% | 0.53% | 0.27% | 0.25% | 0.06% | 0.11% | 0.12% | 0.13% | 0.31% | 0.18% |
| K5 | 27.51% | 2.44% | 0.92% | 0.22% | 0.48% | 0.10% | 0.12% | 0.15% | 0.15% | 0.53% | 0.36% |
| K6 | 20.49% | 1.38% | 0.75% | 0.20% | 0.14% | 0.23% | 0.30% | 0.00% | 0.24% | 1.14% | 0.45% |
| K7 | 23.98% | 1.39% | 0.59% | 0.27% | 0.26% | 0.18% | 0.51% | 0.41% | 0.13% | 0.38% | 0.23% |
| K8 | 22.26% | 1.61% | 0.63% | 0.23% | 0.47% | 0.20% | 0.20% | 0.35% | 0.57% | 0.42% | 0.36% |
| L1 | 31.91% | 3.23% | 1.07% | 0.78% | 0.37% | 0.16% | 0.22% | 0.18% | 0.45% | 0.05% | 0.22% |
| L2 | 15.70% | 2.34% | 0.98% | 0.73% | 0.50% | 0.73% | 0.55% | 0.73% | 0.90% | 0.35% | 0.43% |
| L3 | 31.06% | 3.14% | 1.21% | 1.02% | 1.17% | 1.20% | 0.61% | 0.52% | 0.65% | 0.50% | 0.37% |
| L4 | 32.59% | 3.00% | 1.18% | 0.50% | 0.53% | 0.16% | 0.47% | 0.28% | 0.27% | 0.57% | 0.55% |
| L5 | 23.01% | 2.68% | 0.77% | 0.74% | 0.59% | 0.50% | 0.48% | 0.21% | 0.38% | 0.35% | 0.18% |
| L6 | 22.51% | 3.79% | 1.44% | 0.88% | 0.64% | 0.40% | 0.38% | 0.28% | 0.40% | 0.33% | 0.34% |
| L7 | 23.74% | 4.02% | 1.22% | 1.04% | 1.13% | 0.46% | 0.34% | 0.59% | 0.26% | 0.47% | 0.33% |
| L8 | 24.54% | 5.40% | 1.11% | 1.10% | 0.86% | 0.59% | 0.51% | 0.10% | 0.43% | 0.33% | 0.16% |
| M1 | 35.39% | 3.23% | 1.59% | 0.83% | 0.71% | 0.53% | 0.63% | 0.25% | 0.27% | 0.38% | 0.29% |
| M2 | 26.40% | 5.61% | 1.35% | 0.66% | 1.31% | 0.65% | 1.43% | 0.56% | 0.22% | 0.16% | 0.57% |
| M3 | 34.68% | 3.13% | 0.96% | 0.79% | 0.38% | 0.34% | 0.46% | 0.29% | 0.67% | 0.20% | 0.71% |
| M4 | 29.20% | 2.47% | 1.29% | 1.11% | 1.04% | 0.47% | 0.59% | 0.18% | 0.56% | 0.51% | 0.37% |
| M5 | 27.64% | 3.84% | 0.60% | 1.11% | 0.49% | 0.48% | 0.16% | 0.18% | 0.38% | 0.35% | 0.22% |
| M6 | 31.42% | 2.42% | 0.90% | 0.60% | 0.60% | 0.42% | 0.66% | 0.14% | 0.35% | 0.16% | 0.32% |
| M7 | 25.83% | 2.69% | 1.95% | 0.79% | 0.54% | 0.49% | 0.48% | 0.18% | 0.56% | 0.64% | 0.32% |
| M8 | 28.47% | 3.56% | 1.18% | 0.86% | 0.83% | 0.54% | 0.47% | 0.35% | 0.05% | 0.24% | 0.27% |

*Comments: Day7-M5: urine catch found fallen over in morning/Day 8-L4: urine spilled

| Animal ID | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|
| % Recovered Dose-Female Animals-Feces per Day-Day 7 Necropsy | | | | | | | | | | | |
| A1 | 6.61% | 1.46% | 2.12% | 1.96% | 1.59% | 2.11% | 1.76% | | | | |
| A2 | 9.23% | 2.04% | 2.12% | 2.30% | 2.41% | 1.94% | 1.16% | | | | |
| A3 | 19.65% | 1.71% | 2.26% | 2.19% | 2.22% | 1.87% | 1.88% | | | | |
| A4 | 8.83% | 2.04% | 2.59% | 1.51% | 1.85% | 1.72% | 1.42% | | | | |
| B1 | 8.96% | 13.36% | 5.58% | 3.61% | 2.85% | 1.63% | 1.39% | | | | |
| B2 | 4.64% | 8.81% | 1.92% | 2.93% | 2.91% | 2.50% | 1.95% | | | | |
| B3 | 19.46% | 9.40% | 3.39% | 2.98% | 2.16% | 1.90% | 1.75% | | | | |
| B4 | 9.41% | 8.35% | 2.59% | 1.99% | 2.39% | 2.12% | 1.74% | | | | |
| C1 | 11.51% | 13.77% | 4.51% | 3.35% | 2.71% | 2.52% | 2.15% | | | | |
| C2 | 5.30% | 8.33% | 3.49% | 3.00% | 2.82% | 2.18% | 1.62% | | | | |
| C3 | 8.74% | 12.44% | 4.66% | 3.74% | 2.30% | 2.39% | 1.98% | | | | |
| C4 | 7.20% | 14.41% | 4.88% | 4.08% | 2.85% | 3.01% | 2.66% | | | | |
| D1 | 4.64% | 1.49% | 2.21% | 2.05% | 1.21% | 1.90% | 1.44% | | | | |
| D2 | 8.84% | 1.01% | 1.27% | 1.93% | 2.28% | 1.37% | 1.25% | | | | |
| D3 | 7.52% | 1.07% | 1.66% | 1.54% | 2.24% | 1.45% | 1.64% | | | | |
| D4 | 9.24% | 0.88% | 1.37% | 2.37% | 2.06% | 1.99% | 1.76% | | | | |
| E1 | 6.10% | 8.15% | 2.89% | 2.76% | 1.35% | 1.90% | 2.23% | | | | |
| E2 | 10.77% | 10.30% | 5.25% | 3.97% | 1.95% | 1.34% | 1.29% | | | | |
| E3 | 13.26% | 9.61% | 5.53% | 4.52% | 2.80% | 2.01% | 1.91% | | | | |
| E4 | 10.08% | 15.30% | 2.67% | 2.90% | 2.17% | 2.18% | 2.16% | | | | |
| F1 | 9.32% | 8.03% | 2.78% | 2.68% | 2.30% | 2.40% | 1.39% | | | | |
| F2 | 9.52% | 12.87% | 4.30% | 3.98% | 3.01% | 2.04% | 1.59% | | | | |
| F3 | 7.17% | 9.08% | 4.68% | 3.14% | 3.85% | 2.26% | 2.15% | | | | |
| F4 | 5.19% | 6.87% | 2.63% | 2.89% | 3.00% | 1.91% | 2.13% | | | | |
| % Recovered Dose-Female Animals-Urine per Day-Day 11 Necropsy | | | | | | | | | | | |
| G1 | 15.43% | 2.91% | 2.82% | 2.69% | 1.92% | 1.35% | 2.19% | 1.59% | 1.47% | 0.97% | 1.00% |
| G2 | 12.49% | 2.16% | 2.98% | 2.70% | 2.84% | 2.04% | 2.61% | 1.90% | 1.46% | 1.03% | 0.74% |
| G3 | 7.61% | 1.10% | 0.68% | 2.34% | 1.38% | 1.89% | 1.53% | 0.74% | 1.59% | 0.73% | 0.72% |
| G4 | 7.61% | 0.95% | 1.65% | 2.47% | 1.15% | 1.25% | 1.55% | 1.18% | 1.39% | 1.30% | 0.88% |
| G5 | 14.20% | 1.37% | 2.71% | 2.98% | 2.55% | 3.06% | 2.79% | 2.87% | 1.73% | 1.29% | 0.97% |
| G6 | 12.86% | 1.89% | 2.84% | 3.34% | 1.88% | 2.51% | 1.96% | 1.53% | 1.84% | 1.33% | 1.85% |
| G7 | 12.41% | 1.26% | 1.53% | 1.08% | 1.48% | 1.73% | 1.03% | 1.14% | 1.23% | 0.95% | |
| G8 | 4.72% | 1.34% | 2.86% | 2.48% | 2.21% | 3.02% | 1.60% | 1.02% | 1.00% | 1.39% | 1.19% |
| H1 | 9.33% | 3.78% | 4.12% | 2.95% | 3.24% | 1.23% | 1.33% | 0.66% | 0.40% | 0.31% | 0.25% |
| H2 | 10.42% | 5.22% | 4.15% | 3.74% | 2.72% | 2.05% | 1.66% | 1.22% | 0.85% | 0.47% | 0.49% |
| H3 | 5.66% | 5.30% | 6.39% | 4.22% | 3.06% | 2.60% | 2.35% | 0.77% | 0.75% | 0.39% | 0.32% |
| H4 | 9.35% | 4.96% | 5.55% | 3.34% | 2.44% | 1.54% | 1.27% | 0.75% | 0.43% | 0.29% | 0.27% |

TABLE 4.6-continued

PERCENT RECOVERED DOSE FEMALE ARM

| H5 | 11.13% | 5.23% | 5.41% | 3.22% | 3.11% | 1.89% | 1.38% | 0.78% | 0.47% | 0.19% | 0.37% |
|---|---|---|---|---|---|---|---|---|---|---|---|
| H6 | 9.41% | 5.12% | 4.29% | 4.38% | 2.27% | 1.51% | 1.35% | 0.99% | 0.72% | 0.50% | 0.52% |
| H7 | 6.93% | 3.93% | 3.92% | 2.99% | 1.41% | 0.91% | 1.24% | 0.49% | 0.37% | 0.25% | 0.29% |
| H8 | 9.39% | 5.10% | 3.16% | 5.19% | 2.10% | 1.79% | 1.89% | 1.24% | 0.99% | 0.54% | 0.67% |
| I1 | 7.77% | 14.47% | 5.15% | 2.76% | 2.07% | 1.80% | 1.20% | 0.79% | 0.82% | 0.78% | 0.67% |
| I2 | 13.56% | 0.20% | | | | | | | | | |
| I3 | 9.39% | 15.38% | 4.91% | 3.63% | 2.10% | 2.08% | 1.23% | 1.03% | 0.67% | 0.49% | 0.65% |
| I4 | 8.83% | 21.84% | 4.95% | 3.08% | 1.73% | 1.82% | 1.07% | 0.78% | 0.59% | 0.52% | 0.58% |
| I5 | 9.40% | 16.92% | 3.52% | 3.06% | 1.67% | 1.64% | 1.17% | 0.83% | 0.61% | 0.32% | 0.43% |
| I6 | 8.09% | 19.11% | 6.42% | 4.72% | 1.85% | 2.11% | 1.43% | 0.67% | 0.55% | 0.31% | 0.46% |
| I7 | 8.07% | 11.80% | 5.63% | 3.06% | 1.81% | 1.61% | 1.94% | 0.96% | 0.69% | 0.55% | 0.89% |
| I8 | 7.99% | 17.77% | 7.70% | 4.39% | 1.59% | 1.48% | 1.45% | 0.90% | 0.52% | 0.45% | 0.44% |
| K1 | 7.86% | 1.41% | 1.56% | 1.85% | 0.96% | 1.78% | 1.52% | 1.43% | 1.26% | 0.65% | 0.64% |
| K2 | 4.85% | 1.03% | 1.23% | 1.02% | 1.08% | 0.96% | 1.70% | 1.15% | 1.14% | 0.86% | 1.28% |
| K3 | 8.59% | 2.17% | 2.08% | 2.43% | 1.50% | 2.06% | 2.28% | 1.42% | 0.80% | 0.78% | 1.08% |
| K4 | 5.95% | 1.71% | 1.87% | 1.98% | 2.87% | 2.32% | 1.96% | 1.11% | 0.79% | 0.69% | 0.70% |
| K5 | 6.07% | 1.87% | 2.24% | 1.60% | 2.26% | 1.89% | 2.30% | 2.10% | 1.37% | 1.47% | 1.23% |
| K6 | 10.20% | 1.42% | 1.84% | 1.58% | 1.28% | 1.11% | 1.28% | 1.47% | 0.90% | 1.09% | 1.57% |
| K7 | 8.73% | 2.00% | 3.11% | 1.44% | 1.82% | 2.58% | 2.49% | 1.88% | 1.13% | 1.09% | 1.13% |
| K8 | 7.83% | 2.31% | 3.02% | 2.05% | 1.91% | 2.05% | 2.24% | 1.29% | 0.92% | 0.67% | 0.64% |
| L1 | 5.35% | 9.62% | 5.07% | 4.52% | 2.41% | 1.58% | 2.68% | 2.01% | 0.99% | 1.29% | 0.70% |
| L2 | 10.51% | 11.11% | 4.30% | 3.28% | 2.57% | 1.95% | 4.39% | 6.27% | 3.81% | 1.70% | 1.28% |
| L3 | 3.65% | 5.95% | 2.41% | 1.82% | 6.05% | 4.31% | 2.50% | 1.63% | 0.96% | 0.71% | 0.58% |
| L4 | 5.09% | 8.55% | 3.68% | 3.38% | 2.26% | 3.12% | 2.41% | 1.89% | 0.99% | 1.04% | 0.75% |
| L5 | 9.71% | 8.68% | 5.39% | 3.96% | 2.77% | 2.44% | 2.29% | 1.73% | 1.05% | 1.04% | 0.68% |
| L6 | 8.91% | 12.54% | 4.44% | 3.67% | 2.39% | 1.42% | 1.58% | 1.02% | 0.50% | 0.44% | 0.40% |
| L7 | 9.38% | 10.49% | 3.21% | 4.12% | 2.74% | 1.86% | 2.14% | 1.29% | 0.53% | 0.60% | 0.72% |
| L8 | 5.37% | 9.01% | 5.10% | 5.10% | 3.54% | 2.87% | 2.03% | 1.12% | 0.57% | 0.41% | 0.59% |
| M1 | 8.44% | 6.23% | 2.30% | 3.18% | 1.90% | 2.20% | 1.09% | 1.16% | 0.89% | 0.48% | 0.44% |
| M2 | 9.22% | 7.89% | 3.50% | 2.79% | 2.00% | 3.65% | 4.12% | 1.96% | 0.80% | 0.61% | 0.82% |
| M3 | 6.58% | 7.02% | 4.87% | 3.46% | 3.07% | 3.85% | 3.24% | 1.85% | 0.95% | 0.71% | 0.63% |
| M4 | 5.72% | 10.02% | 4.65% | 4.28% | 4.53% | 2.48% | 1.63% | 1.17% | 0.56% | 0.70% | 0.58% |
| M5 | 8.33% | 10.31% | 3.13% | 3.48% | 2.38% | 2.57% | 2.05% | 1.59% | 0.83% | 1.03% | 0.53% |
| M6 | 7.11% | 12.05% | 1.94% | 2.77% | 1.31% | 1.91% | 0.95% | 1.23% | 0.91% | 1.20% | 1.12% |
| M7 | 8.76% | 7.08% | 3.83% | 2.90% | 2.10% | 3.39% | 2.29% | 1.36% | 1.12% | 1.20% | 0.91% |
| M8 | 7.62% | 9.14% | 3.56% | 3.40% | 2.52% | 2.63% | 2.08% | 1.47% | 1.20% | 1.18% | 0.93% |

*Comments: Day 7-M2: few/watery feces; M7: water feces/Day 8-L2: few feces, M5, M7, and M8: less feces than other groups (on avg)

b. Percent Recovered Dose for Male Arm

TABLE 4.7

PERCENT RECOVERED DOSE MALE ARM

% Recovered Dose-Male Animals-Day-7 Necropsy

| Animal ID | Kidney | Liver | ART | SOFT | SKEL | Combined Body | Total Urine | Total Feces | Combined Excreta |
|---|---|---|---|---|---|---|---|---|---|
| A1 | 0.34% | 27.03% | 1.59% | 2.99% | 26.81% | 58.77% | 25.44% | 15.79% | 41.23% |
| A2 | 0.23% | 34.76% | 1.26% | 3.18% | 24.80% | 642.3% | 15.71% | 20.06% | 35.77% |
| A3 | 0.36% | 19.23% | 1.66% | 3.14% | 41.18% | 65.57% | 19.45% | 14.99% | 34.43% |
| A4 | 0.26% | 23.48% | 1.17% | 2.68% | 40.58% | 68.17% | 13.35% | 18.48% | 31.83% |
| B1 | 0.29% | 30.79% | 2.16% | 3.27% | 15.55% | 52.05% | 25.54% | 22.40% | 47.95% |
| B2 | 0.25% | 12.69% | 1.57% | 3.41% | 20.00% | 37.93% | 21.58% | 40.49% | 62.07% |
| B3 | 0.26% | 22.32% | 1.65% | 2.67% | 23.24% | 50.13% | 23.85% | 26.02% | 49.87% |
| B4 | 0.45% | 19.79% | 1.32% | 3.29% | 20.71% | 45.55% | 22.32% | 32.13% | 54.45% |
| C1 | 0.22% | 15.72% | 1.42% | 2.28% | 24.75% | 44.39% | 21.21% | 34.40% | 55.61% |
| C2 | 0.15% | 12.80% | 1.55% | 2.12% | 21.49% | 38.12% | 29.21% | 32.67% | 61.88% |
| C3 | 0.21% | 16.24% | 1.84% | 3.24% | 23.68% | 45.21% | 4.35% | 50.44% | 54.79% |
| C4 | 0.17% | 16.85% | 1.39% | 2.82% | 17.13% | 38.36% | 26.29% | 35.35% | 61.64% |
| D1 | 0.29% | 26.94% | 1.64% | 2.32% | 30.14% | 61.33% | 18.47% | 20.21% | 38.67% |
| D2 | 0.32% | 22.34% | 1.65% | 3.33% | 39.57% | 67.21% | 17.95% | 14.84% | 32.79% |
| D3 | 0.25% | 19.76% | 1.03% | 2.24% | 35.09% | 58.38% | 24.07% | 17.55% | 41.62% |
| D4 | 0.27% | 20.69% | 1.96% | 2.85% | 29.04% | 54.81% | 26.74% | 18.45% | 45.19% |
| E1 | 0.14% | 9.72% | 1.02% | 1.89% | 17.72% | 30.49% | 28.61% | 40.90% | 69.51% |
| E2 | 0.21% | 15.67% | 1.34% | 1.96% | 20.95% | 40.14% | 19.82% | 40.04% | 59.86% |
| E3 | 0.13% | 11.76% | 1.21% | 1.16% | 20.71% | 34.97% | 25.43% | 39.60% | 65.03% |
| E4 | 0.20% | 13.58% | 1.33% | 2.00% | 20.84% | 37.95% | 22.13% | 39.91% | 62.05% |
| F1 | 0.17% | 7.14% | 1.03% | 2.03% | 20.00% | 30.37% | 26.88% | 42.75% | 69.63% |
| F2 | 0.21% | 17.14% | 1.92% | 2.08% | 18.02% | 39.36% | 24.59% | 36.05% | 60.64% |
| F3 | 0.42% | 15.20% | 2.25% | 2.10% | 16.63% | 36.59% | 18.97% | 44.44% | 63.41% |
| F4 | 0.21% | 10.27% | 1.33% | 2.66% | 16.58% | 31.04% | 30.09% | 38.86% | 68.96% |

TABLE 4.7-continued

PERCENT RECOVERED DOSE MALE ARM

% Recovered Dose-Male Animals-Day-11 Necropsy

| Animal ID | Kidney | Liver | GI Tract | Soft Tissue | Total Bone | Combined Body | Total Urine | Total Feces | Combined Excreta |
|---|---|---|---|---|---|---|---|---|---|
| G1 | 0.29% | 18.07% | 3.00% | 3.47% | 32.56% | 57.39% | 10.93% | 31.68% | 42.61% |
| G2 | 0.25% | 20.65% | 1.54% | 3.47% | 31.30% | 57.21% | 18.06% | 24.73% | 42.79% |
| G3 | 0.62% | 23.13% | 2.78% | 3.91% | 24.95% | 55.39% | 25.71% | 18.91% | 44.61% |
| G4 | 0.30% | 15.89% | 1.58% | 3.47% | 23.93% | 45.17% | 19.63% | 35.20% | 54.83% |
| G5 | 0.23% | 14.89% | 1.44% | 3.79% | 26.67% | 47.02% | 21.67% | 31.31% | 52.98% |
| G6 | 0.23% | 8.17% | 1.40% | 2.87% | 38.98% | 51.66% | 27.52% | 20.82% | 48.34% |
| G7 | 0.46% | 19.39% | 2.04% | 3.64% | 29.92% | 55.46% | 27.80% | 16.74% | 44.54% |
| G8 | 0.27% | 14.01% | 1.94% | 3.74% | 30.93% | 50.89% | 24.29% | 24.82% | 49.11% |
| H1 | 0.14% | 5.98% | 1.75% | 2.40% | 21.31% | 31.58% | 42.91% | 25.51% | 68.42% |
| H2 | 0.28% | 3.55% | 0.46% | 1.47% | 18.54% | 24.29% | 44.82% | 30.89% | 74.71% |
| H3 | 0.20% | 5.50% | 0.91% | 2.34% | 24.85% | 33.79% | 42.18% | 24.03% | 66.21% |
| H4 | 0.21% | 4.81% | 0.70% | 2.95% | 22.27% | 30.93% | 13.18% | 55.88% | 69.07% |
| H5 | 0.11% | 4.85% | 0.71% | 2.10% | 24.22% | 32.00% | 38.78% | 29.23% | 68.00% |
| H6 | 0.15% | 4.26% | 0.57% | 1.91% | 22.15% | 29.03% | 31.74% | 39.23% | 70.97% |
| H7 | 0.14% | 4.33% | 0.52% | 1.81% | 16.34% | 23.14% | 40.70% | 36.16% | 76.86% |
| H8 | 0.17% | 4.96% | 0.47% | 1.44% | 20.37% | 27.41% | 26.43% | 46.15% | 72.59% |
| I1 | 0.08% | 2.60% | 0.43% | 1.04% | 11.74% | 15.90% | 30.06% | 54.04% | 84.10% |
| I2 | 0.11% | 1.91% | 0.47% | 0.98% | 17.07% | 20.53% | 19.00% | 60.47% | 79.47% |
| I3 | 0.10% | 2.22% | 0.44% | 0.83% | 15.87% | 19.46% | 28.76% | 51.78% | 80.54% |
| I4 | 0.14% | 2.29% | 0.49% | 1.42% | 17.81% | 22.16% | 39.36% | 38.48% | 77.84% |
| I5 | 0.10% | 3.02% | 0.64% | 1.37% | 11.38% | 16.51% | 34.31% | 49.18% | 83.49% |
| I6 | 0.10% | 2.09% | 0.58% | 1.04% | 18.21% | 22.02% | 34.20% | 43.78% | 77.98% |
| I7 | 0.13% | 2.92% | 0.71% | 1.22% | 16.06% | 21.03% | 34.38% | 44.59% | 78.97% |
| I8 | 0.16% | 2.34% | 0.49% | 1.20% | 19.05% | 23.25% | 33.18% | 43.58% | 76.75% |
| K1 | 0.20% | 17.09% | 1.22% | 20.37% | 12.76% | 51.64% | 25.42% | 22.94% | 48.36% |
| K2 | 0.23% | 18.06% | 1.26% | 25.30% | 12.61% | 57.46% | 21.74% | 20.80% | 42.54% |
| K3 | 0.20% | 15.87% | 1.21% | 2.10% | 33.51% | 52.90% | 23.59% | 23.51% | 47.10% |
| K4 | 0.28% | 22.74% | 2.38% | 3.06% | 25.63% | 54.09% | 26.83% | 19.07% | 45.91% |
| K5 | 0.37% | 15.70% | 1.41% | 3.92% | 32.17% | 53.57% | 25.97% | 20.45% | 46.43% |
| K6 | 0.23% | 14.20% | 1.39% | 2.03% | 36.93% | 54.76% | 15.89% | 29.35% | 45.24% |
| K7 | 0.31% | 20.85% | 1.47% | 2.55% | 26.21% | 51.39% | 27.49% | 21.12% | 48.61% |
| K8 | 0.37% | 22.02% | 1.39% | 3.37% | 26.32% | 53.48% | 24.87% | 21.65% | 46.52% |
| L1 | 0.10% | 8.71% | 0.99% | 2.91% | 25.77% | 38.48% | 19.82% | 41.70% | 61.52% |
| L2 | 0.15% | 15.99% | 1.04% | 2.09% | 24.60% | 43.87% | 20.73% | 35.40% | 56.13% |
| L3 | 0.19% | 9.13% | 1.13% | 2.06% | 16.37% | 28.88% | 27.24% | 43.87% | 71.12% |
| L4 | 0.19% | 5.50% | 1.03% | 2.29% | 19.43% | 28.44% | 24.82% | 46.74% | 71.56% |
| L5 | 0.15% | 9.51% | 1.21% | 2.57% | 22.08% | 32.53% | 26.43% | 38.04% | 64.47% |
| L6 | 0.14% | 10.88% | 0.97% | 2.02% | 18.56% | 32.57% | 30.12% | 37.30% | 67.43% |
| L7 | 0.14% | 7.89% | 0.90% | 1.97% | 15.85% | 26.76% | 27.17% | 46.07% | 73.24% |
| L8 | 0.14% | 8.10% | 0.93% | 1.69% | 25.23% | 36.08% | 30.39% | 33.53% | 63.92% |
| M1 | 0.08% | 3.86% | 0.61% | 1.50% | 13.99% | 20.04% | 26.10% | 53.86% | 79.96% |
| M2 | 0.17% | 3.49% | 0.50% | 1.55% | 15.68% | 21.39% | 31.92% | 46.68% | 78.61% |
| M3 | 0.28% | 8.37% | 0.89% | 1.52% | 17.58% | 28.64% | 24.91% | 46.45% | 71.36% |
| M4 | 0.16% | 6.17% | 0.48% | 2.24% | 25.41% | 34.45% | 29.67% | 35.88% | 65.55% |
| M5 | 0.25% | 12.45% | 0.99% | 2.53% | 16.78% | 33.00% | 26.20% | 40.81% | 67.00% |
| M6 | 0.24% | 9.96% | 1.00% | 2.16% | 17.24% | 30.60% | 9.95% | 59.45% | 69.40% |
| M7 | 0.20% | 3.83% | 0.73% | 2.01% | 18.80% | 25.58% | 37.71% | 36.72% | 74.42% |
| M8 | 0.13% | 6.08% | 0.76% | 1.95% | 18.71% | 27.62% | 32.94% | 39.43% | 72.38% |

| Animal ID | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|
| % Recovered Dose-Male Animals-Urine per Day-Day 7 Necropsy | | | | | | | | | | | |
| A1 | 23.45% | 0.94% | 0.58% | 0.00% | 0.27% | 0.00% | 0.20% | | | | |
| A2 | 13.24% | 0.92% | 0.45% | 0.45% | 0.37% | 0.17% | 0.11% | | | | |
| A3 | 17.58% | 0.33% | 0.66% | 0.37% | 0.18% | 0.19% | 0.13% | | | | |
| A4 | 9.90% | 1.60% | 0.89% | 0.23% | 0.24% | 0.13% | 0.35% | | | | |
| B1 | 20.65% | 2.02% | 0.61% | 1.30% | 0.61% | 0.18% | 0.17% | | | | |
| B2 | 15.62% | 2.81% | 1.15% | 0.41% | 0.58% | 0.64% | 0.37% | | | | |
| B3 | 19.53% | 2.18% | 1.12% | 0.54% | 0.10% | 0.10% | 0.28% | | | | |
| B4 | 17.05% | 1.96% | 1.18% | 0.89% | 0.65% | 0.10% | 0.50% | | | | |
| C1 | 12.15% | 4.28% | 1.32% | 1.17% | 0.65% | 0.70% | 0.94% | | | | |
| C2 | 23.06% | 3.19% | 0.98% | 0.68% | 0.33% | 0.52% | 0.45% | | | | |
| C3 | 2.56% | 0.38% | 0.50% | 0.55% | 0.19% | 0.07% | 0.11% | | | | |
| C4 | 22.38% | 1.72% | 0.95% | 0.59% | 0.35% | 0.19% | 0.10% | | | | |
| D1 | 15.56% | 1.09% | 0.86% | 0.32% | 0.34% | 0.21% | 0.10% | | | | |
| D2 | 13.36% | 2.69% | 0.85% | 0.34% | 0.62% | 0.09% | 0.00% | | | | |
| D3 | 22.21% | 0.84% | 0.44% | 0.18% | 0.08% | 0.19% | 0.14% | | | | |
| D4 | 24.80% | 0.68% | 0.42% | 0.24% | 0.13% | 0.23% | 0.23% | | | | |
| E1 | 21.72% | 3.64% | 1.49% | 0.67% | 0.39% | 0.49% | 0.21% | | | | |
| E2 | 14.01% | 2.67% | 0.90% | 0.69% | 0.62% | 0.53% | 0.41% | | | | |
| E3 | 18.66% | 3.46% | 1.61% | 0.59% | 0.41% | 0.46% | 0.23% | | | | |
| E4 | 17.47% | 2.04% | 1.12% | 0.53% | 0.39% | 0.31% | 0.27% | | | | |

TABLE 4.7-continued

PERCENT RECOVERED DOSE MALE ARM

| | | | | | | | | | | | |
|---|---|---|---|---|---|---|---|---|---|---|---|
| F1 | 19.31% | 3.62% | 1.51% | 0.98% | 0.45% | 0.45% | 0.55% | | | | |
| F2 | 19.65% | 1.94% | 1.15% | 0.55% | 0.42% | 0.47% | 0.40% | | | | |
| F3 | 13.22% | 2.38% | 1.06% | 0.74% | 0.47% | 0.36% | 0.72% | | | | |
| F4 | 25.18% | 2.07% | 1.06% | 0.83% | 0.41% | 0.29% | 0.26% | | | | |

% Recovered Dose-Female Animals-Urine per Day-Day 11 Necropsy

| | | | | | | | | | | | |
|---|---|---|---|---|---|---|---|---|---|---|---|
| G1 | 5.87% | 1.01% | 0.34% | 0.23% | 0.20% | 0.27% | 1.00% | 0.57% | 0.49% | 0.42% | 0.53% |
| G2 | 14.37% | 0.65% | 0.52% | 0.26% | 0.31% | 0.14% | 0.87% | 0.38% | 0.16% | 0.08% | 0.30% |
| G3 | 22.65% | 0.74% | 0.40% | 0.30% | 0.15% | 0.12% | 0.52% | 0.11% | 0.30% | 0.17% | 0.25% |
| G4 | 16.66% | 1.36% | 0.29% | 0.26% | 0.11% | 0.00% | 0.48% | 0.14% | 0.04% | 0.11% | 0.17% |
| G5 | 18.80% | 1.18% | 0.30% | 0.17% | 0.00% | 0.00% | 0.32% | 0.24% | 0.29% | 0.00% | 0.38% |
| G6 | 24.48% | 0.80% | 0.43% | 0.26% | 0.15% | 0.11% | 0.50% | 0.14% | 0.27% | 0.20% | 0.18% |
| G7 | 25.01% | 0.51% | 0.32% | 0.30% | 0.07% | 0.00% | 0.33% | 0.33% | 0.33% | 0.37% | 0.24% |
| G8 | 19.95% | 1.02% | 0.71% | 0.14% | 0.23% | 0.14% | 0.75% | 0.34% | 0.36% | 0.31% | 0.33% |
| H1 | 20.57% | 7.92% | 3.90% | 3.05% | 1.94% | 1.36% | 1.74% | 0.96% | 0.92% | 0.35% | 0.20% |
| H2 | 20.95% | 8.51% | 4.79% | 3.34% | 1.91% | 1.21% | 1.68% | 0.76% | 0.50% | 0.32% | 0.84% |
| H3 | 19.90% | 7.65% | 4.05% | 2.72% | 2.47% | 1.73% | 1.50% | 0.90% | 1.01% | | 0.25% |
| H4 | 1.76% | 2.69% | 2.57% | 0.84% | 1.16% | 0.80% | 1.67% | 0.53% | 0.62% | 0.27% | 0.28% |
| H5 | 20.72% | 6.20% | 3.66% | 2.10% | 1.62% | 1.18% | 1.63% | 0.64% | 0.49% | 0.21% | 0.33% |
| H6 | 6.70% | 7.54% | 4.86% | 3.61% | 3.01% | 1.69% | 1.84% | 0.85% | 0.72% | 0.49% | 0.44% |
| H7 | 19.37% | 5.46% | 4.80% | 2.55% | 2.10% | 1.57% | 1.87% | 1.18% | 0.87% | 0.38% | 0.55% |
| H8 | 2.05% | 8.58% | 5.85% | 2.58% | 2.23% | 1.37% | 1.77% | 0.65% | 0.69% | 0.35% | 0.31% |
| I1 | 19.74% | 3.96% | 1.65% | 0.77% | 0.94% | 0.65% | 0.87% | 0.32% | 0.20% | 0.58% | 0.39% |
| I2 | 6.58% | 5.51% | 1.23% | 0.85% | 0.87% | 0.41% | 1.16% | 0.70% | 0.51% | 0.74% | 0.44% |
| I3 | 15.30% | 4.41% | 3.48% | 0.98% | 0.59% | 0.44% | 0.64% | 0.71% | 0.73% | 0.92% | 0.55% |
| I4 | 28.39% | 4.63% | 2.00% | 1.08% | 0.63% | 0.32% | 0.59% | 0.52% | 0.48% | 0.42% | 0.31% |
| I5 | 24.31% | 4.05% | 1.41% | 0.65% | 0.79% | 0.35% | 0.75% | 0.77% | 0.39% | 0.40% | 0.43% |
| I6 | 21.90% | 5.30% | 1.65% | 0.92% | 0.76% | 0.48% | 0.99% | 0.79% | 0.60% | 0.38% | 0.43% |
| I7 | 24.69% | 3.86% | 1.46% | 0.89% | 0.28% | 0.51% | 1.27% | 0.51% | 0.51% | 0.38% | 0.00% |
| I8 | 20.49% | 5.05% | 1.93% | 0.93% | 1.05% | 0.55% | 0.64% | 0.79% | 0.63% | 0.41% | 0.71% |
| K1 | 22.09% | 0.70% | 0.23% | 0.15% | 0.26% | 0.28% | 0.36% | 0.26% | 0.10% | 0.37% | 0.61% |
| K2 | 18.42% | 1.10% | 0.29% | 0.13% | 0.25% | 0.00% | 0.51% | 0.41% | 0.11% | 0.00% | 0.53% |
| K3 | 21.15% | 0.62% | 0.11% | 0.14% | 0.07% | 0.15% | 0.11% | 0.30% | 0.46% | 0.06% | 0.43% |
| K4 | 23.56% | 1.10% | 0.49% | 0.00% | 0.29% | 0.09% | 0.45% | 0.29% | 0.00% | 0.40% | 0.15% |
| K5 | 21.23% | 1.44% | 0.39% | 0.66% | 0.27% | 0.11% | 0.39% | 0.29% | 0.26% | 0.51% | 0.45% |
| K6 | 11.82% | 1.14% | 0.37% | 0.00% | 0.17% | 0.08% | 0.54% | 0.39% | 0.64% | 0.59% | 0.15% |
| K7 | 23.04% | 1.25% | 0.78% | 0.00% | 0.23% | 0.07% | 0.20% | 0.45% | 0.60% | 0.38% | 0.49% |
| K8 | 22.37% | 0.73% | 0.58% | 0.17% | 0.24% | 0.11% | 0.21% | 0.15% | 0.32% | 0.00% | 0.00% |
| L1 | 12.59% | 2.90% | 1.04% | 0.50% | 0.64% | 0.60% | 0.61% | 0.30% | 0.21% | 0.24% | 0.20% |
| L2 | 16.03% | 1.60% | 0.84% | 0.38% | 0.28% | 0.06% | 0.22% | 0.16% | 0.30% | 0.45% | 0.41% |
| L3 | 21.48% | 1.70% | 1.21% | 0.59% | 0.60% | 0.37% | 0.72% | 0.05% | 0.20% | 0.12% | 0.20% |
| L4 | 17.40% | 2.41% | 0.62% | 0.77% | 0.52% | 0.49% | 1.23% | 0.55% | 0.22% | 0.20% | 0.40% |
| L5 | 21.11% | 1.15% | 1.08% | 0.45% | 0.67% | 0.33% | 0.46% | 0.30% | 0.55% | 0.21% | 0.14% |
| L6 | 22.45% | 2.95% | 1.06% | 0.81% | 0.60% | 0.48% | 0.44% | 0.60% | 0.27% | 0.30% | 0.18% |
| L7 | 21.35% | 2.14% | 0.54% | 0.67% | 0.50% | 0.37% | 0.51% | 0.16% | 0.25% | 0.34% | 0.34% |
| L8 | 20.51% | 3.00% | 1.49% | 1.28% | 0.69% | 0.43% | 0.75% | 0.62% | 0.67% | 0.63% | 0.31% |
| M1 | 19.50% | 2.27% | 0.81% | 0.47% | 0.66% | 0.38% | 0.73% | 0.40% | 0.40% | 0.12% | 0.35% |
| M2 | 24.06% | 2.99% | 1.49% | 0.64% | 0.36% | 0.35% | 0.69% | 0.36% | 0.45% | 0.23% | 0.30% |
| M3 | 17.35% | 2.82% | 1.40% | 0.77% | 0.19% | 0.46% | 0.76% | 0.42% | 0.37% | 0.16% | 0.22% |
| M4 | 21.87% | 2.82% | 1.64% | 0.68% | 0.53% | 0.26% | 0.65% | 0.32% | 0.42% | 0.28% | 0.20% |
| M5 | 18.70% | 2.73% | 1.14% | 0.62% | 0.60% | 0.36% | 0.63% | 0.43% | 0.40% | 0.21% | 0.36% |
| M6 | 2.45% | 2.07% | 1.43% | 0.31% | 0.47% | 0.41% | 0.83% | 0.34% | 0.61% | 0.62% | 0.43% |
| M7 | 28.31% | 4.97% | 1.07% | 0.58% | 0.30% | 0.12% | 0.47% | 0.74% | 0.41% | 0.46% | 0.26% |
| M8 | 25.46% | 3.05% | 1.00% | 0.72% | 0.22% | 0.61% | 0.38% | 0.33% | 0.48% | 0.27% | 0.42% |

*Comments: Day 10-H3: collected by not calculated

| Animal ID | Day 1 | Day 2 | Day 3 | Day 4 | Day 5 | Day 6 | Day 7 | Day 8 | Day 9 | Day 10 | Day 11 |
|---|---|---|---|---|---|---|---|---|---|---|---|
| | | | | | | | | | | | |

% Recovered Dose-Male Animals-Feces per Day-Day 7 Necropsy

| | | | | | | | | | | | |
|---|---|---|---|---|---|---|---|---|---|---|---|
| A1 | 4.54% | 1.10% | 2.13% | 2.47% | 1.92% | 1.46% | 2.17% | | | | |
| A2 | 11.70% | 1.31% | 2.26% | 1.68% | 0.92% | 0.80% | 1.37% | | | | |
| A3 | 7.30% | 1.16% | 1.31% | 1.60% | 1.17% | 1.11% | 1.35% | | | | |
| A4 | 11.62% | 1.61% | 0.91% | 1.84% | 0.72% | 0.97% | 0.82% | | | | |
| B1 | 4.37% | 7.66% | 2.15% | 3.14% | 1.34% | 2.28% | 1.46% | | | | |
| B2 | 8.32% | 12.16% | 3.85% | 4.08% | 2.97% | 6.44% | 2.68% | | | | |
| B3 | 7.75% | 9.09% | 3.59% | 1.98% | 0.93% | 1.47% | 1.21% | | | | |
| B4 | 4.30% | 13.43% | 3.55% | 4.25% | 2.49% | 2.02% | 2.10% | | | | |
| C1 | 8.78% | 15.31% | 2.49% | 3.01% | 1.70% | 1.91% | 1.21% | | | | |
| C2 | 6.29% | 12.37% | 5.42% | 3.04% | 2.00% | 2.24% | 1.32% | | | | |
| C3 | 9.94% | 22.78% | 4.54% | 5.87% | 3.00% | 2.37% | 1.95% | | | | |
| C4 | 4.97% | 14.58% | 6.24% | 3.77% | 2.15% | 2.32% | 1.31% | | | | |
| D1 | 9.37% | 1.92% | 2.05% | 2.20% | 1.55% | 1.38% | 1.74% | | | | |
| D2 | 6.97% | 0.95% | 1.02% | 2.37% | 1.09% | 1.31% | 1.13% | | | | |
| D3 | 8.18% | 1.35% | 1.67% | 1.63% | 1.38% | 1.64% | 1.70% | | | | |
| D4 | 5.47% | 1.34% | 1.91% | 3.05% | 1.46% | 3.11% | 2.12% | | | | |
| E1 | 6.19% | 19.35% | 3.91% | 5.36% | 1.97% | 2.01% | 2.11% | | | | |

TABLE 4.7-continued

PERCENT RECOVERED DOSE MALE ARM

| | | | | | | | | | | | |
|---|---|---|---|---|---|---|---|---|---|---|---|
| E2 | 11.96% | 15.22% | 2.72% | 3.66% | 1.84% | 2.66% | 1.97% | | | | |
| E3 | 7.28% | 16.75% | 3.36% | 5.40% | 1.67% | 2.92% | 2.22% | | | | |
| E4 | 11.97% | 13.98% | 3.87% | 5.25% | 1.79% | 1.87% | 1.18% | | | | |
| F1 | 6.91% | 14.25% | 13.31% | 4.17% | 1.77% | 1.60% | 0.74% | | | | |
| F2 | 7.78% | 13.00% | 3.36% | 4.09% | 2.34% | 2.84% | 2.65% | | | | |
| F3 | 14.62% | 16.24% | 3.68% | 3.98% | 1.75% | 1.72% | 2.45% | | | | |
| F4 | 9.13% | 15.40% | 5.91% | 3.52% | 1.78% | 1.54% | 1.59% | | | | |

% Recovered Dose-Male Animals-Feces per Day-Day 11 Necropsy

| | | | | | | | | | | | |
|---|---|---|---|---|---|---|---|---|---|---|---|
| G1 | 12.82% | 2.03% | 1.71% | 3.33% | 1.15% | 3.76% | 0.86% | 1.89% | 1.61% | 1.12% | 1.40% |
| G2 | 7.64% | 1.97% | 1.46% | 2.66% | 1.43% | 1.59% | 1.69% | 1.73% | 1.89% | 1.44% | 1.24% |
| G3 | 6.70% | 0.82% | 1.00% | 1.64% | 0.97% | 1.31% | 1.61% | 1.36% | 1.68% | 0.88% | 0.94% |
| G4 | 13.99% | 2.13% | 2.06% | 4.92% | 1.86% | 2.34% | 1.81% | 1.99% | 1.85% | 1.08% | 1.18% |
| G5 | 12.37% | 1.41% | 2.08% | 3.61% | 1.75% | 2.69% | 1.06% | 2.43% | 1.73% | 1.00% | 1.19% |
| G6 | 8.41% | 0.77% | 1.13% | 1.81% | 0.75% | 2.71% | 1.07% | 2.14% | 0.85% | 0.57% | 0.63% |
| G7 | 5.16% | 0.84% | 0.85% | 1.94% | 0.92% | 1.59% | 0.97% | 1.52% | 1.00% | 0.95% | 1.00% |
| G8 | 7.26% | 1.28% | 2.15% | 2.81% | 2.34% | 2.22% | 1.75% | 1.77% | 1.13% | 1.09% | 1.03% |
| H1 | 9.15% | 2.78% | 3.63% | 3.78% | 1.51% | 1.64% | 1.05% | 0.81% | 0.43% | 0.38% | 0.37% |
| H2 | 8.02% | 4.90% | 6.69% | 4.47% | 1.78% | 2.00% | 1.04% | 0.75% | 0.51% | 0.40% | 0.35% |
| H3 | 6.78% | 1.40% | 4.80% | 3.18% | 1.71% | 2.45% | 1.03% | 1.29% | 0.65% | 0.33% | 0.40% |
| H4 | 17.54% | 7.06% | 10.31% | 7.97% | 3.62% | 2.79% | 2.05% | 1.70% | 1.29% | 0.79% | 0.78% |
| H5 | 10.87% | 3.40% | 4.70% | 3.38% | 1.81% | 1.57% | 1.28% | 0.85% | 0.58% | 0.42% | 0.36% |
| H6 | 15.09% | 6.60% | 6.91% | 4.66% | 1.45% | 1.96% | 0.78% | 0.78% | 0.39% | 0.30% | 0.30% |
| H7 | 6.58% | 7.14% | 8.25% | 5.75% | 2.38% | 1.83% | 1.36% | 1.19% | 0.64% | 0.52% | 0.52% |
| H8 | 17.21% | 5.64% | 7.45% | 4.65% | 1.92% | 1.74% | 3.81% | 1.40% | 0.87% | 0.68% | 0.77% |
| I1 | 9.44% | 24.63% | 7.33% | 4.73% | 2.15% | 1.96% | 1.48% | 0.86% | 0.53% | 0.46% | 0.47% |
| I2 | 11.73% | 29.18% | 7.00% | 4.29% | 1.67% | 1.64% | 2.52% | 0.84% | 0.71% | 0.52% | 0.38% |
| I3 | 10.15% | 24.62% | 5.92% | 4.45% | 2.13% | 1.89% | 0.83% | 0.55% | 0.43% | 0.43% | 0.37% |
| I4 | 5.92% | 13.96% | 6.28% | 3.39% | 2.90% | 2.15% | 1.51% | 0.84% | 0.64% | 0.45% | 0.43% |
| I5 | 9.00% | 18.50% | 9.54% | 5.21% | 1.73% | 2.00% | 0.94% | 0.76% | 0.57% | 0.45% | 0.48% |
| I6 | 6.11% | 19.63% | 7.12% | 4.16% | 2.06% | 1.56% | 1.29% | 0.55% | 0.47% | 0.40% | 0.44% |
| I7 | 8.55% | 17.47% | 7.60% | 3.65% | 1.56% | 1.92% | 1.15% | 1.22% | 0.49% | 0.47% | 0.50% |
| I8 | 9.19% | 19.39% | 4.73% | 3.13% | 2.26% | 1.66% | 1.02% | 0.87% | 0.53% | 0.36% | 0.43% |
| K1 | 6.75% | 1.18% | 1.75% | 3.06% | 1.26% | 1.67% | 1.79% | 1.63% | 1.26% | 1.28% | 1.34% |
| K2 | 5.72% | 1.90% | 1.65% | 2.06% | 1.59% | 2.00% | 1.49% | 1.41% | 0.96% | 1.06% | 0.97% |
| K3 | 9.45% | 1.18% | 1.71% | 2.62% | 1.41% | 2.07% | 0.94% | 1.40% | 0.85% | 0.77% | 1.10% |
| K4 | 5.19% | 2.88% | 1.47% | 1.22% | 0.85% | 1.78% | 1.16% | 1.26% | 0.88% | 0.73% | 1.64% |
| K5 | 8.35% | 1.44% | 1.09% | 2.86% | 0.63% | 1.08% | 1.24% | 1.29% | 0.86% | 0.72% | 0.89% |
| K6 | 14.38% | 1.25% | 1.84% | 2.63% | 1.32% | 1.46% | 1.46% | 1.56% | 1.26% | 1.01% | 1.18% |
| K7 | 6.30% | 1.06% | 0.97% | 2.26% | 1.04% | 2.46% | 1.16% | 1.81% | 1.31% | 1.12% | 1.62% |
| K8 | 6.81% | 1.35% | 1.58% | 1.91% | 1.65% | 1.46% | 1.40% | 1.78% | 1.57% | 1.09% | 1.07% |
| L1 | 19.13% | 9.49% | 2.02% | 1.98% | 1.04% | 3.32% | 1.56% | 1.03% | 0.88% | 0.60% | 0.63% |
| L2 | 9.90% | 10.37% | 3.23% | 2.69% | 1.47% | 1.94% | 1.72% | 1.27% | 0.94% | 0.98% | 0.89% |
| L3 | 13.78% | 11.59% | 3.48% | 3.71% | 2.57% | 2.97% | 1.53% | 1.54% | 0.96% | 0.96% | 0.79% |
| L4 | 9.96% | 15.06% | 4.47% | 6.81% | 2.42% | 2.78% | 1.45% | 1.58% | 0.88% | 0.65% | 0.66% |
| L5 | 8.53% | 13.00% | 2.87% | 3.67% | 1.75% | 2.36% | 2.10% | 1.33% | 0.57% | 0.99% | 0.87% |
| L6 | 6.03% | 13.15% | 3.37% | 4.04% | 1.82% | 3.15% | 1.44% | 1.26% | 1.17% | 1.01% | 0.87% |
| L7 | 11.30% | 16.38% | 4.43% | 3.55% | 2.26% | 2.15% | 1.80% | 1.23% | 1.08% | 1.02% | 0.84% |
| L8 | 9.22% | 8.84% | 2.71% | 3.76% | 1.72% | 2.74% | 1.29% | 0.92% | 0.78% | 0.90% | 0.66% |
| M1 | 8.69% | 16.84% | 4.32% | 3.42% | 1.00% | 10.71% | 5.02% | 1.81% | 1.01% | 0.48% | 0.57% |
| M2 | 9.69% | 15.20% | 6.13% | 4.94% | 2.50% | 2.32% | 2.31% | 1.55% | 1.12% | 0.47% | 0.46% |
| M3 | 13.97% | 15.54% | 4.17% | 4.01% | 1.52% | 2.47% | 1.09% | 1.22% | 0.73% | 0.92% | 0.82% |
| M4 | 8.94% | 13.29% | 2.65% | 4.02% | 1.62% | 1.70% | 1.15% | 0.94% | 0.57% | 0.59% | 0.41% |
| M5 | 5.04% | 15.04% | 4.16% | 6.06% | 1.76% | 3.63% | 1.51% | 1.24% | 1.01% | 0.65% | 0.70% |
| M6 | 18.41% | 19.29% | 6.33% | 4.40% | 1.90% | 2.41% | 1.35% | 2.07% | 0.96% | 1.22% | 1.12% |
| M7 | 8.12% | 14.53% | 4.24% | 3.22% | 1.20% | 1.58% | 0.86% | 0.87% | 0.64% | 0.76% | 0.68% |
| M8 | 5.36% | 19.54% | 3.82% | 2.93% | 1.08% | 1.99% | 1.01% | 1.10% | 0.76% | 0.85% | 1.01% |

In EXAMPLE 5-EXAMPLE 9 the treatment dose levels for each in vivo study are presented in μmol/kg and/or mg/kg. Based on the molecular weight of 750.71 g/mol for the API 3,4,3-L1(1,2-HOPO), the mg/kg dose level is divided by 0.7507 to obtain the dose level in μmol/kg, while the μmol/kg dose level is multiplied by 0.7507 to obtain the dose level in mg/kg. Dose levels commonly used in the nonclinical studies are displayed as both μmol/kg and mg/kg in TABLE 0.1 for reference purposes.

TABLE 0.1

COMMONLY USED NON-CLINICAL DOSE LEVELS OF 3,4,3-LI(1,2-HOPO) IN μMOL/KG AND MG/KG

| Dose Level (μmol/kg) | Dose Level (mg/kg) |
|---|---|
| 1 | 0.8 |
| 3 | 2.3 |
| 10 | 7.7 |
| 30 | 22.5 |
| 50 | 37.5 |
| 60 | 45.1 |
| 100 | 75.1 |
| 200 | 150 |
| 300 | 225 |
| 400 | 300 |
| 532 | 400 |
| 600 | 451 |
| 1000 | 751 |
| 1800 | 1352 |

Example 5—Radiolabeled In Vivo ADME Studies in Rodents

Formulated material was used in the single dose in vivo ADME characterization studies in Sprague Dawley rats and Swiss-Webster mice with 14C-labeled 3,4,3-L1(1,2-HOPO).

Pharmacokinetic parameters and disposition/biodistribution of 3,4,3-L1(1,2-HOPO) were characterized in vivo (with the aid of two 14C labels on the spermine backbone of the parent product) in two non-GLP studies using Swiss-Webster mice and Sprague Dawley rats. The study designs for these two studies are shown in TABLE 5.1 and TABLE 5.2, respectively. Groups of six mice (3 male, 3 female) were given a single dose of [14C]-3,4,3-L1(1,2-HOPO) via iv, ip, or po routes, respectively. An additional group of six mice (3 male, 3 female) were administered the 14C-labeled API with permeability enhancer (10% sodium oleate) by oral gavage (po). Similarly, groups of six rats (3 male, 3 female) were administered a single iv dose of the 14C-labeled API or a single po dose of the 14C-labeled API with 10% sodium oleate. In each of these studies, samples were collected at scheduled time points up to 24 hr post-dose and analyzed for 14C content using liquid scintillation counting. Blood, liver, kidney, feces and urine were collected and analyzed from the mice. Blood, brain, liver, kidney, lungs, spleen, skeletal muscle tissues, gastrointestinal (GI) tract samples, carcasses, feces, and urine were collected and analyzed from the rats.

TABLE 5.1

STUDY DESIGN FOR RADIOLABELED IN VIVO ADME STUDIES IN MICE

| Group | Route | Dose Level (μmol/kg) | Dose Level (mg/kg) | $^{14}$C Dose (μCi/kg) | Formulation | No. of Mice | Necropsy Time (min or hr) |
|---|---|---|---|---|---|---|---|
| 1 | iv | 50 | 37.5 | 50 | — | 18M | 5, 15, 30 min; |
| 2 | iv | 100 | 75.1 | 100 | — | 18F | 1, 4, 24 hr |
| 3 | ip | 50 | 37.5 | 50 | — | 18M | |
| 4 | ip | 100 | 75.1 | 100 | — | 18F | |
| 5 | oral | 100 | 75.1 | 100 | — | 18M/18F | 30, 45 min; 1, 2, 6, 24 hr |
| 6 | oral | 100 | 75.0 | 100 | 10% sodium oleate | 18M/18F | 10, 20, 30, 45, 60, 120 min |

TABLE 5.2

STUDY DESIGN FOR RADIOLABELED IN VIVO ADME STUDY IN RATS

| Group | Route | Dose Level (μmol/kg) | Dose Level (mg/kg) | $^{14}$C Dose (μCi/kg) | Formulation | No. of Rats | Necropsy Time (hr) |
|---|---|---|---|---|---|---|---|
| 1 | iv | 100 | 75.1 | 200 | — | 3M/3F | 2 |
| 2 | | | | | | 3M/3F | 6 |
| 3 | | | | | | 3M/3F | 24 |
| 4 | oral | 100 | 75.1 | 200 | 10% sodium oleate | 3M/3F | 2 |
| 5 | | | | | | 3M/3F | 6 |
| 6 | | | | | | 3M/3F | 24 |

The pharmacokinetic parameters determined from these studies are presented in TABLE 5.3. Blood was collected at 6-8 time points from 5 min to 24 post-dose. Plasma concentration-time profiles showed similar log-linear decays after iv administration in mice and rats, and the radiolabeled compound was rapidly distributed throughout the extracellular fluid space with higher peak concentrations and total plasma exposure in rats (C0=463 and 422 Pg-eq/ml, AUC=354 and 211 hr Pg-eq/ml for male and female, respectively) than in mice (C0=342 and 76 Pg-eq/mL, AUC=66.2 and 41.7 hr Pg-eq/ml for female and male, respectively). Radioactivity was cleared from plasma with t½ values of approximately 1.6 and 8 hr for mice and rats, respectively, after iv administration. Intraperitoneal administration of [14C]-3,4,3-L1(1,2-HOPO) in mice resulted in a lower level of radioactivity in plasma than through the iv route, but significantly higher than by the po route. The oral bioavailability (F) of 3,4,3-L1(1,2-HOPO) was limited, as indicated by its low plasma exposure. Bioavailability of the radioactive compound was slightly higher in females compared with males (1.2% vs. 2.6% in male and female mice, respectively; 0.4% vs. 1.1% in male and female rats, respectively), as shown in TABLE 5.3. Formulation of 3,4,3-L1 (1,2-HOPO) with sodium oleate resulted in a moderate improvement in systemic exposure: The Cmax improved by approximately 3-fold from 0.32 to 0.93 Pg-eq/ml in male and 0.55 to 1.4 Pg-eq/ml in female mice. In addition, the AUC, when calculated over 2 hr posttreatment, increased from 8.3±6.2 to 17.4±6.7 min Pg-eq/ml in males and 23.0±15.4 to 35.1±18.9 min Pg-eq/ml in females, which translates into an oral bioavailability improvement of about 2-fold in mice.

TABLE 5.3

MEAN PHARMACOKINETIC PARAMETERS OF RADIOACTIVITY FOR MALE AND FEMALE SWISS-WEBSTER MICE AND SPRAGUE DAWLEY RATS ADMINISTERED [$_{14}$C]-3,4,3-LI(1,2-HOPO)

| Route | Species | Sex (n = 2-3) | Dose (μmol/kg) | $C_0^a$ or $C_{max}$ (μg-eq/ml) | $T_{max}$ (h) | AUC$^b$ (h μg-eq/ml) | $t_{1/2}$ (h) | F$^c$ (%) |
|---|---|---|---|---|---|---|---|---|
| iv | Mouse | Male | 50 | 76 ± 47 | NA$^d$ | 41.7 ± 3.2 | 1.6 ± 0.5 | NA |
|  |  | Female | 100 | 342 ± 211 | NA | 161.6 ± 21.5 | 1.6 ± 0.3 | NA |
|  | Rat | Male | 100 | 463 | NA | 354 ± 26.9 | 8.1 | NA |
|  |  | Female | 100 | 422 | NA | 211 ± 28.7 | 8.6 | NA |
| ip | Mouse | Male | 50 | 16.4 ± 7.1 | 0.33 ± 0.14 | 39.8 ± 10.5 | NA | NA |
|  |  | Female | 100 | 61.7 ± 36.7 | 0.33 ± 0.14 | 187.5 ± 14 | NA | NA |
| po | Mouse | Male | 100 | 0.32 ± 0.23 | 0.63 ± 0.18 | 1.94 ± 2.80 | NC$^e$ | 1.2 |
|  |  | Female | 100 | 0.55 ± 0.29 | 0.67 ± 0.29 | 3.93 ± 3.17 | NC | 2.6 |
|  | Rat | Male | 100 | 0.29 ± 0.20 | 0.67 | 1.30 ± 0.37 | NC | 0.4 |
|  |  | Female | 100 | 0.15 ± 0.04 | 0.68 | 2.40 ± 0.44 | NC | 1.1 |

$^a$C$_0$ is the plasma concentration extrapolated to time zero.
$^b$AUC presented is calculated to the last data point at 24 h.
$^c$The bioavailability F is calculated using the formula: [(Dose$_{iv}$ × AUC$_{po}$)/(Dose$_{po}$ × AUC$_{iv}$)] × 100%
$^d$NA = not applicable.
$^e$NC = not calculated; insufficient data for parameter estimation.

Analysis of radioactivity levels in tissues showed that radioactivity from [$_{14}$C]-3,4,3-L1(1,2-HOPO) was distributed rapidly into the liver and kidneys following an iv injection. In general, the highest level of radioactivity in kidneys and liver was detected early at 1 hr in mice and 2 hr in rats post-dose (FIG. 19A-FIG. 19F and FIG. 20A-FIG. 20D). A similar trend was observed in mice injected ip, in which the highest level of radioactivity in kidneys and liver was detected at 1 hr post-dose. No major differences in the radioactive uptake into liver and kidneys were observed between iv and ip routes of administration in mice, indicating that both routes are effective for [$_{14}$C]-3,4,3-L1(1,2-HOPO) distribution. In the iv treatment group for rats, the general rank order of tissue concentrations at the 2 hr time point was kidney>liver>lung>brain spleen muscle. Liver and kidney tissue radioactivity levels were similar and remained high at all the time points after iv administration, whereas levels in other tissues decreased more rapidly after 2 hr. As a result, after the iv dose, radioactivity tended to concentrate in the elimination organs (kidney and liver); thus tissue-to-plasma ratios increased with time in these tissues. In contrast, after the po dose, the highest concentrations of radioactivity were observed in the feces and GI tract, and very low levels of radioactivity were observed in urine, plasma, and the other tissues (FIG. 19A-FIG. 19F) and FIG. 20A-FIG. 20D).

The principal excretion routes of radioactivity from [14C]-3,4,3-L1(1,2-HOPO) were both the feces and urine after an iv dose based on high levels of radioactivity in both feces and urine as well as significant radioactivity in the excretory tissues, kidney, liver and GI tract. Fecal elimination by 24 hr post-dose accounted for approximately 62% and 16% of the iv administered dose in mice and rats, respectively. Urinary excretion accounted for approximately 12-23% of the iv administered dose in these rodents with renal excretion of 14C beginning as early as 5 min after iv injection in mice. In contrast, following oral administration, excretion was primarily by the fecal route accounting for approximately 89% and 41% of the orally administered dose in mice and rats, respectively, by 24 h post-dose. Urinary excretion accounted for <1% of the orally administered dose and low radioactivity levels were detected in systemic circulation and in tissues except for the GI tract. In mice, the highest accumulation of 14C was seen in the feces after all three administration routes (i.e., iv, ip and po) confirming that the biliary pathway is the main mode of elimination at least for the iv and ip administration routes. Based on the colonic transit time in rats of 15.5 hr, 11 the radioactivity found in the feces in the first 24 hr after po administration is most likely unabsorbed compound. Although hepatic metabolism followed by excretion in the bile is possible for 3,4,3-L1(1,2-HOPO) that is orally bioavailable, the very low level of radioactivity in the blood and tissues in the po group animals suggests that the predominant route of elimination of an oral dose of 3,4,3-L1(1,2-HOPO) is through the feces and is comprised of unabsorbed parent compound and metabolite(s) resulting from the first pass effect of the liver or biotransformations in the gut. Metabolite profiling of [14C]-3,4,3-L1(1,2-HOPO) was performed using an HPLC method on selected urine, feces, kidney, liver, and lung samples from the Sprague Dawley rat. Only samples containing the highest total radioactive levels were selected for analysis. A total of 11 peaks were detected, of which 6 were from uncharacterized interactions between the test article and matrix components because they were also seen in spiked blank matrix controls. These 6 peaks are not metabolites and are considered alternate forms of the parent compound (e.g. complexes of the test article with metallic ions). The 5 other radioactive species (peaks P1-P4 and P10) are considered potential metabolites. Feces-specific metabolite peaks P2, P3, and P10 represented a combined 10.5-11.4% and 0.5-4.2% of the administered dose after po or iv administration, respectively, in rats. Peak P10 was the most abundant peak in all samples analyzed. It represented up to 10% of the administered dose in feces after po administration while the other two feces-specific peaks represented <1% of the administered dose after po administration. Peak P10 was also the predominant, and sometimes the only, peak in feces samples after iv administration. P10 could be of biliary origin, or, more likely, it could be the product of a transformation within the intestinal tract, either through a spontaneous degradation process or mediated by the intestinal flora, since it was not detected in liver samples. P1 was the only metabolite peak identified in urine, representing ≤0.4% of the iv administered dose, and was absent in the single urine sample analyzed after po administration. In conclusion, evaluation of the metabolite profiles demonstrated that a putative major metabolite of [14C]-3,4,3-L1 (1,2-HOPO) is formed (P10) that accounts for ~10% of an administered oral dose. Thus it is likely that the observed low bioavailability of [14C]-3,4,3-L1(1,2-HOPO) is due both to biotransformation processes, likely in the gut, as well as relatively low absorption after oral administration.

Example 6—GLP Single Dose Oral Safety with Pharmacokinetic Assessment Study in Beagle Dogs Pharmacokinetic parameters in beagle dogs after a single oral administration of formulated capsules was determined in a GLP study. A validated bioanalytical method was used to determine the plasma concentration in 3 dogs/sex after capsule administration of 37.5, 75, and 150 mg/kg (50, 100, and 200 µmol/kg) of clinically formulated 3,4,3-L1(1,2-HOPO). Plasma concentrations at all three dose levels peaked at 0.6-1.1 hr post-dose (Tmax), and trended higher in females (FIG. 21B) compared with males (FIG. 21A). Similarly, mean exposure, based on AUCinf, was 1979±777 hr·ng/ml and 4741 hr·ng/ml for low-dose males and females, respectively; 4317±1721 hr·ng/ml and 8610 hr·ng/ml for mid-dose males and females, respectively; and 12022±5458 hr·ng/ml and 8305±1607 hr·ng/ml for high-dose males and females, respectively. Mean Cmax and mean AUCinf values increased relatively proportional to dose (all doses in males, low to mid doses in females) and trended approximately 2-fold higher in females compared with males at the low and mid doses (1.7- to 2.4-fold higher). The mean t½ was consistently short across dose groups and ranged from 0.5 to 0.9 hr.

The pharmacokinetic parameters in two non-GLP 7-day repeat dose studies in beagle dogs (SRI No. B677-13 with formulated capsules and SRI No. M835-11 with oral gavage delivered API) were in general agreement with the single dose GLP study and showed that 3,4,3-L1(1,2-HOPO) did not accumulate in the plasma after 7 days of dosing. These two pilot studies included an iv administration group so that oral bioavailability could be calculated. The oral bioavailability was low at <3% and essentially the same in both studies regardless of whether the dogs received formulated capsules or 3,4,3-L1(1,2-HOPO) dissolved in PBS without sodium oleate. One male and two female dogs were administered 37.6 mg/kg (50 µmol/kg) by the iv route which resulted in an observed peak plasma level of 115±11 µg/ml, mean AUCinf of 64 hr·µg/ml and a t½ value of 0.4 hr. Volume of distribution was 0.3 L/kg, consistent with drug that is distributed primarily to the extracellular space. The clearance (Cl) was 594 ml/hr/kg with an indication that plasma clearance may become saturated at higher plasma concentrations.

Example 7—Conclusions of Pharmacokinetic and ADME Studies from Examples 5 and 6

The pharmacokinetics of 3,4,3-L1(1,2-HOPO) were generally similar across species. Oral bioavailability of formulated and unformulated 3,4,3-L1(1,2-HOPO) was low at <3% in the dog and the bioavailability of total radioactivity from $[_{14}C]$-3,4,3-L1(1,2-HOPO) in mice and rats was also <3%. Formulation of API with sodium oleate enhanced exposure parameters by approximately 2- to 3-fold in mice. When administered orally, 3,4,3-L1(1,2-HOPO) was eliminated almost entirely through the fecal route either as unabsorbed parent compound or as metabolite(s) formed either by the liver or in the small intestine. Evaluation of the metabolite profiles in rats demonstrated that a putative major metabolite of $[_{14}C]$-3,4,3-11(1,2-HOPO) is feces-specific and that it accounts for ~10% of an administered oral dose. This metabolite could be of biliary origin, or, more likely, it is the product of metabolism within the intestinal tract, either through a spontaneous degradation process or mediated by the intestinal flora. Thus it is likely that the observed low bioavailability of $[_{14}C]$-3,4,3-L1(1,2-HOPO) is due both to biotransformation processes as well as relatively low absorption of an oral dose.

When administered to rodents by the iv route, 3,4,3-L1 (1,2-HOPO) was distributed rapidly into the liver and kidneys and eliminated by both the renal and biliary routes. The compound appears to be metabolized in the GI tract, degraded slightly in gastric fluid, and stable in plasma.

Plasma concentrations after an oral dose peaked (Tmax) at similar times post-dose in rodents and with the clinical formulation in dogs (~0.7 hr and 0.6-1.1 hr post-dose in rodents and dogs, respectively). Mean t½ after oral administration was consistently short across dose groups and species at ~1 hr in rats and 0.5 to 0.9 hr in dogs. Cmax, AUC, and oral bioavailability trended ~2-fold higher in females than males in all three species (mice, rats, and dogs) and increased relatively proportional to dose. When co-formulated with sodium oleate as a permeability enhancer, the labeled [14C]-3,4,3-L1(1,2-HOPO) displayed an increased exposure that translates into an oral bioavailability improvement of about 2- to 3-fold in mice. In beagle dogs administered the clinical formulation of 3,4,3-L1(1,2-HOPO), exposure based on Cmax and AUCinf values increased relatively proportional to dose (all doses in males, low to mid doses in females) and trended higher in females compared with males at the low and mid doses (1.7- to 2.4-fold higher). The mean t½ was consistently short across dose groups and ranged from 0.5 to 0.9 hr.

Plasma protein binding differed across species; it was greatest in dog (95%), intermediate in human (29%), and lowest in rat (5%) when tested at 10 µg/ml. In vitro human liver microsome experiments showed that the compound was relatively stable, and these results are consistent with the relatively low extent of metabolism observed in vivo in the rat. 3,4,3-L1(1,2-HOPO) did not inhibit the activity of $CYP1A2$, $CYP2B6$, $CYP2C_9$, $CYP2C19$, $CYP2D6$, and $CYP3A4$ and thus is unlikely to be a source of drug interactions for other agents metabolized by these enzymes.

Example 8—Single Oral Dose GLP Safety Study in Beagle Dogs

The clinical formulation was tested in a single dose GLP toxicology and cardiovascular safety pharmacology study in beagle dogs. The study design is presented in TABLE 8.1. This study demonstrated a NOAEL of 37.5 mg/kg (50 µmol/kg) 3,4,3-L1(1,2-HOPO) in dogs following oral capsule administration of formulated material at 37.5, 75, or 150 mg/kg (50, 100, and 200 µmol/kg).

TABLE 8.1

STUDY DESIGN FOR GLP SINGLE DOSE ORAL SAFETY STUDY IN BEAGLE DOGS

| Group | Treatment | Dose Level (µmol/kg) | Dose Level (mg/kg) | No. of Dogs | No. of Dogs Sacrificed on Day 2 | No. of Dogs Sacrificed on Day 15 |
|---|---|---|---|---|---|---|
| 1 | Empty Capsule | 0 | 0 | 6M/6F | 3M/3F | 3M/3F |
| 2 | Formulated 3,4,3-L1(1,2-HOPO) in Capsule | 50 | 37.5 | 6M/6F | 3M/3F | 3M/3F |
| 3 | Formulated 3,4,3-L1(1,2-HOPO) in Capsule | 100 | 75 | 6M/6F | 3M/3F | 3M/3F |
| 4 | Formulated 3,4,3-L1(1,2-HOPO) in Capsule | 200 | 150 | 6M/6F | 3M/3F | 3M/3F |

Based on this study, the MTD in dogs after a single oral administration is considered to be greater than 150 mg/kg. All dogs (6/sex/group; total 48) survived to their scheduled sacrifice on Day 2 or 15, and administration of 3,4,3-L1(1, 2-HOPO) produced no meaningful changes in body weight, food consumption, ophthalmology, cardiovascular assessments, clinical pathology, urinalysis, gross necropsy observations, or organ weights.

Clinical observations that were associated with test article administration included post-dose diarrhea and emesis. Specifically, dogs in the mid- and high-dose groups experienced slight or extreme diarrhea on Day 1 between 1 and 6 hr post-dose. Diarrhea was absent from the lowdose group. Slight diarrhea was seen in 17% of males and 33% of females in the high-dose group and in 67% of females in the mid-dose group. Extreme diarrhea was seen in 33% of highdose males. By Day 2, 8 of the 9 affected dogs were normal, with the exception of one highdose group female that had continued slight diarrhea. Slight to moderate emesis occurred <2 hr post-dose (and oftentimes <1 hr post-dose) in 1-3 dogs from each of the 3,4,3-L1(1,2-HOPO) treatment groups and in none of the vehicle control-treated dogs. Post-dose emesis appeared to be dose-dependent since it occurred in 0, 1, 2, and 3 dogs out of 12 dogs per group in control, low, mid, and high dose groups, respectively. Post-dose emesis is a common response to oral dose administration in dogs, and a single occurrence of it in the low dose group could be treatment-related rather than test article-related and is not considered a dose-limiting event. Slight post-dose emesis in this one male dog was the only finding present in the 37.5 mg/kg lowdose treatment group. Similar dose dependent, transient emesis and diarrhea were observed ~1 hr post-dose in the non-GLP repeat dose beagle dog study (SRI No. B677-13) where 2 dogs/sex were administered formulated capsules once daily for 7 days at doses of 75.1, 150, or 300 mg/kg (100, 200, and 400 µmol/kg). However, soft stools or diarrhea were not observed in Sprague Dawley rats after oral gavage administration of 400-1300 mg/kg (532-1732 µmol/kg) for 7 days (SRI No. M801-10) or 7.7-76.9 mg/kg (10-102 µmol/kg) for 28 days (SRI No. M512-07).

Renal findings of diffuse, moderate, proximal tubular casts and dilation; moderate interstitial hemorrhage; and mild interstitial hemosiderin pigmentation were observed at the Day 15 recovery sacrifice in 1 of 3 female dogs in the high-dose group (150 mg/kg). No similar renal histopathology findings were found in any of the other on-study dogs. The observation of hemosiderin without fibrosis in the kidney sections from this one dog is consistent with the renal findings having developed within one to three days prior to the Day 15 necropsy. This dog also had corresponding small increases (1.8- and 1.3-fold, respectively) in the renal function markers BUN and CR on Day 15 relative to pre-test. The timing of the renal findings in this recovery group dog is surprising given the fact that 3,4,3-L1(1,2-HOPO) was administered only on Day 1. Therefore, it is unclear if these renal findings are related specifically to high-dose administration of 3,4,3-L1(1,2-HOPO). There were no toxicologically meaningful histopathology findings in any of the dogs on Day 2 or in any of the other dogs on Day 15. Similar renal findings were also absent from the non-GLP 7-day repeat dose dog study (SRI No. B677-13) where 2 dogs/sex received formulated material at higher doses for 4 days followed by equivalent doses for 3 days and then were sacrificed on Day 8. There were also no renal findings in the Sprague Dawley rat studies after 7 and 28 days of oral gavage dose administration (SRI Nos. M801-10 and M512-07, respectively).

An evaluation of the serum levels of iron, unsaturated iron binding capacity, total iron binding capacity, magnesium, and ferritin were included in the clinical pathology analysis during the dog safety studies because 3,4,3-L1(1,2-HOPO) is a potent metal chelator. In the GLP study with 3 dogs/sex, none of these parameters were meaningfully altered with statistical significance on Days 2 or 15 in treated groups when compared with controls although the standard deviations were large and the number of dogs per group was small. In the non-GLP pilot repeat dose study with even smaller numbers (2 dogs/sex) and no control group, there were indications that serum total iron levels increased ~2-fold after treatment when compared with pretest levels while the unsaturated iron binding capacity decreased 16-62% suggesting that the increased iron was bound to transferrin, not 3,4,3-L1(1,2-HOPO). Thus, the results from the nonclinical dog studies suggest that serum iron and magnesium levels are not meaningfully altered after 3,4,3-L1(1,2-HOPO) administration although these parameters are being evaluated in the clinical trial.

Example 9—GLP Single Oral Dose GLP Safety with Cardiovascular Assessment Study in Beagle Dogs Cardiovascular parameters in beagle dogs after a single oral administration of formulated capsules was determined in a GLP study Electrocardiograms and blood pressure were evaluated from 3 male and 3 female beagle dogs per dose group (0, 37.5, 75, or 150 mg/kg) at pretest, 1 and 4 hours post-dose, and 7 days after a single oral dose of formulated material (TABLE 8.1). There were no electrocardiographic, heart rate, or blood pressure findings that were attributed to administration of 3,4,3-L1(1,2-HOPO). Instances of increased or decreased blood pressure (hypertension or hypotension) in various dogs were considered sporadic or due to stress, excitement, or struggling during the time of recording and not test article related. In summary, electrocardiogram and blood pressure assessments in beagle dogs raised no cardiovascular safety concerns.

Example 10—Permeability Enhancement of 3,4,3-L1(1,2-HOPO)

Summary

The objective of the analytical study described in Part C of this report was to assess the feasibility of enhancing the permeability of the active pharmaceutical ingredient 3,4,3-L1(1,2-HOPO) using oral permeation enhancers. Evaluation was performed using an in vitro pK assay based on the Double-Sink™ PAMPA technology developed by pION, Inc.

Fifteen different permeation enhancers were evaluated for their ability at increasing the permeability of 3,4,3-L1(1,2-HOPO), using an in vitro PAMPA assay with artificial GIT lipid membranes. A significant increase was observed in permeability for one formulation containing 10 mg/mL of Polysorbate 80 and 1 mg/mL of API. All other tested formulations showed no or minor improvement in permeability. Formulations containing Polysorbate 80 will be evaluated further in in vivo studies.

1. Purpose of Study

The purpose of this study was to provide data that can be used to support research efforts. It was not conducted in accordance with U.S. Food and Drug Administration (FDA) "Good Laboratory Practice for Nonclinical Laboratory Studies" (GLP) regulations, as described in 21 CFR Part 58. However, the study was planned, performed, recorded, and reported in accordance with standard practices to ensure data quality and integrity.

2. Objective of Study

The objective of this study was to assess the feasibility of enhancing the permeability of the active pharmaceutical ingredient 3,4,3-L1(1,2-HOPO) using oral permeation enhancers. Evaluation was performed using an in vitro pK assay based on the Double-Sink™ PAMPA technology developed by pION, Inc.

3. Experimental Design

The permeability enhancement study was performed in two stages. In the first stage (TABLE 10.1), 15 formulations were prepared and screened. The second stage (TABLE 10.2) was performed to refine the concentrations of the permeability enhancers that seemed to display permeability enhancement in the first screening. The screening conditions for both stages are listed below. The sample solutions were stored throughout the study in 20 mL clear scintillation glass vials with polypropylene cap and pulp foil liner, wrapped in aluminum foil.

TABLE 10.1

PAMPA SCREENING STAGE I
PAMPA Screening Stage 1

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F0 (Control) | 3,4,3-LI(1,2-HOPO) API | None | NA | NA | 1 | 10 |
| F1 | Anionic Surfactant | Sodium lauryl sulfate (SLS) | 0.010% | 0.10 | 1 | 10 |
| F2 | Nitrogen containing Ring | Caprolactam | 1.00% | 2.50 | 1 | 10 |
| F3 | Nonionic Surfactant | Polysorbate 80 | 20 mg/mL | 2.50 | 1 | 10 |
| F4 | Bile Salts | Sodium deoxycholoate | 30 mg/mL | 2.50 | 1 | 10 |
| F5 | Fatty Esters | Isopropyl myristate | 1.00% | 2.50 | 1 | 10 |
| F6 | Nitrogen containing Rings | 1-Phenylpiperazine | 1.00% | 2.50 | 1 | 10 |

TABLE 10.1-continued

PAMPA SCREENING STAGE I
PAMPA Screening Stage 1

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F7 | Natural | Piperine | 1.00% | 2.50 | 1 | 10 |
| F8 | Others | Menthone | 1.00% | 2.50 | 1 | 10 |
| F9 | Lipid | Labrafac Lipophile WL 1349 | 159 mg | 5.00 | 1 | 10 |
| F10 | Lipid | Gelucire 44/14 | 218 mg | 5.00 | 1 | 10 |
| F11 | Lipid | Labrafil M2130 CS | 218 mg | 5.00 | 1 | 10 |
| F12 | Lipid | Labrafil M2125 CS | 300 mg | 5.00 | 1 | 10 |
| F13 | Lipid | Maisine 35-1 | 344 mg | 5.00 | 1 | 10 |
| F14 | Lipid | Peceol | 33.3 | 5.00 | 1 | 10 |
| F15 | Lipid | Labrasol | 70 mg | 5.00 | 1 | 10 |

TABLE 10.2

PAMPA SCREENING STAGE 2
PAMPA Screening Stage 2

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F0 Repeat | 3,4,3-LI(1,2-HOPO) API | | | NA | 1 | 10 |
| F3 Repeat | Nonionic Surfactant | Polysorbate 80 | 20 mg/mL | 2.50 | 1 | 10 |
| F3A | | | | 5.00 | 1 | 10 |
| F3B | | | | 10.00 | 1 | 10 |
| F4 Repeat | Bile Salts | Sodium deoxycholate | 30 mg/mL | 2.50 | 1 | 10 |
| F4A | | | | 10.00 | 1 | 10 |
| F5 Repeat | Fatty Esters | Isopropyl myristate | 1.00% | 2.50 | 1 | 10 |
| F5A | | | | 10.00 | 1 | 10 |
| F10 Repeat | Lipid | Gelucire 44/14 | 218 mg | 5.00 | 1 | 10 |
| F10A | | | | 20.00 | 1 | 10 |
| F13 Repeat | Lipid | Maisine 35-1 | 344 mg | 5.00 | 1 | 10 |
| F13A | | | | 10.00 | 1 | 10 |
| F13B | | | | 20.00 | 1 | 10 |
| F14 Repeat | Lipid | Peceol | 33.3 | 5.00 | 1 | 10 |
| F14A | | | | 10.00 | 1 | 10 |
| F14B | | | | 20.00 | 1 | 10 |

4. Materials And Methods
   a. Test and Control Articles

Test Article: 3,4,3-L1(1,2-HOPO)
Manufacturer: Ash Stevens, Inc. (Detroit, Mich.)
Lot Number: ML-11-276
Physical Description: Pale yellow solid
Storage Conditions: Refrigerated 2-8° C. protected from light.
Materials:

| | |
|---|---|
| Purified Water | HPLC Grade-Supplier: Ricca |
| Sodium lauryl sulfate (SLS) | Spectrum chemicals |
| Caprolactam | Spexcertiprep |
| Polysorbate 80 (Tween 80) | Spectrum chemicals |
| Sodium deoxycholate | Sigma-aldrich |
| Isopropyl myristate | Sigma-aldrich |
| 1-Phenylpiperazine | Sigma-aldrich |
| Piperine | Sigma-aldrich |
| Menthone | TCI |
| Labrafac Lipophile WL 1349 | Gattefosse |
| Gelucire 44/14 | Gattefosse |
| Labrafil M2130 CS | Gattefosse |
| Labrafil M2125 CS | Gattefosse |
| Maisine 35-1 | Gattefosse |
| Peceol | Gattefosse |
| Labrasol | Gattefosse |
| GIT-0 lipid | pIOn, Inc. |
| Acceptor Sink Buffer | pIOn, Inc. |
| Prisma ™ Buffer | pIOn, Inc. |
| DMSO | HPLC Grade, Burdick and Jackson |
| Stirring device | Gut-Box ™, pION, Inc. |

Test Solutions: Vehicles containing the permeation enhancers were prepared by weighing the adequate quantity of enhancer and dissolving it into 100 mL of purified water to reach the designated concentration. Test solutions were then prepared by weighing 10 mg of 3,4,3-L1(1,2-HOPO), dissolving it into 10 mL of each of the vehicles to reach a concentration of 1 mg/mL (purified water was used for the control solution). The final pH and clarity of each solution were recorded.

b. Sample Characterization

Visual Observation: For each sample solution, visual observation consisted in recording color and clarity.

pH Record: The pH of each sample solution prepared for permeability analysis was measured and recorded.

c. Permeability Assay

In vitro PK assay based on Double-Sink™ PAMPA assay layout:

The PAMPA Evolution96™ instrument was used for the liquid handling, UV data collection and results processing. The system consisted of a 96-well Double-Sink PAMPA Sandwich with pre-loaded stirrers. A PAMPA sandwich was formed such that each composite well was divided into two chambers, separated by a 125 μm microfilter disc (0.45 μm pores), coated with Pion GIT-0 phospholipids mixture. Formulations were suspended in Prisma™ buffer. GIT-0 lipid painted on a filter support created an artificial membrane separating two chamber of the permeation system while the free of drug Acceptor Sink Buffer (ASB, pH 7.4) was placed in the receiving compartment.

After introducing the formulations in the donor compartments, the PAMPA sandwich was incubated for 15-30 min or up to 24 hours and only the UV spectra of the receiver were collected. Calibrated for in vivo conditions, individual-well stirring was provided by the Gut-Box™ (Pion Inc.).

The appearance rate of a compound in the receiving compartment of the PAMPA Sandwich containing formulation in the donor compartment was compared to the corresponding rate in a formulation-free system. The ratio between these two rates was reported as a Flux Ratio.

Sample Mapping Schemes (Table 10.3 and Table 10.4)

TABLE 10.3

Stage 1 Screening:

| | 1 | 2 | 3 | 4 | 5 | 6 | 7 | 8 | 9 | 10 | 11 | 12 |
|---|---|---|---|---|---|---|---|---|---|---|---|---|
| A | Formulation 1 | | | Vehicle 1 | | | Formulation 9 | | | Vehicle 9 | | |
| B | Formulation 2 | | | Vehicle 2 | | | Formulation 10 | | | Vehicle 10 | | |
| C | Formulation 3 | | | Vehicle 3 | | | Formulation 11 | | | Vehicle 11 | | |
| D | Formulation 4 | | | Vehicle 4 | | | Formulation 12 | | | Vehicle 12 | | |
| E | Formulation 5 | | | Vehicle 5 | | | Formulation 13 | | | Vehicle 13 | | |
| F | Formulation 6 | | | Vehicle 6 | | | Formulation 14 | | | Vehicle 14 | | |
| G | Formulation 7 | | | Vehicle 7 | | | Formulation 115 | | | Vehicle 15 | | |
| H | Formulation 8 | | | Vehicle 8 | | | Formulation 0-Control | | | Vehicle 0-Control | | |

TABLE 10.4

Stage 2 Screening:

| | 1 | 2 | 3 | 4 | 5 | 6 | 7 | 8 | 9 | 10 | 11 | 12 |
|---|---|---|---|---|---|---|---|---|---|---|---|---|
| A | Formulation 3 | | | F3 Vehicle | | | Formulation 14B | | | F14B Vehicle | | |
| B | Formulation 3A | | | F3A Vehicle | | | Formulation 4 | | | F4 Vehicle | | |
| C | Formulation 3B | | | F3B Vehicle | | | Formulation 4A | | | F4A Vehicle | | |
| D | Formulation 13 | | | F13 Vehicle | | | Formulation 5 | | | F5 Vehicle | | |
| E | Formulation 13A | | | F13A Vehicle | | | Formulation 5A | | | F5A Vehicle | | |
| F | Formulation 13B | | | F13B Vehicle | | | Formulation 10 | | | F10 Vehicle | | |
| G | Formulation 14 | | | F14 Vehicle | | | Formulation 10A | | | F10A Vehicle | | |
| H | Formulation 14A | | | F14A Vehicle | | | Formulation 0-Control | | | F0-Control Vehicle | | |

5. Results a. PAMPA Assay Results

Observations (formulation appearance and pH) and PAMPA permeation results are summarized in TABLE 10.5 below for both screening stages. Based on the data obtained from the permeation assay, the GIT lipid-covered membranes were stable in the presence of all tested formulations and formulation vehicles, and no leakage was detected. The API 3,4,3-L1(1,2-HOPO) indicated very low permeability, comparable or even lower than the permeability level of the references compound Ranitidine.

TABLE 10.5

PAMPA SCREENING RESULTS STAGES 1 AND 2

| | | Formulation Vehicle Preparation & pH in 100 mL Purified Water | | | Observations/Results API's Concentration: 1 mg/mL, 10 mL Vehicle | | |
|---|---|---|---|---|---|---|---|
| Formulation Code | Enhancer Selected | Enhancer's Target Conc (mg/mL) | Quantity (mg) | PH | Appearance | pH | Flux Ration (In vitro pK PAMPA Assay) |
| F0 (Control) | None | NA | NA | 7.21 | Clear solution | 3.73 | 1.00 |
| F0 Repeat | | NA | NA | 7.20 | Clear solution | 3.70 | 1.00 ± 0.09 |
| F1 | Sodium lauryl sulfate | 0.10 | 10 | 6.58 | Clear solution | 3.74 | NA |
| F2 | Caprolactam | 2.50 | 250 | 6.68 | Clear solution | 3.72 | NA |
| F3 | Polysorbate 80 | 2.50 | 250 | 6.07 | Clear solution | 3.74 | 2.22 ± 0.96 |
| F3 Repeat | | 2.50 | 250 | 6.34 | Clear solution | 3.70 | 0.77 ± 0.08 |
| F3A | | 5.00 | 500 | 6.30 | Clear solution | 3.83 | 0.94 ± 0.09 |
| F3B | | 10.00 | 1000 | 6.54 | Clear solution | 3.72 | 75.57 ± 5.22 |
| F4 | Sodium deoxycholate | 2.50 | 250 | 7.63 | White Dispersion | 6.85 | 1.04 ± 0.43 |
| F4 Repeat | | 2.50 | 250 | 7.47 | White Dispersion | 7.08 | NA |
| F4A | | 10.00 | 1000 | 7.82 | Opaque dispersion | 7.07 | NA |
| F5 | Isopropyl myristate | 2.50 | 250 | 6.55 | Clear solution | 3.77 | 1.06 ± 0.72 |
| F5 Repeat | | 2.50 | 250 | 6.73 | Clear solution | 3.79 | 1.86 ± 0.22 |
| F5A | | 10.00 | 1000 | 6.82 | Clear solution with oily drops | 3.72 | 1.39 ± 0.14 |
| F6 | 1-Phenylpiperazine | 2.50 | 250 | 9.99 | Clear solution | 9.12 | NA |
| F7 | Piperine | 2.50 | 250 | 6.93 | Clear solution | 3.79 | NA |
| F8 | Menthone | 2.50 | 250 | 6.76 | Clear solution | 3.72 | NA |
| F9 | Labrafac Lipophile WL | 5.00 | 500 | 5.73 | Oily globules | 3.75 | NA |
| F10 | Gelucire 44/14 | 5.00 | 500 | 3.87 | Clear solution | 3.62 | 0.84 ± 0.45 |
| F10 Repeat | | 5.00 | 500 | 4.17 | Clear solution | 3.72 | NA |
| F10A | | 20.00 | 2000 | 3.41 | Opaque dispersion | 3.44 | 0.77 ± 0.09 |
| F11 | Labrafil M2130 CS | 5.00 | 500 | 5.65 | White Dispersion | 3.73 | NA |
| F12 | Labrafil M2125 CS | 5.00 | 500 | 6.16 | White Dispersion | 3.79 | NA |
| F13 | Maisine 35-1 | 5.00 | 500 | 6.23 | Opaque dispersion | 3.74 | 2.30 ± 0.93 |
| F13 Repeat | | 5.00 | 500 | 6.37 | Opaque dispersion | 3.67 | 0.71 ± 0.12 |
| F13A | | 10.00 | 1000 | 6.35 | White Dispersion | 3.68 | 0.95 ± 0.07 |
| F13B | | 20.00 | 2000 | 6.41 | Opaque dispersion | 3.92 | 1.04 ± 0.08 |
| F14 | Perceol | 5.00 | 500 | 5.22 | Clear solution | 3.70 | 1.18 ± 0.60 |
| F14 Repeat | | 5.00 | 500 | 6.03 | Clear solution | 3.74 | 1.15 ± 0.12 |
| F14A | | 10.00 | 1000 | 6.08 | Clear solution | 3.7 | 0.97 ± 0.30 |

TABLE 10.5-continued

PAMPA SCREENING RESULTS STAGES 1 AND 2

| Formulation Code | Enhancer Selected | Formulation Vehicle Preparation & pH in 100 mL Purified Water | | | Observations/Results API's Concentration: 1 mg/mL, 10 mL Vehicle | | Flux Ration (In vitro pK PAMPA Assay) |
|---|---|---|---|---|---|---|---|
| | | Enhancer's Target Conc (mg/mL) | Quantity (mg) | PH | Appearance | pH | |
| F14B | | 20.00 | 2000 | 6.03 | Clear solution | 3.83 | 1.63 ± 0.43 |
| F15 | Labrasol | 5.00 | 500 | 5.27 | White Dispersion | 3.71 | NA |

For Formulations 1, 2, 4A, 8, 9, 11, 12, and 15, the UV-Visible signal in the acceptor compartment was below the detection limit and the flux ratio could not be determined. Formulations 6 and 7 showed very high penetration rates for their corresponding vehicles that completely saturated the UV-Visible signal in the acceptor compartment, precluding the signal detection of the API under the strong vehicle background. Formulations 3, 3A, 4, 5, 5A, 10, 10A, 13, 13A, 13B, 14, 14A, and 14B showed no or minor improvement in flux in comparison to the control API, while formulation 3B showed significant improvement of permeability.

b. Flux Ratio Comparison

Flux ratios obtained for the different formulations of 3,4,3-L1(1,2-HOPO) are summarized in TABLE 10.6 and charted in FIG. 22. The only formulation 3B resulting in a 75-fold permeability increase was obtained with 10 mg/mL Polysorbate 80 and 1 mg/mL API, with a recorded pH of 3.72.

TABLE 10.6

FLUX RATIO COMPARISONS FOR TESTED FORMULATIONS

| Formulation Code | Flux Ratio | SD |
|---|---|---|
| F0 (API Control) | 1.00 | |
| F0 Repeat | 1.00 | 0.09 |
| F3 | 2.22 | 0.96 |
| F3 Repeat | 0.77 | 0.08 |
| F3A | 0.94 | 0.09 |
| F3B | 75.57 | 5.22 |
| F4 | 1.04 | 0.43 |
| F5 | 1.06 | 0.72 |

TABLE 10.6-continued

FLUX RATIO COMPARISONS FOR TESTED FORMULATIONS

| Formulation Code | Flux Ratio | SD |
|---|---|---|
| F5 Repeat | 1.86 | 0.22 |
| F5A | 1.39 | 0.14 |
| F10 | 0.84 | 0.45 |
| F10A | 0.77 | 0.09 |
| F13 | 2.3 | 0.93 |
| F13 Repeat | 0.71 | 0.12 |
| F13A | 0.95 | 0.07 |
| F13B | 1.04 | 0.08 |
| F14 | 1.18 | 0.6 |
| F14 Repeat | 1.15 | 0.12 |
| F14A | 0.97 | 0.3 |
| F14B | 1.63 | 0.43 |

6. Part C Conclusion

Fifteen different permeation enhancers were evaluated for their ability at increasing the permeability of 3,4,3-L1(1,2-HOPO), using an in vitro PAMPA assay with artificial GIT lipid membranes. A significant increase was observed in permeability for one formulation containing 10 mg/mL of Polysorbate 80 and 1 mg/mL of API. All other tested formulations showed no or minor improvement in permeability. Formulations containing Polysorbate 80 will be evaluated further in in vivo studies.

Analysis of 3,4,3-L1(1,2-HOPO) Lot ML-11-276 was performed and a certificate of analysis was prepared regarding appearance, identification by IR and $^1$H-NMR, related compounds by HPLC, HPLC purity, heavy metal content, residual solvent content, water content by Karl Fischer, residue on ignition, and purity.

TABLE 10.7

DISTRIBUTION COEFFICIENT MEASUREMENT SUMMARY

Buffering Agent 1: 7.5 E−02 M HCl

| | Standard A1 | | | Standard B1 | | |
|---|---|---|---|---|---|---|
| | $A_{st}$ | 0.885 | | $A_{st}$ | 1.906 | |
| | $\varepsilon_{aq}$ | 17735 | | $\varepsilon_{aq}$ | 18193 | |
| Samples | A11 | A12 | A13 | B11 | B12 | B13 |
| pH | 1.18 | 1.18 | 1.18 | 1.20 | 1.20 | 1.20 |
| $A_{aq}$ | 1.578 | 1.587 | 1.592 | 1.446 | 1.436 | 1.483 |
| $C_{aq}$ | 8.90E−05 | 8.95E−05 | 8.98E−05 | 7.95E−05 | 7.89E−05 | 8.15E−05 |
| $C_{or}$ | 1.08E−05 | 1.03E−05 | 1.00E−05 | 2.53E−05 | 2.58E−05 | 2.33E−05 |
| $D_{ow}$ | 0.122 | 0.115 | 0.112 | 0.318 | 0.327 | 0.285 |
| $Log(D_{ow})$ | −0.915 | −0.938 | −0.952 | −0.497 | −0.485 | −0.545 |
| | | −0.935 | 0.011 | | −0.509 | 0.018 |

TABLE 10.7-continued

| Buffering Agent 2: 7.5 E−03 M HCl | | | | | | |
|---|---|---|---|---|---|---|
| Standard A2 | | | | Standard B2 | | |
| $A_{st}$ | 0.998 | | | $A_{st}$ | 1.88 | |
| $\varepsilon_{aq}$ | 19999 | | | $\varepsilon_{aq}$ | 17945 | |
| Samples | A11 | A12 | A13 | B11 | B12 | B13 |
| pH | 2.15 | 2.15 | 2.15 | 2.16 | 2.16 | 2.16 |
| $A_{aq}$ | 1.826 | 1.807 | 1.798 | 1.251 | 1.261 | 1.280 |
| $C_{aq}$ | 9.13E−05 | 9.04E−05 | 8.99E−05 | 6.97E−05 | 7.03E−05 | 7.13E−05 |
| $C_{or}$ | 8.50E−06 | 9.45E−06 | 9.90E−06 | 3.51E−05 | 3.45E−05 | 3.34E−05 |
| $D_{ow}$ | 0.093 | 0.105 | 0.110 | 0.503 | 0.491 | 0.469 |
| $\text{Log}(D_{ow})$ | −1.031 | −0.980 | −0.958 | −0.299 | −0.309 | −0.329 |
| | | −0.990 | 0.022 | | −0.312 | 0.009 |

| Buffering Agent 3: 7.5 E−04 M HCl | | | | | | |
|---|---|---|---|---|---|---|
| Standard A3 | | | | Standard B3 | | |
| $A_{st}$ | 0.75 | | | $A_{st}$ | 1.892 | |
| $\varepsilon_{aq}$ | 15029 | | | $\varepsilon_{aq}$ | 18059 | |
| Samples | A31 | A32 | A33 | B31 | B32 | B33 |
| pH | 3.21 | 3.21 | 3.21 | 3.13 | 3.13 | 3.13 |
| $A_{aq}$ | 1.271 | 1.282 | 1.267 | 1.834 | 1.808 | 1.852 |
| $C_{aq}$ | 8.46E−05 | 8.53E−05 | 8.43E−05 | 1.02E−04 | 1.00E−04 | 1.03E−04 |
| $C_{or}$ | 1.52E−05 | 1.45E−05 | 1.55E−05 | 3.21E−06 | 4.65E−06 | 2.21E−06 |
| $D_{ow}$ | 0.180 | 0.170 | 0.184 | 0.032 | 0.046 | 0.022 |
| $\text{Log}(D_{ow})$ | −0.744 | −0.769 | −0.735 | −1.500 | −1.333 | −1.666 |
| | | −0.750 | 0.010 | | −1.499 | 0.096 |

| Buffering Agent 4: 1 E−02 M Acetic Acid | | | | | | |
|---|---|---|---|---|---|---|
| Standard A4 | | | | Standard B4 | | |
| $A_{st}$ | 0.885 | | | $A_{st}$ | 1.883 | |
| $\varepsilon_{aq}$ | 17735 | | | $\varepsilon_{aq}$ | 17973 | |
| Samples | A41 | A42 | A43 | B41 | B42 | B43 |
| pH | 4.19 | 4.19 | 4.19 | 4.00 | 4.00 | 4.00 |
| $A_{aq}$ | 1.645 | 1.669 | 1.657 | 1.804 | 1.802 | 1.864 |
| $C_{aq}$ | 9.28E−05 | 9.41E−05 | 9.34E−05 | 1.00E−04 | 1.00E−04 | 1.04E−04 |
| $C_{or}$ | 7.05E−06 | 5.70E−06 | 6.37E−06 | 4.40E−06 | 4.51E−06 | 1.06E−06 |
| $D_{ow}$ | 0.076 | 0.061 | 0.068 | 0.044 | 0.045 | 0.010 |
| $\text{Log}(D_{ow})$ | −1.119 | −1.218 | −1.166 | −1.359 | −1.347 | −1.922 |
| | | −1.168 | 0.029 | | −1.566 | 0.213 |

| Buffering Agent 5: 1 E−02 M Acetic Acid | | | | | | |
|---|---|---|---|---|---|---|
| Standard A5 | | | | Standard B5 | | |
| $A_{st}$ | 0.753 | | | $A_{st}$ | 1.505 | |
| $\varepsilon_{aq}$ | 15090 | | | $\varepsilon_{aq}$ | 14365 | |
| Samples | A51 | A52 | A53 | B51 | B52 | B53 |
| pH | 5.13 | 5.13 | 5.13 | 5.20 | 5.20 | 5.20 |
| $A_{aq}$ | 1.443 | 1.466 | 1.434 | 1.425 | 1.391 | 1.365 |
| $C_{aq}$ | 9.56E−05 | 9.72E−05 | 9.50E−05 | 9.92E−05 | 9.68E−05 | 9.50E−05 |
| $C_{or}$ | 4.18E−06 | 2.65E−06 | 4.77E−06 | 5.57E−06 | 7.94E−06 | 9.75E−06 |
| $D_{ow}$ | 0.044 | 0.027 | 0.050 | 0.056 | 0.082 | 0.103 |
| $\text{Log}(D_{ow})$ | −1.360 | −1.564 | −1.299 | −1.251 | −1.086 | −0.989 |
| | | −1.408 | 0.080 | | −1.109 | 0.076 |

| Buffering Agent 6: 1 E−02 M MES | | | | | | |
|---|---|---|---|---|---|---|
| Standard A6 | | | | Standard B6 | | |
| $A_{st}$ | 0.719 | | | $A_{st}$ | 1.356 | |
| $\varepsilon_{aq}$ | 14408 | | | $\varepsilon_{aq}$ | 12943 | |
| Samples | A61 | A62 | A63 | B61 | B62 | B63 |
| pH | 6.30 | 6.30 | 6.30 | 6.15 | 6.15 | 6.15 |
| $A_{aq}$ | 1.351 | 1.335 | 1.329 | 1.356 | 1.301 | 1.326 |

TABLE 10.7-continued

| | | | | | | |
|---|---|---|---|---|---|---|
| $C_{aq}$ | 9.38E−05 | 9.27E−05 | 9.22E−05 | 1.05E−04 | 1.01E−04 | 1.02E−04 |
| $C_{or}$ | 6.04E−06 | 7.15E−06 | 7.57E−06 | 0.00E+00 | 4.25E−06 | 2.32E−06 |
| $D_{ow}$ | 0.064 | 0.077 | 0.082 | 0.000 | 0.042 | 0.023 |
| $Log(D_{ow})$ | −1.191 | −1.113 | −1.086 | #NUM! | −1.374 | −1.645 |
| | | −1.130 | 0.032 | | −1.510 | 0.136 |

Buffering Agent 7: 1 E−02 M HEPES

| | Standard A7 | | | Standard B7 | | |
|---|---|---|---|---|---|---|
| $A_{st}$ | 0.669 | | | $A_{st}$ | 1.418 | |
| $\varepsilon_{aq}$ | 13406 | | | $\varepsilon_{aq}$ | 13535 | |

| Samples | A71 | A72 | A73 | B71 | B72 | B73 |
|---|---|---|---|---|---|---|
| pH | 6.75 | 6.75 | 6.75 | 6.83 | 6.83 | 6.83 |
| $A_{aq}$ | 1.268 | 1.302 | 1.319 | 1.341 | 1.381 | 1.374 |
| $C_{aq}$ | 8.68E−05 | 8.91E−05 | 9.03E−05 | 1.00E−04 | 1.03E−04 | 1.03E−04 |
| $C_{or}$ | 1.30E−05 | 1.07E−05 | 9.51E−06 | 4.27E−06 | 1.27E−06 | 1.80E−06 |
| $D_{ow}$ | 0.150 | 0.120 | 0.105 | 0.043 | 0.012 | 0.017 |
| $Log(D_{ow})$ | −0.824 | −0.921 | −0.977 | −1.372 | −1.910 | −1.758 |
| | | −0.908 | 0.045 | | −1.680 | 0.160 |

Buffering Agent 8: 1 E−02 M HEPES

| | Standard A8 | | | Standard B8 | | |
|---|---|---|---|---|---|---|
| $A_{st}$ | 0.667 | | | $A_{st}$ | 1.516 | |
| $\varepsilon_{aq}$ | 13366 | | | $\varepsilon_{aq}$ | 14470 | |

| Samples | A81 | A82 | A83 | B81 | B82 | B83 |
|---|---|---|---|---|---|---|
| pH | 7.42 | 7.42 | 7.42 | 7.46 | 7.46 | 7.46 |
| $A_{aq}$ | 1.290 | 1.288 | 1.317 | 1.329 | 1.325 | 1.264 |
| $C_{aq}$ | 8.83E−05 | 8.82E−05 | 9.02E−05 | 9.96E−05 | 9.93E−05 | 9.47E−05 |
| $C_{or}$ | 1.15E−05 | 1.16E−05 | 9.65E−06 | 5.17E−06 | 5.47E−06 | 1.00E−05 |
| $D_{ow}$ | 0.130 | 0.132 | 0.107 | 0.052 | 0.055 | 0.106 |
| $Log(D_{ow})$ | −0.885 | −0.879 | −0.970 | −1.285 | −1.259 | −0.975 |
| | | −0.912 | 0.029 | | −1.173 | 0.099 |

Buffering Agent 9: 1 E−02 M HEPES

| | Standard A9 | | | Standard B9 | | |
|---|---|---|---|---|---|---|
| $A_{st}$ | 0.622 | | | $A_{st}$ | 1.481 | |
| $\varepsilon_{aq}$ | 12464 | | | $\varepsilon_{aq}$ | 14136 | |

| Samples | A91 | A92 | A93 | B91 | B92 | B93 |
|---|---|---|---|---|---|---|
| pH | 8.00 | 8.00 | 8.00 | 8.00 | 8.00 | 8.00 |
| $A_{aq}$ | 1.313 | 1.357 | 1.288 | 1.367 | 1.391 | 1.377 |
| $C_{aq}$ | 8.99E−05 | 9.29E−05 | 8.82E−05 | 1.02E−04 | 1.04E−04 | 1.03E−04 |
| $C_{or}$ | 9.93E−06 | 6.91E−06 | 1.16E−05 | 2.32E−06 | 5.25E−07 | 1.57E−06 |
| $D_{ow}$ | 0.110 | 0.074 | 0.132 | 0.023 | 0.005 | 0.015 |
| $Log(D_{ow})$ | −0.957 | −1.128 | −0.879 | −1.644 | −2.298 | −1.817 |
| | | −0.988 | 0.074 | | −1.920 | 0.196 |

TABLE 10.8

PAMPA MEASUREMENT SUMMARY
Screening Stage 1

| Sample | Average $C_{ACC}$, μm | SD $C_{ACC}$ | Flux Ratio | SD Ratio |
|---|---|---|---|---|
| Formulation 1 | <0.1 | | | |
| Formulation 2 | <0.1 | | | |
| Formulation 3 | 0.41 | 0.06 | 2.22 | 0.96 |
| Formulation 4 | 0.19 | 0.02 | 1.04 | 0.43 |
| Formulation 5 | 0.19 | 0.02 | 1.06 | 0.72 |
| Formulation 6 | See Discussion Section | | | |
| Formulation 7 | See Discussion Section | | | |
| Formulation 8 | <0.1 | | | |
| Formulation 9 | <0.1 | | | |
| Formulation 10 | 0.15 | 0.05 | 0.84 | 0.45 |
| Formulation 11 | <0.1 | | | |
| Formulation 12 | <0.1 | | | |
| Formulation 13 | 0.42 | 0.02 | 2.30 | 0.93 |
| Formulation 14 | 0.22 | 0.07 | 1.18 | 0.60 |
| Formulation 15 | <0.1 | | | |
| Formulation-0 Control | 0.18 | 0.07 | 1.00 | |

| Sample | $C_{acc}$, μm | SD $C_{acc}$ | Ratio | SD Ratio |
|---|---|---|---|---|
| Formulation 3 | 0.12 | 0.01 | 0.77 | 0.08 |
| Formulation 14B | 0.25 | 0.06 | 1.63 | 0.43 |
| Formulation 3A | 0.14 | 0.01 | 0.94 | 0.09 |
| Formulation 3B | 11.45 | 0.38 | 75.57 | 5.22 |
| Formulation 13 | 0.11 | 0.02 | 0.71 | 0.12 |
| Formulation 5 | 0.28 | 0.03 | 1.86 | 0.22 |
| Formulation 13A | 0.14 | 0.01 | 0.95 | 0.07 |
| Formulation 5A | 0.21 | 0.02 | 1.39 | 0.14 |

TABLE 10.8-continued

PAMPA MEASUREMENT SUMMARY
Screening Stage 1

| | | | | |
|---|---|---|---|---|
| Formulation 13B | 0.16 | 0.01 | 1.04 | 0.08 |
| Formulation 14 | 0.17 | 0.02 | 1.15 | 0.12 |
| Formulation 10A | 0.12 | 0.01 | 0.77 | 0.09 |
| Formulation 14A | 0.15 | 0.04 | 0.97 | 0.30 |
| Formulation-0 Control | 0.15 | 0.01 | 1.00 | 0.09 |
| Formulation 4 | <0.1 | | | |
| Formulation 4A | <0.1 | | | |
| Formulation 10 | <0.1 | | | |

Sample—compound name based on provided information
Average $C_{ACC}$—average value of API concentration determined in the acceptor compartment after 18 hours of incubation
Flux Ratio—calculated based on a ratio between UV signals in the acceptor compartment when corresponding donor compartment has formulated product and pure API respectively
SD $C_{ACC}$—standard deviation of concentration from a triplicate measurements
SD Ratio—standard deviation of a ratio calculated taking into account propagation of errors Example 11—Permeability Enhancement of 3,4,3-L1(1,2-HOPO)

Summary

The objective of the analytical study described in this report was to evaluate additional oral permeation enhancers for their ability at enhancing the permeability of the active pharmaceutical ingredient 3,4,3-L1(1,2-HOPO). Evaluation was performed using an in vitro pK assay based on the Double-Sink™ PAMPA technology developed by pION, Inc.

Thirty one different permeation enhancers were evaluated, in addition to the original fifteen described in study 12-003-C, for their ability at increasing the permeability of 3,4,3-L1(1,2-HOPO), using an in vitro PAMPA assay with artificial GIT lipid membranes. Significant increases were observed in permeability for two formulations containing 2-Octyl-1-dodecanol and sodium oleate, respectively. All other tested formulations showed no or minor improvement in permeability. Formulations containing Polysorbate 80 were re-evaluated and previous enhancement results (as described in 12-003-C) could not be reproduced.

1. Purpose of Study

The purpose of this study was to provide data that can be used to support research efforts. It was not conducted in accordance with U.S. Food and Drug Administration (FDA) "Good Laboratory Practice for Nonclinical Laboratory Studies" (GLP) regulations, as described in 21 CFR Part 58. However, the study was planned, performed, recorded, and reported in accordance with standard practices to ensure data quality and integrity.

2. Objective of Study

The objective of this study was to evaluate additional oral permeation enhancers for their ability at enhancing the permeability of the active pharmaceutical ingredient 3,4,3-L1(1,2-HOPO). Evaluation was performed using an in vitro pK assay based on the Double-Sink™ PAMPA technology developed by pION, Inc. This a follow-up study to LBNL No. 12-003-C, in which fifteen oral permeation enhancers were initially tested.

3. Experimental Design

The permeability enhancement study was performed in two additional stages (stages 3 and 4, following the stages 1 and 2 described in EXAMPLE 10). In stage 3, 32 formulations were prepared and screened (including 31 new formulations and 1 repeat of the most successful formulation from EXAMPLE 10). Stage 4 was performed to refine the concentrations of the permeability enhancers that seemed to display permeability enhancement in the first three screenings and verify reproducibility. The screening conditions for both stages 3 and 4 are listed below in TABLE 11.1 and TABLE 11.2, respectively. The sample solutions were stored throughout the study in 20 mL clear scintillation glass vials with polypropylene cap and pulp foil liner, wrapped in aluminum foil.

TABLE 11.1

PAMPA SCREENING STAGE 3
PAMPA Screening Stage 3

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F0 Repeat 2&3 | 3,4,3-LI(1,2-HOPO)API | None | NA | NA | 1 | 10 |
| F16 | Anionic Surfactant | Sodium decyl sulfate | 0.010% | 0.20 | 1 | 10 |
| F17 | Anionic Surfactant | Sodium octyl sulfate | 0.01% | 0.20 | 1 | 10 |
| F18 | Cationic Surfactant | Decyltrimethyl-ammoniumbromide | 0.10% | 1.00 | 1 | 10 |
| F19 | Nonionic Surfactant | Span-80 (Sorbitan monooleate) | 1.7 MG (Oral tablet) | 2.50 | 1 | 10 |
| F20 | Nonionic Surfactant | Triton X-100 | N/A | 2.50 | 1 | 10 |
| F21 | Bile Salts | Sodium glycocholate hydrate | 30 mg/mL | 1.00 | 1 | 10 |
| F22 | Fatty Acid | Cholic acid | N/A | 2.50 | 1 | 10 |
| F23 | Fatty Acid | Heptanoic acid | N/A | 2.50 | 1 | 10 |
| F24 | Fatty Ester | Isopropyl Palmitate | 0.1 to 1% | 2.50 | 1 | 10 |
| F25 | Fatty Ester | Methyl laurate | 0.1 to 1% | 2.50 | 1 | 10 |
| F26 | Fatty Amine | Sodium oleate | N/A | 2.50 | 1 | 10 |
| F27 | Sodium Salts of Fatty Acid | Urea | 0.018 MG (Oral tablet, coated) | 2.50 | 1 | 10 |

TABLE 11.1-continued

PAMPA SCREENING STAGE 3
PAMPA Screening Stage 3

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F28 | Nitrogen containing Rings | 1-Octyl-2-pyrrolidone | 0.1 to 1% | 2.50 | 1 | 10 |
| F29 | Nitrogen containing Rings | 1-Methylpiperazine | 0.1 to 1% | 2.50 | 1 | 10 |
| F30 | Nitrogen containing Rings | 1-Methyl-2-Pyrrolidinone | 0.1 to 1% | 2.50 | 1 | 10 |
| F31 | Nitrogen containing Rings | n-Caproic Acid | 0.1 to 1% | 2.50 | 1 | 10 |
| F32 | Others | Sodium Salicylate | N/A | 2.50 | 1 | 10 |
| F33 | Others | (=)-Limonene | N/A | 2.50 | 1 | 10 |
| F34 | Others | L-Fenchone | N/A | 2.50 | 1 | 10 |
| F35 | Others | Cineole | N/A | 2.50 | 1 | 10 |
| F36 | Others | Pinene oxide | N/A | 2.50 | 1 | 10 |
| F37 | Others | 2-Octyl-1-dodecanol | N/A | 2.50 | 1 | 10 |
| F38 | Natural | Cumin seed oil | N/A | 2.50 | 1 | 10 |
| F39 | Lipid Excipient | Caproyl PGMC | N/A | 5.00 | 1 | 10 |
| F40 | Lipid Excipient | Caproyl 90 (Propylene glycol dicaprylate) | N/A | 5.00 | 1 | 10 |
| F41 | Lipid Excipient | Lauroglycol FCC | N/A | 5.00 | 1 | 10 |
| F42 | Lipid Excipient | Lauroglycol 80 | N/A | 5.00 | 1 | 10 |
| F43 | Lipid Excipient | Labrafac PG | N/A | 5.00 | 1 | 10 |
| F44 | Lipid Excipient | Transcutol | N/A | 5.00 | 1 | 10 |
| F45 | Lipid Excipient | Gelucire 50/13 | N/A | 5.00 | 1 | 10 |
| F46 | Lipid Excipient | Labrafil M1944 CS | N/A | 5.00 | 1 | 10 |
| F3B Repeat 1 | Noninonic Surfactant | Polysorbate 80 | N/A | 10.00 | 1 | 10 |

TABLE 11.2

PAMPA SCREENING STAGE 4
PAMPA Screening Stage 4

| | Permeation Enhancer | | | Formulation Vehicle Preparation | | |
|---|---|---|---|---|---|---|
| Formulation Code | Class | Enhancer Selected | Max. IIG limit or Literature report | Enhancer's Target Conc (mg/mL) | API's Target Conc (mg/mL) | Vehicle Volume (mL) |
| F0 Repeat 4 | 3,4,3-LI(1,2-HOPO) API | None | NA | NA | 1 | 10 |
| F0 Repeat 5 | 3,4,3-LI(1,2-HOPO) API | None | NA | NA | 1 | 10 |
| F3B Repeat 2 | Noninonic Surfactant | Polysorbate 80 | N/A | 10.00 | 1 | 10 |
| F3B Repeat 3 | Noninonic Surfactant | Polysorbate 80 | N/A | 10.00 | 1 | 10 |
| F3B Repeat 4 | Noninonic Surfactant | Polysorbate 80 | N/A | 10.00 | 1 | 10 |
| F26 Repeat 1 | Fatty Amine | Sodium oleate | N/A | 2.50 | 1 | 10 |
| F26 Repeat 2 | Fatty Amine | Sodium oleate | N/A | 2.50 | 1 | 10 |

4. Materials And Methods a. Test and Control Articles

Test Article: 3,4,3-L1(1,2-HOPO)

Manufacturer: Ash Stevens, Inc. (Detroit, Mich.)

Lot Number: ML-11-276

Physical Description: Pale yellow solid

Storage Conditions: Refrigerated 2-8° C. protected from light.

Materials:

| | |
|---|---|
| Purified Water | HPLC Grade - Supplier: Ricca |
| Sodium lauryl sulfate (SLS) | Spectrum chemicals |
| Caprolactam | Spexcertiprep |
| Polysorbate 80 (Tween 80) | Spectrum chemicals |
| Sodium decyl sulfate | Sigma-aldrich |
| Sodium octyl sulfate | Sigma-aldrich |
| Decyltrimethylammonium bromide | Sigma-aldrich |
| Span-80 (Sorbitan monooleate) | Sigma-aldrich |
| Triton X-100 | Sigma-aldrich |
| Sodium glycocholate hydrate | Sigma-aldrich |
| Cholic acid | Sigma-aldrich |
| Heptanoic acid | Sigma-aldrich |
| Isopropyl Palmitate | Sigma-aldrich |
| Methyl laurate | Sigma-aldrich |
| Sodium oleate | TCI |
| Urea | Sigma-aldrich |
| 1-Octyl-2-pyrrolidone | Sigma-aldrich |
| 1-Methylpiperazine | Sigma-aldrich |
| 1-Methyl-2-Pyrrolidinone | Sigma-aldrich |
| n-Caproic acid | TCI |
| Sodium Salicylate | Sigma-aldrich |
| (±)-Limonene | TCI |
| L-Fenchone | Sigma-aldrich |
| Cineole | Sigma-aldrich |
| Pinene oxide | Sigma-aldrich |
| 2-Octyl-1-dodecanol | Sigma-aldrich |
| Cumin seed oil | Sigma-aldrich |
| Caproyl PGMC | Gattefosse |
| Caproyl 90 (Propylene glycol dicaprylate) | Gattefosse |
| Lauroglycol FCC | Gattefosse |
| Lauroglycol 90 | Gattefosse |
| Labrafac PG | Gattefosse |
| Transcutol | Gattefosse |
| Gelucire 50/13 | Gattefosse |
| Labrafil M1944 CS | Gattefosse |
| GIT-0 lipid | pIOn, Inc. |
| Acceptor Sink Buffer | pIOn, Inc. |
| Prisma ™ Buffer | pIOn, Inc. |
| DMSO | HPLC Grade, Burdick and Jackson |
| Stirring device | Gut-Box ™, pION, Inc. |

Test Solutions: Vehicles containing the permeation enhancers were prepared by weighing the adequate quantity of enhancer and dissolving it into 100 mL of purified water to reach the designated concentration. Test solutions were then prepared by weighing 10 mg of 3,4,3-L1(1,2-HOPO), dissolving it into 10 mL of each of the vehicles to reach a concentration of 1 mg/mL (purified water was used for the control solution). The final pH and clarity of each solution were recorded.

b. Sample Characterization

Visual Observation: For each sample solution, visual observation consisted in recording color and clarity.

pH Record: The pH of each sample solution prepared for permeability analysis was measured and recorded.

c. Permeability Assay

In vitro PK assay based The PAMPA Evolution96™ instrument was used for the liquid on Double-Sink™ handling, UV data collection and results processing. The PAMPA assay layout: system consisted of a 96-well Double-Sink PAMPA Sandwich with preloaded stirrers. A PAMPA sandwich was formed such that each composite well was divided into two chambers, separated by a 125 µm microfilter disc (0.45 µM pores), coated with Pion GIT-0 phospholipids mixture. Formulations were suspended in Prisma™ buffer. GIT-0 lipid painted on a filter support created an artificial membrane separating two chamber of the permeation system while the free of drug Acceptor Sink Buffer (ASB, pH 7.4) was placed in the receiving compartment. After introducing the formulations in the donor compartments, the PAMPA sandwich was incubated for 15-30 min or up to 24 hours and only the UV spectra of the receiver were collected. Calibrated for in vivo conditions, individual-well stirring was provided by the Gut-Box™ (Pion Inc.).

The appearance rate of a compound in the receiving compartment of the PAMPA Sandwich containing formulation in the donor compartment was compared to the corresponding rate in a formulation-free system. The ratio between these two rates was reported as a Flux Ratio.

Sample Preparation: The formulations were gently shaken before the assay and the aliquots of the samples were transferred in the donor compartment of the PAMPA Sandwich. In order to verify that the lipid-coated membrane was stable in the presence of the formulations and to take into account possible affect of the formulation vehicle on the UV spectra, the corresponding formulation vehicles solutions containing no API were transferred in the donor compartment. The samples and the corresponding vehicles were assayed in triplicates.

5. Results a. PAMPA Assay Results

Observations (formulation appearance and pH) and PAMPA permeation results are summarized in TABLE 11.3 for screening stages 1 and 2 and in TABLE 11.4 for screening stages 3 and 4. Based on the data obtained from the permeation assay, the GIT lipid-covered membranes were stable in the presence of all tested formulations and formulation vehicles, and no leakage was detected. The API 3,4,3-L1(1,2-HOPO) indicated very low permeability, comparable or even lower than the permeability level of the references compound Ranitidine.

TABLE 11.3

PAMPA SCREENING RESULTS STAGES 1 AND 2

| Formulation Code | Enhancer Selected | Formulation Vehicle Preparation & pH in 100 mL | | | Observations/Results API's Concentration: 1 mg/mL, 10 mL Vehicle | | Flux Ratio |
|---|---|---|---|---|---|---|---|
| | | Purified Water | | | | | |
| | | Enhancer's Target Conc (mg/mL) | Quantity (mg) | pH | Appearance | pH | (In vitro pK PAMPA Assay) |
| F0 (Control) | None | NA | NA | 7.21 | Clear Solution | 3.73 | 1.00 |
| F0 Repeat | | NA | NA | 7.20 | Clear Solution | 3.70 | 1.00 ± 0.09 |
| F1 | Sodium lauryl sulfate | 0.10 | 10 | 6.58 | Clear Solution | 3.74 | N/A |
| F2 | Caprolactam | 2.50 | 250 | 6.68 | Clear Solution | 3.72 | N/A |
| F3 | Polysorbate 80 | 2.50 | 250 | 6.07 | Clear Solution | 3.74 | 2.22 ± 0.96 |
| F3 Repeat | | 2.50 | 250 | 6.34 | Clear Solution | 3.70 | 0.77 ± 0.08 |
| F3A | | 5.00 | 500 | 6.30 | Clear Solution | 3.83 | 0.94 ± 0.09 |
| F3B | | 10.00 | 1000 | 6.54 | Clear Solution | 3.72 | 75.57 ± 5.22 |
| F4 | Sodium deoxycholate | 2.50 | 250 | 7.63 | White dispersion | 6.85 | 1.04 ± 0.43 |
| F4 Repeat | | 2.50 | 250 | 7.47 | White dispersion | 7.08 | N/A |
| F4A | | 10.00 | 1000 | 7.82 | Opaque dispersion | 7.07 | N/A |
| F5 | Isopropyl myristate | 2.50 | 250 | 6.55 | Clear Solution | 3.77 | 1.06 ± 0.72 |
| F5 Repeat | | 2.50 | 250 | 6.73 | Clear Solution | 3.79 | 1.86 ± 0.22 |
| F5A | | 10.00 | 1000 | 6.82 | Clear Solution with oily drops | 3.72 | 1.39 ± 0.14 |
| F6 | 1-Phenylpiperazine | 2.50 | 250 | 9.99 | Clear Solution | 9.12 | N/A |
| F7 | Piperine | 2.50 | 250 | 6.93 | Clear Solution | 3.79 | N/A |
| F8 | Menthone | 2.50 | 250 | 6.76 | Clear Solution | 3.72 | N/A |
| F9 | Labrafac Lipophile WL | 5.00 | 500 | 5.73 | Oily globules | 3.75 | N/A |
| F10 | Gelucire 44/14 | 5.00 | 500 | 3.87 | Clear Solution | 3.62 | 0.84 ± 0.45 |
| F10 Repeat | | 5.00 | 500 | 4.17 | Clear Solution | 3.72 | N/A |
| F10A | | 20.00 | 2000 | 3.41 | Opaque dispersion | 3.44 | 0.77 ± 0.09 |
| F11 | Labrafil M2130 CS | 5.00 | 500 | 5.65 | White dispersion | 3.73 | N/A |
| F12 | Labrafil M2125 CS | 5.00 | 500 | 6.16 | White Dispersion | 3.79 | N/A |
| F13 | Maisine 35-1 | 5.00 | 500 | 6.23 | Opaque dispersion | 3.74 | 2.30 ± 0.93 |
| F13 Repeat | | 5.00 | 500 | 6.37 | Opaque dispersion | 3.67 | 0.71 ± 0.12 |
| F13A | | 10.00 | 1000 | 6.35 | White Dispersion | 3.68 | 0.95 ± 0.07 |
| F13B | | 20.00 | 2000 | 6.4.1 | Opaque dispersion | 3.92 | 1.04 ± 0.08 |
| F14 | Peceol | 5.00 | 500 | 5.22 | Clear Solution | 3.70 | 1.18 ± 0.60 |
| F14 Repeat | | 5.00 | 500 | 6.03 | Clear Solution | 3.74 | 1.15 ± 0.12 |
| F14A | | 10.00 | 1000 | 6.08 | Clear Solution | 3.7 | 0.97 ± 0.30 |
| F14B | | 20.00 | 2000 | 6.03 | Clear Solution | 3.83 | 1.63 ± 0.43 |
| F15 | Labrasol | 5.00 | 5000 | 5.27 | White Dispersion | 3.71 | N/A |

TABLE 11.4

PAMPA SCREENING RESULTS STAGES 3 AND 4
PAMPA Screening Results Stage 3

| | | Formulation Vehicle Preparation & pH in 100 mL Purified Water | | | Observations/Results API's Concentration: 1 mg/mL, 10 mL Vehicle | | |
|---|---|---|---|---|---|---|---|
| Formulation Code | Enhancer Selected | Enhancer's Target Conc (mg/mL) | Quantity (mg) | pH | Appearance | pH | Flux Ratio (In vitro pK PAMPA Assay) |
| F0 Repeat 2 | None | NA | NA | 6.76 | Clear Solution | 3.73 | 1.00 ± 0.55 |
| F0 Repeat 3 | None | NA | NA | 6.76 | Clear Solution | 3.73 | 1.00 ± 0.61 |
| F1 | Sodium lauryl sulfate (SLS) | 0.10 | 10 | 6.58 | Clear Solution | 3.74 | N/A |
| F2 | Caprolactam | 2.50 | 250 | 6.68 | Clear Solution | 3.72 | N/A |
| F3B Repeat 1 | Polysorbate 80 | 10.00 | 1000 | 6.29 | Clear Solution | 3.89 | N/A |
| F16 | Sodium decyl sulfate | 0.20 | 20 | 5.99 | Clear Solution | 3.74 | 2.79 ± 2.09 |
| F17 | Sodium octyl sulfate | 0.20 | 20 | 6.08 | Clear Solution | 3.86 | N/A |
| F18 | Decyltrimethylammoniu monooleate | 1.00 | 100 | 7.21 | Clear Solution | 3.68 | N/A |
| F19 | Span-80 (Sorbitan monooleate) | 2.50 | 250 | 6.27 | White Dispersion | 3.78 | 1.23 ± 0.75 |
| F20 | Triton X-100 | 2.50 | 250 | 5.27 | Clear Solution | 3.83 | N/A |
| F21 | Sodium glycocholate hydrate | 1.00 | 100 | 7.06 | Clear Solution | 4.24 | 1.13 ± 0.54 |
| F22 | Cholic acid | 2.50 | 250 | 4.67 | White Dispersion | 3.86 | N/A |
| F23 | Heptanoic acid | 2.50 | 250 | 3.41 | Clear Solution | 3.45 | N/A |
| F24 | Isopropyl Palmitate | 2.50 | 250 | 6.37 | Dispersion | 3.81 | N/A |
| F25 | Methyl laurate | 2.50 | 250 | 5.95 | Oily Dispersion | 3.84 | 1.40 ± 1.07 |
| F26 | Sodium oleate | 2.50 | 250 | 10.61 | White Dispersion | 8.81 | 17.35 ± 6.77 |
| F27 | Urea | 2.50 | 250 | 9.17 | Clear Solution | 3.91 | N/A |
| F28 | 1-Octyl-2-pyrrolidone | 2.50 | 250 | 7.78 | Clear Solution | 3.77 | N/A |
| F29 | 1-Methylpiperazine | 2.50 | 250 | 10.91 | Clear Solution | 9.80 | N/A |
| F30 | 1-Methyl-2-Pyrrolidinone | 2.50 | 250 | 6.84 | Clear Solution | 3.82 | 1.79 ± 0.91 |
| F31 | n-Caproic Acid | 2.50 | 250 | 3.35 | Clear Solution | 3.37 | 1.64 ± 1.79 |
| F32 | Sodium Salicylate | 2.50 | 250 | 6.80 | Clear Solution | 4.32 | N/A |
| F33 | (±)-Limonene | 2.50 | 250 | 6.41 | Clear Solution | 3.72 | 2.79 ± 1.36 |
| F34 | L-Fenchone | 2.50 | 250 | 7.38 | Clear Solution | 3.71 | 0.57 ± 0.49 |
| F35 | Cineole | 2.50 | 250 | 7.37 | Clear Solution | 3.75 | 1.71 ± 0.73 |
| F36 | Pinene oxide | 2.50 | 250 | 5.91 | Clear Solution | 3.74 | 2.64 ± 1.27 |
| F37 | 2-Octyl-1-dodecanol | 2.50 | 250 | 7.26 | Clear Solution | 3.75 | 3.14 ± 1.36 |
| F38 | Cumin seed oil | 2.50 | 250 | 4.47 | Clear Solution | 3.75 | N/A |
| F39 | Caproyl PGMC | 5.00 | 500 | 6.44 | Oily Solution | 3.75 | N/A |
| F40 | Caproyl 90 (Propylene glycol dicaprylate) | 5.00 | 500 | 6.59 | Oily Solution | 3.73 | N/A |
| F41 | Lauroglycol FCC | 5.00 | 500 | 6.03 | Oily Solution | 3.86 | N/A |
| F42 | Lauroglycol 90 | 5.00 | 500 | 6.35 | Oily Solution | 3.77 | N/A |
| F43 | Labrafac PG | 5.00 | 500 | 6.63 | Oily Solution | 3.74 | N/A |
| F44 | Transcutol | 5.00 | 500 | 6.64 | Oily Solution | 3.77 | N/A |
| F45 | Gelucire 50/13 | 5.00 | 500 | 5.95 | Opaque Solution | 3.84 | N/A |
| F46 | Labrafil M1944 CS | 5.00 | 500 | 6.29 | White Dispersion | 3.91 | N/A |

TABLE 11.4-continued

PAMPA SCREENING RESULTS STAGES 3 AND 4
PAMPA Screening Results Stage 3

| Formulation Code | Enhancer Selected | Enhancer's Target Conc (mg/mL) | Quantity (mg) | pH | Appearance | pH | Flux Ratio (In vitro pK PAMPA Assay) |
|---|---|---|---|---|---|---|---|

PAMPA Screening Results Stage 4

Formulation Vehicle Preparation & pH in 100 mL Purified Water

Observations/Results — API's Concentration: 1 mg/mL, 10 mL Vehicle

| Formulation Code | Enhancer Selected | Enhancer's Target Conc (mg/mL) | Quantity (mg) | Appearance | pH | Flux Ratio 1 | Flux Ratio 2 |
|---|---|---|---|---|---|---|---|
| F0 Repeat 4 | None | NA | NA | 7.21 | Clear solution | 1.22 ± 0.66 | 1.00 ± 0.40 |
| F0 Repeat 5 |  | NA | NA | 7.20 | Clear solution | 1.00 ± 0.65 | 0.82 ± 0.44 |
| F3B Repeat 2 | Polysorbate 80 | 10.00 | 1000 | 6.54 | Clear solution | 34.16 ± 16.61 | 28.06 ± 9.05 |
| F3B Repeat 3 |  | 10.00 | 1000 | 6.29 | Clear solution | 1.51 ± 0.89 | 1.24 ± 0.57 |
| F3B Repeat 4 |  | 10.00 | 1000 | 6.29 | Clear solution | 0.98 ± 0.50 | 0.81 ± 0.29 |
| F26 Repeat 1 | Sodium oleate | 2.50 | 250 | 10.61 | White Dispersion | 8.22 ± 3.82 | 6.75 ± 1.95 |
| F26 Repeat 2 |  | 2.50 | 250 | 10.61 | White Dispersion | 12.16 ± 6.82 | 9.99 ± 4.27 |

For Formulations 17, 18, 20, 22, 23, 24, 27, 28, 29, 40, 42, 43, 44, 45, and 3B, the UV/Visible signal in the acceptor compartment was below the detection limit and the flux ratio could not be determined. Formulations 32 and 38 showed very high penetration rates for their corresponding vehicles that completely saturated the UV-Visible signal in the acceptor compartment, precluding the signal detection of the API under the strong vehicle background. The significant improvement of permeability seen previously for formulation 3B was not reproducible in the subsequent repeats. Significant and reproducible improvement was noted for formulation 26, and significant improvement was also observed for formulation 37. Formulations 16, 19, 21, 25, 30, 31, 33, 34, 35, and 36 showed no or minor improvement in flux in comparison to the control API.

b. Flux Ratio Comparison

Flux ratios obtained for the different newly tested formulations of 3,4,3-L1(1,2-HOPO) are summarized in TABLE 11.5. The repeats for formulation 3B did not reproduce the initial 75-fold permeability increase. However, Formulation 26 did result in reproducible enhancement, obtained with 2.50 mg/mL sodium oleate and 1 mg/mL API, with a recorded pH of 8.81.

TABLE 11.5

FLUX RATIO COMPARISONS FOR TESTED FORMULATIONS

| Formulation Code | Flux Ratio | SD |
|---|---|---|
| F0 (API Control) | 1.00 |  |
| F0 Repeat 1 | 1.00 | 0.09 |
| F0 Repeat 2 | 1.00 |  |
| F0 Repeat 3 | 1.00 | 0.09 |
| F0 Repeat 4 | 1.22 | 0.66 |
|  | 1.00 | 0.40 |
| F0 Repeat 5 | 1.00 | 0.65 |
|  | 0.82 | 0.44 |
| F3 | 2.22 | 0.96 |
| F3 Repeat | 0.77 | 0.08 |
| F3A | 0.94 | 0.09 |
| F3B | 75.57 | 5.22 |
| F3B Repeat 1 | NA | NA |
| F3B Repeat 2 | 34.16 | 16.61 |
|  | 28.06 | 9.05 |
| F3B Repeat 3 | 1.51 | 0.89 |
|  | 1.24 | 0.57 |
| F3B Repeat 4 | 0.98 | 0.50 |
|  | 0.81 | 0.29 |
| F4 | 1.04 | 0.43 |
| F5 | 1.06 | 0.72 |
| F5 Repeat | 1.86 | 0.22 |
| F5A | 1.39 | 0.14 |
| F10 | 0.84 | 0.45 |
| F10A | 0.77 | 0.09 |
| F13 | 2.30 | 0.93 |
| F13 Repeat | 0.71 | 0.12 |
| F13A | 0.95 | 0.07 |
| F13B | 1.04 | 0.08 |
| F14 | 1.18 | 0.60 |
| F14 Repeat | 1.15 | 0.12 |
| F14A | 0.97 | 0.30 |
| F14B | 1.63 | 0.43 |
| F16 | 2.79 | 2.09 |
| F19 | 1.23 | 0.75 |

TABLE 11.5-continued

FLUX RATIO COMPARISONS FOR TESTED FORMULATIONS

| Formulation Code | Flux Ratio | SD |
|---|---|---|
| F21 | 1.13 | 0.54 |
| F25 | 1.40 | 1.07 |
| F26 | 17.35 | 6.77 |
| F26 Repeat 1 | 8.22 | 3.82 |
|  | 6.75 | 1.95 |
| F26 Repeat 2 | 12.16 | 6.82 |
|  | 9.99 | 4.27 |
| F30 | 1.79 | 0.91 |
| F31 | 1.64 | 1.79 |
| F33 | 2.79 | 1.36 |
| F34 | 0.57 | 0.49 |
| F35 | 1.71 | 0.73 |
| F36 | 2.64 | 1.27 |
| F37 | 3.14 | 1.36 |

6. Conclusion

Thirty one additional permeation enhancers were evaluated for their ability at increasing the permeability of 3,4,3-L1(1,2-HOPO), using an in vitro PAMPA assay with artificial GIT lipid membranes. The significant increase in permeability originally observed for one formulation containing 10 mg/mL of Polysorbate 80 and 1 mg/mL of API was not reproducible. While most other tested formulations showed no or minor improvement in permeability, improvement was noted for formulations containing 2.50 mg/mL sodium oleate or 2-octyl-1-dodecanol. Formulations containing sodium oleate or 2-octyl-1-dodecanol will be evaluated further in vivo.

Analysis of 3,4,3-L1(1,2-HOPO) Lot ML-11-276 was performed and a certificate of analysis was prepared regarding appearance, identification by IR and $^1$H-NMR, related compounds by HPLC, HPLC purity, heavy metal content, residual solvent content, water content by Karl Fischer, residue on ignition, and purity.

TABLE 11.6

PAMPA MEASUREMENT SUMMARY
Screening Stage 3

| Sample | $C_{ACC}$, μm | SD $C_{ACC}$ | Flux Ratio | SD Ratio |
|---|---|---|---|---|
| Set 1 | | | | |
| Formulation 16 | 0.30 | 0.19 | 2.79 | 2.09 |
| Formulation 17 | <0.1 | | | |
| Formulation 18 | <0.1 | | | |
| Formulation 19 | 0.13 | 0.06 | 1.23 | 0.75 |
| Formulation 20 | <0.1 | | | |
| Formulation 21 | 0.12 | 0.03 | 1.13 | 0.54 |
| Formulation 22 | <0.1 | | | |
| Formulation 23 | <0.1 | | | |
| Formulation 24 | <0.1 | | | |
| Formulation 25 | 0.15 | 0.10 | 1.40 | 1.07 |
| Formulation 26 | 1.85 | 0.09 | 17.35 | 6.77 |
| Formulation 27 | <0.1 | | | |
| Formulation 0-Control | 0.11 | 0.04 | 1.00 | 0.55 |
| Set 2 | | | | |
| Formulation 28 | <0.1 | | | |
| Formulation 29 | <0.1 | | | |
| Formulation 30 | 0.25 | 0.07 | 1.79 | 0.91 |
| Formulation 31 | 0.23 | 0.23 | 1.64 | 1.79 |
| Formulation 32 | und | | | |
| Formulation 33 | 0.39 | 0.09 | 2.79 | 1.36 |
| Formulation 34 | 0.08 | 0.06 | 0.57 | 0.49 |

TABLE 11.6-continued

PAMPA MEASUREMENT SUMMARY
Screening Stage 3

| Formulation 35 | 0.24 | 0.00 | 1.71 | 0.73 |
|---|---|---|---|---|
| Formulation 36 | 0.37 | 0.08 | 2.64 | 1.27 |
| Formulation 37 | 0.44 | 0.03 | 3.14 | 1.36 |
| Formulation 38 | und | | | |
| Formulation 0-Control | 0.14 | 0.06 | 1.00 | 0.61 |
| Set 3 | | | | |
| Formulation 39 | 0.14 | 0.04 | | |
| Formulation 40 | <0.1 | | | |
| Formulation 41 | 0.12 | 0.04 | | |
| Formulation 42 | <0.1 | | | |
| Formulation 43 | <0.1 | | | |
| Formulation 44 | <0.1 | | | |
| Formulation 45 | <0.1 | | | |
| Formulation 46 | 0.27 | 0.10 | | |
| Formulation 3B | <0.1 | | | |
| Formulation 0-Control | <0.1 | | | |

| Sample | $C_{ACC}$, μm | SD $C_{ACC}$ | Ratio (1) | SD Ratio | Ratio (2) | SD Ratio |
|---|---|---|---|---|---|---|
| F3B_2444 | 5.04 | 0.79 | 34.16 | 16.61 | 28.06 | 9.05 |
| F3B_2487 | 0.22 | 0.08 | 1.51 | 0.89 | 1.24 | 0.57 |
| F3B_2509 | 0.14 | 0.03 | 0.98 | 0.50 | 0.81 | 0.29 |
| F26_2487 | 1.21 | 0.08 | 8.22 | 3.82 | 6.75 | 1.95 |
| F26_2509 | 1.79 | 0.58 | 12.16 | 6.82 | 9.99 | 4.27 |
| F0-Control_2487 | 0.18 | 0.05 | 1.22 | 0.66 | 1.00 | 0.40 |
| F0-Control_2509 | 0.15 | 0.07 | 1.00 | 0.65 | 0.82 | 0.44 |

Sample compound name based on provided information, four last digits numbers refer to the project number associated with the originally submitted samples.
$C_{ACC}$, μM average value of API concentration determined in the acceptor compartment after 18 hours of incubation
Flux Ratio calculated based on a ratio between UV signals in the acceptor comparmient when corresponding donor compartment has formulated product and pure API respectively
Flux Ratio (1) calculated based on the control submitted for the project 132509
Flux Ratio (2) calculated based on the control submitted for the project 132487
SD $C_{ACC}$ standard deviation of concentration from a replicate measurements
SD Ratio standard deviation of a ratio calculated taking into account propagation of errors.

Example 12

The feasibility of developing oral formulations for 3,4,3-L1(1,2-HOPO) was evaluated.

Four oral dosage forms were investigated: (i) powder in bottle, (ii) dispersible/dissolvable granules, (iii) chewable tablets, and (iv) conventional immediate release tablets. Based on the studies performed, nine formulation prototypes that showed immediate drug release behavior and required physical properties were identified and selected for API verification, gastric fluid dissolution, and related substance testing following defined liquid chromatography methods. Among these selected compositions, two are powder in bottle formulations, two are granule formulations, three are chewable tablet formulations, and two are conventional tablet formulations. The respective compositions of these prototype formulations are summarized and tabulated below. All assays confirmed that these prototypes are suitable for further development.

| Dosage Form → | Powder in Bottle | | Granules | | Chewable Tablets | | | Conventional Tablets | |
|---|---|---|---|---|---|---|---|---|---|
| Ingredients  Formulation ID → | A2 | A11 | G11 | G12 | C11 | C13 | C21 | T50 | T51 |
| Intra-Granular Materials (for granules and conventional tablets) | | | | | | | | | |
| 3,4,3-LI(1,2-HOPO) | 1.000 | 1.000 | 1.000 | 1.000 | 0.500 | 0.500 | 0.500 | 0.500 | 0.500 |
| Sodium Oleate | 0.092 | 0.092 | 0.092 | 0.092 | 0.046 | 0.046 | 0.046 | 0.046 | 0.046 |
| Microcrystalline Cellulose and Carboxymethyl Cellulose, NF (Avivel RC-591) | — | 1.000 | — | — | — | — | — | — | — |
| Croscarmellose Sodium, NF (Ac-Di-Sol) | — | — | 0.075 | 0.075 | 0.075 | — | 0.075 | 0.084 | 0.092 |
| Microcrystalline Cellulose and guar gum, NF (Avicel CE-15) | — | — | 1.833 | — | 1.854 | — | 0.927 | — | — |
| Lactose Monohydrate, NF (Pharmatose 300M) | — | — | — | 1.533 | — | — | — | — | — |
| Lactose Monohydrate, Povidone and Crospovidone, NF (Ludipress) | — | — | — | — | — | 1.929 | — | — | — |
| Mannitol, USP (Mannogem) | — | — | — | — | — | — | 0.9227 | — | — |
| Magensium sterate, NF (HyQual) | — | — | — | — | 0.025 | 0.025 | 0.025 | — | — |
| Microcrystalline Cellulose, NF (Avicel PH 102) | — | — | — | — | — | — | — | 0.410 | 0.501 |
| Colloidal silicone dioxide, NF (Cab-O-Sil M5P) | — | — | — | — | — | — | — | 0.005 | 0.006 |
| Purified water, USP | — | — | Q.S. | Q.S. | — | — | — | — | — |
| Magensium sterate, NF (HyQual) | — | — | — | — | — | — | — | — | — |
| Extra-Granular Materials (for granules and conventional tablet) | | | | | | | | | |
| Hypromellose, 50 cps | — | — | — | 0.300 | — | — | — | — | — |
| Magensium sterate, NF (HyQual) | — | — | — | — | — | — | — | 0.005 | 0.006 |
| Unit weight (g) | 1.092 | 2.0962 | 3.000 | 3.000 | 2.500 | 2.500 | 2.500 | 1.050 | 1.151 |

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

What is claimed is:

1. A pharmaceutical composition comprising:
   a 1,2-HOPO chelating agent in an amount from about 100 to about 1500 mg; and
   sodium oleate,
   wherein the 1,2-HOPO chelating agent is 3,4,3-L1-1,2-HOPO.

2. The pharmaceutical composition of claim 1, wherein sodium oleate is present at about 70 to about 130 mg.

3. The pharmaceutical composition of claim 1, wherein sodium oleate is present at 8 to 12% of a total weight of the composition.

4. The pharmaceutical composition of claim 3, wherein sodium oleate is about 11% of a total weight of the composition.

5. The pharmaceutical composition of claim 3, wherein the 3,4,3-L1-1,2-HOPO chelating agent is present in an amount from 300 to 1500 mg.

6. The pharmaceutical composition of claim 4, wherein the 3,4,3-L1-1,2-HOPO chelating agent is present in an amount from 400 to 1200 mg.

7. The pharmaceutical composition of claim 4, wherein the 3,4,3-L1-1,2-HOPO chelating agent is present in an amount from 100 to 300 mg.

8. The pharmaceutical composition of claim 4, wherein the 3,4,3-L1-1,2-HOPO chelating agent is present in an amount of 600 mg.

9. The pharmaceutical composition of claim 1, wherein the 3,4,3-L1-1,2-HOPO chelating agent is present in an amount from 300 to 1500 mg.

10. The pharmaceutical composition of claim 1, wherein the 3,4,3-L1-1,2-HOPO chelating agent is present in an amount from 400 to 1200 mg.

11. The pharmaceutical composition of claim 1, wherein the 3,4,3-L1-1,2-HOPO chelating agent is present in an amount from 100 to 300 mg.

12. The pharmaceutical composition of claim 1, wherein the 3,4,3-L1-1,2-HOPO chelating agent is present in an amount of 600 mg.

13. The pharmaceutical composition of claim 1, wherein the pharmaceutical composition is packaged as a tablet.

14. The pharmaceutical composition of claim 1, wherein the pharmaceutical composition is within a capsule.

15. The pharmaceutical composition of claim 1, wherein the pharmaceutical composition is within one or more granules.

16. The pharmaceutical composition of claim 7, wherein the pharmaceutical composition is packaged as a tablet.

17. The pharmaceutical composition of claim 7, wherein the pharmaceutical composition is within a capsule.

18. The pharmaceutical composition of claim 7, wherein the pharmaceutical composition is within one or more granules.

* * * * *